US007993642B2

(12) United States Patent
Tsunoda et al.

(10) Patent No.: US 7,993,642 B2
(45) Date of Patent: Aug. 9, 2011

(54) ANTI-MPL ANTIBODIES

(75) Inventors: Hiroyuki Tsunoda, Ibaraki (JP); Kiyotaka Nakano, Ibaraki (JP); Tetsuro Orita, Ibaraki (JP); Masayuki Tsuchiya, Shizuoka (JP); Yuichi Hirata, Ibaraki (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 366 days.

(21) Appl. No.: 10/551,504

(22) PCT Filed: Dec. 10, 2004

(86) PCT No.: PCT/JP2004/018506

§ 371 (c)(1), (2), (4) Date: May 12, 2006

(87) PCT Pub. No.: WO2005/056604

PCT Pub. Date: Jun. 23, 2005

(65) Prior Publication Data

US 2006/0222643 A1 Oct. 5, 2006

(30) Foreign Application Priority Data

Dec. 12, 2003 (JP) ................................ 2003-415746
Mar. 12, 2004 (JP) ................................ 2004-071763
Aug. 27, 2004 (JP) ................................ 2004-248323

(51) Int. Cl.
*A61K 39/395* (2006.01)
*C12P 21/08* (2006.01)
*C07K 16/00* (2006.01)

(52) U.S. Cl. ............... 424/141.1; 530/388.1; 530/387.3; 530/387.9; 530/388.15; 530/388.22

(58) Field of Classification Search ........................ None
See application file for complete search history.

(56) References Cited

U.S. PATENT DOCUMENTS 4,946,778 A 8/1990 Ladner et al.
5,618,920 A 4/1997 Robinson et al.
5,780,021 A 7/1998 Sobel
5,789,554 A 8/1998 Leung et al.
5,837,242 A 11/1998 Holliger et al.
5,837,821 A 11/1998 Wu
5,840,344 A 11/1998 Fukushima
5,885,574 A 3/1999 Elliott
5,892,020 A 4/1999 Mezes et al.
5,977,322 A 11/1999 Marks et al.
6,126,980 A 10/2000 Smith et al.
6,132,992 A 10/2000 Ledbetter et al.
6,361,760 B1 3/2002 Tovey
6,579,692 B1 6/2003 Fukushima
6,699,686 B1 3/2004 Brocard et al.
6,719,972 B1 4/2004 Gribben et al.
6,759,043 B2 7/2004 Fukushima
7,115,373 B2 10/2006 Hashida et al.
7,262,278 B2 8/2007 Tawara et al.
7,456,260 B2 11/2008 Rybak et al.
2002/0028178 A1 3/2002 Hanna et al.
2002/0155537 A1 10/2002 Carter et al.
2002/0197706 A1 12/2002 Nadkarni et al.
2003/0082612 A1 5/2003 Snodgrass et al.
2003/0103979 A1 6/2003 Leung et al.
2003/0147894 A1 8/2003 Fukushima et al.
2003/0157100 A1 8/2003 Fukushima et al.
2003/0157577 A1 8/2003 Fukushima et al.
2003/0202975 A1 10/2003 Tedder
2003/0211108 A1 11/2003 Fukushima et al.
2004/0001828 A1 1/2004 Tuscano et al.
2004/0058393 A1 3/2004 Fukishima et al.
2004/0073013 A1 4/2004 Fukushima et al.
2004/0219643 A1 11/2004 Winter et al.
2005/0130224 A1 6/2005 Saito et al.
2005/0214278 A1 9/2005 Kakuta et al.
2005/0267222 A1 12/2005 Iwata et al.
2006/0058511 A1 3/2006 Tanikawa et al.
2006/0159673 A1 7/2006 Kojima
2006/0269989 A1 11/2006 Miyazaki et al.
2007/0087381 A1 4/2007 Kojima
2007/0280951 A1 12/2007 Kimura et al.
2007/0281327 A1 12/2007 Nakano et al.
2008/0009038 A1 1/2008 Ohtomo et al.
2008/0107654 A1 5/2008 Kikuchi et al.
2008/0206229 A1 8/2008 Ono et al.
2008/0248037 A1 10/2008 Li et al.
2008/0274110 A1 11/2008 Ozaki et al.
2008/0286280 A1 11/2008 Kallmeyer et al.

(Continued)

FOREIGN PATENT DOCUMENTS

AU 755822 3/1999

(Continued)

OTHER PUBLICATIONS

Bowie et al, 1990, Science 247:1306-1310.* Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
Burrone et al., "Stimulation of HLA-A,B,C by IFN-alpha. The derivation of Molt 4 variants and the differential expression of HLA-A,B,C subsets," *The EMBO Journal*, 4(11):2855-2860 (1985).
Cangemi et al., "IFN-alpha mediates the up-regulation of HLA class I on melanoma cells without switching proteasome to immunoproteasome," *International Immunology*, 15(12):1415-1421 (2005).
CAPLUS Accession No. 2005:547624, 2 pages (2008).
DeJonge et al., "In vivo retargeting of T cell effector function by recombinant bispecific single chain Fv (anti-DC3 x anti-idiotype) induces long term survival of the murine BCL1 lymphoma model," *J. Immunol.*, 161(3):1454-1461 (1998).

(Continued)

*Primary Examiner* — Shulamith H Shafer
(74) *Attorney, Agent, or Firm* — Fish & Richardson P.C.

(57) ABSTRACT

Anti-human Mpl antibodies were isolated and purified. Anti-human Mpl diabodies and anti-human Mpl sc(Fv)2 were prepared using genetic engineering techniques and anti-human Mpl sc(Fv)2 was also humanized. The diabodies and sc(Fv)2 were assayed for TPO-like agonistic activity, and were found to have activities higher than those of anti-human Mpl antibodies, or activities equivalent to or higher than those of naturally-occurring human TPO ligand.

27 Claims, 22 Drawing Sheets

U.S. PATENT DOCUMENTS

| | | | |
|---|---|---|---|
| 2009/0022687 | A1 | 1/2009 | Matsumoto et al. |
| 2009/0028854 | A1 | 1/2009 | Igawa et al. |
| 2009/0117097 | A1 | 5/2009 | Igawa et al. |
| 2009/0214535 | A1 | 8/2009 | Igawa |
| 2009/0297501 | A1 | 12/2009 | Igawa et al. |
| 2009/0311718 | A1 | 12/2009 | Fukushima et al. |
| 2010/0015133 | A1 | 1/2010 | Igawa et al. |
| 2010/0040600 | A1 | 2/2010 | Yoshikubo et al. |
| 2010/0092457 | A1 | 4/2010 | Aburatani et al. |

FOREIGN PATENT DOCUMENTS

| | | | |
|---|---|---|---|
| AU | 2004297111 | | 6/2005 |
| AU | 2002210917 | | 5/2006 |
| CA | 2272245 | | 5/1998 |
| CA | 2 331 641 | | 11/1999 |
| CN | 1723036 | | 1/2006 |
| DE | 198 19 846 | | 11/1999 |
| EP | 437 622 | | 7/1991 |
| EP | 0 562 125 | | 9/1993 |
| EP | 0 721 015 | | 7/1996 |
| EP | 0 774 511 | | 5/1997 |
| EP | 811 691 | | 12/1997 |
| EP | 1 035 132 | | 9/2000 |
| EP | 1 327 681 | A1 | 10/2001 |
| EP | 1 327 680 | A1 | 7/2003 |
| EP | 1369431 | A1 | 12/2003 |
| EP | 1 396 500 | | 3/2004 |
| EP | 1561759 | | 8/2005 |
| EP | 1712565 | | 10/2006 |
| EP | 1757686 | | 2/2007 |
| EP | 1870458 | | 12/2007 |
| EP | 1900814 | | 3/2008 |
| EP | 1 262 548 | | 8/2008 |
| JP | 3-41033 | | 2/1991 |
| JP | 7-503622 | | 4/1995 |
| JP | 7236475 | | 9/1995 |
| JP | 8-500979 | | 2/1996 |
| JP | 9-289892 | | 11/1997 |
| JP | 10-505231 | | 5/1998 |
| JP | 10510842 | A1 | 10/1998 |
| JP | 11-500916 | | 1/1999 |
| JP | 11-092500 | | 4/1999 |
| JP | 2000-95800 | | 4/2000 |
| JP | 2001/506135 | | 5/2001 |
| JP | 2001-513999 | | 9/2001 |
| JP | 2001-518930 | | 10/2001 |
| JP | 2001-523971 | | 11/2001 |
| JP | 2002-543822 | | 12/2002 |
| JP | 2002-544173 | | 12/2002 |
| JP | 2003-515323 | | 5/2003 |
| JP | 2004-086862 | | 3/2004 |
| JP | 2004-0866862 | | 3/2004 |
| JP | 2004222502 | A1 | 8/2004 |
| JP | 2004-292455 | | 10/2004 |
| JP | 2005204539 | A1 | 8/2005 |
| JP | 2005539082 | A1 | 12/2005 |
| MX | 9905856 | A | 7/2000 |
| WO | 9100739 | | 1/1991 |
| WO | WO 91/16928 | | 11/1991 |
| WO | WO 92/19759 | | 11/1992 |
| WO | WO 93/06862 | | 4/1993 |
| WO | WO 94/05690 | | 3/1994 |
| WO | WO 94/13806 | | 6/1994 |
| WO | WO 96/26648 | | 9/1996 |
| WO | WO 96/27011 | | 9/1996 |
| WO | WO 96/34892 | | 11/1996 |
| WO | WO 96/36360 | | 11/1996 |
| WO | 9640218 | | 12/1996 |
| WO | WO 97/01633 | | 1/1997 |
| WO | WO 97/10354 | | 3/1997 |
| WO | WO 97/32601 | | 9/1997 |
| WO | WO9734632 | | 9/1997 |
| WO | WO 98/22136 | | 5/1998 |
| WO | WO 98/44001 | | 8/1998 |
| WO | WO 98/50431 | | 11/1998 |
| WO | WO 99/03495 | | 1/1999 |
| WO | WO 99/10494 | | 3/1999 |
| WO | WO 99/12973 | | 3/1999 |
| WO | WO 99/17364 | | 4/1999 |
| WO | WO 00/23593 | | 4/2000 |
| WO | WO 00/44788 | | 8/2000 |
| WO | WO 00/53634 | | 9/2000 |
| WO | WO 00/67795 | | 11/2000 |
| WO | WO 00/69462 | | 11/2000 |
| WO | WO 00/75191 | | 12/2000 |
| WO | WO 01/36486 | | 5/2001 |
| WO | WO 01/44282 | | 6/2001 |
| WO | WO 01/64713 | | 9/2001 |
| WO | WO 01/66737 | | 9/2001 |
| WO | WO 01/70775 | | 9/2001 |
| WO | WO 01/74388 | | 10/2001 |
| WO | WO 01/77342 | | 10/2001 |
| WO | WO 01/79494 | | 10/2001 |
| WO | WO 01/87337 | | 11/2001 |
| WO | WO 01/97858 | | 12/2001 |
| WO | WO 02/04021 | | 1/2002 |
| WO | WO 02/22212 | | 3/2002 |
| WO | WO 02/33072 | | 4/2002 |
| WO | WO 02/078612 | | 10/2002 |
| WO | WO 02/094880 | | 11/2002 |
| WO | WO 02/096457 | | 12/2002 |
| WO | WO 02/097033 | | 12/2002 |
| WO | WO03002607 | A1 | 9/2003 |
| WO | WO 03/086324 | | 10/2003 |
| WO | WO 03/087163 | | 10/2003 |
| WO | WO 03/107218 | | 12/2003 |
| WO | WO 2004/003019 | | 1/2004 |
| WO | WO 2004/019966 | | 3/2004 |
| WO | 2004026332 | | 4/2004 |
| WO | WO 2004/026332 | | 4/2004 |
| WO | WO 2004/037293 | | 5/2004 |
| WO | WO 2004/111233 | | 12/2004 |
| WO | 2005056604 | | 6/2005 |
| WO | 2005056798 | | 6/2005 |
| WO | WO 2005/056602 | | 6/2005 |
| WO | WO 2005/056603 | | 6/2005 |
| WO | WO 2005/056604 | | 6/2005 |
| WO | WO 2005/056605 | | 6/2005 |
| WO | WO 2005/056798 | | 6/2005 |
| WO | WO 2005/100560 | | 10/2005 |
| WO | WO 2005/107784 | | 11/2005 |
| WO | WO 2008/071394 | | 6/2008 |

OTHER PUBLICATIONS

Kriangkum et al., "Bispecific and bifunctional single chain recombinant antibodies," *Biomol. Eng.*, 18(2):31-40 (2001).

Kumar et al., "The second PDZ domain of INAD is a type I domain involved in binding to eye protein kinase C. Mutational analysis and naturally occurring variants," *J. Biol. Chem.*, 276(27):24971-2497 (2001).

Mack et al., "A small bispecific antibody construct expressed as a functional single-chain molecule with high tumor cell cytotoxicity," *Proc. Natl. Acad. Sci. USA*, 92(15):7021-7025 (1995).

Mallender et al., "Construction, expression and activity of a bivalent bispecific single-chain antibody," *J. Biol. Chem.*, 269(1):199-206 (1994).

McInnes and Schett, "Cytokines in the pathogenesis of rheumatoid arthritis," *Nature Reviews/Immunology*, 7:429-442 (2007).

Sal-man et al., "Arginine mutations within a transmembrane domain of Tar, an *Escherichia coli* aspartate receptor, can drive monodimer dissociation and heterodimer association n vivo," *Biochem. J.*, 385(1):29-36 (2005).

Scott, "The Problem with Potency," *Nature Biotechnology*, 23(9):1037-1039 (2005).

Seikomoto et al., "A Single-Chain Fv Diabody Against Human Leukocyte Antigen-A Molecules Specifically Induces Myeloma Cell Death in the Bone Marrow Environment," *Cancer Res.*, 67(3):1184-1192 (2007).

Sekimoto et al., "Eradication of Human Myeloma Cells by a Recombinant HLA Class I-Specific Single Chain Fv Diabody," *Blood*, 102:932a, XP009106629 (Abstract #3469) (Nov. 2003) [Abstract of the American Society of Hematology 45$^{th}$ Annual Meeting, Dec. 6-9, 2003, San Diego, California].

Ozaki et al., "A Recombinant HLA Class I-Specific Single Chain Fv Diabody Induces Cell Death in Human Lymphoid Malignancies," *Blood*, 102:933a, XP002987122 (Abstract #3474) (Nov. 2003) [Abstract of the American Society of Hematology 45th Annual Meeting, Dec. 6-9, 2003, San Diego, California].

Stein et al., "Characterization of humanized IgG4 anti-HLA-DR monoclonal antibody that lacks effector cell functions but retains direct antilymphoma activity and increases the potency of rituximab," *Blood*, 108(8):2736-2744 (2006).

Reff et al., "A review of modifications to recombinant antibodies: attempt to increase efficacy in oncology applications", Critical Reviews in Oncology and Hematology, 40:25-35, 2001.

Boger et al., "Cytokine receptor dimerization and activation: prospects for small molecule agonists," *Bioorganic and Medicinal Chemistry*, 9(3):557-562 (2001).

Milligan, "G Protein-Coupled Receptor Dimerization: Function and Ligand Pharmacology," *Mol. Pharm*., 66:1-7 (2004).

Abe et al., "Surrogate thrombopoietin", Immunology Letters 61:73-78, 1998.

Casset et al., "A peptide mimetic of an anti-CD4 monoclonal antibody by rational design", Biochemical and Biophysical Research Communications 307:198-205, 2003.

Chen et al., "Selection and analysis of an optimized anti-VEGF antibody: Crystal structure of an affinity-matured Fab in complex with antigen", Journal of Molecular Biology 293:865-881, 1999.

De Pascalis et al., "Grafting of 'abbreviated' complementary-determining regions containing specificity-determining residues essential for ligand contact to engineer a less immunogenic humanized monoclonal antibody", Journal of Immunology 169:3076-3084, 2002.

Holm et al., "Functional mapping and single chain construction of the anti-cytokeratin 8 monoclonal antibody TS1", Molecular Immunology 44:1075-1084, 2007.

MacCallum et al., "Antibody-antigen interactions: Contact analysis and binding site topography", Journal of Molecular Biology 262:732-745, 1996.

Palacios et al., "IL-3-dependent mouse clones that express B-220 surface antigen, contain Ig genes in germ-line configuration, and generate B lymphocutes in vivo", Cell 41:727-734, 1985.

Rudikoff et al., "Single amino acid substitution altering antigen-binding specificity", Proc. Natl. Acad. Sci. USA, 79:1979-1983, 1982.

Skolnick et al., "From genes to protein structure and function: novel applications of computational approaches in the genomic era", Trends in Biotechnology 18:34-39, 2000.

Souyri et al., "A putative truncated cytokine receptor gene transduced by the myeloproliferative leukemia virus immortalizes hematopoietic progenitors", Cell 63:1137-1147, 1990.

Vajdos et al., "Comprehensive functional maps of the antigen-binding site of an anti-ErbB2 antibody obtained with shotgun scanning mutagenesis", Journal of Molecular Biology 320:415-428, 2002.

Wu et al., "Humanization of a murine monoclonal antibody by simultaneous optimization of framework and CDR residues", Journal of Molecular Biology 294:151-162, 1999.

Ledbetter et al., Agonistic Activity of a CD4O-Specific Single-Chain Fv Constructed from the Variable Regions of mAb G28-5, Critical Reviews in Immunology, vol. 17, pp. 427-435 (1997).

Kong et al., "A Single Residue, Aspartic Acid 95, in the δOpioid Receptor Specifies Selective High Affinity Agonist Binding", The Journal of Biological Chemistry, vol. 268(31), pp. 23056-23058 (1993).

Medline Plus Drug Information: Dexamethasone Oral www.nlm.nih.gov/medlineplus/druginfo/meddmaster/a682792.html, downloaded Jul. 19, 2007; last revised Apr. 1, 2003 (see p. 3) (4 pages).

Arndt et al., "Factors Influencing the Dimer to Monomer Transition of an Antibody Single-Chain Fv Fragment," *Biochemistry*, 37:12918-12926 (1998).

Dufner et al., "Harnessing phage and ribosome display for antibody optimization," *Trends Biotechnol*., 24(11):523-529 (2006).

Ichikawa et al., "Tumoricidal activity of a novel anti-human DR5 monoclonal antibody without hepatocyte cytotoxicity," *Nat. Med*., 7:954-960 (2001).

Mateo et al., "CD47 ligation induces caspase-independent cell death in chronic lymphocytic leukemia," *Nat. Med*., 5(11):1277-1284 (1999).

Paul, *Fundamental Immunology*, 3rd Edition, Raven Press, NY, Chapter 8, pp. 292-295 (1993).

Wakelee et al., "Phase I and pharmacokinetic study of lexatumumab (HGS-ETR2) given every 2 weeks in patients with advanced solid tumors," *Ann. Oncol*. On-line publication (Jul. 24, 2009).

Ward et al., "Binding activities of a repertoire of single immunoglobulin variable domains secreted from *Escherichia coli*," *Nature*, 341:544-546 (1989).

Whitlow et al., "Multivalent Fvs: characterization of single-chain Fv oligomers and preparation of a bispecific Fv," *Protein Eng*., 7(8):1017-1026 (1994).

Yagita et al., "TRAIL and its receptors as targets for cancer therapy," *Cancer Sci*., 95:777-783 (2004).

Fish & Richardson P.C., Amendment in Reply to Action dated Mar. 16, 2009 in U.S. Appl. No. 10/550,934, filed Sep. 10, 2009, 75 pages.

U.S. Examiner Anne Gussow, USPTO Non-Final Office Action in U.S. Appl. No. 10/582,304, mailed Sep. 15, 2009, 22 pages.

U.S. Appl. No. 11/910,117, filed Aug. 2007, Igawa et al.

U.S. Appl. No. 11/910,128, filed Sep. 2007, Igawa et al.

U.S. Appl. No. 11/916,979, filed Aug. 2008, Igawa.

U.S. Appl. No. 12/304,514, filed Dec. 2008, Yoshikubo et al.

Andris-Widhopf et al. , "Methods for the generation of chicken monoclonal antibody fragments by phage display," *Journal of Immunological Methods*, 242:159-181 (2000).

Arndt et al. , "Generation of a highly stable, internalizing anti-DC22 single-chain Fv fragment for targeting non-Hodgkin's lymphoma," *Int. J. Cancer*, 107(5):822-829 (2003).

Avent et al. , "Monoclonal antibodies that recognize different membrane proteins that are deficient in Rhnull human erythrocytes. One group of antibodies reacts with a variety of cells and tissues whereas the other group is erythroid-specific," *Biochem. J*., 251:499-505 (1988).

Bartley et al. , "Identification and Cloning of a Megakaryocyte Growth and Development Factor That is a Ligand for the Cytokine Receptor Mpl," *Cell*, 77:1117-1124 (1994).

Bazil et al. , "Apoptosis of human hematopoietic progenitor cells induced by crosslinking of surface CD43, the major sialoglycoprotein of leukocytes," *Blood*, 86:502-511 (1995).

Bazzoni et al. , "Chimeric tumor necrosis factor receptors with constitutive signaling activity," *Proc. Natl. Acad. Sci. USA*, 92(12):5376-5580 (1995).

Beresford et al., "Binding Characteristics and Tumor Targeting of a Covalently Linked Divalent CC49 Single-Chain Antibody," *Int. J. Cancer*, 81:911-917 (1999).

Berger et al. , "Inhibition of intractable nucleases with ribonucleoside-vanadyl complexes: isolation of messenger ribonucleic acid from resting lymphocytes," *Biochemistry*, 18(23):5143-5149 (1979).

Bodmer et al. , "TRAIL Receptor-2 Signals Apoptosis Through FADD and Caspase-8," *Nat. Cell Biol*., 2:241-243 (2000).

Brown et al. , "Integrin-associated protein: a 50-kD plasma membrane antigen physically and functionally associated with integrins," *J. Cell Biology*, 111(6 Pt 1):2785-2794 (1990).

Brown et al. , "Integrin-associated protein (CD47) and its ligands," *Trends Cell Biology*, 11(3):130-135 (2001).

Buchsbaum et al. , "Antitumor Efficacy of TRA-8 Anti-DR5 Monoclonal Antibody Alone or in Combination with Chemotherapy and/or Radiation Therapy in a Human Breast Cancer Model," *Clin. Cancer Res*., 9:3731-3741 (2003).

Burgess et al. , "Possible dissociation of the heparin-binding and mitogenic activities of heparin-binding (acidic fibroblast) growth factor-1 from its receptor-binding activities by site-directed mutagenesis of a single lysine residue," *J. Cell Biol*., 111:2129-2138 (1990).

Burthem et al. , "Hairy cell interactions with extracellular matrix: expression of specific integrin receptors and their role in the cell's response to specific adhesive proteins," *Blood*, 84(3):873-882 (1994).

Caldas et al. , "Humanization of the anti-CD18 antibody 6.7: an unexpected effect of a framework residue in binding to antigen," *Mol. Immunol.*, 39:941-952 (2003).
Caron et al., "Engineered Humanized Dimeric Forms of IgG Are More Effective Antibodies," J. Exp. Med., 176:1191-1195 (1992).
Carpenter et al. , "Rational design of stable lyophilized protein formulations: some practical advice," *Pharmaceutical Research*, 14(8):969-975 (1997).
Carpenter et al. , "Rational design of stable lyophilized protein formulations: theory and practice," *Pharma Biotechnol.*, 13:109-133 (2001).
Carter, "Bispecific human IgG by design," *J. Immunol. Methods*, 248:7-15 (2001).
Cekaite et al. , "Protein Arrays: A versatile toolbox for target identification and monitoring of patient immune responses," *Methods Mol. Biol.*, 360:335-348 (2007).
Chien et al. , "Significant structural and functional change of an antigen-binding site by a distant amino acid substitution: Proposal of a structural mechanism," *Proc. Nat. Acad. Sci. USA*, 86:5532-5536 (1989).
Chirgwin et al. , "Isolation of biologically active ribonucleic acid from sources enriched in ribonuclease," *Biochemistry*, 18(24):5294-5299 (1979).
Chuntharapai et al. "Isotype-Dependent Inhibition of Tumor Growth In Vivo by Monoclonal Antibodies to Death Receptor 4," *J. Immunol.*, 166:4891-4898 (2001).
Clackson et al. , "Making antibody fragments using phage display libraries," *Nature*, 352:624-628 (1991).
Cleland et al. , "A specific molar ratio of stabilizer to protein is required for storage stability of a lyophilized monoclonal antibody," *Journal of Pharmaceutical Sciences*, 90(3):310-321 (2001).
Cochlovius et al., "Cure of Burkitt's Lymphoma in Severe Combined Immunodeficiency Mice by T Cells, Tetravalent CD3×CD19 Tandem Diabody and CD28 Costimulation," *Cancer Res.*, 60:4336-4341 (2000).
Cochlovius et al. , "Treatment of human B cell lymphoma xenografts with a CD3×CD19 diabody and T cells," *The Journal of Immunology*, 165:888-895 (2000).
Cooper et al. , "Transendothelial migration of neutrophils involves integrin-associated protein (CD47)," *Proc. Natl. Acad. Sci. USA*, 92:3978-3982 (1995).
Creighton, T., "Protein folding," *Biochem. J.*, 270(1):1-16 (1990).
Daniel et al. , "Pathway of apoptosis induced in Jurkat T Lymphoblasts by anti-HLA Class I antibodies," *Human Immunology*, 65(3):189-199 (2004).
De Jonge et al. , "Production and Characterization of Bispecific Single-Chain Antibody Fragments," *Mol. Immunol.*, 32:1405-1412 (1995).
De Leon et al. , "High resolution human leukocyte antigen (HLA) class I and class II allele typing in Mexican mestizo women with sporadic breast cancer: case-control study," *BMC Cancer*, 9(48):1-9 (2009).
Degli-Esposti et al. , "Cloning and Characterization of TRAIL-R3, a Novel Member of the Emerging TRAIL Receptor Family," *J. Exp. Med.*, 186:1165-1170 (1997).
De Sauvage et al. , "Stimulation of Megakaryocytopoiesis and Thrombopoiesis by the c-Mpl Ligand," *Nature*, 369:533-538 (1994).
Desplancq et al. , "Multimerization behaviour of single chain Fv variants for the tumour-binding antibody B72.3," *Protein Engineering*, 7(8):1027-1033 (1994).
De St. Groth et al. , "Production of Monoclonal Antibodies: Strategy and Tactics," *Journal of Immunological Methods*, 35:1-21 (1980).
Dillman, "Monoclonal antibodies for treating cancer," *Ann. Int. Med.*, 11(7):592-603 (1989).
Dorai et al. , "Mammalian cell expression of single-chain Fv (sFv) antibody proteins and their C-terminal fusions with interleukin-2 and other effector domains," *Biotechnology*, 12(9):890-897 (1994).
Eijsink et al. , "Rational engineering of enzyme stability," *Journal of Biotechnology*, 113:105-120 (2004).
Emery et al. , "Osteoprotegerin Is a Receptor for the Cytotoxic Ligand TRAIL," *J. Biol. Chem.*, 273:14363-14367 (1998).
Ewert et al. , "Biophysical properties of human antibody variable domains," *J. Mol. Biol.*, 325:531-553 (2003).
Ewert et al. , "Stability improvement of antibodies for extracellular and intracellular applications: CDR grafting to stable frameworks and structure-based framework engineering," *Methods*, 34:184-199 ( 2004).
Ewert et al. , "Structure-based improvement of the biophysical properties of immunoglobulin $V_H$ domains with a generalizable approach," *Biochemistry*, 42:1517-1528 (2003).
Felgenhauer et al. "Nucleotide Sequences of the cDNAs Encoding the V-Regions of H- and L-Chains of a Human Monoclonal Antibody Specific to HIV-1—gp41," *Nucleic Acids Research*, 18(16):4927 (1990).
Frokjaer et al. , "Protein drug stability: a formulation challenge," Nature Rev Drug Discov. 4:298-306 (2005).
Fujimoto et al. , "50-kD integrin-associated protein does not detectably influence several functions of glycoprotein IIb-IIIa complex in human platelets," *Blood*, 86(6):2174-2182 (1995).
Fukushima et al. , "Enhanced hematopoiesis in vivo and in vitro by splenic stromal cells derived from the mouse with recombinant granulocyte colony-stimulating factor," *Blood*, 80(8):1914-1922 (1992).
Fukushima et al. , "Apoptosis of Bone Marrow Cells Via Integrin Associated Protein by the Novel Monoclonal Antibody," *Blood*, 94(10):479A (1999).
Galfre et al. , "Preparation of monoclonal antibodies: strategies and procedures," *Methods in Enzymology*, 73:3-46 (1981).
Galfre et al. , "Rat x rat hybrid myelomas and a monoclonal anti-Fd portion of mouse IgG," *Nature*, 277:131-133 (1979).
Garcia-Gonzalez et al. , "Purification of murine IgG3 and IgM monoclonal antibodies by euglobulin precipitation," *Journal of Immunological Methods*, 111:17-23 (1988).
Giusti et al. ,"Somatic diversification of S107 from an antiphosphocholine to an anti-DNA autoantibody is due to a single base change in its heavy chain variable region," *Proc. Natl. Acad. Sci. USA*, 84:2926-2930 (1987).
Goding, "Monoclonal Antibodies: Principles and Practice," *Academic Press*, second Ed., 125:129 (1986).
Goldstein et al. , "Cytolytic and Cytostatic Properties of an Anti-Human FcγRI (CD64) x Epidermal Growth Factor Bispecific Fusion Protein," *J. Immunol.*, 158:872-879 (1997).
Gombotz et al. , "The stabilization of a human IgM monoclonal antibody with poly(vinylpyrrolidone)," *Pharmaceutical Research*, 11(5):624-632 (1994).
Greenspan et at., "Defining epitopes: It's not as easy as it seems," *Nature Biotechnology*, 17:936-937 (1999).
Grell et al. , "TR60 and TR80 tumor necrosis factor (TNF)-receptors can independently mediate cytolysis," *Lymphokine and Cytokine Research*, 12(3):143-148 (1993).
Griffith et al. , "Functional Analysis of TRAIL Receptors Using Monoclonal Antibodies," *J. Immunol.*, 162:2597-2605 (1999).
Gruber et al. , "Efficient tumor cell lysis mediated by a bispecific single chain antibody expressed in *Escherichia coli," Journal of Immunology*, 152:5368-5374 (1994).
Güssow and Seemann, "Humanization of Monoclonal Antibodies," *Methods in Enzymology*, 203:99-121 (1991).
Holliger el at., "Specific Killing of Lymphoma Cells by Cytotoxic T-Cells Mediated by a Bispecific Diabody," *Protein Engineering*, 9(3):299-305 (1996).
Hoogenboom et al. , "Multi-subunit proteins on the surface of filamentous phage: methodologies for displaying antibody (Fab) heavy and light chains," *Nucleic Acids Res.*, 19:4133-4137 (1991).
Hopp et al. , "A Short Polypeptide Marker Sequence Useful for Recombinant Protein Identification and Purification," *Biotechnology*, 6:1204-1210 (1988).
Horan et al. , "Dimerization of the extracellular domain of granuloycte-colony stimulating factor receptor by ligand binding: a monovalent ligand induces 2:2 complexes," *Biochemistry*, 35:4886-4896 (1996).
Hozumi and Tonegawa, "Evidence for somatic rearrangement of immunoglobulin genes coding for variable and constant regions," *Proc. Natl. Acad. Sci. USA*, 73(10):3628-3632 (1976).

Huston et al. , "Protein Engineering of Antibody Binding Sites: Recovery of Specific Activity in an Anti-Digoxin Single-Chain Fv Analogue Produced in *Escherichia coli," Proc. Natl. Acad. Sci. USA*, 85:5879-5883 (1988).

Itoh et al. , "The Polypeptide Encoded by the cDNA for Human Cell Surface Antigen Fas Can Mediate Apoptosis," *Cell*, 66:233-243 (1991).

Jäger et al. , "Folding and assembly of an antibody Fv fragment, a heterodimer stabilized by antigen," *Journal of Molecular Biology*, 285:2005-2019 (1999).

Jiang et al. , "A Novel Peptide Isolated from a Phage Display Peptide Library with Trastuzumab Can Mimic Antigen Epitope of HER-2," *J. Biol. Chem.*, 280(6):4656-4662 (2005).

Jones et al. , "Rapid PCR-Cloning of Full-Length Mouse Immunoglobulin Variable Regions," *Biotechnology*, 9:88-89 (1991).

Kearney, et al. , "A New Mouse Myeloma Cell Line That Has Lost immunoglobulin Expression But Permits The Construction of Antibody-Secreting Hybrid Cells Lines," *The Journal of Immunology*, 123(4):1548-1550 (1979).

Keen et al. , "The use of serum-free medium for the production of functionally active humanized monoclonal antibody from NSO mouse myeloma cells engineered using glutamine synthetase as a selectable marker," *Cytotechnology*, 18(3):207-217 (Abstract) (1994).

Kipriyanov and Little, "Generation of Recombinant Antibodies," *Molecular Biotechnology*, 12:173-201 (1999) (from 148 family).

Kipriyanov et al. , "Bispecific CD3×CD19 diabody for T cell-mediated lysis of malignant human B cells," *In. J. Cancer*, 77:763-772 (1998).

Kipriyanov et al. , "Bispecific tandem diabody for tumor therapy with improved antigen binding and pharmacokinetics," *Journal of Molecular Biology*, 293:41-56 (1999).

Kohler, et al. , "Derivation of specific antibody-producing tissue culture and tumor lines by cell fusion," *Eur. J Immunol.*, 6:511-519 (1976).

Kontermann, R., "Recombinant bispecific antibodies for cancer therapy," *Acta Pharmacol. Sin.*, 26(1):1-9 (2005).

Korn et al. , "Recombinant bispecific antibodies for the targeting of adenoviruses to CEA-expressing tumour cells: a comparative analysis of bacterially expressed single-chain diabody and tandem scFv," *The Journal of Gene Medicine*, 6:642-651 (2004).

Kortt et al. , "Recombinant anti-sialidase single-chain variable fragment antibody: Characterization, formation of dimmer and higher-molecular-mass multimers and the solution of the crystal structure of the single-chain variable fragment/sialidase complex," *Eur. J. Biochem.*, 221:151-157 (1994).

Kortt et al. , "Single-chain Fv fragments of anti-neuraminidase antibody NC10 containing five-and ten- residue linkers form dimmers and with zero-residue linker a trimer," *Protein Engineering*, 10(4):423-433 (1997).

Kozak, M., "At Least Six Nucleotides Preceding the AUG Initiator Codon Enhance Translation in Mammalian Cells," *J. Mol. Biol.*, 196:947-950 (1987).

Krebber et al. , "Reliable cloning of functional antibody variable domains from hybridomas and spleen cell repertoires employing a reengineered phage display system," *J. Immunol. Methods*, 201:35-55 (1997).

Kumar et al. , "Molecular cloning and expression of the fabs of human autoantibodies in *Escherichia coli," The Journal of Biological Chemistry*, 275(41):35129-35136 (2000).

Kurucz et al. , "Retargeting of CTL by an efficiently refolded bispecific single-chain Fv dimer produced in bacteria," *The Journal of Immunology*, 154:4576-4582 (1995).

Larrick, et al. , "Polymerase Chain Reaction Using Mixed Primers: Cloning of Human Monoclonal Antibody Variable Region Genes From Single Hybridoma Cells," *Biotechnology*, 7:934-938 (1989).

Law et al. , "Observations On The Effect Of A Folic-Acid Antagonist On Transplantable Lymphoid Leukemias In Mice," *Journal of the National Cancer Institute*, 10:179-193 (1949).

Lazar et al. , "Transforming growth factor a: mutation of aspartic acid 47 and leucine 48 results in different biological activities," *Molecular and Cellular Biology*, 8:1247-1252 (1988).

Le Gall et al. , "Effect of linker sequences between the antibody variable domains on the formation, stability and biological activity of a bispecific tandem diabody," *Protein Engineering Design & Selection*, 17(4):357-366 (2004).

Lee et al. , "Reversible dimer formation and stability of the anti-tumour single chain Fv antibody MFE-23 by neutron scattering, analytical ultracentrifugation, and NMR and FR-IR spectroscopy," *J. Mol. Biol.*, 320:107-127 (2002).

Lei et al. , "Characterization of the *Erwinia carotovora pelB* Gene and Its Product Pectate Lyase," *Journal of Bacteriology*, 169:4379-4383 (1987).

Lin et al. , "Structure-function relationships in glucagon: properties of highly purified des-His-1-, monoiodo-, and (des-Asn-28, Thr-29)(homoserine lactone-27)-glucagon," *Biochemistry*, 14:1559-1563 (1975).

Lindberg et al. , "Molecular Cloning of Integrin-Associated Protein: An Immunoglobulin Family Member with Multiple Membrane-Spanning Domains Implicated in $\alpha_v\beta_3$-Dependent Ligand Binding," *The Journal of Cell Biology*, 123(2):485-496, The Rockefeller University Press (1993).

Lindberg et al. , "Rh-Related Antigen CD47 is the Signal-Transducer Integrin-Associated Protein," *J. Biol. Chem.*, 269:1567-1570 (1994).

Little et al. , "Of mice and men: hybridoma and recombinant antibodies," *Immunol. Today*, 21:364-370 (2000).

Liu et al. , "Functional interactions between arginine-133 and aspartate-88 in the human reduced folate carrier: evidence for a charge-pair association," *Biochem. J.*, 358:511-516 (2001).

Maity et al. , "Equilibrium unfolding of dimeric and engineered monomeric forms of Cro (F58W) repressor and the effect of added salts: evidence for the formation of folded monomer induced by sodium perchlorate," *Archives of Biochemistry and Biophysics*, 434:93-107 (2005).

Margulies et al. , "Somatic Cell Hybridization of Mouse Myeloma Cells," *Cell*, 8:405-415 (1976).

Mariuzza et al. , "The structural basis of antigen-antibody recognition," *Annu. Rev. Biophys. Biophys. Chem.*, 16:139-159 (1987).

Marsters et al. , "A Novel Receptor for Apo2L/TRAIL Contains a Truncated Death Domain," *Curr. Biol.*, 7:1003-1006 (1997).

Martsev et al. , "Antiferritin single-chain antibody: a functional protein with incomplete folding?" *FEBS Letters*, 441:458-462 (1998).

Mateo et al., "Induction of Apoptosis in B-Cells From Chronic Lymphocytic Leukemia (B-CLLs) by CD47," *FASEB Journal*, 12(5):A1082 (1998).

Mawby et al. , "Isolation and characterization of CD47 glycoprotein: a multispanning membrane protein which is the same as integrin-associated protein (IAP) and the ovarian tumor marker OA3," *Biochem. J.*, 304:525-530 (1994).

McGuinness et al. , "Phage diabody repertoires for selection of large number of bispecific antibody fragments," *Nature Biotechnology*, 14(9):1149-1154 (1996).

Meng et al. , "The evaluation of recombinant, chimeric, tetravalent antihuman CD22 antibodies," *Clinical Cancer Research*, 10:1274-1281 (2004).

Methia et al. , "Oligodeoxynucleotides Antisense to the Proto-Oncogene *c-Mpl* Specifically Inhibit In Vitro Megakaryocytopoiesis," *Blood*, 82(5):1395-1401 (1993).

Merchant et al. , "An efficient route to human bispecific IgG," *Nature Biotechnology*, 16:677-681 (1996).

Milili et al. , "The VDJ Repertoire Expressed in Human preB Cells Reflects the Selection of *Bona Fide* Heavy Chains," *Eur. J. Immunol.*, 26:63-69 (1996).

Mizushima et al. , "pEF-BOS, a Powerful Mammalian Expression Vector," *Nucleic Acids Research*, 18(17):5322 (1990).

Moore et al. , "Kinetics and thermodynamics of dimer formation and dissociation for a recombinant humanized monoclonal antibody to vascular endothelial growth factor," *Biochemistry*, 38:13960-13967 (1999).

Mori et al. , "Human normal hepatocytes are susceptible to apoptosis signal mediated by both TRAIL-R1 and TRAIL-R2," *Cell Death and Differentiation*, 11:203-207 (2004).

Mulligan et al. , "Synthesis of Rabbit β-Globin in Cultured Monkey Kidney Cells Following Infection with a SV40 β-Globin Recombinant Genome," *Nature*, 277:108-114 (1979).

Nakayama et al. , "Thrombocytosis in preterm infants: a possible involvement of thrombopoietin receptor gene expression," *Journal of Molecular Medicine*, 83:316-320 (2005).
Nieba et al. , "Disrupting the hydrophobic patches at the antibody variable/constant domain interface: improved in vivo folding and physical characterization of an engineered scFv fragment," *Protein Engineering*, 10(4):435-444 (1997).
Nohaile et al. , "Altering dimerization specificity by changes in surface electrostatics," *PNAS* 98(6):3109-3114 (2001).
O'Brien et al. , "Monoclonal antibodies for the human insulin receptor stimulate intrinsic receptor-kinase activity," *Biochim. Soc. Trans.*, 14(6):1021-1023 (1986).
Ohtsuka et al. , "Synergistic induction of tumor cell apoptosis by death receptor antibody and chemotherapy agent through JNK/p38 and mitochondrial death pathway," Oncogene, 22:2034-2044 (2003).
Pan et al. , "An Antagonist Decoy Receptor and a Death Domain-Containing Receptor for TRAIL," *Science*, 277:815-818 (1997).
Pan et al. , "The Receptor for the Cytotoxic Ligand TRAIL," *Science*, 276:111-113 (1997).
Paul, *Fundamental Immunology*, Raven Press, NY, Chapter 8, p. 242 (1993).
Peipp et al. , "Bispecific antibodies targeting cancer cells," *Biochem. Soc. Trans.*, 30:507-511 (2002).
Petterson et al. , "CD47 Signals T Cell Death," *J. Immunol.*, 7031-7040 (1999).
Petterson, "CD47 and death signaling in the immune system," *Apoptosis*, 5:299-306 (2000).
Rajagopal et al. , "A form of anti-Tac (Fv) which is both single-chain and disulfide stabilized: comparison with its single-chain and disulfide-stabilized homologs," *Protein Engineering*, 10(12):1453-1459 (1997).
Reinhold et al. , "In vivo expression of alternatively spliced forms of integrin-associated protein (CD47)," *J. Cell Science*, 108:3419-3425 (1995).
Ridgway et al. , "'Knobs-into-holes' engineering of antibody $C_H3$ domains for heavy chain heterodimerization," *Protein Eng.*, 9:617-621 (1996).
Riechmann et al. , "Reshaping Human Antibodies for Therapy," *Nature*, 332:323-327 (1988).
Reiter et al. , "Engineering interchain disulfide bonds into conserved framework regions of Fv fragments: improved biochemical characteristics of recombinant immunotoxins containing disulfide-stabilized Fv," *Protein Enginering*, 7(5):697-704 (1994).
Reiter et al. , "Stabilization of the Fv Fragments in Recombinant Immunotoxins by Disulfide Bonds Engineered into Conserved Framework Regions," *Biochemistry*, 33:5451-5459 (1994).
Roue et al. "Mitochondrial dysfunction in CD47-mediated caspase-independent cell death: ROS production in the absence of cytochrome c and AIF release," *Biochimie.*, 85:741-746 (2003).
Rousch et al. , "Somatostatin displayed on filamentous phage as a receptor-specific agonist," *Br. J. Pharmacol.*, 125:5-16 (1998) (from 148 family).
Rozsnyay et al. , "Phenylarsine oxide (PAO) blocks antigen receptor-induced calcium response and tyrosine phosphroylation of a distinct group of proteins," *Immunology Lett.*, 37(2-3):197-205 (1993).
Sato et al. , "Reshaping a Human Antibody to Inhibit the Interleukin 6-Dependent Tumor Cell Growth," *Cancer Research*, 53:851-856 (1993).
Schickel, et al. , "Gene for Integrin-Associated Protein (IAP, CD47): Physical Mapping, Genomic Structure, and Expression Studies in Skeletal Muscle," *Biochem. Cell. Biol.*, 80(2):169-176 (2002).
Schwartz et al. , "A superactive insulin: [B10-aspartic acid]insulin(human)," *Proc. Natl. Acad. Sci. U.S.A.*, 84:6408-6411 (1987).
Schwartz et al. , "A 50-kDa Integrin-associated Protein Is Required for Integrin-regulated Calcium Entry in endothelial Cells," *J. Biol. Chem.*, 268(27):19931-19934 (1993).
Schmidt et al. , "A bivalent single-chain antibody-toxin specific for ErbB-2 and the EGF receptor," *Int. J. Cancer*, 65(4):538-546 (1996).
Segal et al. , "Bispecific antibodies in cancer therapy," *Current Opinion in Immunology*, 11:558-582 (1999).
Shalaby et al. , "Development of Humanized Bispecific Antibodies Reactive with Cytotoxic Lymphocytes and Tumor Cells Overexpressing the HER2 Protooncogene," *J. Exp. Med.*, 175:217-225 (1992).
Sharma et al. , "Study of IgM aggregation in serum of patients with macroglobulinemia," *Clin Chem Lab Med*, 38(8):759-764 (2000).
Sheridan et al. , "Control of TRAIL-Induced Apoptosis by a Family of Signaling and Decoy Receptors," *Science*, 277:818-821 (1997).
Shigeta et al. , "Sperm-immobilizing monoclonal antibody to human seminal plasma antigens," *Clin. Exp. Immunol.*, 42:458-462 (1980).
Shimba et al. , "Comparative thermodynamic analyses of the Fv, Fab* and Fab fragments of anti-dansyl mouse monoclonal antibody," *FEBS Letters*, 360:247-250 (1995).
Shire et al. , "Challenges in the development of high protein concentration formulations," *Journal of Pharmaceutical Sciences*, 93(6):1390-1402 (2004).
Shulman et al. , "A better cell line for making hybridomas secreting specific antibodies," *Nature*, 276:269-270 (1978).
Skerra, "Use of the tetracycline promoter for the tightly regulated production of a murine antibody fragment in *Escherichia coli," Gene*, 151:131-135 (1994).
Smith-Gill et al. , "Contributions of immunoglobulin heavy and light chains to antibody specificity for lysozyme and two haptens," *The Journal of Immunology*, 139:4135-4144 (1987).
Song et al. , "Light chain of natural antibody plays a dominant role in protein antigen binding," *Biochemical and Biophysical Research Communications*, 268:390-394, (2000).
Souyri, M., "Mpl: from an acute myeloproliferative virus to the isolation of the long sought thrombopoietin," *Seminars in Hematology*, 35(3):222-231 (1998).
Spaargaren et al. , "Antibody-induced Dimerization Activates the Epidermal Growth Factor Receptor Tyrosine Kinase," *The J. Biol. Chem.*, 266(3):1733-1739 (1981).
Stancovski et al. , "Mechanistic aspects of the opposing effects of monoclonal antibodies to the ERBB2 receptor on tumor growth," *Proc. Natl. Acad. Sci. USA*, 88:8691-8695 (1991).
Tan et al. , "Contributions of a highly conserved $V_H/V_L$ hydrogen bonding interaction to scFv folding stability and refolding efficiency," *Biophysical Journal*, 75:1473-1482 (1998).
Tang et al. , "Selection of linkers for a catalytic single-chain antibody using phage display technology", *The Journal of Biological Chemistry*, 271(26):15682-15686 (1996).
Trowbridge, I.S., "Interspecies Spleen-Myeloma Hybrid Producing Monoclonal Antibodies Against Mouse Lymphocyte Surface Glycoprotein, T200," *J. Exp. Med.*, 148:313-323 (1978).
Turner et al. , "Importance of the linker in expression of single-chain Fv antibody fragments: optimization of peptide sequence using phage display technology," *Journal of Immunological Methods*, 205:43-54 (1997).
Van Den Burg et al. , "Selection of mutations for increased protein stability," *Curr. Opin. Biotechnol.*, 13(4):333-337 (2002).
Van Geelen et al. , "Differential modulation of the TRAIL receptors and the CD95 receptor in colon carcinoma cell lines," *Br. J. Cancer*, 89(2):363-373 (2003).
Verma et al. , "Antibody engineering: Comparison of bacterial, yeast, insect and mammalian expression systems," *Journal of Immunological Methods*, 216:165-181 (1998).
Vieille et al. , "Hyperthermophilic enzymes: sources, uses, and molecular mechanisms for thermostability," *Microbiology and Molecular Biology Reviews*, 65(1):1-43 (2001).
Volkel et al. , "Optimized linker sequences for the expression of monomeric and dimeric bispecific single-chain diabodies," *Protein Engineering*, 14(10):815-823 (2001).
Walczak et al. , "TRAIL-R2: A Novel Apoptosis-Mediating Receptor for TRAIL," *EMBO J.*, 16:5386-5397 (1997).
Wang et al. , "Instability, stabilization, and formulation of liquid protein pharmaceuticals," *International Journal of Pharmaceutics*, 185:129-188 (1999).
Wang et al. , "Lyophilization and development of solid protein pharmaceuticals," *International Journal of Pharmaceutics*, 203:1-60 (2000).

Wang et al. , "Protein aggregation and its inhibition in biopharmaceutics," *International Journal of Pharmaceutics*, 289:1-30 (2005).
Whitlow et al. , "An improved linker for single-chain Fv with reduced aggregation and enhanced proteolytic stability," *Protein Engineering*, 6(8):989-995 (1993).
Wiley et al. , "Identification and Characterization of a New Member of the TNF Family that Induces Apoptosis," *Immunity*, 3:673-682 (1995).
Winkler et al. , "Changing the Antigen Binding Specificity by Single Point Mutations of an Anti-p24 (HIV-1) Antibody," *J. Immunol.*, 265:4505-4514 (2000).
Worn et al. , "Stability engineering of antibody single-chain Fv fragments," *J. Mol. Biol.*, 305:989-1010 (2001).
Xie et al. , "Direct Demonstration of MuSK Involvement in Acetylcholine Receptor Clustering Through Identification of Agonist ScFv," *Nature Biotechnology*, 15(8):768-771 (1997).
Yanabu et al. , "Tyrosine phosphorylation and p72syk activation by an anti-glycoprotein lb monoclonal antibody," *Blood*, 89(5):1590-1598 (1997).
Yarden et al. , "Self-phosphorylation of epidermal growth factor receptor: evidence for a model of intermolecular allosteric activation," *Biochemistry*, 26(5):1434-1442 (1987).
Yelton et al. , "Fusion of Mouse Myeloma and Spleen Cells," *Current Topics in Microbiology and Immunology*, 81:1-7 (1978).
Zhu et al. , "Remodeling domain interfaces to enhance heterodimer formation," *Protein Science*, 6:781-788 (1997).
Zhu et al. , "An efficient route to the production of an IgG-like bispecific antibody", Protein Eng., 13:361-367 (2000).
USPTO Restriction Requirement in U.S. Appl. No. 10/530,696, mailed Oct. 19, 2006, 8 pages.
Fish & Richardson P.C., Response to Restriction Requirement dated Oct. 19, 2006, in U.S. Appl. No. 10/530,696, filed Nov. 16, 2006, 1 page.
USPTO Non-Final Office Action in U.S. Appl. No. 10/530,696, mailed Dec. 21, 2006, 19 pages.
Fish & Richardson P.C., Amendment in Reply to Office Action dated Dec. 21, 2006 in U.S. Appl. No. 10/530,696, filed Apr. 23, 2007, 16 pages.
USPTO Final Office Action in U.S. Appl. No. 10/530,696, mailed Aug. 8, 2007, 13 pages.
USPTO Interview Summary in U.S. Appl. No. 10/530,696, mailed Nov. 26, 2007, 3 pages.
Fish & Richardson P.C., Amendment in Reply to Office Action dated Aug. 8, 2007 in U.S. Appl. No. 10/530,696, filed Dec. 6, 2007, 12 pages.
USPTO Advisory Action in U.S. Appl. No. 10/530,696, mailed Dec. 14, 2007, 4 pages.
USPTO Non-Final Office Action in U.S. Appl. No. 10/530,696, mailed Feb. 5, 2008, 9 pages.
Fish & Richardson, Amendment in Reply to Action dated Feb. 5, 2008 in U.S. Appl. No. 10/530,696, filed Aug. 5, 2008, 7 pages.
USPTO Non-Final Office Action in U.S. Appl. No. 10/530,696, mailed Nov. 17, 2008, 18 pages.
Fish & Richardson, Amendment in Reply to Action dated Nov. 17, 2008 in U.S. Appl. No. 10/530,696, filed Feb. 17, 2009, 14 pages.
Japanese Patent Office, International Search Report for App. Ser. No. PCT/JP2003/013063, mailed Nov. 18, 2003, 2 pages.
Japanese Patent Office, International Preliminary Report on Patentability for App. Ser. No. PCT/JP2003/013063, dated Feb. 6, 2004, 4 pages.
European Search Report for App. Ser. No. EP 03 75 1456, dated Apr. 4, 2006, 2 pages.
USPTO Final Office Action in U.S. Appl. No. 10/530,696, mailed Jun. 8, 2009, 10 pages.
USPTO Restriction Requirement in U.S. Appl. No. 10/548,727, mailed Apr. 12, 2007, 6 pages.
Fish & Richardson P.C., Reply to Restriction Requirement dated Apr. 12, 2007 in U.S. Appl. No. 10/548,727, filed May 3, 2007, 1 page.
USPTO Non-Final Office Action in U.S. Appl. No. 10/548,727, mailed Aug. 3, 2007, 21 pages.
Fish & Richardson P.C., Reply to Office Action dated Aug. 3, 2007 in U.S. Appl. No. 10/548,727, filed Jan. 15, 2008, 15 pages.
USPTO Final Office Action in U.S. Appl. No. 10/548,727, mailed Apr. 29, 2008, 23 pages.
USPTO Advisory Action in U.S. Appl. No. 10/548,727, mailed Sep. 24, 2008, 6 pages.
USPTO Non-Final Office Action in U.S. Appl. No. 10/548,727, mailed Jan. 28, 2009, 16 pages.
Japanese Patent Office, International Search Report for App. Ser. No. PCT/JP2004/003334, mailed Jun. 15, 2004, 3 pages.
Japanese Patent Office, International Preliminary Report on Patentability for App. Ser. No. PCT/JP2004/003334, dated May 2, 2005, 6 pages.
USPTO Restriction Requirement in U.S. Appl. No. 10/550,934, mailed Nov. 21, 2007, 7 pages.
Fish & Richardson P.C., Response to Restriction Requirement dated Nov. 21, 2007 in U.S. Appl. No. 10/550,934, filed Apr. 16, 2008, 2 pages.
USPTO Non-Final Office Action in U.S. Appl. No. 10/550,934, mailed Jun. 12, 2008, 27 pages.
Fish & Richardson P.C., Amendment in Reply to Action dated Jun. 12, 2008 in U.S. Appl. No. 10/550,934, filed Dec. 12, 2008, 45 pages.
USPTO Final Office Action in U.S. Appl. No. 10/550,934, mailed Mar. 16, 2009, 19 pages.
Japanese Patent Office, International Search Report for App. Ser. No. PCT/JP2004/004696, mailed Jul. 27, 2004, 5 pages.
Japanese Patent Office, International Preliminary Report on Patentability for App. Ser. No. PCT/JP2004/004696, dated Feb. 9, 2005, 10 pages.
European Search Report for App. Ser. No. EP 04 72 4770, dated Mar. 31, 2006, 4 pages.
USPTO Restriction Requirement in U.S. Appl. No. 10/560,098, mailed Jul. 13, 2007, 9 pages.
Fish & Richardson P.C., Response to Restriction Requirement dated Jul. 13, 2007 in U.S. Appl. No. 10/560,098, filed Aug. 10, 2007, 6 pages.
USPTO Non-Final Office Action in U.S. Appl. No. 10/560,098, mailed Oct. 23, 2007, 17 pages.
USPTO Final Office Action in U.S. Appl. No. 10/560,098, mailed Sep. 11, 2008, 20 pages.
USPTO Interview Summary for U.S. Appl. No. 10/560,098, mailed Jun. 5, 2009, 8 pages.
Fish & Richardson P.C., Amendment in Reply to Office Action dated Sep. 11, 2008 in U.S. Appl. No. 10/560,098, filed Jun. 10, 2009, 12 pages.
USPTO Office Action in U.S. Appl. No. 10/560,098, mailed Aug. 13, 2009, 21 pages.
Japanese Patent Office, International Search Report for App. Ser. No. PCT/JP2004/008585, mailed Sep. 7, 2004, 4 pages.
Japanese Patent Office, International Preliminary Report on Patentability for App. Ser. No. PCT/JP2004/008585, 10 pages.
Japanese Patent Office, International Search Report for App. Ser. No. PCT/JP2004/018499, mailed Jan. 18, 2005, 2 pages.
Japanese Patent Office, International Preliminary Report on Patentability for App. Ser. No. PCT/JP2004/018499, dated Jan. 26, 2006, 5 pages.
USPTO Restriction Requirement in U.S. Appl. No. 10/582,413, mailed Jan. 4, 2008, 8 pages.
Fish & Richardson P.C., Response to Restriction Requirement dated Jan. 4, 2008 in U.S. Appl. No. 10/582,413, filed Feb. 4, 2008, 2 pages.
USPTO Non-Final Office Action in U.S. Appl. No. 10/582,413, mailed Mar. 31, 2008, 17 pages.
Fish & Richardson P.C., Amendment in Reply to Action dated Mar. 31, 2008 in U.S. Appl. No. 10/582,413, filed Jun. 30, 2008, 20 pages.
USPTO Interview Summary in U.S. Appl. No. 10/582,413, mailed Jun. 30, 2008, 2 pages.
USPTO Notice of Informal or Non-Responsive Amendment in U.S. Appl. No. 10/582,413, mailed Oct. 20, 2008, 3 pages.
USPTO Interview Summary in U.S. Appl. No. 10/582,413, mailed Nov. 12, 2008, 4 pages.
Fish & Richardson P.C., Amendment in Reply to Notice of Informal or Non-Responsive Amendment dated Oct. 20, 2008 in U.S. Appl. No. 10/582,413, filed Nov. 17, 2008, 10 pages.
USPTO Interview Summary in U.S. Appl. No. 10/582,413, mailed Nov. 25, 2008, 4 pages.

USPTO Interview Summary in U.S. Appl. No. 10/582,413, mailed Dec. 24, 2008, 4 pages.
USPTO Restriction Requirement in U.S. Appl. No. 10/582,413, mailed Mar. 11, 2009, 8 pages.
Fish & Richardson P.C., Response to Restriction Requirement dated Mar. 11, 2009 in U.S. Appl. No. 10/582,413, filed Apr. 8, 2009, 8 pages.
USPTO Final Office Action in U.S. Appl. No. 10/582,413, mailed Jun. 25, 2009, 28 pages.
Japanese Patent Office, International Search Report for App. Ser. No. PCT/JP2004/018493, mailed Mar. 22, 2005, 2 pages.
Japanese Patent Office, International Preliminary Report on Patentability for App. Ser. No. PCT/JP2004/018493, dated Dec. 20, 2005, 7 pages.
European Search Report for App. Ser. No. EP 04 82 0305, dated Oct. 6, 2008, 3 pages.
USPTO Restriction Requirement in U.S. Appl. No. 10/582,304, mailed Nov. 20, 2008, 7 pages.
Fish & Richardson P.C., Response to Restriction Requirement dated Nov. 20, 2008 in U.S. Appl. No. 10/582,304, filed Dec. 16, 2008, 3 pages.
USPTO Non-Final Office Action in U.S. Appl. No. 10/582,304, mailed Apr. 1, 2009, 38 pages.
Fish & Richardson P.C., Amendment in Reply to Office Action dated Apr. 1, 2009 in U.S. Appl. No. 10/582,304, filed Jun. 30, 2009, 15 pages.
Japanese Patent Office, International Search Report for App. Ser. No. PCT/JP2004/018501, mailed Mar. 29, 2005, 2 pages.
Japanese Examiner Yoshiko Kuwahara, International Preliminary Report on Patentability for App. Ser. No. PCT/JP2004/018501, dated Nov. 4, 2005, 7 pages.
European Search Report for App. Ser. No. EP 04 82 0311, dated Jan. 28, 2009, 4 pages.
Japanese Patent Office, International Search Report for App. Ser. No. PCT/JP2004/005152, mailed Jul. 20, 2004, 2 pages.
Japanese Patent Office, International Preliminary Report on Patentability for App. Ser. No. PCT/JP2004/005152, dated Feb. 14, 2005, 6 pages.
European Search Report for App. Ser. No. EP 04 72 6750, dated Feb. 4, 2008, 3 pages.
USPTO Non-Final Office Action in U.S. Appl. No. 11/547,747, mailed Jun. 1, 2009, 41 pages.
Japanese Patent Office, International Search Report for App. Ser. No. PCT/JP2006/306800, mailed May 16, 2006, 4 pages.
International Preliminary Report on Patentability for App. Ser. No. PCT/JP2006/306800, dated Oct. 3, 2007, 6 pages.
Japanese Patent Office, International Search Report for App. Ser. No. PCT/US2006/306803, mailed Jul. 11, 2006, 4 pages.
International Preliminary Report on Patentability for App. Ser. No. PCT/US2006/306803, dated Oct. 3, 2007, 6 pages.
Japanese Patent Office, International Search Report for App. Ser. No. PCT/JP2006/309890, mailed Jul. 18, 2006, 2 pages.
International Preliminary Report on Patentability for App. Ser. No. PCT/JP2006/309890, dated Nov. 19, 2007, 5 pages.
Japanese Patent Office, International Search Report for App. Ser. No. PCT/JP2006/311575, mailed Sep. 26, 2006, 3 pages.
International Preliminary Report on Patentability for App. Ser. No. PCT/JP2006/311575, dated Dec. 11, 2007, 5 pages.
Japanese Patent Office, International Search Report for App. Ser. No. PCT/JP2006/311600, mailed Aug. 29, 2006, 2 pages.
International Preliminary Report on Patentability for App. Ser. No. PCT/JP2006/31160, dated Dec. 11, 2007, 8 pages.
Japanese Patent Office, International Search Report for App. Ser. No. PCT/JP2006/311625, mailed Aug. 22, 2006, 2 pages.
International Preliminary Report on Patentability for App. Ser. No. PCT/JP2006/311625, dated Dec. 11, 2007, 4 pages.
Japanese Patent Office, International Search Report for App. Ser. No. PCT/JP2007/061850, mailed Aug. 7, 2007, 8 pages.
International Preliminary Report on Patentability for App. Ser. No. PCT/JP2007/061850, dated Dec. 16, 2008, 8 pages.
USPTO Restriction Requirement in U.S. Appl. No. 10/582,654, mailed May 26, 2009, 9 pages.
USPTO Restriction Requirement in U.S. Appl. No. 10/399,518, mailed Nov. 25, 2005, 9 pages.
Foley & Lardner LLP, Response to Restriction Requirement dated Nov. 25, 2005 in U.S. Appl. No. 10/399,518, filed Dec. 23, 2005, 3 pages.
USPTO Non-Final Office Action in U.S. Appl. No. 10/399,518, mailed Mar. 27, 2006, 38 pages.
Foley & Lardner LLP, Amendment in Reply to Action dated Mar. 27, 2006 in U.S. Appl. No. 10/399,518, filed Sep. 26, 2006, 26 pages.
Foley & Lardner LLP, Supplemental Amendment in Reply to Action dated Mar. 27, 2006 in U.S. Appl. No. 10/399,518, filed Oct. 11, 2006, 11 pages.
Foley & Lardner LLP, Supplemental Amendment in Reply to Action dated Mar. 27, 2006 in U.S. Appl. No. 10/399,518, filed Oct. 13, 2006, 11 pages.
USPTO Non-Final Office Action in U.S. Appl. No. 10/399,518, mailed Dec. 28, 2006, 29 pages.
Foley & Lardner LLP, Amendment in Reply to Action dated Dec. 28, 2006 in U.S. Appl. No. 10/399,518, filed May 3, 2007, 22 pages.
USPTO Final Office Action in U.S. Appl. No. 10/399,518, mailed Jun. 7, 2007, 13 pages.
Foley & Lardner LLP, Amendment in Reply to Action dated Jun. 7, 2007 in U.S. Appl. No. 10/399,518, filed Sep. 7, 2007, 9 pages.
Advisory Action in U.S. Appl. No. 10/399,518, mailed Sep. 27, 2007, 5 pages.
Interview Summary in U.S. Appl. No. 10/399,518, mailed Nov. 13, 2007, 3 pages.
USPTO Non-Final Office Action in U.S. Appl. No. 10/399,518, mailed Jan. 31, 2008, 14 pages.
Foley & Lardner LLP, Amendment in Reply to Action dated Jan. 31, 2008 in U.S. Appl. No. 10/399,518, filed Apr. 30, 2008, 7 pages.
USPTO Final Office Action in U.S. Appl. No. 10/399,518, mailed Aug. 4, 2008, 8 pages.
Advisory Action in U.S. Appl. No. 10/399,518, mailed Nov. 7, 2008, 4 pages.
Foley & Lardner LLP, Amendment in Reply to Action dated Nov. 7, 2008 in U.S. Appl. No. 10/399,518, filed Oct. 23, 2008, 8 pages.
USPTO Non-Final Office Action in U.S. Appl. No. 10/399,518, mailed Feb. 17, 2009, 12 pages.
Foley & Lardner LLP, Amendment in Reply to Action dated Feb. 17, 2009 in U.S. Appl. No. 10/399,518, filed May 18, 2009, 26 pages.
Fish & Richardson P.C., Reply to Office Action dated Jan. 28, 2009 in U.S. Appl. No. 10/548,727, filed Jun. 26, 2009, 9 pages.
USPTO Restriction Requirement in U.S. Appl. No. 11/913,229, mailed Jul. 8, 2009, 6 pages.
Fish & Richardson P.C., Response to Restriction Requirement dated Jul. 8, 2009 in U.S. Appl. No. 11/913,229, filed Aug. 4, 2009, 1 page.
Japanese Patent Office, International Search Report for App. Ser. No. PCT/JP2004/018506, mailed Mar. 22, 2005, 3 pages.
International Preliminary Report on Patentability for App. Ser. No. PCT/JP2004/018506, 8 pages.
European Search Report for App. Ser. No. EP 04 82 0316, dated Jul. 17, 2008, 3 pages.
European Search Report for App. Ser. No. EP 06 73 0748, dated Apr. 22, 2009, 7 pages.
European Search Report for App. Ser. No. EP 06 74 6578, dated Jun. 25, 2009, 2 pages.
Sackstein, "The lymphocyte homing receptors: gatekeepers of the multistep paradigm," Current Opinion in Hematology, 12:444-450 (2005).
USPTO Restriction Requirement in U.S. Appl. No. 10/582,176, mailed October 19, 2009, 6 pages.
USPTO Interview Summary in U.S. Appl. No. 10/582,413, mailed October 27, 2009, 4 pages.
Alexander et al., "Studies of the c-Mpl Thrombopoietin Receptor through Gene Disruption and Activation," Stem Cells, 14(suppl 1):124-132 (1996).
Borden et al., "Lymphokines and Cytokines as Cancer Treatment," Cancer, 65:800-814 (1990).
Byers, "What Can Randomized Controlled Trials Tell us About Nutrition and Cancer Prevention?," CA Cancer J. Clin., 49:353-361 (1999).

Fox et al., "Thrombopoietin expands hematopoietic stem cells after transplantation," J. Clin. Invest., 110(3):389-394 (2002).
Granziero et al., "Adoptive immunotherapy prevents prostate cancer in a transgenic animal model," Eur. J. Immunol., 29:1127-1138 (1999).
Higa et al., "Administration of anti-interleukin 18 antibody fails to inhibit development of dermatitis in atopic dermatitis-model mice NC/Nga," Br. J. Dermatol., 149(1):39-45 (2003).
Miyazaki et al., "Future Prospects of Thrombopoietin," Jpn. J. Transfusion Medicine, 46(3):311-316 (2000).
Nagayama et al., "Transient hematopoietic stem cell rescue using umbilical cord blood for a lethally irradiated nuclear accident victim," Bone Marrow Transplant. 29(3):197-204 (2002).
Nakamura et al., "A Novel Non-Peptidyl Human C-Mpl Agonist, NIP-004, Stimulates Human Megakaryopoiesis and Thrombopoiesis," Blood (ASH Annual Meeting Abstracts), Abstract 3148 (2005).
Nakamura et al., "A novel non-peptidyl human c-Mpl activator stimulates human megakaryopoiesis and thrombopoiesis," Blood, 107(11):4300-4307 (2006). Epub DOI 10.1182/blood-2005-11-4433 (2006).
Suzuki et al., "YM477, a Novel Orally-Active Thrombopoietin Receptor Agonist," Blood (ASH Annual Meeting Abstracts), 106:Abstract 2298 (2005).
Verstegen et al., "Thrombopoietin is a major limiting factor for selective outgrowth of human umbilical cord blood cells in non-obese diabetic/severe combined immunodeficient recipient mice," Br. J. Haematol., 122(5):837-846 (2003).
Fish & Richardson P.C., Response to Restriction Requirement dated Oct. 19, 2009 in U.S. Appl. No. 10/582,176, filed Nov. 4, 2009, 1 page.
USPTO Non-Final Office Action in U.S. Appl. No. 11/913,229, mailed Nov. 3, 2009, 40 pages.
Fish & Richardson, Amendment in Reply to Action dated Jun. 8, 2009 in U.S. Appl. No. 10/530,696, filed Nov. 30, 2009, 10 pages.
USPTO Notice of Allowance in U.S. Appl. No. 10/548,727, mailed Nov. 25, 2009, 29 pages.
USPTO Non-Final Office Action in U.S. Appl. No. 10/550,934, mailed Dec. 8, 2009, 33 pages.
USPTO Interview Summary in U.S. Appl. No. 10/582,413, mailed Dec. 2, 2009, 4 pages.
Fish & Richardson P.C., Amendment in Reply to Action dated Jun. 1, 2009 in U.S. Appl. No. 11/547,747, filed Nov. 30, 2009, 12 pages.
Klarquist Sparkman, LLP Response to Restriction Requirement dated May 26, 2009 in U.S. Appl. No. 10/582,654, filed Jun. 23, 2009, 2 pages.
USPTO Office Action in U.S. Appl. No. 10/582,654, mailed Sep. 1, 2009, 36 pages.
USPTO Final Office Action in U.S. Appl. No. 10/399,518, mailed Sep. 11, 2009, 24 pages.
USPTO Restriction Requirement in U.S. Appl. No. 10/257,864, mailed Feb. 1, 2006, 14 pages.
USPTO Non-Final Office Action in U.S. Appl. No. 10/530,696, mailed Apr. 23, 2010, 9 pages.
USPTO Non-Final Office Action in U.S. Appl. No. 10/582,413, mailed Apr. 16, 2010, 27 pages.
USPTO Restriction Requirement in U.S. Appl. No. 11/910,117, mailed May 3, 2010, 9 pages.
Fish & Richardson P.C., Amendment in Reply to Office Action dated Aug. 13, 2009 in U.S. Appl. No. 10/560,098, filed Feb. 16, 2010, 14 pages.
USPTO Non-Final Office Action in U.S. Appl. No. 10/582,176, mailed Jan. 25, 2010, 7 pages.
Fish & Richardson P.C., Amendment in Reply to Office Action dated Sep. 15, 2009 in U.S. Appl. No. 10/582,304, filed Jan. 13, 2010, 13 pages.
USPTO Final Office Action in U.S. Appl. No. 11/547,747, mailed Feb. 19, 2010, 15 pages.
European Search Report for App. Ser. No. EP 06 76 6512, dated Nov. 30, 2009, 6 pages.
USPTO Non-Final Office Action in U.S. Appl. No. 10/582,304, mailed Mar. 24, 2010, 10 pages.
Fish & Richardson P.C., Amendment in Reply to Action dated Nov. 3, 2009 in U.S. Appl. No. 11/913,229, filed Apr. 7, 2010, 15 pages.
USPTO Restriction Requirement in U.S. Appl. No. 11/916,981, mailed Mar. 31, 2010, 5 pages.
Foley & Lardner LLP, Amendment in Reply to Action dated Sep. 11, 2009 in U.S. Appl. No. 10/399,518, filed Dec. 11, 2009, 9 pages.
USPTO Non-Final Office Action in U.S. Appl. No. 10/399,518, mailed Mar. 23, 2010, 19 pages.
Arndt et al., "Factors influencing the dimer to monomer transition of an antibody single-chain Fv fragment," Biochemistry, 37(37):12918-26 (1998).
Brooke et al., "Human lymphocytes interact directly with CD47 through a novel member of the signal regulatory protein (SIRP) family," J. Immunol., 173:2562-2570 (2004).
Chatellier et al., "Functional mapping of conserved residues located at the VL and VH domain interface of a Fab," J. Mol. Biol., 264(1):1-6 (1996).
Chowdhury et al., "Engineering scFvs for improved stability," Methods Mol. Biol., 207:237-54 (2003).
Davies et al., "Antibody VH domains as small recognition units," Biotechnology (N.Y.), 13(5):475-9 (1995).
Jung et al., "The importance of framework residues H6, H7 and H10 in antibody heavy chains: experimental evidence for a new structural subclassification of antibody V(H) domains," J. Mol. Biol., 309(3):701-16 (2001).
Kaushansky, "Lineage-specific hematopoietic growth factors," N. Engl. J. Med., 354(19):2034-45 (2006).
Khalifa et al., "Effects on interaction kinetics of mutations at the VH-VL interface of Fabs depend on the structural context," J. Mol. Recognit., 13(3):127-39 (2000).
Vargas-Madrazo et al., "An improved model of association for VH-VL immunoglobulin domains: asymmetries between VH and VL in the packing of some interface residues," J. Mol. Recognit., 16(3):113-20 (2003).
Vernon-Wilson et al., "CD47 is a ligand for rat macrophage membrane signal regulatory protein SIRP (OX41) and human SIRPalpha 1," Eur. J. Immunol., 30:2130-2137 (2000).
Wu et al., "Multimerization of a chimeric anti-CD20 single-chain Fv-Fc fusion protein is mediated through variable domain exchange," Protein Eng., 14(12):1025-33 (2001).
USPTO Final Office Action in U.S. Appl. No. 10/560,098, mailed Jun. 3, 2010, 16 pages.
Fish & Richardson P.C., Amendment in Reply to Action dated Jan. 25, 2010 in U.S. Appl. No. 10/582,176, filed Jul. 23, 2010, 11 pages.
Fish & Richardson P.C., Amendment in Reply to Action dated Mar. 24, 2010 in U.S. Appl. No. 10/582,304, filed Jul. 26, 2010, 14 pages.
Fish & Richardson P.C., Amendment in Reply to Action dated Feb. 19, 2010 in U.S. Appl. No. 11/547,747, filed Jun. 18, 2010, 13 pages.
European Search Report for App. Ser. No. EP 06 73 0751, dated Jul. 16, 2010, 6 pages.
USPTO Final Office Action in U.S. Appl. No. 11/913,229, mailed Jun. 10, 2010, 10 pages.
USPTO Restriction Requirement in U.S. Appl. No. 11/916,351, mailed Sep. 3, 2010, 8 pages.
European Search Report for App. Ser. No. EP 06 75 7198, dated Jun. 11, 2010, 2 pages.
USPTO Restriction Requirement in U.S. Appl. No. 11/916,979, mailed Jul. 1, 2010, 7 pages.
Supplementary European Search Report for App. Ser. No. EP 07 74 5133, dated May 21, 2010, 2 pages.
USPTO Restriction Requirement in U.S. Appl. No. 12/874,872, mailed Dec. 15, 2010, 6 pages.
Fish & Richardson P.C., Reply to Restriction Requirement dated Dec. 15, 2010 in U.S. Appl. No. 12/874,872, filed Jan. 18, 2011, 8 pages.
Fish & Richardson P.C., Amendment in Reply to Action dated Apr. 16, 2010 in U.S. Appl. No. 10/582,413, filed Oct. 15, 2010, 11 pages.
USPTO Final Office Action in U.S. Appl. No. 10/582,413, mailed Dec. 23, 2010, 12 pages.
Fish & Richardson P.C., Amendment and Response to Restriction Requirement mailed May 3, 2010 in U.S. Appl. No. 11/910,117, filed Nov. 2, 2010, 11 pages.

USPTO Non-Final Office Action in U.S. Appl. No. 11/910,117, mailed Jan. 24, 2011, 10 pages.
Fish & Richardson P.C., Amendment and Response to Restriction Requirement dated Sep. 3, 2010 in U.S. Appl. No. 11/916,351, filed Dec. 2, 2010, 9 pages.
Fish & Richardson P.C., Amendment and Response to Restriction Requirement dated Jul. 1, 2010 in U.S. Appl. No. 11/916,979 filed Nov. 30, 2010, 9 pages.
USPTO Non-Final Office Action in U.S. Appl. No. 11/916,979, mailed Jan. 21, 2011, 15 pages.
USPTO Non-Final Office Action in U.S. Appl. No. 11/916,981, mailed Dec. 3, 2010, 8 pages.
USPTO Restriction Requirement in U.S. Appl. No. 12/304,514, dated Jan. 5, 2011, 5 pages.
Fish & Richardson P.C., Amendment and Reply to Restriction Requirement dated Jan. 5, 2011 in U.S. Appl. No. 12/304,514, filed Feb. 7, 2011, 9 pages.

* cited by examiner

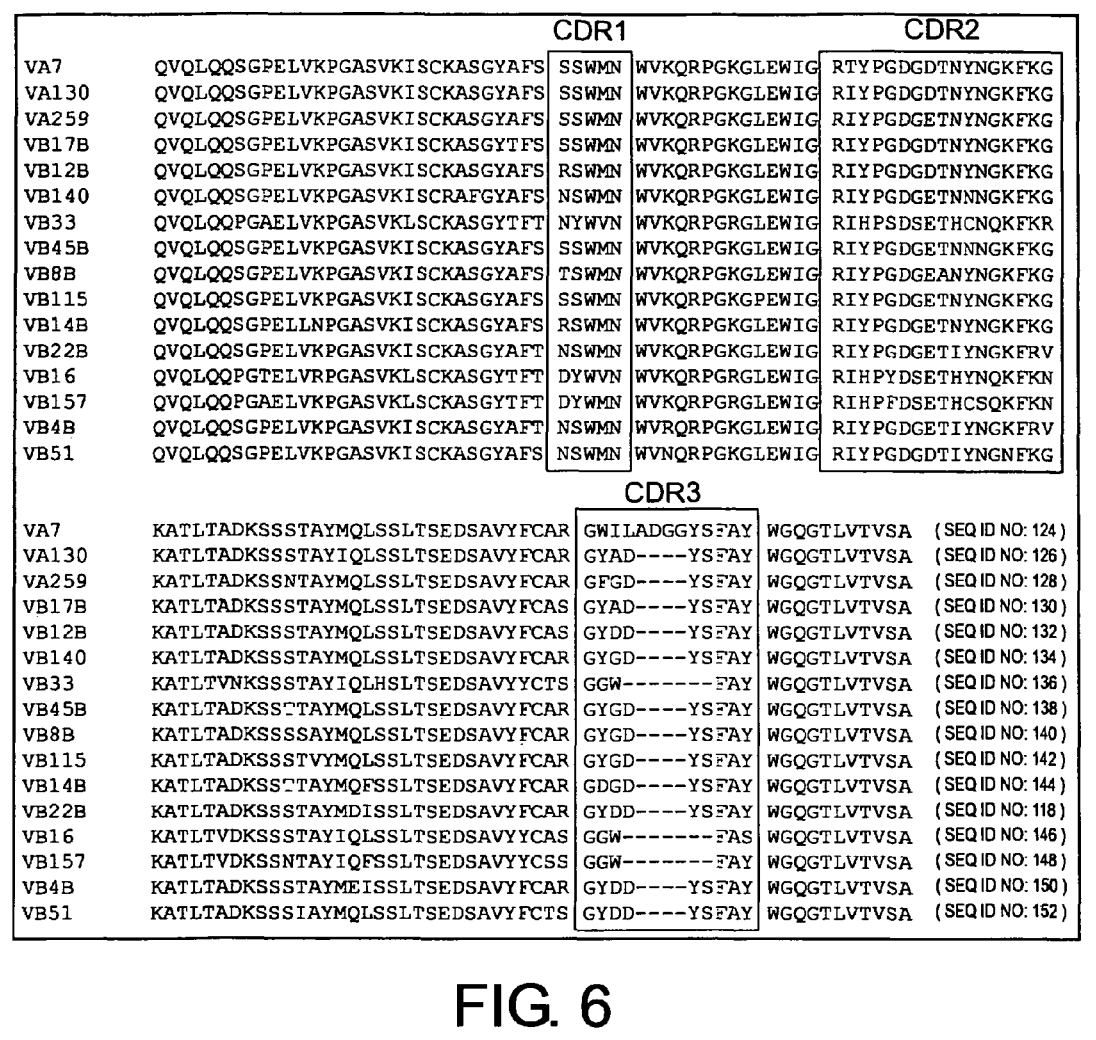

| | | CDR1 | | CDR2 |
|---|---|---|---|---|
| VA7 | QVQLQQSGPELVKPGASVKISCKASGYAFS | SSWMN | WVKQRPGKGLEWIG | RTYPGDGDTNYNGKFKG |
| VA130 | QVQLQQSGPELVKPGASVKISCKASGYAFS | SSWMN | WVKQRPGKGLEWIG | RIYPGDGDTNYNGKFKG |
| VA259 | QVQLQQSGPELVKPGASVKISCKASGYAFS | SSWMN | WVKQRPGKGLEWIG | RIYPGDGETNYNGKFKG |
| VB17B | QVQLQQSGPELVKPGASVKISCKASGYTFS | SSWMN | WVKQRPGKGLEWIG | RIYPGDGDTNYNGKFKG |
| VB12B | QVQLQQSGPELVKPGASVKISCKASGYAFS | RSWMN | WVKQRPGKGLEWIG | RIYPGDGDTNYNGKFKG |
| VB140 | QVQLQQSGPELVKPGASVKISCRAFGYAFS | NSWMN | WVKQRPGKGLEWIG | RIYPGDGETNNNGKFKG |
| VB33 | QVQLQQPGAELVKPGASVKLSCKASGYTFT | NYWVN | WVKQRPGRGLEWIG | RIHPSDSETHCNQKFKR |
| VB45B | QVQLQQSGPELVKPGASVKISCKASGYAFS | SSWMN | WVKQRPGKGLEWIG | RIYPGDGETNNNGKFKG |
| VB8B | QVQLQQSGPELVKPGASVKISCKASGYAFS | TSWMN | WVKQRPGKGLEWIG | RIYPGDGEANYNGKFKG |
| VB115 | QVQLQQSGPELVKPGASVKISCKASGYAFS | SSWMN | WVKQRPGKGPEWIG | RIYPGDGETNYNGKFKG |
| VB14B | QVQLQQSGPELLNPGASVKISCKASGYAFS | RSWMN | WVKQRPGKGLEWIG | RIYPGDGETNYNGKFKG |
| VB22B | QVQLQQSGPELVKPGASVKISCKASGYAFT | NSWMN | WVKQRPGKGLEWIG | RIYPGDGETIYNGKFRV |
| VB16 | QVQLQQPGTELVRPGASVKLSCKASGYTFT | DYWVN | WVKQRPGRGLEWIG | RIHPYDSETHYNQKFKN |
| VB157 | QVQLQQPGAELVKPGASVKLSCKASGYTFT | DYWMN | WVKQRPGRGLEWIG | RIHPFDSETHCSQKFKN |
| VB4B | QVQLQQSGPELVKPGASVKISCKASGYAFT | NSWMN | WVRQRPGKGLEWIG | RIYPGDGETIYNGKFRV |
| VB51 | QVQLQQSGPELVKPGASVKISCKASGYAFS | NSWMN | WVNQRPGKGLEWIG | RIYPGDGDTIYNGNFKG |

| | | CDR3 | | |
|---|---|---|---|---|
| VA7 | KATLTADKSSSTAYMQLSSLTSEDSAVYFCAR | GWILADGGYSFAY | WGQGTLVTVSA | (SEQ ID NO: 124) |
| VA130 | KATLTADKSSSTAYIQLSSLTSEDSAVYFCAR | GYAD----YSFAY | WGQGTLVTVSA | (SEQ ID NO: 126) |
| VA259 | KATLTADKSSNTAYMQLSSLTSEDSAVYFCAR | GFGD----YSFAY | WGQGTLVTVSA | (SEQ ID NO: 128) |
| VB17B | KATLTADKSSSTAYMQLSSLTSEDSAVYFCAS | GYAD----YSFAY | WGQGTLVTVSA | (SEQ ID NO: 130) |
| VB12B | KATLTADKSSSTAYMQLSSLTSEDSAVYFCAS | GYDD----YSFAY | WGQGTLVTVSA | (SEQ ID NO: 132) |
| VB140 | KATLTADKSSSTAYMQLSSLTSEDSAVYFCAR | GYGD----YSFAY | WGQGTLVTVSA | (SEQ ID NO: 134) |
| VB33 | KATLTVNKSSSTAYIQLHSLTSEDSAVYYCTS | GGW-------FAY | WGQGTLVTVSA | (SEQ ID NO: 136) |
| VB45B | KATLTADKSSTTAYMQLSSLTSEDSAVYFCAR | GYGD----YSFAY | WGQGTLVTVSA | (SEQ ID NO: 138) |
| VB8B | KATLTADKSSSSAYMQLSSLTSEDSAVYFCAR | GYGD----YSFAY | WGQGTLVTVSA | (SEQ ID NO: 140) |
| VB115 | KATLTADKSSSTVYMQLSSLTSEDSAVYFCAR | GYGD----YSFAY | WGQGTLVTVSA | (SEQ ID NO: 142) |
| VB14B | KATLTADKSSTTAYMQFSSLTSEDSAVYFCAR | GDGD----YSFAY | WGQGTLVTVSA | (SEQ ID NO: 144) |
| VB22B | KATLTADKSSSTAYMDISSLTSEDSAVYFCAR | GYDD----YSFAY | WGQGTLVTVSA | (SEQ ID NO: 118) |
| VB16 | KATLTVDKSSSTAYIQLSSLTSEDSAVYYCAS | GGW-------FAS | WGQGTLVTVSA | (SEQ ID NO: 146) |
| VB157 | KATLTVDKSSNTAYIQFSSLTSEDSAVYYCSS | GGW-------FAY | WGQGTLVTVSA | (SEQ ID NO: 148) |
| VB4B | KATLTADKSSSTAYMEISSLTSEDSAVYFCAR | GYDD----YSFAY | WGQGTLVTVSA | (SEQ ID NO: 150) |
| VB51 | KATLTADKSSSIAYMQLSSLTSEDSAVYFCTS | GYDD----YSFAY | WGQGTLVTVSA | (SEQ ID NO: 152) |

FIG. 6

| | | CDR1 | | CDR2 |
|---|---|---|---|---|
| VA7 | DIVMTQAAPSIPVTPGESVSISC | RSSKSLLHSNGNTYLY | WFLQRPGQSPQLLIY | RMSNLAS |
| VA130 | DIVMTQAAPSVPVTPGESVSISC | RSSKSLLHSNGNTYLY | WFLQRPGQSPQLLIY | RMSNLAS |
| VA259 | DIVMTQAAPSVPVTPGESVSISC | RSSKSLLHSNGNTYLY | WFLQRPGQSPQLLIY | RMSNLAS |
| VB17B | DIVMTQAAPSVPVTPGESVSISC | RSSKSLLHSNGNTYLY | WFLQRPGQSPQLLIY | RMSNLAS |
| VB12B | DIVMTQAAPSVPVTPGESVSISC | RSSKSLLHSNGNTYLY | WFLQRPGQSPQLLIY | RMSNLAS |
| VB140 | DIVMTQAAPSVPVTPGESVSISC | RSSKSLLHSNGNTYLY | WFLQRPGQSPQLLIY | RMSNLAS |
| VB33 | DIVMTQAAPSVPVTPGESVSISC | RSSKSLLYSNGNIYLY | WFLQRPGQSPQLLIY | RMSNLAS |
| VB45B | DIVMTQAAPSVPVTPGESVSISC | RSSKSLLHSNGNTYLY | WFLQRPGQSPQLLIY | RMSNLAS |
| VB8B | DIVMTQAAPSVPVTPGESVSISC | RSSKSLLHSNGNTYLY | WFMQRPGQSPQLLIY | RMSNLAS |
| VB115 | DIVMTQAAPSVPVTPGESVSISC | RSSKSLLHSNGNTYLY | WFLQRPGQSPQLLIY | RMSNLAS |
| VB14B | DIVMTQAAPSVPVTPGESVSISC | RSSKSLLHSNGNTYLY | WFLQRPGQSPQLLIY | RMSNLAS |
| VB22B | DIVMTQAAPSIPVTPGESVSISC | RSSKSLLHSNGNTYLY | WFLQRPGQSPQLLIY | RMSNLAS |
| VB16 | DIVMTQAAPSVPVTPGESVSISC | RSSKSLLYSNGNTYLY | WFLQRPGQSPQLLIY | RMSNLAS |
| VB157 | DIVMTQAAPSVSVTPGESVSISC | RSSKSLLYSNGNIYLY | WFLQRPGQSPQLLIY | RMSNLAS |
| VB4B | DIVMTQAAPSVPVTPGESVSISC | RSSKSLLHNNGNTYLY | WFLQRPGQSPQLLIY | RMSNLAS |
| VB51 | DIVMTQAAPSLPVTPGESVSISC | RSSKSLLHSNGNTYLY | WFLQRPGQSPQLLIY | RMSNLAS |

| | | CDR3 | | |
|---|---|---|---|---|
| VA7 | GVPDRFSGSGSGTAFTLRISRVEAEDVGIYYC | MQHLEYPFT | FGTGTKLEIK | (SEQ ID NO: 125) |
| VA130 | GVPDRFSGSGSGTAFTLRISRVEAEDVGVYYC | MQHLEYPYT | FGSGTKLEIK | (SEQ ID NO: 127) |
| VA259 | GAPDRFSGSGSGTAFTLRISRVETEDVGVYYC | MQHLEYPYT | FGSGTKLEIK | (SEQ ID NO: 129) |
| VB17B | GVPDRFSGSGSGTAFTLRISRVEAEDVGVYYC | MQHLEYPYT | FGSGTKLEIK | (SEQ ID NO: 131) |
| VB12B | GVPDRFSGSGSGTAFTLRISRVEAEDVGVYYC | MQHLEYPYT | FGSGTKLEIK | (SEQ ID NO: 133) |
| VB140 | GVPDRFSGSGSGAAFTLRISRVEAEDVGVYYC | MQHLEYPYT | FGSGTKLEIK | (SEQ ID NO: 135) |
| VB33 | GVPDRFSGSGSGTAFTLRISRVEAEDVGVYYC | MQHLEYPYT | FGSGTKLEIK | (SEQ ID NO: 137) |
| VB45B | GVPDRFSGSGSGAAFTLRISRVEAEDVGVYYC | MQHLEYPYT | FGSGTKLEIK | (SEQ ID NO: 139) |
| VB8B | GVPDRFSGSGSGTAFTLRISRVEAEDVGVYYC | MQHVEYPYT | FGSGTKLEIK | (SEQ ID NO: 141) |
| VB115 | GVPDRFSGSGSGTAFTLRISRVEAEDVGVYYC | MQHLEYPYT | FGSGTKLEIK | (SEQ ID NO: 143) |
| VB14B | GVPDRFSGSGSGTAFTLRISRVEAEDVGVYYC | MQHLEYPYT | FGSGTKLEIK | (SEQ ID NO: 145) |
| VB22B | GVPDRFSGSGSGTAFTLRISRVEAEDVGVYYC | MQHIEYPFT | FGSGTKLEIK | (SEQ ID NO: 120) |
| VB16 | GVPDRFSGSGSGTAFTLTISSVEAEDVGVYYC | MQHLEYPYT | FGSGTKLEIK | (SEQ ID NO: 147) |
| VB157 | GVPDRFSGSGSGTAFTLKISRVEAEDVGVYYC | MQHLEYPYT | FGSGTKLEIK | (SEQ ID NO: 149) |
| VB4B | GVPDRFSGSGSGTAFTLRISRVEAEDVGVYYC | MQHIEYPFT | FGSGTKLEIK | (SEQ ID NO: 151) |
| VB51 | GVPDRFSGSGSGTAFTLRISRVEAEDVGVYYC | MQHLEYPYT | FGSGTKLEIK | (SEQ ID NO: 153) |

FIG. 7

HUMANIZED HEAVY CHAIN

| | FR1 | CDR1 | FR2 | CDR2 |
|---|---|---|---|---|
| hVB22B u2-wz4 | QVQLVQSGPEVKKPGASVKVSCKASGYTFT | NSWMN | WVRQRPGKGLEWIG | RIYPGDGETIYNGKFRV |
| hVB22B q-wz5 | QVQLVQSGPEVKKPGASVKVSCKASGYTFT | NSWMN | WVRQRPGKGLEWIG | RIYPGDGETIYNGKFRV |
| hVB22B p-z | QVQLVQSGPEVKKPGASVKVSCKASGYTFT | NSWMN | WVRQRPGKGLEWMG | RIYPGDGETIYNGKFRV |
| hVB22B g-e | QVQLVQSGPEVKKPGASVKVSCKASGYTFT | NSWMN | WVRQRPGKGLEWVG | RIYPGDGETIYNGKFRV |
| hVB22B e | QVQLVQSGPEVKKPGASVKVSCKASGYTFT | NSWMN | WIRQRPGKGLEWIG | RIYPGDGETIYNGKFRV |

| | FR3 | CDR3 | FR4 | |
|---|---|---|---|---|
| hVB22B u2-wz4 | RVTITADESTSTAYMQLSSLRSEDTAVYYCAR | GYDDYSFAY | WGQGTTVTVSS | ( SEQ ID NO: 289 ) |
| hVB22B q-wz5 | RVTITADESTSTAYMELSSLRSEDTAVYYCAR | GYDDYSFAY | WGQGTTVTVSS | ( SEQ ID NO: 295 ) |
| hVB22B p-z | RVTITADESTSTAYMELSSLRSEDTAVYYCAR | GYDDYSFAY | WGQGTTVTVSS | ( SEQ ID NO: 229 ) |
| hVB22B g-e | RVTITADESTSTAYMELSSLRSEDTAVYYCAR | GYDDYSFAY | WGQGTTVTVSS | ( SEQ ID NO: 256 ) |
| hVB22B e | RVTITADESTSTAYMELSSLRSEDTAVYYCAR | GYDDYSFAY | WGQGTLVTVSS | ( SEQ ID NO: 262 ) |

FIG. 18-1

HUMANIZED LIGHT CHAIN

| | FR1 | CDR1 | FR2 | CDR2 |
|---|---|---|---|---|
| hVB22B u2-wz4 | DIVMTQSPLSLPVTPGEPASISC | RSSKSLLHSNGNTYLY | WFLQKPGQSPQLLIY | RMSNLAS |
| hVB22B q-wz5 | DIVMTQSPLSLPVTPGEPASISC | RSSKSLLHSNGNTYLY | WFQQKPGQAPRLLIY | RMSNLAS |
| hVB22B p-z | DIVMTQSALSLPVTPGEPASISC | RSSKSLLHSNGNTYLY | WFQQKPGQSPQLLIY | RMSNLAS |
| hVB22B g-e | DIVMTQSALSLPVTPGEPASISC | RSSKSLLHSNGNTYLY | WYLQKPGQSPQLLIY | RMSNLAS |
| hVB22B e | DIVMTQSALSLPVTPGEPASISC | RSSKSLLHSNGNTYLY | WYLQKPGQSPQLLIY | RMSNLAS |

| | FR3 | CDR3 | FR4 | |
|---|---|---|---|---|
| hVB22B u2-wz4 | GVPDRFSGSGSGTDFTLKISRVEAEDVGVYYC | MQHIEYPFT | FGQGTKLEIK | ( SEQ ID NO: 291 ) |
| hVB22B q-wz5 | GVPDRFSGSGSGTAFTLKISRVEAEDVGVYYC | MQHIEYPFT | FGQGTKLEIK | ( SEQ ID NO: 297 ) |
| hVB22B p-z | GVPDRFSGSGSGTAFTLKISRVEAEDVGVYYC | MQHIEYPFT | FGQGTKLEIK | ( SEQ ID NO: 238 ) |
| hVB22B g-e | GVPDRFSGSGSGTAFTLKISRVEAEDVGVYYC | MQHIEYPFT | FGQGTKLEIK | ( SEQ ID NO: 258 ) |
| hVB22B e | GVPDRFSGSGSGTAFTLKISRVEAEDVGVYYC | MQHIEYPFT | FGQGTKLEIK | ( SEQ ID NO: 258 ) |

FIG. 18-2

ANTI-MPL ANTIBODIES

CROSS-REFERENCE TO RELATED APPLICATIONS

This application is the National Stage of International Application No. PCT/JP2004/018506, filed Dec. 10, 2004, which claims the benefit of Japanese Patent Applications Ser. No. 2003-415746, filed on Dec. 12, 2003, Ser. No. 2004-071763, filed on Mar. 12, 2004, and Serial No. 2004-248323, filed on Aug. 27, 2004. The contents of all of the foregoing applications are hereby incorporated by reference in their entireties.

TECHNICAL FIELD

The present invention relates to anti-Mpl antibodies.

BACKGROUND ART

Thrombopoietin (TPO) is a factor that enhances the differentiation and maturation of megakaryocytes (platelet precursor cells) from hemopoietic stem cells into platelets. TPO also functions as a cytokine with an important role in the regulation of platelet number. TPO is converted into its active form through the cleavage of a TPO precursor comprising 353 amino acids.

Mpl is a TPO receptor, and human Mpl molecules are known to exist in two forms comprising 572 and 635 amino acids. The human Mpl gene sequence has already been analyzed (see Non-Patent Document 1 and GenBank accession No. NM_005373).

Most cytokine receptors dimerize upon ligand binding, and transduce signals into cells. It has been reported that TPO similarly binds to its own specific receptor MPL, which leads to dimerization of the receptor, thereby transducing signals into cells and exerting physiological effects (see Non-Patent Document 2).

Antibodies exhibiting agonistic activity have been reported among those antibodies that bind to receptors having the above features.

For example, an antibody against the erythropoietin (EPO) receptor has been reported to substitute for erythropoietin function. The monovalent form (Fab) of the antibody is capable of binding to the EPO receptor but is unable to transduce signals. Thus, dimerization of the erythropoietin receptor via bivalent binding is assumed to be essential for signal transduction (see Non-Patent Document 3).

Antibodies that bind to Mpl and exhibit TPO agonistic activity have also been reported (see Non-Patent Documents 4 and 5). This suggests that receptor dimerization is induced upon binding of a bivalent antibody with regards to MPL as well.

Meanwhile, a single-chain antibody (scFv) has been reported to exhibit TPO agonistic activity (see Patent Document 1). However, it has been revealed that, the underlying mechanism of scFv exhibiting TPO agonistic activity is that a part of scFv dimerizes (diabody) and this diabody becomes the actual active unit (see Patent Documents 2 to 4).

[Patent Document 1] U.S. Pat. No. 6,342,220
[Patent Document 2] WO 01/79494
[Patent Document 3] WO 02/33072
[Patent Document 4] WO 02/33073
[Non-Patent Document 1] Palacios et al., *Cell,* 1985, 41, 727-734
[Non-Patent Document 2] Souyri et al., *Cell,* 1990, 63, 1137-1147

[Non-Patent Document 3] Elliott, S. et al., *J. Biol. Chem.,* 1996, 271(40), 24691-24697
[Non-Patent Document 4] Abe et al., Immunol. Lett., 1998, 61, 73-78
[Non-Patent Document 5] Bijia Deng et al., Blood, 1998, 92, 1981-1988

DISCLOSURE OF THE INVENTION

Problems to be Solved by the Invention

The present invention was achieved in view of the above circumstances. An objective of the present invention is to provide novel anti-Mpl antibodies having TPO agonistic activity.

Means to Solve the Problems

The present inventors performed exhaustive research to solve the above objective. The present inventors prepared and purified anti-human Mpl antibody VB22B, and established a single-chain antibody expression system using genetic engineering techniques. Specifically, the variable region of anti-human Mpl antibody was first cloned, and a diabody expression vector pCXND3-VB22B db for the anti-human Mpl antibody was prepared. This pCXND3-VB22B db vector was then used to generate an expression vector pCXND3-VB22B sc$(Fv)_2$ for anti-human Mpl antibody sc(Fv)2. Anti-human Mpl sc(Fv)2 was expressed in CHO-DG44 cells using the expression vector pCXND3-VB22B sc(Fv)2, and then purified from the culture supernatant. In control experiments, VB22B diabody was transiently expressed in COS7 cells using the above pCXND3-VB22B db vector, and then purified from the culture supernatant.

In addition, VB22B diabody and VB22B sc(Fv)2 were evaluated for their TPO-like agonistic activities. The results showed that VB22B diabody and VB22B sc(Fv)2 exhibit higher agonistic activities compared to VB22B IgG, and thus activities equivalent to or higher than that of the natural ligand, human TPO.

Furthermore, the present inventors succeeded in preparing five types of humanized VB22B sc(Fv)2. The TPO-like agonistic activity was also proven to be unaltered by humanization.

More specifically, the present invention provides the following (1) to (38):

(1) an antibody comprising a single-chain polypeptide having binding activity against TPO receptor (Mpl), wherein said antibody comprises two heavy chain variable regions and two light chain variable regions;

(2) the antibody of (1), wherein the two heavy chain variable regions and the two light chain variable regions are arranged in the order of heavy chain variable region, light chain variable region, heavy chain-variable region, and light chain variable region from the N terminus of the single-chain polypeptide;

(3) the antibody of (1) or (2), wherein the two heavy chain variable regions and the two light chain variable regions are linked by linkers;

(4) the antibody of (3), wherein the linkers comprise 15 amino acids;

(5) a chimeric antibody that binds to Mpl;

(6) the antibody of (5), which is a humanized antibody;

(7) the antibody of (5) or (6), which is a minibody;

(8) an antibody that binds to soluble Mpl;

(9) an antibody that binds to human Mpl and monkey Mpl;

(10) an antibody having agonistic activity against human Mpl and monkey Mpl;

(11) an antibody whose binding activity to soluble Mpl is $KD=10^{-6}$ M or lower;

(12) an antibody whose binding activity to soluble Mpl is KD=$10^{-7}$ M or lower;

(13) an antibody whose TPO agonistic activity is EC50=100 nM or lower;

(14) an antibody whose TPO agonistic activity is EC50=30 nM or lower;

(15) an antibody whose TPO agonistic activity is EC50=10 nM or lower;

(16) an antibody which comprises a heavy chain variable region, wherein said heavy chain variable regions comprises CDR1, CDR2 and CDR3 consisting of an amino acid sequence of any one of:

[1] SEQ ID NOs: 3, 4, and 5
[2] SEQ ID NOs: 6, 7, and 8
[3] SEQ ID NOs: 9, 10, and 11
[4] SEQ ID NOs: 15, 16, and 17
[5] SEQ ID NOs: 18, 19, and 20
[6] SEQ ID NOs: 21, 22, and 23
[7] SEQ ID NOs: 24, 25, and 26
[8] SEQ ID NOs: 27, 28, and 29
[9] SEQ ID NOs: 30, 31, and 32
[10] SEQ ID NOs: 33, 34, and 35
[11] SEQ ID NOs: 36, 37, and 38
[12] SEQ ID NOs: 39, 40, and 41
[13] SEQ ID NOs: 42, 43, and 44
[14] SEQ ID NOs: 48, 49, and 50
[15] SEQ ID NOs: 51, 52, and 53
[16] SEQ ID NOs: 54, 55, and 56
[17] SEQ ID NOs: 57, 58, and 59;

(17) an antibody which comprises a light chain variable region, wherein said light chain variable region comprises CDR1, CDR2 and CDR3 consisting of an amino acid sequence of any one of:

[1] SEQ ID NOs: 60, 61, and 62
[2] SEQ ID NOs: 63, 64, and 65
[3] SEQ ID NOs: 78, 79, and 80
[4] SEQ ID NOs: 84, 85, and 86
[5] SEQ ID NOs: 93, 94, and 95
[6] SEQ ID NOs: 96, 97, and 98
[7] SEQ ID NOs: 102, 103, and 104
[8] SEQ ID NOs: 108, 109, and 110
[9] SEQ ID NOs: 111, 112, and 113
[10] SEQ ID NOs: 114, 115, and 116;

(18) an antibody that comprises a heavy chain variable region and a light chain variable region of any one of:

[1] a heavy chain variable region that comprises CDR1, CDR2, and CDR3 comprising the amino acid sequences consisting of SEQ ID NOs: 3, 4, and 5, and a light chain variable region that comprises CDR1, CDR2, and CDR3 comprising the amino acid sequences consisting of SEQ ID NOs: 60, 61, and 62;

[2] a heavy chain variable region that comprises CDR1, CDR2, and CDR3 comprising the amino acid sequences consisting of SEQ ID NOs: 6, 7, and 8, and a light chain variable region that comprises CDR1, CDR2, and CDR3 comprising the amino acid sequences consisting of SEQ ID NOs: 63, 64, and 65;

[3] a heavy chain variable region that comprises CDR1, CDR2, and CDR3 comprising the amino acid sequences consisting of SEQ ID NOs: 9, 10, and 11, and a light chain variable region that comprises CDR1, CDR2, and CDR3 comprising the amino acid sequences consisting of SEQ ID NOs: 63, 64, and 65;

[4] a heavy chain variable region that comprises CDR1, CDR2, and CDR3 comprising the amino acid sequences consisting of SEQ ID NOs: 15, 16, and 17, and a light chain variable region that comprises CDR1, CDR2, and CDR3 comprising the amino acid sequences consisting of SEQ ID NOs: 63, 64, and 65;

[5] a heavy chain variable region that comprises CDR1, CDR2, and CDR3 comprising the amino acid sequences consisting of SEQ ID NOs: 18, 19, and 20, and a light chain variable region that comprises CDR1, CDR2, and CDR3 comprising the amino acid sequences consisting of SEQ ID NOs: 63, 64, and 65;

[6] a heavy chain variable region that comprises CDR1, CDR2, and CDR3 comprising the amino acid sequences consisting of SEQ ID NOs: 21, 22, and 23, and a light chain variable region that comprises CDR1, CDR2, and CDR3 comprising the amino acid sequences consisting of SEQ ID NOs: 78, 79, and 80;

[7] a heavy chain variable region that comprises CDR1, CDR2, and CDR3 comprising the amino acid sequences consisting of SEQ ID NOs: 24, 25, and 26, and a light chain variable region that comprises CDR1, CDR2, and CDR3 comprising the amino acid sequences consisting of SEQ ID NOs: 63, 64, and 65;

[8] a heavy chain variable region that comprises CDR1, CDR2, and CDR3 comprising the amino acid sequences consisting of SEQ ID NOs: 27, 28, and 29, and a light chain variable region that comprises CDR1, CDR2, and CDR3 comprising the amino acid sequences consisting of SEQ ID NOs: 84, 85, and 86;

[9] a heavy chain variable region that comprises CDR1, CDR2, and CDR3 comprising the amino acid sequences consisting of SEQ ID NOs: 30, 31, and 32, and a light chain variable region that comprises CDR1, CDR2, and CDR3 comprising the amino acid sequence consisting of SEQ ID NOs: 63, 64, and 65;

[10] a heavy chain variable region that comprises CDR1, CDR2, and CDR3 comprising the amino acid sequences consisting of SEQ ID NOs: 33, 34, and 35, and a light chain variable region that comprises CDR1, CDR2, and CDR3 comprising the amino acid sequences consisting of SEQ ID NOs: 63, 64, and 65;

[11] a heavy chain variable region that comprises CDR1, CDR2, and CDR3 comprising the amino acid sequences consisting of SEQ ID NOs: 36, 37, and 38, and a light chain variable region that comprises CDR1, CDR2, and CDR3 comprising the amino acid sequences consisting of SEQ ID NOs: 93, 94, and 95;

[12] a heavy chain variable region that comprises CDR1, CDR2, and CDR3 comprising the amino acid sequences consisting of SEQ ID NOs: 39, 40, and 41, and a light chain variable region that comprises CDR1, CDR2, and CDR3 comprising the amino acid sequences consisting of SEQ ID NOs: 96, 97, and 98;

[13] a heavy chain variable region that comprises CDR1, CDR2, and CDR3 comprising the amino acid sequences consisting of SEQ ID NOs: 42, 43, and 44, and a light chain variable region that comprises CDR1, CDR2, and CDR3 comprising the amino acid sequences consisting of SEQ ID NOs: 78, 79, and 80;

[14] a heavy chain variable region that comprises CDR1, CDR2, and CDR3 comprising the amino acid sequences consisting of SEQ ID NOs: 45, 46, and 47, and a light chain variable region that comprises CDR1, CDR2, and CDR3 comprising the amino acid sequences consisting of SEQ ID NOs: 102, 103, and 104;

[15] a heavy chain variable region that comprises CDR1, CDR2, and CDR3 comprising the amino acid sequences consisting of SEQ ID NOs: 48, 49, and 50, and a light chain variable region that comprises CDR1, CDR2, and CDR3 comprising the amino acid sequences consisting of SEQ ID Nos: 63, 64, and 65;

[16] a heavy chain variable region that comprises CDR1, CDR2, and CDR3 comprising the amino acid sequences consisting of SEQ ID NOs: 51, 52, and 53, and a light chain variable region that comprises CDR1, CDR2, and CDR3 comprising the amino acid sequences consisting of SEQ ID NOs: 108, 109, and 110,

[17] a heavy chain variable region that comprises CDR1, CDR2, and CDR3 comprising the amino acid sequences consisting of SEQ ID NOs: 54, 55, and 56, and a light chain variable region that comprises CDR1, CDR2, and CDR3 comprising the amino acid sequences consisting of SEQ ID NOs: 111, 112, and 113;

[18] a heavy chain variable region that comprises CDR1, CDR2, and CDR3 comprising the amino acid sequences consisting of SEQ ID NOs: 57, 58, and 59, and a light chain variable region that comprises CDR1, CDR2, and CDR3 each comprising the amino acid sequences consisting of SEQ ID NOs: 114, 115, and 116;

(19) an antibody that comprises a heavy chain variable region comprising the amino acid sequence of SEQ ID NO: 118;

(20) an antibody that comprises a light chain variable region comprising the amino acid sequence of SEQ ID NO: 120;

(21) an antibody that comprises a heavy chain variable region comprising the amino acid sequence of SEQ ID NO: 118 and a light chain variable region comprising the amino acid sequence of SEQ ID NO: 120;

(22) an antibody comprising the amino acid sequence of SEQ ID NO: 122 or 264;

(23) an antibody that comprises a heavy chain variable region, wherein said heavy chain variable region comprises FR1, FR2, FR3, and FR4 consisting of amino acid sequences of any one of:

[1] SEQ ID NOs: 230, 232, 234, and 236

[2] SEQ ID NOs: 265, 267, 269, and 271

[3] SEQ ID NOs: 279, 281, 283, and 285

[4] SEQ ID NOs: 298, 299, 300, and 301

[5] SEQ ID NOs: 298, 299, 306, and 301.

(24) an antibody comprising a light chain variable region, wherein said light chain variable region comprises FR1, FR2, FR3, and FR4 consisting of amino acid sequences of any one of:

[1] SEQ ID NOs: 239, 241, 243, and 245

[2] SEQ ID NOs: 272, 274, 276, and 278

[3] SEQ ID NOs: 302, 303, 304, and 305

[4] SEQ ID NOs: 302, 307, 308, and 305;

(25) an antibody that comprises a heavy chain variable region and a light chain variable region of any one of:

[1] a heavy chain variable region which comprises FR1, FR2, FR3, and FR4 having the amino acid sequences consisting of SEQ ID NOs: 230, 232, 234, and 236, and a light chain variable region which comprises FR1, FR2, FR3, and FR4 having the amino acid sequences consisting of SEQ ID NOs: 239, 241, 243, and 245;

[2] a heavy chain variable region which comprises FR1, FR2, FR3, and FR4 having the amino acid sequences consisting of SEQ ID NOs: 265, 267, 269, and 271, and a light chain variable region which comprises FR1, FR2, FR3, and FR4 having the amino acid sequences consisting of SEQ ID NOs: 272, 274, 276, and 278;

[3] a heavy chain variable region which comprises FR1, FR2, FR3, and FR4 having the amino acid sequences consisting of SEQ ID NOs: 279, 281, 283, and 285, and a light chain variable region which comprises FR1, FR2, FR3, and FR4 having the amino acid sequences consisting of SEQ ID NOs: 272, 274, 276, and 278;

[4] a heavy chain variable region which comprises FR1, FR2, FR3, and FR4 having the amino acid sequences consisting of SEQ ID NOs: 298, 299, 300, and 301, and a light chain variable region which comprises FR1, FR2, FR3, and FR4 having the amino acid sequences consisting of SEQ ID NOs: 302, 303, 304, and 305;

[5] a heavy chain variable region which comprises FR1, FR2, FR3, and FR4 having the amino acid sequences consisting of SEQ ID NOs: 298, 299, 306, and 301, and a light chain variable region which comprises FR1, FR2, FR3, and FR4 having the amino acid sequences consisting of SEQ ID NOs: 302, 307, 308, and 305;

(26) an antibody that comprises a heavy chain variable region, wherein said heavy chain variable region comprises the amino acid sequence of SEQ ID NO: 229, 256, 262, 289, or 295;

(27) an antibody that comprises a light chain variable region, wherein said light chain variable region comprises the amino acid sequence of SEQ ID NO: 238, 258, 291, or 297;

(28) an antibody that comprises a heavy chain variable region and a light chain variable region of any one of:

[1] a heavy chain variable region comprising the amino acid sequence of SEQ ID NO: 229, and a light chain variable region comprising the amino acid sequence of SEQ ID NO: 238;

[2] a heavy chain variable region comprising the amino acid sequence of SEQ ID NO: 256, and a light chain variable region comprising the amino acid sequence of SEQ ID NO: 258;

[3] a heavy chain variable region comprising the amino acid sequence of SEQ ID NO: 262, and a light chain variable region comprising the amino acid sequence of SEQ ID NO: 258;

[4] a heavy chain variable region comprising the amino acid sequence of SEQ ID NO: 289, and a light chain variable region comprising the amino acid sequence of SEQ ID NO: 291;

[5] a heavy chain variable region comprising the amino acid sequence of SEQ ID NO: 295, and a light chain variable region comprising the amino acid sequence of SEQ ID NO: 297;

(29) an antibody that comprises the amino acid sequence of SEQ ID NO: 2, 254, 260, 287, or 293;

(30) an antibody having an activity equivalent to that of an antibody of any one of (16) to (29), wherein said antibody comprises the amino acid sequence set forth in any one of (16) to (29), in which one or more amino acids have been substituted, deleted, added and/or inserted;

(31) an antibody that recognizes an epitope recognized by an antibody of any one of (16) to (30);

(32) an antibody that recognizes the region of amino acids 26 to 274 of human Mpl;

(33) an antibody of any one of (1) to (32), which has TPO agonistic activity;

(34) a polynucleotide encoding an antibody of any one of (1) to (33);

(35) a polynucleotide hybridizing to the polynucleotide of (34) under stringent conditions, wherein said polynucleotide encodes an antibody having activity equivalent to that of an antibody of any one of (1) to (33);

(36) a vector comprising the polynucleotide of (34) or (35);

(37) a host cell that carries the polynucleotide of (34) or (35), or the vector of (36); and

(38) a pharmaceutical composition comprising an antibody of any one of (1) to (33).

BRIEF DESCRIPTION OF THE DRAWINGS

FIG. 6 shows the amino acid sequences of anti-human Mpl antibodies (H chains) that exhibit higher agonistic activities when converted into minibodies.

FIG. 7 shows the amino acid sequences of anti-human Mpl antibodies (L chains) which exhibit higher agonistic activities when converted into minibodies.

FIG. 18 shows the positions of FRs and CDRs in humanized heavy chain sequences (hVB22B p-z, hVB22B g-e, hVB22B e, hVB22B u2-wz4, and hVB22B q-wz5:VH), and humanized light chain sequences (hVB22B p-z, hVB22B g-e, hVB22B e, hVB22B u2-wz4, and hVB22B q-wz5:VL).

BEST MODE FOR CARRYING OUT THE INVENTION

Figure 1:
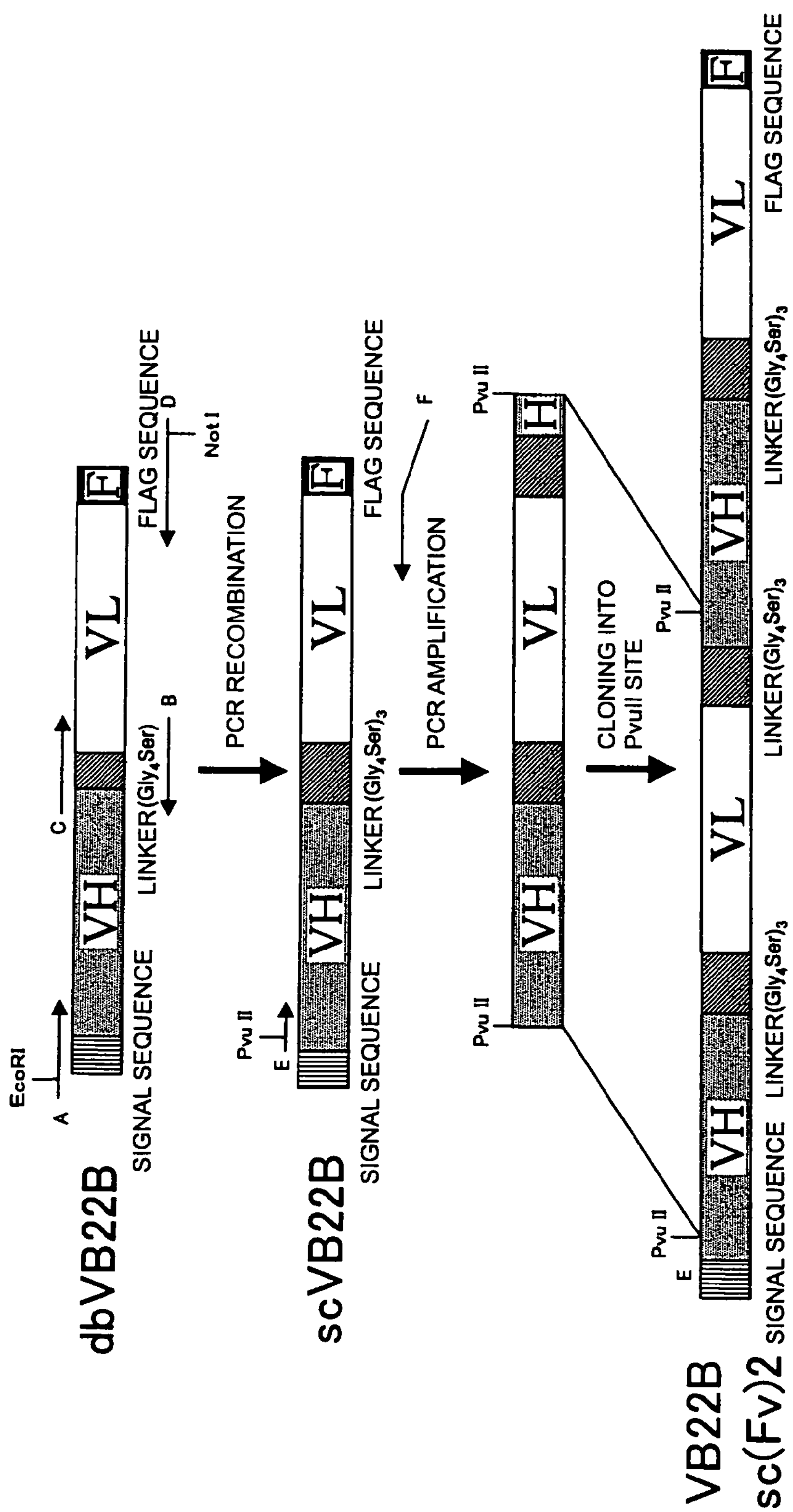
FIG. 1 demonstrates the strategy for preparing single-chain antibody sc(Fv)2.

The present invention provides antibodies that bind to the TPO receptor (Mpl).

The antibodies of the present invention comprise all types of antibodies, including antibodies with modified amino acid sequences, such as minibodies, humanized antibodies, and chimeric antibodies; antibodies that have been modified by binding with other molecules (for example, polymers such as polyethylene glycol); and antibodies whose sugar chains have been modified.

Mpl of the present invention may be a mutant receptor. A mutant receptor of the present invention is usually a receptor that exists at a frequency lower than 50%, preferably lower than 20%, more preferably lower than 10%, and even more preferably lower than 1%. The frequency is generally calculated using randomly selected subjects. However, the frequency may vary depending on the country, area, sex, and such. Therefore, the frequency may also be calculated, for example, within a defined country or area, such as Japan, the United States, and Europe, or calculated for one sex. When there are two or more mutations in a receptor, the frequency may be calculated for multiple mutation sites or for any one of the mutation sites. Mutant receptors are preferably evaluated by a frequency as described above. However, mutant receptors can also be evaluated, for example, by their signal transducing ability and such. Specifically, for example, when two different receptors are present, the one with stronger transducing signals upon natural ligand-binding maybe be used as a non-mutant type receptor, and the one with weaker transducing signals as a mutant receptor.

In one embodiment, the mutant receptors of the present invention comprise receptors that are associated with disease onset. The phrase "mutant receptors associated with disease onset" means that the loss of reactivity to a natural ligand becomes part of the reason that triggers disease onset. In the present invention, the mutant receptor may be a contributing factor, but not necessarily the sole factor triggering disease onset. Many reports have been previously published that describe the association of mutant receptors with disease onset. In addition to those that have been reported, associations of mutant receptors and disease onset can also be identified by statistical analysis methods (for example, correlation analyses). Correlation analyses, also called "case control studies", are well known to those skilled in the art (for example, Nishimura, Y., 1991, "Statistical analysis of polymorphisms", Saishin Igaku, 46:909-923; Oka, A. et al., 1990, Hum. Mol. Genetics 8, 2165-2170; Ota; M. et al., 1999, Am. J. Hum. Genet. 64, 1406-1410; Ozawa, A. et al., 1999, Tissue Antigens 53, 263-268). For example, the correlation between a mutant receptor and a disease can be studied by computing the frequency of the mutant receptor in patients and healthy subjects, and testing whether the patient population has a higher mutant receptor frequency. Typically, differences in frequency are evaluated using the $\chi$-test. $\chi$ is obtained by the equation $\chi^2=\Sigma$(observed value−expected value)$^2$/expected value. A p value is obtained from the $\chi^2$ value determined. Based on this p value, it can be determined whether there is a correlation between the mutant receptor and the disease. For example, when $p<0.05$, the mutant receptor is considered to correlate with the disease. Mutant thrombopoietin (TPO) receptors have already been reported (Matthias Ballmaier et al., 2001, BLOOD, 97 (1), 139; and others).

It is preferable that the antibodies of the present invention have agonistic activity against Mpl.

In a preferred embodiment, the antibodies of the present invention comprise, for example, minibodies.

The minibodies comprise antibody fragments lacking portions of the whole antibody (for example, whole IgG). The minibodies are not particularly limited as long as they have binding activity to their antigens. The minibodies of the present invention have higher activities compared to their corresponding whole antibodies. There are no particular limitations on the antibody fragments of the present invention as long as they are portions of the whole antibody, and preferably contain heavy chain variable regions (VH) and/or light chain variable regions (VL). The amino acid sequences of VH or VL may contain substitutions, deletions, additions and/or insertions. Furthermore, the antibody fragment may also lack portions of VH or/and VL, as long as it has binding ability to its antigen. In addition, the variable regions may be chimerized or humanized. Such antibody fragments include, for example, Fab, Fab', $F(ab')_2$, and Fv. An example of a minibody includes Fab, Fab', $F(ab')_2$, Fv, scFv (single-chain Fv), diabody, and sc(Fv)2 (single-chain (Fv)2).

Herein, an "Fv" fragment is the smallest antibody fragment and contains a complete antigen recognition site and a binding site. The "Fv" fragment is a dimer (VH-VL dimer) in which a single VH and a single VL are strongly linked by a non-covalent bond. The three complementarity-determining regions (CDRs) of each of the variable regions interact with each other to form an antigen-binding site on the surface of the VH-VL dimer. Six CDRs confer the antigen-binding site of an antibody. However, a single variable region (or a half of Fv containing only three CDRs specific to an antigen) alone is also capable of recognizing and binding an antigen although its affinity is lower than the affinity of the entire binding site.

scFv contains the VH and VL regions of an antibody, and these regions exist on a single polypeptide chain. Generally, an Fv polypeptide further contains a polypeptide linker between VH and VL, and therefore an scFv can form a structure required for antigen binding. See, Pluckthun "The Pharmacology of Monoclonal Antibodies" Vol. 113 (Rosenburg and Moore eds. (Springer Verlag, New York, pp. 269-315, 1994) for the review of scFv. In the present invention, linkers are not especially limited as long as they do not inhibit expression of antibody variable regions linked at both ends of the linkers.

The term "diabody" refers to a bivalent antibody fragment constructed by gene fusion (Holliger P et al., 1993, Proc. Natl. Acad. Sci. USA 90: 6444-6448; EP 404,097; WO 93/11161 and others). Diabodies are dimers comprising two polypeptide chains, where each polypeptide chain comprises a VL and a VH connected with a linker short enough to prevent interaction of these two domains, for example, a linker of about five residues. The VL and VH encoded on the same polypeptide chain will form a dimer because the linker between them is too short to form a single-chain variable region fragment. As a result, the polypeptide chains form a dimer, and thus the diabody has two antigen binding sites.

sc(Fv) 2 is a single-chain minibody produced by linking two units of VH and two units of VL with linkers and such (Hudson et al., 1999, J Immunol. Methods 231:177-189). sc(Fv)2 exhibits a particularly high agonistic activity compared to the whole antibody and other minibodies. sc (Fv) 2 can be produced, for example, by linking two scFv molecules.

In a preferable antibody, the two VH units and two VL units are arranged in the order of VH, VL, VH, and VL ([VH]-linker-[VL]-linker-[VH]-linker-[VL]) beginning from the N terminus of a single-chain polypeptide.

The order of the two VH units and two VL units is not limited to the above arrangement, and they may be arranged in any order. Examples of the arrangements are listed below.

[VL]-linker-[VH]-linker-[VH]-linker-[VL]
[VH]-linker-[VL]-linker-[VL]-linker-[VH]
[VH]-linker-[VH]-linker-[VL]-linker-[VL]
[VL]-linker-[VL]-linker-[VH]-linker-[VH]
[VL]-linker-[VH]-linker-[VL]-linker-[VH]

The linkers to be used for linking the variable regions of an antibody comprise arbitrary peptide linkers that can be introduced by genetic engineering, synthetic linkers, and linkers disclosed in, for example, Holliger, P. et al., Protein Engineering, 9(3), 299-305, 1996. Peptide linkers are preferred in the present invention. There are no limitations as to the length of the peptide linkers. The length can be selected accordingly by those skilled in the art depending on the purpose, and is typically 1-100 amino acids, preferably 3-50 amino acids, more preferably 5-30 amino acids, and even more preferably 12-18 amino acids (for example, 15 amino acids).

For example, such peptide linkers include:

```
Ser
Gly-Ser
Gly-Gly-Ser
Ser-Gly-Gly
Gly-Gly-Gly-Ser
Ser-Gly-Gly-Gly
Gly-Gly-Gly-Gly-Ser
Ser-Gly-Gly-Gly-Gly
Gly-Gly-Gly-Gly-Gly-Ser
Ser-Gly-Gly-Gly-Gly-Gly
Gly-Gly-Gly-Gly-Gly-Gly-Ser
Ser-Gly-Gly-Gly-Gly-Gly-Gly
(Gly-Gly-Gly-Gly-Ser)n
(Ser-Gly-Gly-Gly-Gly)n
```

where n is an integer of 1 or larger. The lengths and sequences of peptide linkers can be selected accordingly by those skilled in the art depending on the purpose.

In an embodiment of the present invention, a particularly preferable sc(Fv)2 includes, for example, the sc(Fv)2 below.

[VH]-peptide linker (15 amino acids)-[VL]-peptide linker (15 amino acids)-[VH]-peptide linker (15 amino acids)-[VL]

Synthetic linkers (chemical crosslinking agents) include crosslinking agents routinely used to crosslink peptides, for example, N-hydroxy succinimide (NHS), disuccinimidyl suberate (DSS), bis(succinimidyl) suberate ($BS^3$), dithiobis (succinimidyl propionate) (DSP), dithiobis (succinimidyl propionate) (DTSSP), ethylene glycol bis(succinimidyl succinate) (EGS), ethylene glycol bis(sulfosuccinimidyl succinate) (sulfo-EGS), disuccinimidyl tartrate (DST), disulfosuccinimidyl tartrate (sulfo-DST), bis[2-

(succinimidoxycarbonyloxy)ethyl] sulfone (BSOCOES), and bis[2-(succinimidoxycarbonyloxy)ethyl] sulfone (sulfo-BSOCOES). These crosslinking agents are commercially available.

In general, three linkers are required to link four antibody variable regions together. The linkers to be used may be of the same type or different types. In the present invention, a preferable minibody is a diabody, even more preferably, an sc(Fv)2. Such a minibody can be prepared by treating an antibody with an enzyme, for example, papain or pepsin, to generate antibody fragments, or by constructing DNAs encoding those antibody fragments and introducing them into expression vectors, followed by expression in an appropriate host cell (see, for example, Co, M. S. et al., 1994, J. Immunol. 152, 2968-2976; Better, M. and Horwitz, A. H., 1989, Methods Enzymol. 178, 476-496; Pluckthun, A. and Skerra, A., 1989, Methods Enzymol. 178, 497-515; Lamoyi, E., 1986, Methods Enzymol. 121, 652-663; Rousseaux, J. et al., 1986, Methods Enzymol. 121, 663-669; Bird, R. E. and Walker, B. W., 1991, Trends Biotechnol. 9, 132-137).

An antibody having exceedingly high agonistic activity can be prepared by reducing the molecular weight of a full-length antibody, particularly by converting it into an sc(Fv)2.

In a preferred embodiment, the antibodies of the present invention comprise modified antibodies, such as chimeric antibodies and humanized antibodies that bind to Mpl. These modified antibodies can be produced by known methods.

Chimeric antibodies are antibodies prepared by combining sequences derived from different animal species, and include for example, antibodies comprising the heavy chain and light chain variable regions of a murine antibody, and the heavy chain and light chain constant regions of a human antibody. Chimeric antibodies can be prepared by known methods. For example, a DNA encoding the V region of an antibody is linked to a DNA encoding the C region of a human antibody, and the construct is inserted into an expression vector and introduced into a host to produce chimeric antibodies.

Humanized antibodies are also referred to as “reshaped human antibodies”. Such a humanized antibody is obtained by transferring the complementarity-determining region (CDR) of an antibody derived from a non-human mammal, for example mouse, to the complementarity-determining region of a human antibody, and the general gene recombination procedure for this is also known (see European Patent Application No. 125023 and WO 96/02576).

Specifically, a DNA sequence designed to link a murine antibody CDR to the framework region (FR) of a human antibody can be synthesized by PCR, using primers prepared from several oligonucleotides containing overlapping portions of both CDR and FR terminal regions (see methods described in WO 98/13388).

The human antibody framework region to be linked by CDR is selected in order to form a favorable antigen-binding site in the complementarity-determining region. Amino acids of the framework region in the antibody variable region may be substituted, as necessary, for the complementarity-determining region of the reshaped human antibody to form a suitable antigen-binding site (Sato, K. et al., 1993, Cancer Res. 53, 851-856).

The constant region of a human antibody is used as the constant region of a chimeric antibody or humanized antibody. For example, Cγ1, Cγ2, Cγ3, and Cγ4 can be used as the H chain, and Cκ and Cλ can be used as the L chain. The human antibody constant region may be modified to improve the antibody or the stability of the antibody production.

Generally, chimeric antibodies comprise the variable region of an antibody from a non-human mammal and the constant region derived from a human antibody. On the other hand, humanized antibodies comprise the complementarity-determining region of an antibody from a non-human mammal, and the framework region and constant region derived from a human antibody.

In addition, after a chimeric antibody or a humanized antibody is prepared, amino acids in the variable region (for example, FR) and the constant region may be replaced with other amino acids, and such.

The origin of the variable regions in chimeric antibodies or that of the CDRs in humanized antibodies is not particularly limited, and may be derived from any type of animal. For example, sequences of murine antibodies, rat antibodies, rabbit antibodies, camel antibodies may be used.

In general, it is difficult to chimerize or humanize an antibody without losing the agonistic activity of the original antibody. Nevertheless, the present invention succeeded in preparing humanized antibodies having agonistic activity equivalent to that of the original murine antibody.

A preferred humanized antibody of the present invention is an antibody comprising a heavy chain variable region that comprises the amino acid sequence of SEQ ID NO: 229 (humanized heavy chain sequence: hVB22B p-z VH), SEQ ID NO: 256 (humanized heavy chain sequence: hVB22B g-e VH), SEQ ID NO: 262 (humanized heavy chain sequence: hVB22B e VH), SEQ ID NO: 289 (humanized heavy chain sequence: hVB22B u2-wz4 VH), or SEQ ID NO: 295 (humanized heavy chain sequence: hVB22B q-wz5 VH); or an antibody comprising a light chain variable region that comprises the amino acid sequence of SEQ ID NO: 238 (humanized light chain hVB22B p-z VL), SEQ ID NO: 258 (humanized light chain hVB22B g-e VL or hVB22B e VL), SEQ ID NO: 291 (humanized light chain hVB22B u2-wz4 VL), or SEQ ID NO: 297 (humanized light chain hVB22B q-wz5 VL). In particular, a preferred antibody is an antibody comprising a heavy chain variable region and a light chain variable region of any one of (1) to (5) indicated below:

(1) a heavy chain variable region comprising the amino acid sequence of SEQ ID NO: 229, and a light chain variable region comprising the amino acid sequence of SEQ ID NO: 238;

(2) a heavy chain variable region comprising the amino acid sequence of SEQ ID NO: 256, and a light chain variable region comprising the amino acid sequence of SEQ ID NO: 258;

(3) a heavy chain variable region comprising the amino acid sequence of SEQ ID NO: 262, and a light chain variable region comprising the amino acid sequence of SEQ ID NO: 258;

(4) a heavy chain variable region comprising the amino acid sequence of SEQ ID NO: 289, and a light chain variable region comprising the amino acid sequence of SEQ ID NO: 291; and (5) a heavy chain variable region comprising the amino acid sequence of SEQ ID NO: 295, and a light chain variable region comprising the amino acid sequence of SEQ ID NO: 297.

Such antibodies include, for example, antibodies comprising the amino acid sequence of SEQ ID NO: 2, 254, 260, 287, or 293 (humanized sc(Fv)2 sequence (hVB22B p-z sc(Fv)2, hVB22B g-e sc(Fv)2, hVB22B e sc(Fv)2, hVB22B u2-wz4, or hVB22B q-wz5).

The nucleotide sequence of hVB22B p-z VH is shown in SEQ ID NO: 228; the nucleotide sequence of hVB22B g-e VH is shown in SEQ ID NO: 255; the nucleotide sequence of hVB22B e VH is shown in SEQ ID NO: 261; the nucleotide sequence of hVB22B u2-wz4 VH is shown in SEQ ID NO:

288; the nucleotide sequence of hVB22B q-wz5 VH is shown in SEQ ID NO: 294; the nucleotide sequence of hVB22B p-z VL is shown in SEQ ID NO: 237; the nucleotide sequences of hVB22B g-e VL and hVB22B e VL are shown in SEQ ID NO: 257; the nucleotide sequence of hVB22B u2-wz4 VL is shown in SEQ ID NO: 290; and the nucleotide sequence of hVB22B q-wz5 VL is shown in SEQ ID NO: 296.

In the amino acid sequence of SEQ ID NO: 229 (humanized heavy chain sequence: hVB22B p-z VH), SEQ ID NO: 256 (humanized heavy chain sequence: hVB22B g-e VH), SEQ ID NO: 262 (humanized heavy chain sequence: hVB22B e VH), SEQ ID NO: 289 (humanized heavy chain sequence: hVB22B u2-wz4 VH), or SEQ ID NO: 295 (humanized heavy chain sequence: hVB22B q-wz5 VH), amino acids 31-35 correspond to CDR1;
amino acids 50-66 correspond to CDR2;
amino acids 99-107 correspond to CDR3;
amino acids 1-30 correspond to FR1;
amino acids 36-49 correspond to FR2;
amino acids 67-98 correspond to FR3; and
amino acids 108-118 correspond to FR4.

In the amino acid sequence of SEQ ID NO: 238 (humanized light chain sequence: hVB22B p-z VL), SEQ ID NO: 258 (humanized light chain sequence: hVB22B g-e VL or hVB22B e VL), SEQ ID NO: 291 (humanized light chain sequence: hVB22B u2-wz4 VL), or SEQ ID NO: 297 (humanized light chain sequence: hVB22B q-wz5 VL), amino acids 24-39 correspond to CDR1;
amino acids 55-61 correspond to CDR2;
amino acids 94-102 correspond to CDR3;
amino acids 1-23 correspond to FR1;
amino acids 40-54 correspond to FR2;
amino acids 62-93 correspond to FR3; and
amino acids 103-112 correspond to FR4.

In the present invention, SEQ ID NOs of the CDRs and FRs in the hVB22B p-z VH sequence are shown below:

hVB22B p-z VH: FR1/SEQ ID NO: 230
hVB22B p-z VH: CDR1/SEQ ID NO: 36
hVB22B p-z VH: FR2/SEQ ID NO: 232
hVB22B p-z VH: CDR2/SEQ ID NO: 37
hVB22B p-z VH: FR3/SEQ ID NO: 234
hVB22B p-z VH: CDR3/SEQ ID NO: 38
hVB22B p-z VH: FR4/SEQ ID NO: 236.

In the present invention, SEQ ID NOs of the CDRs and FRs in the hVB22B p-z VL sequence are shown below:

hVB22B p-z VL: FR1/SEQ ID NO: 239
hVB22B p-z VL: CDR1/SEQ ID NO: 93
hVB22B p-z VL: FR2/SEQ ID NO: 241
hVB22B p-z VL: CDR2/SEQ ID NO: 94
hVB22B p-z VL: FR3/SEQ ID NO: 243
hVB22B p-z VL: CDR3/SEQ ID NO: 95
hVB22B p-z VL: FR4/SEQ ID NO: 245.

In the present invention, SEQ ID NOs of the CDRs and FRs in the hVB22B g-e VH sequence are shown below:

hVB22B g-e VH: FR1/SEQ ID NO: 265
hVB22B g-e VH: CDR1/SEQ ID NO: 36
hVB22B g-e VH: FR2/SEQ ID NO: 267
hVB22B g-e VH: CDR2/SEQ ID NO: 37
hVB22B g-e VH: FR3/SEQ ID NO: 269
hVB22B g-e VH: CDR3/SEQ ID NO: 38
hVB22B g-e VH: FR4/SEQ ID NO: 271.

In the present invention, SEQ ID NOs of the CDRs and FRs in the hVB22B g-e VL sequence are shown below:

hVB22B g-e VL: FR1/SEQ ID NO: 272
hVB22B g-e VL: CDR1/SEQ ID NO: 93
hVB22B g-e VL: FR2/SEQ ID NO: 274
hVB22B g-e VL: CDR2/SEQ ID NO: 94
hVB22B g-e VL: FR3/SEQ ID NO: 276
hVB22B g-e VL: CDR3/SEQ ID NO: 95
hVB22B g-e VL: FR4/SEQ ID NO: 278.

In the present invention, SEQ ID NOs of the CDRs and FRs in the hVB22B e VH sequence are shown below:

hVB22B e VH: FR1/SEQ ID NO: 279
hVB22B e VH: CDR1/SEQ ID NO: 36
hVB22B e VH: FR2/SEQ ID NO: 281
hVB22B e VH: CDR2/SEQ ID NO: 37
hVB22B e VH: FR3/SEQ ID NO: 283
hVB22B e VH: CDR3/SEQ ID NO: 38
hVB22B e VH: FR4/SEQ ID NO: 285.

In the present invention, SEQ ID NOs of the CDRs and FRs in the hVB22B e VL sequence are shown below:

hVB22B e VL: FR1/SEQ ID NO: 272
hVB22B e VL: CDR1/SEQ ID NO: 93
hVB22B e VL: FR2/SEQ ID NO: 274
hVB22B e VL: CDR2/SEQ ID NO: 94
hVB22B e VL: FR3/SEQ ID NO: 276
hVB22B e VL: CDR3/SEQ ID NO: 95
hVB22B e VL: FR4/SEQ ID NO: 278.

In the present invention, SEQ ID NOs of the CDRs and FRs in the hVB22B u2-wz4 VH sequence are shown below:

hVB22B u2-wz4 VH: FR1/SEQ ID NO: 298
hVB22B u2-wz4 VH: CDR1/SEQ ID NO: 36
hVB22B u2-wz4 VH: FR2/SEQ ID NO: 299
hVB22B u2-wz4 VH: CDR2/SEQ ID NO: 37
hVB22B u2-wz4 VH: FR3/SEQ ID NO: 300
hVB22B u2-wz4 VH: CDR3/SEQ ID NO: 38
hVB22B u2-wz4 VH: FR4/SEQ ID NO: 301.

In the present invention, SEQ ID NOs of the CDRs and FRs in the hVB22B u2-wz4 VL sequence are shown below:

hVB22B u2-wz4 VL: FR1/SEQ ID NO: 302
hVB22B u2-wz4 VL: CDR1/SEQ ID NO: 93
hVB22B u2-wz4 VL: FR2/SEQ ID NO: 303
hVB22B u2-wz4 VL: CDR2/SEQ ID NO: 94
hVB22B u2-wz4 VL: FR3/SEQ ID NO: 304
hVB22B u2-wz4 VL: CDR3/SEQ ID NO: 95
hVB22B u2-wz4 VL: FR4/SEQ ID NO: 305.

In the present invention, SEQ ID NOs of the CDRs and FRs in the hVB22B q-wz5 VH sequence are shown below:

hVB22B q-wz5 VH: FR1/SEQ ID NO: 298
hVB22B q-wz5 VH: CDR1/SEQ ID NO: 36
hVB22B q-wz5 VH: FR2/SEQ ID NO: 299
hVB22B q-wz5 VH: CDR2/SEQ ID NO: 37
hVB22B q-wz5 VH: FR3/SEQ ID NO: 306
hVB22B q-wz5 VH: CDR3/SEQ ID NO: 38
hVB22B q-wz5 VH: FR4/SEQ ID NO: 301.

In the present invention, SEQ ID NOs of the CDRs and FRs in the hVB22B q-wz5 VL sequence are shown below:

hVB22B q-wz5 VL: FR1/SEQ ID NO: 302
hVB22B q-wz5 VL: CDR1/SEQ ID NO: 93
hVB22B q-wz5 VL: FR2/SEQ ID NO: 307
hVB22B q-wz5 VL: CDR2/SEQ ID NO: 94
hVB22B q-wz5 VL: FR3/SEQ ID NO: 308
hVB22B q-wz5 VL: CDR3/SEQ ID NO: 95
hVB22B q-wz5 VL: FR4/SEQ ID NO: 305.

The CDRs and FRs in the hVB22B p-z sequence, hVB22B g-e sequence, hVB22B e sequence, hVB22B u2-wz4 sequence, and hVB22B q-wz5 sequence are shown in FIG. 18.

In other embodiments, preferred humanized antibodies of the present invention include:

humanized antibodies comprising a heavy chain variable region which has FR1, 2, 3, and 4 comprising amino acid sequences of any one of (1) to (5) indicated below:

(1) SEQ ID NOs: 230, 232, 234, and 236 (hVB22B p-z: H chain FR1, 2, 3, and 4),
(2) SEQ ID NOs: 265, 267, 269, and 271 (hVB22B g-e: H chain FR1, 2, 3, and 4),
(3) SEQ ID NOs: 279, 281, 283, and 285 (hVB22B e: H chain FR1, 2, 3, and 4),
(4) SEQ ID NOs: 298, 299, 300, and 301 (hVB22B u2-wz4: H chain FR1, 2, 3, and 4), and
(5) SEQ ID NOs: 298, 299, 306, and 301 (hVB22B q-wz5: H chain FR1, 2, 3, and 4);

humanized antibodies comprising a light chain variable region which has FR1, 2, 3, and 4 comprising amino acid sequences of any one of (1) to (4) listed below:
(1) SEQ ID NOs: 239, 241, 243, and 245 (hVB22B p-z: L chain FR1, 2, 3, and 4),
(2) SEQ ID NOs: 272, 274, 276, and 278 (hVB22B g-e or hVB22B e: L chain FR1, 2, 3, and 4),
(3) SEQ ID NOs: 302, 303, 304, and 305 (hVB22B u2-wz4: L chain FR1, 2, 3, and 4), and
(4) SEQ ID NOs: 302, 307, 308, and 305 (hVB22B q-wz5: L chain FR1, 2, 3, and 4);

humanized antibodies comprising a heavy chain variable region which has CDR1, 2 and 3 comprising amino acid sequences according to the SEQ ID NOs listed below:

SEQ ID NOs: 36, 37, and 38 (hVB22B p-z, hVB22B g-e, hVB22B e, hVB22B u2-wz4, or hVB22B q-wz5: H chain CDR1, 2, and 3); and humanized antibodies comprising a light chain variable region which has CDR1, 2 and 3 comprising amino acid sequences according to the SEQ ID NOs listed below:

SEQ ID NOs: 93, 94, and 95 (hVB22B p-z hVB22B g-e, hVB22B e, hVB22B u2-wz4, or hVB22B q-wz5: L chain CDR1, 2, and 3).

In yet another preferred embodiment, preferred humanized antibodies of the present invention include:

humanized antibodies comprising heavy chain and light chain variable regions of any one of (1) to (5) indicated below.
(1) a heavy chain variable region which comprises FR1, 2, 3, and 4 comprising the amino acid sequences of SEQ ID NOs: 230, 232, 234, and 236, respectively, and a light chain variable region which comprises FR1, 2, 3, and 4 comprising the amino acid sequences of SEQ ID NOs: 239, 241, 243, and 245, respectively;
(2) a heavy chain variable region which comprises FR1, 2, 3, and 4 comprising the amino acid sequences of SEQ ID NOs: 265, 267, 269, and 271, respectively, and a light chain variable region which comprises FR1, 2, 3, and 4 comprising the amino acid sequences of SEQ ID NOs: 272, 274, 276, and 278, respectively;
(3) a heavy chain variable region which comprises FR1, 2, 3 and 4 comprising the amino acid sequences of SEQ ID NOs: 279, 281, 283, and 285, respectively, and a light chain variable region which comprises FR1, 2, 3, and 4 comprising the amino acid sequences of SEQ ID NOs: 272, 274, 276, and 278, respectively;
(4) a heavy chain variable region which comprises FR1, 2, 3, and 4 comprising the amino acid sequences of SEQ ID NOs: 298, 299, 300, and 301, and a light chain variable region which comprises FR1, 2, 3, and 4 comprising the amino acid sequences of SEQ ID NOs: 302, 303, 304, and 305, respectively;
(5) a heavy chain variable region which comprises FR1, 2, 3, and 4 comprising the amino acid sequences of SEQ ID NOs: 298, 299, 306, and 301, respectively, and a light chain variable region which comprises FR1, 2, 3, and 4 comprising the amino acid sequences of SEQ ID NOs: 302, 307, 308, and 305, respectively; and humanized antibodies comprising heavy chain and light chain variable regions described below:

a heavy chain variable region which comprises CDR1, 2, and 3 comprising the amino acid sequences of SEQ ID NOs: 36, 37, and 38, respectively, and a light chain variable region which comprises CDR1, 2, and 3 comprising the amino acid sequences of SEQ ID NOs: 93, 94, and 95, respectively.

Chimeric antibodies and humanized antibodies exhibit lower antigenicity in the human body, and thus are expected to be useful when administered to humans for therapeutic purposes.

In one embodiment, the preferred antibodies of the present invention include antibodies that bind to soluble Mpl. The term "soluble Mpl" herein refers to Mpl molecules excluding those expressed on the cell membrane. A specific example of a soluble Mpl is an Mpl lacking the entire or a portion of the transmembrane domain. The transmembrane domain of human Mpl corresponds to amino acids 492-513 in SEQ ID NO: 123.

An antibody that binds to soluble recombinant Mpl can be used in detailed epitope analysis and kinetic analysis of receptor-ligand binding, as well as for assessing the blood concentration and dynamic behavior of the antibody in in vivo tests.

In one embodiment, the preferred antibodies of the present invention include antibodies having binding activity against both human and monkey Mpl. The present invention also provides antibodies having agonistic activity to human Mpl and monkey Mpl. Antibodies having agonistic activity to both human and monkey Mpl are expected to be highly useful since the dynamic behavior and in vivo effects of the antibody, which are generally difficult to determine in human body, can be examined with monkeys.

Such antibodies may also have binding activity or agonistic activity against Mpl from animals other than humans and monkeys (for example, mice).

In addition, the antibodies of the present invention include antibodies with TPO agonistic activity (agonistic activity against Mpl) of EC50=100 nM or lower, preferably EC50=30 nM or lower, more preferably EC50=10 nM or lower.

The agonistic activity can be determined by methods known to those skilled in the art, for example, by the method described below. The sequences for human Mpl (Palacios et al., Cell 41:727-734, (1985); GenBank Accession NO. NM_005373), cynomolgus monkey Mpl (the nucleotide sequence and amino acid sequence are shown in SEQ ID NO: 164 and SEQ ID NO: 165, respectively), and mouse Mpl (GenBank Accession NO. NM_010823) are already known.

In addition, the present invention includes antibodies whose binding activities to soluble Mpl are $KD=10^{-6}$ M or lower, preferably $KD=10^{-7}$ M or lower.

In the present invention, whether the binding activity of an antibody to soluble recombinant Mpl is $KD=10^{-6}$ M or lower can be determined by methods known to those skilled in the art. For example, the activity can be determined using surface plasmon resonance with Biacore. Specifically, soluble MPL-Fc protein, soluble MPL protein, or epitope peptides recognized by antibodies are immobilized onto sensor chips. Reaction rate constant can be determined by assessing the interaction between the antibody and the soluble Mpl-Fc protein, the soluble Mpl protein, or the epitope peptide recognized by the antibody. The proteins to be immobilized on chips are not limited in particular, and include, for example, MG10 (from Gln213 to Ala231)-GST fusion protein and Mpl-IgG Fc fusion protein described in the Examples. Since the antibodies are divalent and have two antigen-binding sites, the binding activities of these antibodies may be determined as those for the monovalent or divalent antibodies, or for mixtures of both. Any of these can be used in the present invention.

The binding activity can be evaluated by ELISA (enzyme-linked immunosorbent assays), EIA (enzyme immunoassays), RIA (radio immunoassays), or fluorescent antibody techniques. For example, in enzyme immunoassays, a sample containing a test antibody, such as purified antibody or culture supernatant of cells producing the test antibody, is added to a plate coated with an antigen to which the test antibody can bind. After incubating the plate with a secondary antibody labeled with an enzyme such as alkaline phosphatase, the plate is washed and an enzyme substrate such as p-nitrophenyl phosphate is added. The antigen-binding activity can then be evaluated by determining the absorbance.

There is no specific limitation as to the upper limit of the binding activity; for example, the upper limit may be set within a technically feasible range by those skilled in the art. However, the technically feasible range may expand with the advancement of technology.

In an embodiment, the preferred antibodies of the present invention include antibodies recognizing epitopes that are recognized by any one of the antibodies indicated in (I) to (XII) below. The antibody of any one of (I) to (XII) is preferably a minibody.

(I) Antibody comprising a VH that has CDR1, 2, and 3 comprising the amino acid sequences according to SEQ ID NOs in any one of (1) to (17) indicated below (name of each antibody and the H chain CDR contained in the antibody are indicated inside the parentheses):

(1) SEQ ID NOs: 3, 4, and 5 (VA7: H chain CDR1, 2, and 3),
(2) SEQ ID NOs: 6, 7, and 8 (VA130 or VB17B: H chain CDR1, 2, and 3),
(3) SEQ ID NOs: 9, 10, and 11 (VA259: H chain CDR1, 2, and 3),
(4) SEQ ID NOs: 15, 16, and 17 (VB12B: H chain CDR1, 2, and 3),
(5) SEQ ID NOs: 18, 19, and 20 (VB140: H chain CDR1, 2, and 3),
(6) SEQ ID NOs: 21, 22, and 23 (VB33: H chain CDR1, 2, and 3),
(7) SEQ ID NOs: 24, 25, and 26 (VB45B: H chain CDR1, 2, and 3),
(8) SEQ ID NOs: 27, 28, and 29 (VB8B: H chain CDR1, 2, and 3),
(9) SEQ ID NOs: 30, 31, and 32 (VB115: H chain CDR1, 2, and 3),
(10) SEQ ID NOs: 33, 34, and 35 (VB14B: H chain CDR1, 2, and 3),
(11) SEQ ID NOs: 36, 37, and 38 (VB22B, VB4B, hVB22B p-z, hVB22B g-e, hVB22B e, hVB22B u2-wz4 or hVB22B q-wz5: H chain CDR1, 2, and 3),
(12) SEQ ID NOs: 39, 40, and 41 (VB16: H chain CDR1, 2, and 3),
(13) SEQ ID NOs: 42, 43, and 44 (VB157: H chain CDR1, 2, and 3),
(14) SEQ ID NOs: 48, 49, and 50 (VB51: H chain CDR1, 2, and 3),
(15) SEQ ID NOs: 51, 52, and 53 (AB317: H chain CDR1, 2, and 3),
(16) SEQ ID NOs: 54, 55, and 56 (AB324: H chain CDR1, 2, and 3),
(17) SEQ ID NOs: 57, 58, and 59 (TA136: H chain CDR1, 2, and 3).

(II) Antibody comprising a VL which has CDR1, 2, and 3 comprising the amino acid sequences according to SEQ ID NOs in any one of (1) to (10) indicated below (name of each antibody and the L chain CDR in the antibody are indicated inside the parentheses):

(1) SEQ ID NOs: 60, 61, and 62 (VA7: L chain CDR1, 2, and 3),
(2) SEQ ID NOs: 63, 64, and 65 (VA130, VA259, VB17B, VB12B, VB140, VB45B, VB115, VB14B or VB51: L chain CDR1, 2, and 3),
(3) SEQ ID NOs: 78, 79, and 80 (VB33 or VB157: L chain CDR1, 2, and 3),
(4) SEQ ID NOs: 84, 85, and 86 (VB8B: L chain CDR1, 2, and 3),
(5) SEQ ID NOs: 93, 94, and 95 (VB22B, hVB22B p-z, hVB22B g-e, hVB22B e, hVB22B u2-wz4 or hVB22B q-wz5: L chain CDR1, 2, and 3),
(6) SEQ ID NOs: 96, 97, and 98 (VB16: L chain CDR1, 2, and 3),
(7) SEQ ID NOs: 102, 103, and 104 (VB4B: L chain CDR1, 2, and 3),
(8) SEQ ID NOs: 108, 109, and 110 (AB317: L chain CDR1, 2, and 3),
(9) SEQ ID NOs: 111, 112, and 113 (AB324: L chain CDR1, 2, and 3),
(10) SEQ ID NOs: 114, 115, and 116 (TA136: L chain CDR1, 2, and 3).

(III) Antibody comprising a VH that comprises an amino acid sequence of the SEQ ID NO in any one of (1) to (24):

(1) SEQ ID NO: 124 (VA7: VH),
(2) SEQ ID NO: 126 (VA130: VH),
(3) SEQ ID NO: 128 (VA259: VH),
(4) SEQ ID NO: 130 (VB17B: VH),
(5) SEQ ID NO: 132 (VB12B: VH),
(6) SEQ ID NO: 134 (VB140: VH),
(7) SEQ ID NO: 136 (VB33: VH),
(8) SEQ ID NO: 138 (VB45B: VH),
(9) SEQ ID NO: 140 (VB8B: VH),
(10) SEQ ID NO: 142 (VB115: VH),
(11) SEQ ID NO: 144 (VB14B: VH),
(12) SEQ ID NO: 118 (VB22B: VH),
(13) SEQ ID NO: 146 (VB16: VH),
(14) SEQ ID NO: 148 (VB157: VH),
(15) SEQ ID NO: 150 (VB4B: VH),
(16) SEQ ID NO: 152 (VB51: VH),
(17) SEQ ID NO: 155 (AB317: VH),
(18) SEQ ID NO: 159 (AB324: VH),
(19) SEQ ID NO: 162 (TA136: VH),
(20) SEQ ID NO: 229 (hVB22B p-z: VH),
(21) SEQ ID NO: 256 (hVB22B g-e: VH),
(22) SEQ ID NO: 262 (hVB22B e: VH),
(23) SEQ ID NO: 289 (hVB22B u2-wz4: VH),
(24) SEQ ID NO: 295 (hVB22B q-wz5: VH).

(IV) Antibody comprising a VL that comprises an amino acid sequence of the SEQ ID NO in any one of (1) to (18):

(1) SEQ ID NO: 125 (VA7: VL),
(2) SEQ ID NO: 127 (VA130, VB17B, VB12B, VB115 or VB14B: VL),
(3) SEQ ID NO: 129 (VA259: VL),
(4) SEQ ID NO: 135 (VB140 or VB45B: VL),
(5) SEQ ID NO: 137 (VB33: VL),
(6) SEQ ID NO: 141 (VB8B: VL),
(7) SEQ ID NO: 120 (VB22B: VL),
(8) SEQ ID NO: 147 (VB16: VL),
(9) SEQ ID NO: 149 (VB157: VL),
(10) SEQ ID NO: 151 (VB4B: VL),
(11) SEQ ID NO: 153 (VB51: VL),
(12) SEQ ID NO: 157 (AB317: VL),
(13) SEQ ID NO: 161 (AB324: VL),

(14) SEQ ID NO: 163 (TA136: VL),
(15) SEQ ID NO: 238 (hVB22B p-z: VL),
(16) SEQ ID NO: 258 (hVB22B g-e: VL or hVB22B e: VL),
(17) SEQ ID NO: 291 (hVB22B u2-wz4: VL),
(18) SEQ ID NO: 297 (hVB22B q-wz5: VL).

(V) Antibody comprising a VH and VL according to any one of (1) to (18):

(1) SEQ ID NOs: 3, 4, and 5 (VA7: H chain CDR1, 2, and 3); SEQ ID NOs: 60, 61, and 62 (VA7: L chain CDR1, 2, and 3),
(2) SEQ ID NOs: 6, 7, and 8 (VA130 or VB17B: H chain CDR1, 2, and 3), SEQ ID NOs: 63, 64, and 65 (VA130 or VB17B: L chain CDR1, 2, and 3),
(3) SEQ ID NOs: 9, 10, and 11 (VA259: H chain CDR1, 2, and 3); SEQ ID NOs: 66, 67, and 68 (VA259: L chain CDR1, 2, and 3),
(4) SEQ ID NOs: 15, 16, and 17 (VB12B: H chain CDR1, 2, and 3); SEQ ID NO: 72, 73, and 74 (VB12B: L chain CDR1, 2, and 3),
(5) SEQ ID NOs: 18, 19, and 20 (VB140: H chain CDR1, 2, and 3); SEQ ID NOs: 75, 76, and 77 (VB140: L chain CDR1, 2, and 3),
(6) SEQ ID NOs: 21, 22, and 23 (VB33: H chain CDR1, 2, and 3); SEQ ID NOs: 78, 79, and 80 (VB33: L chain CDR1, 2, and 3),
(7) SEQ ID NOs: 24, 25, and 26 (VB45B: H chain CDR1, 2, and 3); SEQ ID NOs: 81, 82, and 83 (VB45B: L chain CDR1, 2, and 3),
(8) SEQ ID NOs: 27, 28, and 29 (VB8B: H chain CDR1, 2, and 3); SEQ ID NOs: 84, 85, and 86 (VB8B: L chain CDR1, 2, and 3),
(9) SEQ ID NOs: 30, 31, and 32 (VB115: H chain CDR1, 2, and 3); SEQ ID NOs: 87, 88, and 89 (VB115: L chain CDR1, 2, and 3),
(10) SEQ ID NOs: 33, 34, and 35 (VB14B: H chain CDR1, 2, and 3); SEQ ID NOs: 90, 91, and 92 (VB14B: L chain CDR1, 2, and 3),
(11) SEQ ID NOs: 36, 37, and 38 (VB22B, hVB22B p-z, hVB22B g-e, hVB22B e, hVB22B u2-wz4 or hVB22B q-wz5: H chain CDR1, 2, and 3); SEQ ID NOs: 93, 94, and 95 (VB22B, hVB22B p-z, hVB22B g-e, hVB22B e, hVB22B u2-wz4 or hVB22B q-wz5: L chain CDR1, 2, and 3),
(12) SEQ ID NOs: 39, 40, and 41 (VB16: H chain CDR1, 2, and 3); SEQ ID NOs: 96, 97, and 98 (VB16: L chain CDR1, 2, and 3),
(13) SEQ ID NOs: 42, 43, and 44 (VB157: H chain CDR1, 2, and 3); SEQ ID NOs: 99, 100, and 101 (VB157: L chain CDR1, 2, and 3),
(14) SEQ ID NOs: 45, 46, and 47 (VB4B: H chain CDR1, 2, and 3); SEQ ID NOs: 102, 103, and 104 (VB4B: L chain CDR1, 2, and 3),
(15) SEQ ID NOs: 48, 49, and 50 (VB51: H chain CDR1, 2, and 3); SEQ ID NOs: 105, 106, and 107 (VB51: L chain CDR1, 2, and 3),
(16) SEQ ID NOs: 51, 52, and 53 (AB317: H chain CDR1, 2, and 3); SEQ ID NOs: 108, 109, and 110 (AB317: L chain CDR1, 2, and 3),
(17) SEQ ID NOs: 54, 55, and 56 (AB324: H chain CDR1, 2, and 3); SEQ ID NOs: 111, 112, and 113 (AB324: L chain CDR1, 2, and 3),
(18) SEQ ID NOs: 57, 58, and 59 (TA136: H chain CDR1, 2, and 3); SEQ ID NOs: 114, 115, and 116 (TA136: L chain CDR1, 2, and 3).

(VI) Antibody comprising a VH and a VL that comprise the amino acid sequences according to SEQ ID NOs in any one of (1) to (24) indicated below:

(1) SEQ ID NO: 124 (VA7: VH), SEQ ID NO: 125 (VA7: VL),
(2) SEQ ID NO: 126 (VA130: VH), SEQ ID NO: 127 (VA130: VL),
(3) SEQ ID NO: 128 (VA259: VH), SEQ ID NO: 129 (VA259: VL),
(4) SEQ ID NO: 130 (VB17B: VH), SEQ ID NO: 127 (VB17B: VL),
(5) SEQ ID NO: 132 (VB12B: VH), SEQ ID NO: 127 (VB12B: VL),
(6) SEQ ID NO: 134 (VB140: VH), SEQ ID NO: 135 (VB140: VL),
(7) SEQ ID NO: 136 (VB33: VH), SEQ ID NO: 137 (VB33: VL),
(8) SEQ ID NO: 138 (VB45B: VH), SEQ ID NO: 135 (VB45B: VL),
(9) SEQ ID NO: 140 (VB8B: VH), SEQ ID NO: 141 (VB8B: VL),
(10) SEQ ID NO: 142 (VB115: VH), SEQ ID NO: 127 (VB115: VL),
(11) SEQ ID NO: 144 (VB14B: VH), SEQ ID NO: 127 (VB14B: VL),
(12) SEQ ID NO: 118 (VB22B: VH), SEQ ID NO: 120 (VB22B: VL),
(13) SEQ ID NO: 146 (VB16: VH), SEQ ID NO: 147 (VB16: VL),
(14) SEQ ID NO: 148 (VB157: VH), SEQ ID NO: 149 (VB157: VL),
(15) SEQ ID NO: 150 (VB4B: VH), SEQ ID NO: 151 (VB4B: VL),
(16) SEQ ID NO: 152 (VB51: VH), SEQ ID NO: 153 (VB51: VL),
(17) SEQ ID NO: 155 (AB317: VH), SEQ ID NO: 157 (AB317: VL),
(18) SEQ ID NO: 159 (AB324: VH), SEQ ID NO: 161 (AB324: VL),
(19) SEQ ID NO: 162 (TA136: VH), SEQ ID NO: 163 (TA136: VL),
(20) SEQ ID NO: 229 (hVB22B p-z: VH), SEQ ID NO: 238 (hVB22B p-z: VL),
(21) SEQ ID NO: 256 (hVB22B g-e: VH), SEQ ID NO: 258 (hVB22B g-e: VL),
(22) SEQ ID NO: 262 (hVB22B e: VH), SEQ ID NO: 258 (hVB22B e: VL),
(23) SEQ ID NO: 289 (hVB22B u2-wz4: VH), SEQ ID NO: 291 (hVB22B u2-wz4: VL),
(24) SEQ ID NO: 295 (hVB22B q-wz5: VH), SEQ ID NO: 297 (hVB22B q-wz5: VL).

(VII) Antibody comprising the amino acid sequence of SEQ ID NO: 122 (VB22B: scFv).

(VIII) Humanized antibody comprising an amino acid sequence according to any one of SEQ ID NO: 2 (hVB22B p-z: sc(Fv)2), SEQ ID NO: 254 (hVB22B g-e: sc(Fv)2), SEQ ID NO: 260 (hVB22B e: sc(Fv)2), SEQ ID NO: 287 (hVB22B u2-wz4: sc(Fv)2), and SEQ ID NO: 293 (hVB22B q-wz5: sc(Fv)2).

(IX) Antibody comprising a VH which has FR1, 2, 3, and 4 comprising amino acid sequences according to SEQ ID NOs in any one of (1) to (5) indicated below:

(1) SEQ ID NOs: 230, 232, 234, and 236 (hVB22B p-z: H chain FR1, 2, 3, and 4),
(2) SEQ ID NOs: 265, 267, 269, and 271 (hVB22B g-e: H chain FR1, 2, 3, and 4),
(3) SEQ ID NOs: 279, 281, 283, and 285 (hVB22B e: H chain FR1, 2, 3, and 4), (4) SEQ ID NOs: 298, 299, 300, and 301 (hVB22B u2-wz4: H chain FR1, 2, 3, and 4), (5) SEQ ID NOs: 298, 299, 306, and 301 (hVB22B q-wz5: H chain FR1, 2, 3, and 4).

(X) Antibody comprising a VL which has FR1, 2, 3 and 4 comprising amino acid sequences according to SEQ ID NOs in any one of (1) to (4) indicated below:

(1) SEQ ID NOs: 239, 241, 243, and 245 (hVB22B p-z: L chain FR1, 2, 3, and 4), (2) SEQ ID NOs: 272, 274, 276, and 278 (hVB22B g-e or hVB22B e: L chain FR1, 2, 3, and 4), (3) SEQ ID NOs: 302, 303, 304, and 305 (hVB22B u2-wz4: L chain FR1, 2, 3, and 4), (4) SEQ ID NOs: 302, 307, 308, and 305 (hVB22B q-wz5: L chain FR1, 2, 3, and 4).

(XI) Antibody comprising VH and VL according to any one of (1) to (5) indicated below:

(1) VH having FR1, 2, 3, and 4 comprising the amino acid sequences of SEQ ID NOs: 230, 232, 234, and 236, respectively, and VL having FR1, 2, 3, and 4 comprising the amino acid sequences of SEQ ID NOs: 239, 241, 243, and 245, respectively;

(2) VH having FR1, 2, 3, and 4 comprising the amino acid sequences of SEQ ID NOs: 265, 267, 269, and 271, respectively, and VL having FR1, 2, 3, and 4 comprising the amino acid sequences of SEQ ID NOs: 272, 274, 276, and 278, respectively;

(3) VH having FR1, 2, 3, and 4 comprising the amino acid sequences of SEQ ID NOs: 279, 281, 283, and 285, respectively, and VL having FR1, 2, 3, and 4 comprising the amino acid sequences of SEQ ID NOs: 272, 274, 276, and 278, respectively;

(4) VH having FR1, 2, 3, and 4 comprising the amino acid sequences of SEQ ID NOs: 298, 299, 300, and 301, respectively, and VL having FR1, 2, 3, and 4 comprising the amino acid sequences of SEQ ID NOs: 302, 303, 304, and 305, respectively;

(5) VH having FR1, 2, 3, and 4 comprising the amino acid sequences of SEQ ID NOs: 298, 299, 306, and 301, respectively, and VL having FR1, 2, 3, and 4 comprising the amino acid sequences of SEQ ID NOs: 302, 307, 308, and 305, respectively.

(XII) Antibody comprising the amino acid sequence of SEQ ID NO: 264 (VB22B: sc(Fv)2).

An antibody comprising an amino acid sequence of any one of (I) to (XII) indicated above, in which one or more amino acids have been substituted, deleted, added, and/or inserted, wherein the antibody has activity equivalent to that of the antibody of any one of (I) to (XII).

Herein, the phrase "functionally equivalent" means that an antibody of interest has a biological or biochemical activity comparable to that of an antibody of the present invention. Such activities include, for example, binding activities and agonistic activities.

Methods for preparing polypeptides functionally equivalent to a certain polypeptide are well known to those skilled in the art, and include methods of introducing mutations into polypeptides. For example, those skilled in the art can prepare an antibody functionally equivalent to the antibodies of the present invention by introducing appropriate mutations into the antibody using site-directed mutagenesis (Hashimoto-Gotoh, T. et al. Gene 152, 271-275, (1995); Zoller, M J, and Smith, M. Methods Enzymol. 100, 468-500, (1983); Kramer, W. et al., Nucleic Acids Res. 12, 9441-9456, (1984); Kramer, W. and Fritz H J, Methods Enzymol. 154, 350-367, (1987); Kunkel, T A, Proc. Natl. Acad. Sci. USA. 82, 488-492, (1985); Kunkel, Methods Enzymol. 85, 2763-2766, (1988)), or such. Amino acid mutations may occur naturally. Thus, the present invention also comprises antibodies functionally equivalent to the antibodies of the present invention and comprising the amino acid sequences of these antibodies, in which one or more amino acids is mutated. In such mutants, the number of amino acids that may be mutated is not particularly restricted, so long as the activity is maintained. Generally, the number of amino acids that are mutated is 50 amino acids or less, preferably 30 or less, more preferably 10 or less (for example, five amino acids or less). Likewise, the site of mutation is not particularly restricted, so long as the mutation does not result in the disruption of activity.

Amino acid mutations may be made at one or more predicted, preferably nonessential, amino acid residues. A "nonessential" amino acid residue is a residue that can be altered from the wild-type sequence of a protein without altering the biological activity, whereas an "essential" amino acid residue is required for biological activity. An amino acid is preferably substituted for a different amino acid(s) that allows the properties of the amino acid side-chain to be conserved. Accordingly, throughout the present application, a "conservative amino acid substitution" means a replacement of an amino acid residue belonging to one of the following groups with another amino acid in the same group having a chemically similar side chain. Groups of amino acid residues having similar side chains have been defined in the art. Examples of amino acid side chain properties are: hydrophobic amino acids (A, I, L, M, F, P, W, Y, and V), hydrophilic amino acids (R, D, N, C, E, Q, G, H, K, S, and T), amino acids comprising the following side chains: aliphatic side chains (G, A, V, L, I, and P); hydroxyl-containing side chains (S, T, and Y); sulfur-containing side chains (C and M); carboxylic acid- and amide-containing side chains (D, N, E, and Q); basic side chains (R, K, and H); aromatic ring-containing side chains (H, F, Y, and W) (amino acids are represented by one-letter codes in parentheses).

A polypeptide comprising a modified amino acid sequence, in which one or more amino acid residues is deleted, added, and/or replaced with other amino acids, is known to retain its original biological activity (Mark, D. F. et al., Proc. Natl. Acad. Sci. USA 81, 5662-5666 (1984); Zoller, M. J. & Smith, M. Nucleic Acids Research 10, 6487-6500 (1982); Wang, A. et al., Science 224, 1431-1433; Dalbadie-McFarland, G. et al., Proc. Natl. Acad. Sci. USA 79, 6409-6413 (1982)).

Fusion proteins containing antibodies that comprise the amino acid sequence of an antibody of the present invention, in which two or more amino acid residues have been added, are included in the present invention. The fusion protein results from a fusion between one of the above antibodies and a second peptide or protein, and is included in the present invention. The fusion protein can be prepared by ligating a polynucleotide encoding an antibody of the present invention and a polynucleotide encoding a second peptide or polypeptide in frame, inserting this into an expression vector, and expressing the fusion construct in a host. Some techniques known to those skilled in the art are available for this purpose. The partner peptide or polypeptide to be fused with an antibody of the present invention may be a known peptide, for example, FLAG (Hopp, T. P. et al., BioTechnology 6, 1204-1210 (1988)), 6×His consisting of six His (histidine) residues, 10× His, influenza hemagglutinin (HA), human c-myc fragment, VSV-GP fragment, p18HIV fragment, T7-tag, HSV-tag, E-tag, SV40 T antigen fragment, lck tag, α-tubulin fragment, B-tag, Protein C fragment. Other partner polypeptides to be fused with the antibodies of the present invention include, for example, GST (glutathione-S-transferase), HA (influenza hemagglutinin), immunoglobulin constant region, β-galactosidase, and MBP (maltose-binding protein). A polynucleotide encoding one of these commercially available peptides or polypeptides can be fused with a polynucleotide encoding an antibody of the present invention. The fusion polypeptide can be prepared by expressing the fusion construct.

As described below, the antibodies of the present invention may differ in amino acid sequence, molecular weight, isoelectric point, presence/absence of sugar chains, and conformation depending on the cell or host producing the antibody, or purification method. However, a resulting antibody is included in the present invention, as long as it is functionally equivalent to an antibody of the present invention. For example, when an antibody of the present invention is expressed in prokaryotic cells, for example *E. Coli* a methionine residue is added to the N terminus of the original antibody amino acid sequence. Such antibodies are included in the present invention.

An antibody that recognizes an epitope recognized by the antibody according to any one of (I) to (XII) indicated above is expected to have a high agonistic activity. Such antibodies can be prepared by methods known to those skilled in the art. The antibody can be prepared by, for example, determining the epitope recognized by the antibody according to any one of (I) to (XII) by conventional methods, and using a polypeptide comprising one of the epitope amino acid sequences as an immunogen. Alternatively, the antibody can be prepared by determining the epitopes of conventionally prepared antibodies and selecting an antibody that recognizes the epitope recognized by an antibody of any one of (I) to (XII).

In the present invention, a particularly preferred antibody is an antibody that recognizes the epitope recognized by the antibody comprising the amino acid sequence of SEQ ID NO: 2. The antibody comprising the amino acid sequence of SEQ ID NO: 2 is predicted to recognize the region from Glu 26 to Leu 274, preferably the region from Ala 189 to Gly 245, more preferably the region from Gln 213 to Ala 231 of human Mpl. Thus, antibodies recognizing the region of amino acids 26 to 274, or amino acids 189 to 245, or amino acids 213 to 231 of human Mpl are also included in the present invention.

Antibodies recognizing regions of amino acids 26 to 274, amino acids 189 to 245, or amino acids 213 to 231 of the human Mpl amino acid sequence (SEQ ID NO: 123) can be obtained by methods known to those skilled in the art. Such antibodies can be prepared by, for example, using a peptide comprising amino acids 26 to 274, amino acids 189 to 245, or amino acids 213 to 231 of the human Mpl amino acid sequence (SEQ ID NO: 123) as an immunogen. Alternatively, such antibodies can be prepared by determining the epitope of a conventionally prepared antibody and selecting an antibody that recognizes the same epitope recognized by an antibody of the present invention.

The present invention provides antibodies described above in (I) to (XII). In an embodiment of the present invention, a preferred antibody is the one shown in (V), a more preferred antibody is the one shown in (VI), and a still more preferred is the one shown in (VIII).

The present invention also provides vectors comprising polynucleotides encoding the antibodies of the present invention, or polynucleotides which hybridize under stringent conditions to the polynucleotides of the present invention and encode antibodies having activities equivalent to those of the antibodies of the present invention. The polynucleotides of the present invention are polymers comprising multiple bases or base pairs of deoxyribonucleic acids (DNA) or ribonucleic acids (RNA), and are not particularly limited, as long as they encode the antibodies of the present invention. They may also contain non-natural nucleotides. The polynucleotides of the present invention can be used to express antibodies using genetic engineering techniques. The polynucleotides of this invention can also be used as probes in the screening of antibodies functionally equivalent to the antibodies of the present invention. Specifically, DNAs that hybridize under stringent conditions to a polynucleotide encoding an antibody of the present invention, and encode antibodies having activity equivalent to those of the antibodies of the present invention can be obtained by techniques such as hybridization and gene amplification (for example, PCR), using a polynucleotide of the present invention or a portion thereof as a probe. Such DNAs are also included in the polynucleotides of the present invention. Hybridization techniques are well known to those skilled in the art (Sambrook, J et al., Molecular Cloning 2nd ed., 9.47-9.58, Cold Spring Harbor Lab. press, 1989). Such hybridization conditions include, for example, conditions of low stringency. Examples of conditions of low stringency include post-hybridization washing in 0.1×SSC and 0.1% SDS at 42° C., and preferably in 0.1×SSC and 0.1% SDS at 50° C. More preferable hybridization conditions include those of high stringency. Highly stringent conditions include, for example, washing in 5×SSC and 0.1% SDS at 65° C. In these conditions, the higher the temperature, the higher the expectation of efficiently obtaining polynucleotides with a high homology. However, several factors, such as temperature and salt concentration, can influence hybridization stringency, and those skilled in the art can suitably select these factors to accomplish similar stringencies.

Antibodies that are encoded by polynucleotides obtained by the hybridization and gene amplification techniques, and are functionally equivalent to the antibodies of the present invention generally exhibit high homology to the antibodies of the this invention at the amino acid level. The antibodies of the present invention include antibodies that are functionally equivalent to the antibodies of the present invention, and exhibit high amino acid sequence homology to the antibodies of this invention. The term "high homology" generally means identity at the amino acid level of at least 50% or higher, preferably 75% or higher, more preferably 85% or higher, still more preferably 95% or higher. Polypeptide homology can be determined by the algorithm described in the report: Wilbur, W. J. and Lipman, D. J. Proc. Natl. Acad. Sci. USA 80, 726-730 (1983).

When *E. coli* is used as a host, there is no particular limitation as to the type of vector of the present invention, as long as the vector contains an "ori" responsible for its replication in *E. coli* and a marker gene. The "ori" ensures the amplification and mass production of the vector in *E. coli* (for example, JM109, DH5α, HB101, and XL1Blue). The marker gene is used to select the *E. coli* transformants (for example, a drug resistance gene selected by an appropriate drug such as ampicillin, tetracycline, kanamycin, and chloramphenicol). The vectors include, for example, M13 vectors, pUC vectors, pBR322, pBluescript, and pCR-Script. In addition to the above vectors, for example, pGEM-T, pDIRECT, and pT7 can also be used for the subcloning and excision of cDNAs.

In particular, expression vectors are useful as vectors of the present invention. When an expression vector is expressed, for example, in *E. coli*, it should have the above characteristics in order to be amplified in *E. coli*. Additionally, when *E. coli*, such as JM109, DH5α, HB101, or XL1-Blue are used as the host cell, the vector preferably has a promoter, for example, lacZ promoter (Ward et al. (1989) Nature 341:544-546; (1992) FASEB J. 6:2422-2427), araB promoter (Better et al. (1988) Science 240:1041-1043), or T7 promoter, that allows efficient expression of the desired gene in *E. coli*. Other examples of the vectors include pGEX-5×-1 (Pharmacia), "QIAexpress system" (QIAGEN), pEGFP, and pET (where BL21, a strain expressing T7 RNA polymerase, is preferably used as the host).

Furthermore, the vectors may comprise a signal sequence for polypeptide secretion. When producing polypeptides into the periplasm of *E. coli*, the pelB signal sequence (Lei, S. P. et al. J. Bacteriol. 169:4379 (1987)) may be used as a signal sequence for polypeptide secretion. For example, calcium chloride methods or electroporation methods may be used to introduce the vector into a host cell.

In addition to *E. coli*, expression vectors derived from mammals (e.g., pcDNA3 (Invitrogen), pEGF-BOS (Nucleic Acids Res. (1990) 18(17):5322), PEF, pCDM8), insect cells (e.g., "Bac-to-BAC baculovirus expression system" (GIBCO-BRL), pBacPAK8), plants (e.g., pMH1, pMH2), animalviruses (e.g., pHSV, pMV, pAdexLcw), retroviruses (e.g., pZIPneo), yeasts (e.g., "*Pichia* Expression Kit" (Invitrogen), pNV11, SP-Q01), and *Bacillus subtilis* (e.g., pPL608, pKTH50) may also be used as a vector of the present invention.

In order to express proteins in animal cells such as CHO, COS, and NIH3T3 cells, the vector preferably has a promoter necessary for expression in such cells, for example, an SV40 promoter (Mulligan et al. (1979) Nature 277:108), MMLV-LTR promoter, EF1α promoter (Mizushima et al. (1990) Nucleic Acids Res. 18:5322), CMV promoter, etc.). It is even more preferable that the vector also carries a marker gene for selecting transformants (for example, a drug-resistance gene selected by a drug such as neomycin and G418. Examples of vectors with such characteristics include pMAM, pDR2, pBK-RSV, pBK-CMV, pOPRSV, and pOP13, and such.

In addition, to stably express a gene and amplify the gene copy number in cells, CHO cells that are defective in the nucleic acid synthesis pathway are introduced with a vector containing a DHFR gene (for example, pCHOI) to compensate for the defect, and the copy number is amplified using methotrexate (MTX). Alternatively, a COS cell, which carries an SV40 T antigen-expressing gene on its chromosome, can be transformed with a vector containing the SV40 replication origin (for example, pcD) for transient gene expression. The replication origin may be derived from polyoma virus, adenovirus, bovine papilloma virus (BPV), and such. Furthermore, to increase the gene copy number in host cells, the expression vector may contain, as a selection marker, aminoglycoside transferase (APH) gene, thymidine kinase (TK) gene, *E. coli* xanthine guanine phosphoribosyl transferase (Ecogpt) gene, dihydrofolate reductase (dhfr) gene, and such.

In the present invention, next, the vector is introduced into a host cell. The host cells into which the vector is introduced are not particularly limited, for example, *E. coli* and various animal cells are available for this purpose. The host cells may be used, for example, as a production system to produce and express the antibodies of the present invention. In vitro and in vivo production systems are available for polypeptide production systems. Production systems that use eukaryotic cells or prokaryotic cells are examples of in vitro production systems.

Eukaryotic cells that can be used are, for example, animal cells, plant cells, and fungal cells. Known animal cells include: mammalian cells, for example, CHO (J. Exp. Med. (1995)108, 945), COS, 3T3, myeloma, BHK (baby hamster kidney), HeLa, Vero, amphibian cells such as *Xenopus laevis* oocytes (Valle, et al. (1981) Nature 291, 358-340), or insect cells (e.g., Sf9, Sf21, and Tn5). In the present invention, CHO-DG44, CHO-DXB11, COS7 cells, and BHK cells can be suitably used. Among animal cells, CHO cells are particularly favorable for large-scale expression. Vectors can be introduced into a host cell by, for example, calcium phosphate methods, the DEAE-dextran methods, methods using cationic liposome DOTAP (Boehringer-Mannheim), electroporation methods, lipofection methods.

Plant cells include, for example, *Nicotiana tabacum*-derived cells known as a protein production system. Calluses may be cultured from these cells. Known fungal cells include yeast cells, for example, genus *Saccharomyces* such as *Saccharomyces cerevisiae* and *Saccharomyces* pombe; and filamentous fungi, for example, genus *Aspergillus* such as *Aspergillus niger*.

Bacterial cells can be used in the prokaryotic production systems. Examples of bacterial cells include *E. coli* (for example, JM109, DH5α, HB101 and such); and *Bacillus subtilis*.

Next, the above host cells are cultured. Antibodies can be obtained by transforming the cells with a polynucleotide of interest and in vitro culturing of these transformants. Transformants can be cultured using known methods. For example, DMEM, MEM, RPMI 1640, or IMDM may be used as the culture medium for animal cells, and may be used with or without serum supplements such as FBS or fetal calf serum (FCS). Serum-free cultures are also acceptable. The preferred pH is about 6 to 8 during the course of culturing. Incubation is carried out typically at a temperature of about 30 to 40° C. for about 15 to 200 hours. Medium is exchanged, aerated, or agitated, as necessary.

On the other hand, production systems using animal or plant hosts may be used as systems for producing polypeptides in vivo. For example, a polynucleotide of interest is introduced into an animal or plant and the polypeptide is produced in the body of the animal or plant and then recovered. The "hosts" of the present invention includes such animals and plants.

Animals to be used for the production system include mammals or insects. Mammals such as goats, pigs, sheep, mice, and cattle may be used (Vicki Glaser SPECTRUM Biotechnology Applications (1993)). Alternatively, the mammals may be transgenic animals.

For example, a polynucleotide of interest is prepared as a fusion gene with a gene encoding a polypeptide specifically produced in milk, such as the goat β-casein gene. DNA fragments containing the fusion gene are injected into goat embryos, which are then introduced back to female goats. The desired antibody can be obtained from milk produced by the transgenic goats, which are born from the goats that received the embryos, or from their offspring. Appropriate hormones may be administered to increase the volume of milk containing the antibody produced by the transgenic goats (Ebert, K. M. et al., Bio/Technology 12, 699-702 (1994)).

Insects, such as silkworms, may also be used. Baculoviruses carrying a polynucleotide encoding an antibody of interest can be used to infect silkworms, and the antibody of interest can be obtained from the body fluids (Susumu, M. et al., Nature 315, 592-594 (1985)).

Plants used in the production system include, for example, tobacco. When tobacco is used, a polynucleotide encoding an antibody of interest is inserted into a plant expression vector, for example, pMON 530, and then the vector is introduced into a bacterium, such as *Agrobacterium tumefaciens*. The bacteria are then used to infect tobacco such as *Nicotiana tabacum*, and the desired antibodies can be recovered from the leaves (Julian K.-C. Ma et al., Eur. J. Immunol. 24, 131-138 (1994)).

The resulting antibody may be isolated from the inside or outside (such as the medium) of host cells, and purified as a substantially pure and homogenous antibody. Methods are not limited to any specific method and any standard method for isolating and purifying antibodies may be used. Polypeptides may be isolated and purified, by selecting an appropriate combination of, for example, chromatographic columns, filtration, ultrafiltration, salting out, solvent precipitation, solvent extraction, distillation, immunoprecipitation, SDS-polyacrylamide gel electrophoresis, isoelectric focusing, dialysis, recrystallization, and others. The term "substantially pure" as used herein in reference to a given polypeptide means that the polypeptide is substantially free from contaminants such as other biological macromolecules, culture media (if recombinantly produced), or chemical precursors (if chemically synthesized). The substantially pure polypeptide is at least 75%, preferably at least about 80%, more preferably at least about 85, 90, 95, or 99% pure by dry weight. Purity can be measured by any appropriate standard method, for example by a chromatography method, polyacrylamide gel electrophoresis, or HPLC analysis.

Chromatographies include, for example, affinity chromatographies, ion exchange chromatographies, hydrophobic chromatographies, gel filtrations, reverse-phase chromatographies, and adsorption chromatographies (Strategies for Protein Purification and characterization: A Laboratory Course Manual. Ed Daniel-R. Marshak et al., Cold Spring Harbor Laboratory Press, 1996). These chromatographies can be carried out using liquid phase chromatographies such as HPLC and FPLC. Examples of the affinity chromatography columns include protein A columns and protein G columns. Examples of the proteins A columns include Hyper D, POROS, and Sepharose F. F. (Pharmacia).

An antibody can be modified freely and peptide portions deleted by treating the antibody with an appropriate protein modifying enzyme before or after antibody purification. Such protein modifying enzymes include, for example, trypsins, chymotrypsins, lysyl endopeptidases, protein kinases, and glucosidases.

Antibodies that bind to Mpl can be prepared by methods known to those skilled in the art.

For example, monoclonal antibody-producing hybridomas can be essentially generated by known technologies as follows: immunizing animals with Mpl proteins or Mpl-expressing cells as sensitized antigens using conventional immunological methods; fusing the obtained immunocytes with known parental cells by conventional cell fusion methods; and screening for monoclonal antibody-producing cells by conventional methods.

Specifically, monoclonal antibodies can be prepared by the method below.

First, Mpl protein, which is used as a sensitized antigen for preparing antibodies, is prepared by expressing the Mpl gene/amino acid sequence (GenBank accession number: NM_005373). More specifically, the gene sequence encoding Mpl is inserted into a known expression vector, which is then transfected into an appropriate host cell. The subject human Mpl protein is purified from the host cell or culture supernatant using known methods.

The purified Mpl protein is then used as a sensitized antigen. Alternatively, a partial Mpl peptide may be used as a sensitized antigen. In this case, the partial peptide can also be chemically synthesized based on the amino acid sequence of human Mpl.

The epitopes of Mpl molecule that are recognized by an anti-Mpl antibody of the present invention are not limited to a particular epitope, and may be any epitope on the Mpl molecule. Thus, any fragment can be used as an antigen for preparing anti-Mpl antibodies of the present invention, as long as the fragment comprises an epitope of the Mpl molecule.

There is no limitation as to the type of mammalian species to be immunized with the sensitized antigen. However, a mammal is preferably selected based on its compatibility with the parental cell to be used in cell fusion. Generally, rodents (for example, mice, rats, and hamsters), rabbits, and monkeys can be used.

Animals can be immunized with a sensitized antigen by known methods such as a routine method of injecting a sensitized antigen into a mammal intraperitoneally or subcutaneously. Specifically, the sensitized antigen is diluted appropriately with phosphate-buffered saline (PBS), physiological saline and such, and then suspended. An adequate amount of a conventional adjuvant, for example, Freund's complete adjuvant, is mixed with the suspension, as necessary. An emulsion is then prepared for administering to a mammal several times over a 4- to 21-day interval. An appropriate carrier may be used for the sensitized antigen in immunization.

A mammal is immunized as described above. After a titer increase of target antibody in the serum is confirmed, immunocytes are collected from the mammal and then subjected to cell fusion. Spleen cells are the preferred immunocytes.

Mammalian myeloma cells are used as the parental cells to be fused with the above immunocytes. Preferable myeloma cells to be used include various known cell lines, for example, P3 (P3x63Ag8.653) (Kearney J F, et al., J. Immunol. 123, 1548-1550 (1979)), P3x63Ag8U.1 (Yelton D E, et al., Current Topics in Microbiology and Immunology 81, 1-7 (1978)), NS-1 (Kohler, G. and Milstein, C. Eur. J. Immunol. 6, 511-519 (1976)), MPC-11 (Margulies, D. H. et al., Cell 8, 405-415 (1976)), SP2/0 (Shulman, M. et al., Nature 276, 269-270 (1978)), FO (deSt. Groth, S. F. et al., J. Immunol. Methods 35, 1-21 (1980)), S194 (Trowbridge, I. S., J. Exp. Med. 148, 313-323 (1978)), and R210 (Galfre, G. et al., Nature 277, 131-133 (1979)).

Cell fusions between the immunocytes and the myeloma cells as described above can be essentially carried out using known methods, for example, a method by Kohler and Milstein (Kohler, G. and Milstein, C., Methods Enzymol. 73, 3-46 (1981)).

More specifically, the above-described cell fusions are carried out, for example, in a conventional culture medium in the presence of a cell fusion-promoting agent. The fusion-promoting agents include, for example, polyethyleneglycol (PEG) and Sendaivirus (HVJ). If required, an auxiliary substance such as dimethyl sulfoxide may also be added to improve fusion efficiency.

The ratio of immunocytes to myeloma cells may be determined at one's own discretion, preferably, for example, one myeloma cell for every one to ten immunocytes. Culture media to be used for the above cell fusions include, for example, media that are suitable for the growth of the above myeloma cell lines, such as RPMI 1640 media and MEM media, and other conventional culture media used for this type of cell culture. In addition, serum supplements such as fetal calf serum (FCS) may also be used in combination.

Cell fusion is carried out as follows. As described above, predetermined amounts of immunocytes and myeloma cells are mixed well in the culture medium. PEG solution (for example, mean molecular weight of about 1,000-6,000) preheated to 37° C. is added to the cell suspension typically at a concentration of 30% to 60% (w/v), and mixed to produce fused cells (hybridomas). Then, an appropriate culture medium is successively added to the mixture, and the sample is centrifuged to remove supernatant. This treatment is repeated several times to remove the unwanted cell fusion-promoting agent and others that are unfavorable to hybridoma growth.

Screening of the resulting hybridomas can be carried out by culturing them in a conventional selective medium, for example, hypoxanthine, aminopterin, and thymidine (HAT) medium. Culturing in the above-descried HAT medium is continued for a period long enough (typically, for several days to several weeks) to kill cells (non-fused cells) other than the desired hybridomas. Then, hybridomas are screened for single-cell clones capable of producing the target antibody by conventional limiting dilution methods.

In addition to the method for preparing the above-descried hybridomas by immunizing non-human animals with antigens, preferred human antibodies having binding activity to Mpl can also be obtained by: sensitizing human lymphocytes with Mpl in vitro; and fusing the sensitized lymphocytes with human myeloma cells capable of dividing permanently (see, Examined Published Japanese Patent Application No. (JP-B) Hei 1-59878). Alternatively, it is possible to obtain human antibodies against Mpl from immortalized cells producing anti-Mpl antibodies. In this method, the cells producing anti-Mpl antibodies are prepared by administering Mpl as an antigen to transgenic animals comprising a repertoire of the entire human antibody genes (see, WO 94/25585, WO 93/12227, WO 92/03918, and WO 94/02602).

The monoclonal antibody-producing hybridomas thus prepared can be passaged in a conventional culture medium, and stored in liquid nitrogen over long periods of time.

Monoclonal antibodies can be prepared from the above-described hybridomas by, for example, a routine procedure of culturing the hybridomas and obtaining antibodies from the culture supernatants. Alternatively, monoclonal antibodies can be prepared by injecting the hybridomas into a compatible mammal; growing these hybridomas in the mammal; and obtaining antibodies from the mammal's ascites. The former method is suitable for preparing highly purified antibodies, while the latter is suitable for preparing antibodies on a large scale.

Recombinant antibodies can also be prepared by: cloning an antibody gene from a hybridoma; inserting the gene into an appropriate vector; introducing the vector into a host; and producing the antibodies by using genetic recombination techniques (see, for example, Vandamme, A. M. et al., Eur. J. Biochem. 192, 767-775, (1990)).

Specifically, an mRNA encoding the variable (V) region of anti-Mpl antibody is isolated from hybridomas producing the anti-Mpl antibodies. For mRNA isolation, total RNAs are first prepared by conventional methods such as guanidine ultracentrifugation methods (Chirgwin, J. M. et al., Biochemistry 18, 5294-5299 (1979)), or acid guanidinium thiocyanate-phenol-chloroform (AGPC) methods (Chomczynski, P. et al., Anal. Biochem. 162, 156-159 (1987)), and then the target mRNA is prepared using an mRNA Purification Kit (Pharmacia) and such. Alternatively, the mRNA can be directly prepared using the QuickPrep mRNA Purification Kit (Pharmacia).

A cDNA of the antibody V region is synthesized from the resulting mRNA using reverse transcriptase. cDNA synthesis is carried out using the AMV Reverse Transcriptase First-strand cDNA. Synthesis Kit (Seikagaku Co.), or such. Alternatively, cDNA can be synthesized and amplified by the 5'-RACE method (Frohman, M. A. et al., Proc. Natl. Acad. Sci. USA 85, 8998-9002 (1988); Belyavsky, A. et al., Nucleic Acids Res. 17, 2919-2932 (1989)) using the 5'-Ampli FINDER RACE Kit (Clontech) and PCR.

Target DNA fragments are purified from the obtained PCR products and then ligated with vector DNAs to prepare recombinant vectors. The vectors are introduced into *E. coli* and such, and colonies are selected for preparing the recombinant vector of interest. The target DNA nucleotide sequence is then confirmed by conventional methods such as the dideoxynucleotide chain termination method.

Once a DNA encoding the V region of target anti-Mpl antibody is obtained, the DNA is inserted into an expression vector which comprises a DNA encoding the constant region (C region) of a desired antibody.

The method for producing anti-Mpl antibodies to be used in the present invention typically comprises the steps of: inserting an antibody gene into an expression vector, so that the gene is expressed under the regulation of expression regulatory regions, such as enhancer and promotor; and transforming host cells with the resulting vectors to express antibodies.

For expressing the antibody gene, polynucleotides encoding H chain and L chain, respectively, are inserted into separate expression vectors and co-transfected into a host cell. Alternatively, polynucleotides encoding both H chain and L chain are inserted into a single expression vector and transfected into a host cell (see WO 94/11523).

The term "agonistic activity" refers to an activity to induce changes in some biological activities through signal transduction into cells and such, due to the binding of an antibody to a receptor antigen. The biological activities include, for example, proliferation-promoting activities, proliferation activities, viability activities, differentiation-inducing activities, differentiation activities, transcriptional activities, membrane transport activities, binding activities, proteolytic activities, phosphorylation/dephosphorylation activities, oxidation/reduction activities, transfer activities, nucleolytic activities, dehydration activities, cell death-inducing activities, and apoptosis-inducing activities, but is not limited thereto.

The term "agonistic activity against Mpl" typically refers to the activity of promoting the differentiation of megakaryocytes or their parental hemopoietic stem cells into platelets, or the activity of stimulating platelet proliferation.

Agonistic activity can be assayed by methods known to those skilled in the art. The agonistic activity may be determined using the original activity or a different activity as an indicator.

For example, agonistic activity can be determined by a method using cell growth as an indicator as described in Examples. More specifically, an antibody whose agonistic activity is to be determined is added to cells which proliferate in an agonist-dependent manner, followed by incubation of the cells. Then, a reagent such as WST-8 which shows a coloring reaction at specific wavelengths depending on the viable cell count, is added to the culture and absorbance is measured. The agonistic activity can be determined using the measured absorbance as an indicator.

Cells that proliferate in an agonist-dependent manner can also be prepared by methods known to those skilled in the art. For example, when the antigen is a receptor capable of transducing cell growth signals, cells expressing the receptor may be used. Alternatively, when the antigen is a receptor that cannot transduce signals, a chimeric receptor consisting of the intracellular domain of a receptor that transduces cell growth signals and the extracellular domain of a receptor that does not transduce cell growth signals can be prepared for cellular expression. Receptors that transduce cell growth signals include, for example, G-CSF receptors, mpl, neu, GM-CSF receptors, EPO receptors, c-kit, and FLT-3. Cells that can be used to express a receptor include, for example, BaF3, NFS60, FDCP-1, FDCP-2, CTLL-2, DA-1, and KT-3.

There is no limitation as to the type of detection indicators to be used for determining agonistic activity, as long as the indicator can monitor quantitative and/or qualitative changes. For example, it is possible to use cell-free assay indicators, cell-based assay indicators, tissue-based assay indicators, and in vivo assay indicators. Indicators that can be used in cell-free assays include enzymatic reactions, quantitative and/or qualitative changes in proteins, DNAs, or RNAs. Such enzymatic reactions include, for example, amino acid transfers, sugar transfers, dehydrations, dehydrogenations, and substrate cleavages. Alternatively, protein phosphorylations, dephosphorylations, dimerizations, multimerizations, hydrolyses, dissociations and such; DNA or RNA amplifications, cleavages, and extensions can be used as the indicator in cell-free assays. For example, protein phosphorylations downstream of a signal transduction pathway may be used as a detection indicator. Alterations in cell phenotype, for example, quantitative and/or qualitative alterations in products, alterations in growth activity, alterations in cell number, morphological alterations, or alterations in cellular properties, can be used as the indicator in cell-based assays. The products include, for example, secretory proteins, surface antigens, intracellular proteins, and mRNAs. The morphological alterations include, for example, alterations in dendrite formation and/or dendrite number, alteration in cell flatness, alteration in cell elongation/axial ratio, alterations in cell size, alterations in intracellular structure, heterogeneity/homogeneity of cell populations, and alterations in cell density. Such morphological alterations can be observed under a microscope. Cellular properties to be used as the indicator include anchor dependency, cytokine-dependent response, hormone dependency, drug resistance, cell motility, cell migration activity, pulsatory activity, and alteration in intracellular substances. Cell motility includes cell infiltration activity and cell migration activity. The alterations in intracellular substances include, for example, alterations in enzyme activity, mRNA levels, levels of intracellular signaling molecules such as $Ca^{2+}$ and cAMP, and intracellular protein levels. When a cell membrane receptor is used, alterations in the cell proliferating activity induced by receptor stimulation can be used as the indicator. The indicators to be used in tissue-based assays include functional alterations adequate for the subject tissue. In in vivo assays, alterations in tissue weight, alterations in the blood system (for example, alterations in blood cell counts, protein contents, or enzyme activities), alterations in electrolyte levels, and alterations in the circulating system (for example, alterations in blood pressure or heart rate).

The methods for measuring such detection indices are not particularly limited. For example, absorbance, luminescence, color development, fluorescence, radioactivity, fluorescence polarization, surface plasmon resonance signal, time-resolved fluorescence, mass, absorption spectrum, light scattering, and fluorescence resonance energy transfer may be used. These measurement methods are known to those skilled in the art and may be selected appropriately depending on the purpose. For example, absorption spectra can be obtained by using a conventional photometer, plate reader, or such; luminescence can be measured with a luminometer or such; and fluorescence can be measured with a fluorometer or such. Mass can be determined with a mass spectrometer. Radioactivity can be determined with a device such as a gamma counter depending on the type of radiation. Fluorescence polarization can be measured with BEACON (TaKaRa). Surface plasmon resonance signals can be obtained with BIACORE. Time-resolved fluorescence, fluorescence resonance energy transfer, or such can be measured with ARVO or such. Furthermore, a flow cytometer can also be used for measuring. It is possible to use one of the above methods to measure two or more different types of detection indices. A greater number of detection indices may also be examined by using two or more measurement methods simultaneously and/or consecutively. For example, fluorescence and fluorescence resonance energy transfer can be measured at the same time with a fluorometer.

The present invention also provides pharmaceutical compositions comprising antibodies of this invention. The pharmaceutical compositions comprising antibodies of the present invention are useful for treating and/or preventing thrombocytopenia and such. Time required for the platelet count to recover to the normal level can be shortened by administering an antibody of the present invention after donation of platelet components. The amount of platelet components at the time of blood collection can be increased by pre-administering an antibody of the present invention.

When used as pharmaceutical compositions, the antibodies of the present invention can be formulated by methods known to those skilled in the art. For example, the antibodies can be administered parenterally by injection of a sterile solution or suspension in water or other pharmaceutically acceptable solvents. For example, the antibodies can be formulated by appropriately combining with pharmaceutically-acceptable carriers or solvents, specifically, sterile water or physiological saline, vegetable oils, emulsifiers, suspending agents, surfactants, stabilizers, flavoring agents, excipients, vehicles, preservatives, binding agents, and such, and mixing at a unit dosage and form required by accepted pharmaceutical implementations. In such formulations, the amount of the thus obtained active ingredient should be within the required range.

A sterile composition to be injected can be formulated using a vehicle such as distilled water used for injection, according to standard protocols.

Aqueous solutions used for injections include, for example, physiological saline and isotonic solutions comprising glucose or other adjunctive agents such as D-sorbitol, D-mannose, D-mannitol, and sodium chloride. They may also be combined with an appropriate solubilizing agent such as alcohol, specifically, ethanol, polyalcohol such as propylene glycol or polyethylene glycol, or non-ionic detergent such as polysorbate 80™ or HCO-50, as necessary.

Oil solutions include sesame oils and soybean oils, and can be combined with solubilizing agents such as benzyl benzoate or benzyl alcohol. Injection solutions may also be formulated with buffers, for example, phosphate buffers or sodium acetate buffers; analgesics, for example, procainehydrochloride; stabilizers, for example, benzyl alcohol or phenol; or anti-oxidants. The prepared injections are typically aliquoted into appropriate ampules.

The administration is preferably carried out parenterally, specifically, by injection, intranasal administration, intrapulmonary administration, percutaneous administration, or such. Injections include, for example, intravenous injections, intramuscular injections, intraperitoneal injections, and subcutaneous injections. The injection solutions can be also administered systemically or locally.

The administration methods can be selected properly according to the patient's age, condition, and such. The applied dose of a pharmaceutical composition comprising an antibody or polynucleotide encoding the antibody may be, for example, in the range of 0.0001 to 1,000 mg/kg body weight. Alternatively, the dosage may be, for example, in the range of 0.001 to 100,000 mg/kg body weight. However, the dosage is not restricted to the values described above. The dosage and administration methods depend on the patient's weight, age, and condition, and are appropriately selected by those skilled in the art.

Furthermore, the present invention relates to methods for inducing signals in Mpl-expressing cells by using the antibodies of the present invention. More specifically, the present invention relates methods for inducing signals in Mpl-expressing cells, in which the methods comprise the step of contacting the cells with the antibodies of the present invention.

All patents, published patent applications, and publications cited herein are incorporated by reference in their entirety.

EXAMPLES

The present invention is specifically illustrated below with reference to Examples, but it is not to be construed as being limited thereto.

Example 1

Preparation of Anti-Human Mpl Antibodies 1.1 Establishment of Mpl-Expressing BaF3 Cell Lines BaF3 cell lines expressing the full-length Mpl gene were established to obtain cell lines that proliferate in a TPO-dependent manner.

A full-length human Mpl cDNA (Palacios, R. et al., Cell, 41, 727-734 (1985)) (GenBank accession NO. NM_005373) was amplified by PCR. The cDNA was cloned into a pCOS2 expression vector to construct pCOS2-hMplfull. The expression vector pCOS2 was constructed by removing the DHFR gene expression region from pCHOI (Hirata, Y. et al., FEBS Letter, 356, 244-248 (1994)), where the expression region of the neomycin resistance gene HEF-VH-gγ1 (Sato, K. et al., Mol Immunol., 31, 371-381 (1994)) is inserted.

The cynomolgus monkey Mpl cDNA (SEQ ID NO: 164) was cloned from total RNA extracted from the bone marrow cells of cynomolgus monkey, using a SMART RACE cDNA Amplification Kit (Clontech). The resulting cynomolgus monkey cDNA was inserted into pCOS2 to construct pCOS2-monkeyMplfull.

Then, the full-length mouse Mpl cDNA (GenBank accession NO. NM_010823) was amplified by PCR, and inserted into pCOS2 to construct pCOS2-mouseMplfull.

Each vector (20 μg) prepared as described above was mixed with BaF3 cells ($1\times10^7$ cells/mL) suspended in PBS in Gene Pulser cuvettes. This mixture was then pulsed at 0.33 kV and 950 μFD using a Gene Pulser II (Bio-Rad). The BaF3 cells introduced with the above DNAs by electroporation were added to RPMI 1640 medium (Invitrogen) containing 1 ng/mL mouse interleukin 3 (hereinafter abbreviated as mIL-3; Peprotech), 500 μg/mL Geneticin (Invitrogen), and 10% FBS (Invitrogen), and selected to establish a human Mpl-expressing BaF3 cell line (hereinafter abbreviated as "BaF3-human Mpl"), monkey Mpl-expressing BaF3 cell line (hereinafter abbreviated as BaF3-monkey Mpl), and mouse Mpl-expressing BaF3 cell line (hereinafter abbreviated as "BaF3-mouse Mpl"). Following selection, these cells were cultured and maintained in RPMI 1640 containing 1 ng/mL rhTPO (R&D) and 10% FBS.

1.2 Establishment of Mpl-Expressing CHO Cell Lines

CHO cell lines expressing the full-length Mpl gene were established to obtain cell lines to be used for assessing binding activity by flow cytometry.

First, the DHFR gene expression site from pCHOI was inserted into pCXN2 (Niwa, H. et al., Gene, 108, 193-199 (1991)) at the HindIII site to prepare a pCXND3expression vector. The respective Mpl genes were amplified by PCR using pCOS2-hMplfull, pCOS2-monkeyMplfull, and pCOS2-mouseMplfull as templates, and primers with a His-tag sequence. The PCR products were cloned into pCXND3 to construct pCXND3-hMpl-His, pCXND3-monkey Mpl-His, and pCXND3-mouse Mpl-His, respectively.

Vectors thus prepared (25 μg each) were mixed with a PBS suspension of CHO-DG44 cells ($1\times10^7$ cells/mL) in Gene Pulser cuvettes. The mixture was then pulsed at 1.5 kV and 25 μFD using Gene Pulser II (Bio-Rad). The CHO cells introduced with these DNAs by electroporation were added to CHO-S-SFMII medium (Invitrogen) containing 500 μg/mL Geneticin and 1×HT (Invitrogen). A human Mpl-expressing CHO cell line (hereinafter abbreviated as "CHO-human Mpl"), monkey Mpl-expressing CHO cell line (hereinafter abbreviated as "CHO-monkey Mpl"), and mouse Mpl-expressing CHO cell line (hereinafter abbreviated as "CHO-mouse Mpl") were established through selection.

1.3 Preparation of Soluble Human Mpl Protein

To prepare soluble human Mpl protein, an expression system using insect Sf9 cells for production and secretion of the protein was constructed as described below.

A DNA construct encoding the extracellular region of human Mpl (Gln 26 to Trp 491) with a downstream FLAG tag was prepared. The construct was inserted into a pBACSurf-1 Transfer Plasmid (Novagen) between the PstI and SmaI sites to prepare pBACSurf1-hMpl-FLAG. Then, Sf9 cells were transformed with 4 μg of pBACSurf1-hMpl-FLAG using the Bac-N-Blue Transfection Kit (Invitrogen). The culture supernatant was collected after a three-day incubation. Recombinant virus was isolated by plaque assays. The prepared virus stock was used to infect Sf9 cells, and the culture supernatant was collected.

Soluble human Mpl protein was purified from the obtained culture supernatant as described below. The culture supernatant was loaded onto a Q Sepharose Fast Flow (Amersham Biosciences) for adsorption, and the adsorbed protein was then eluted with 50 mM Na-phosphate buffer (pH7.2) containing 0.01% (v/v) Tween 20 and 500 mM NaCl. After the eluates were loaded onto a FLAG M2-Agarose (Sigma-Aldrich) for adsorption, the protein adsorbed was eluted with 100 mM glycine-HCl buffer (pH3.5) containing 0.01% (v/v) Tween 20. Immediately after elution, the fraction obtained was neutralized with 1 M Tris-HCl Buffer (pH8.0) and the buffer was exchanged with PBS(−) and 0.01% (v/v) Tween 20 using PD-10 columns (Amersham Biosciences). The purified soluble Mpl protein was referred to as "shMpl-FLAG".

1.4 Preparation of Human Mpl-IgG Fc Fusion Protein

Human fusion protein Mpl-IgG Fc gene was prepared according to the method by Bennett et al. (Bennett, B. D. et al., J. Biol. Chem. 266, 23060-23067 (1991)). A nucleotide sequence encoding the extracellular region of human Mpl (Gln 26 to Trp 491) was linked to a nucleotide sequence encoding the Fc region of human IgG-γ1 (a region downstream of Asp 216). A BstEII sequence (amino acids: Val-Thr) was attached to the junction as a fusion linker between these two regions. A 19-amino acid signal peptide derived form human IgG H chain variable region was used as the signal sequence. The resulting human fusion protein Mpl-IgG Fc gene was cloned into pCXND3 to construct pCXND3-hMpl-Fc.

The vector thus prepared (25 μg) was mixed with a PBS suspension of CHO-DG44 cells ($1\times10^7$ cells/mL) in Gene Pulser cuvettes. The mixture was then pulsed at 1.5 kV and 25 μFD using Gene Pulser II (Bio-Rad). The CHO cells introduced with the DNA by electroporation were added to CHO-S-SFMII medium containing 500 μg/mL Geneticin and 1×HT (Invitrogen). shMPL-Fc-expressing CHO cell line (CHO-hMpl-Fc) was then established through selection.

Human Mpl-IgG Fc fusion protein was purified from the culture supernatant as described below.

The culture supernatant was loaded onto a Q Sepharose Fast Flow (Amersham Biosciences) for adsorption, and then the adsorbed protein were eluted with 50 mM Na-phosphate buffer (pH7.6) containing 0.01% (v/v) Tween 20 and 1 M NaCl. After the eluates were loaded onto a HiTrap protein G HP column (Amersham Biosciences) for adsorption, the adsorbed protein was eluted with 0.1 M glycine-HCl buffer (pH2.7) containing 150 mM NaCl and 0.01% (v/v) Tween 20. Immediately after elution, the obtained fraction was neutralized with 1 M Tris-HCl Buffer (pH8.0) and the buffer was exchanged with PBS(−) and 0.01% (v/v) Tween 20 using PD-10 columns (Amersham Biosciences). The purified soluble Mpl protein was referred to as "hMpl-Fc".

1.5 Immunization with shMpl-FLAG or BaF3-Human Mpl and Hybridoma Selection

MRL/MpJUmmCrj-lpr/lpr mice (hereinafter abbreviated as "MRL/lpr mice"; purchased from Charles River, Japan) were immunized; the primary immunization was carried out at eight weeks of age. For every single mouse, an emulsion containing 100 μg of shMPL-FLAG combined with Freund's complete adjuvant (H37 Ra; Beckton Dickinson), was administered subcutaneously as the primary injection. As a booster injection, an emulsion containing shMPL-FLAG (50 μg per mouse) combined with Freund's incomplete adjuvant (Beckton Dickinson) was administered subcutaneously. Three mice which have been immunized six times in total were subjected to a final injection of shMPL-FLAG (50 μg per mouse) through the caudal vein. Cell fusion was achieved by mixing the mouse myeloma P3-X63Ag8U1 cells (P3U1; purchased from ATCC) and mouse splenocytes using polyethylene glycol 1500 (Roche Diagnostics). Hybridoma selection in HAT medium began the following day and culture supernatants were obtained. Screening was carried out by ELISA, using immunoplates immobilized with shMpl-FLAG or hMpl-Fc and the assayed cell growth activity of BaF3-human Mpl as an index. In addition, Balb/C mice were immunized eleven times in total by administering BaF3-human Mpl ($1.0\times10^7$ cells per mouse) intraperitoneally over a period of one week to five months. Hybridomas were similarly prepared by cell fusion, and screened using the assayed cell growth activity of BaF3-human Mpl as an index. Positive clones were isolated as single clones by limiting dilution and then cultured in a large scale. The culture supernatants were collected.

1.6 Analyses of Anti-Human Mpl Antibodies

Antibody concentrations were determined by carrying out a mouse IgG sandwich ELISA using goat anti-mouse IgG (gamma) (ZYMED) and alkaline phosphatase-goat anti-mouse IgG (gamma) (ZYMED), generating a calibration curve by GraphPad Prism (GraphPad Software; USA), and calculating the antibody concentrations from the calibration curve. Commercially available antibodies of the same isotype were used as standards.

Antibody isotypes were determined by antigen-dependent ELISA using isotype-specific secondary antibodies. hMpl-Fc was diluted to 1 μg/mL with a coating buffer (0.1 mM $NaHCO_3$, pH9.6) containing 0.02% (w/v) $NaN_3$, and then added to ELISA plates. The plates were incubated overnight at 4° C. for coating. The plates were blocked with a diluent buffer (50 mM Tris-HCl (pH8.1) containing 1 mM $MgCl_2$, 150 mM NaCl, 0.05% (v/v) Tween 20, 0.02% (w/v) $NaN_3$, 1% (w/v) BSA). After the addition of hybridoma culture supernatants, the plates were allowed to stand at room temperature for 1 hr. After washing with a rinse buffer (0.05% (v/v) Tween 20 in PBS), alkaline phosphatase-labeled isotype-specific secondary antibodies were added to the plates. Then, the plates were allowed to stand at room temperature for 1 hr. Color development was carried out using SIGMA104 (Sigma-Aldrich) diluted to 1 mg/mL with a substrate buffer (50 mM $NaHCO_3$, pH9.8) containing 10 mM $MgCl_2$, and absorbance was measured at 405 nm using Benchmark Plus (Bio-Rad).

The binding activities of an antibody to shMpl-FLAG and hMPL-Fc were determined by ELISA. ELISA plates were coated with 1 μg/mL of purified shMpl-FLAG or hMPL-Fc, and blocked with a diluent buffer. Hybridoma culture supernatants were added to the plates, and the plates were allowed to stand at room temperature for 1 hr. Then, alkaline phosphatase-labeled anti-mouse IgG antibodies (Zymed) were added to the plates. Color development was similarly carried out using the above method. Following a one-hour coloring reaction at room temperature, absorbance was measured at 405 nm and $EC_{50}$ values were computed using GraphPad Prism.

CHO-human Mpl cells and CHO-monkey Mpl cells were harvested, and suspended in FACS Buffer (1% FBS/PBS) to a final concentration of $1\times10^6$ cells/mL. The suspensions were aliquoted into Multiscreen (Millipore) at 100 μl/well, and the culture supernatants were removed by centrifugation. Culture supernatants diluted to 5 μg/mL were added to the plates and incubated on ice for 30 min. The cells were washed once with FACS buffer, and incubated on ice for 30 min following the addition of an FITC-labeled anti-mouse IgG antibody (Beckman Coulter). After incubation, the mixture was centrifuged at 500 rpm for 1 min. The supernatants were removed, and then the cells were suspended in 400 μL of FACS buffer. The samples were analyzed by flow cytometry using EPICS ELITE ESP (Beckman Coulter). An analysis gate was set on the forward and side scatters of a histogram to include viable cell populations.

Agonistic activities of an antibody were evaluated using BaF3-human Mpl and BaF3-monkey Mpl which proliferate in a TPO-dependent manner. Cells of each cell line were suspended at $4\times10^5$ cells/ml in RPMI 1640/10% FBS (Invitrogen), and each suspension was aliquoted into a 96-well plate at 60 μl/well. A 40-μL aliquot of rhTPO (R&D) and hybridoma culture supernatants prepared at various concentrations was added into each well. The plates were then incubated at 37° C. under 5% $CO_2$ for 24 hr. A 10-μL aliquot of the Cell Count Reagent SF (Nacalai Tesque) was added into each well. After incubation for 2 hr, absorbance was measured at 450 nm (and at 655 nm as a control) using a Benchmark Plus. $EC_{50}$ values were calculated using GraphPad Prism.

The above analysis yielded a total of 163 clones of mouse monoclonal antibodies that bind to human Mpl.

Among the anti-human Mpl antibodies to be described, TA136 was established from mice immunized with BaF3-human Mpl and the others were established from mice immunized with shMpl-Flag.

1.7 Purification of Anti-Human Mpl Antibodies

Anti-human Mpl antibodies were purified from hybridoma culture supernatants as described below.

After the culture supernatants were loaded onto HiTrap protein G HP columns (Amersham Biosciences) for adsorption, the antibodies were eluted with 0.1 M glycine-HCl (pH2.7) Buffer. Immediately after elution, the fractions were neutralized with 1 M Tris-HCl Buffer (pH9.0), and dialyzed against PBS to replace the buffer for one day.

1.8 Determination of Epitopes for the Anti-Human Mpl Antibody VB22B

Since the anti-human Mpl antibody VB22B can be used for Western blotting, a GST-fusion protein containing a partial sequence of human Mpl was constructed for VB22B epitope analysis. MG1 (Gln26 to Trp491) and MG2 (Gln26 to Leu274) regions were each amplified by PCR, and cloned into pGEX-4T-3 (Amersham Biosciences) to be expressed as GST fusion proteins. The resulting plasmid DNAs were transformed into DH5α to give transformants. A final concentration of 1 mM IPTG was added to the transformants in their logarithmic growth phase to induce the expression of GST fusion proteins. The bacterial cells were harvested after two hours of incubation. The cells were lysed by sonication. The lysates were centrifuged in XL-80 Ultracentrifuge (Beckman, Rotor 70.1Ti) at 35,000 rpm for 30 min. The culture supernatants were removed, and then the fusion proteins were purified using GST Purification Modules (Amersham Biosciences). The samples were separated by 10%-SDS-PAGE, and then transferred onto a PVDF membrane. The membrane was analyzed by the murine antibody VB22B in Western Btotting. VB22B was found to recognize both MG-1 and MG-2, indicating that the VB22B epitope is located in the (Gln26 to Leu274) region.

Then, GST fusion proteins containing the respective regions of human Mpl: MG3 (Gln26 to Ala189), MG4 (Gln26 to Pro106), MG5 (Gln26 to Glu259), and MG6 (Gln26 to Gly245) were prepared and analyzed by Western blotting using the same procedure described above. VB22B was found to recognize MG5 and MG6, but not MG3 and MG4. This suggests that the VB22B epitope is located within the (Ala189 to Gly245) region. In addition, GST was fused with MG7 (Gln26 to Ala231) and MG8 (Gln26 to Pro217) to prepare GST fusion proteins. VB22B recognized MG7 but not MG8, suggesting that the VB22B epitope is located in the (Gln217 to Ala231) region. Furthermore, GST fusion protein containing MG10 (Gln213 to Ala231) was recognized by VB22B, suggesting that the VB22B epitope is located within the limited region of 19 amino acids between Gln213 and Ala231.

1.9 Kinetic Analyses of the Antigen-Antibody Reaction for Anti-Human Mpl Antibody VB22B Since the anti-human Mpl antibody VB22B binds to soluble recombinant Mpl, kinetic analyses of the antigen-antibody reaction between VB22B IgG and human Mpl-IgG Fc fusion protein were carried out as described in Example 1.4. The Sensor Chip CM5 (Biacore) was placed in Biacore 2000 (Biacore), and human Mpl-IgG Fc fusion protein was immobilized onto the chip by amine-coupling methods. Then, 1.25 to 20 μg/mL of VB22B IgG solution was prepared using HBS-EP Buffer (Biacore), and injected over the chip surface for 2 min to reveal the binding region. Then, HBS-EP Buffer was injected over the chip surface for 2 min to reveal the dissociation region. VB22B IgG bound to the human Mpl-IgG Fc fusion protein on the sensor chip was removed by injecting 10 mM NaOH over the sensor chip for 15 sec, and the chip was recovered. HBS-EP Buffer was used as the running buffer, and the flow rate was 20 μL/min. Using the BIAevaluation Version 3.1 (Biacore) software, the reaction rate constant at each concentration was calculated from the sensorgrams. The dissociation constant (KD) for VB22B IgG was determined to be $1.67\pm0.713\times10^{-9}$ M.

Example 2

Preparation of Single-Chain Anti-Human Mpl Antibodies

Among the prepared anti-human Mpl antibodies, 23 types of antibodies, which exhibit higher binding activities and agonistic activities, were selected to construct expression systems for single-chain antibodies using genetic engineering techniques. An exemplary method for constructing a single-chain antibody derived from the anti-human Mpl antibody VB22B is described below.

2.1 Cloning of the Anti-Human Mpl Antibody Variable Region

The variable region was amplified by RT-PCR using total RNA extracted from hybridomas producing anti-human Mpl antibodies. Total RNA was extracted from $1\times10^7$ hybridoma cells using the RNeasy Plant Mini Kit (QIAGEN).

A 5'-terminal fragment of the gene was amplified from 1 μg of total RNA by the SMART RACE cDNA Amplification Kit (Clontech), using a synthetic oligonucleotide MHC-IgG2b (SEQ ID NO: 166) complementary to mouse IgG2b constant region or a synthetic oligonucleotide kappa (SEQ ID NO: 167) complementary to mouse κ chain constant region. Reverse transcription was carried out at 42° C. for 1.5 hr.

The composition of the PCR reaction solution (50 μL in total) is shown below.

| | |
|---|---|
| 10x Advantage 2 PCR Buffer (Clontech) | 5 μL |
| 10x Universal Primer A Mix (Clontech) | 5 μL |
| dNTPs (dATP, dGTP, dCTP, and dTTP) (Clontech) | 0.2 mM |
| Advantage 2 Polymerase Mix (Clontech) | 1 μL |
| Reverse transcription product | 2.5 μL |
| Synthetic oligonucleotide, MHC-IgG2b or kappa | 10 pmol |

The PCR reaction conditions were:

94° C. (initial temperature) for 30 sec;

five cycles of 94° C. for 5 sec and 72° C. for 3 min;

five cycles of 94° C. for 5 sec, 70° C. for 10 sec, and 72° C. for 3 min;

25 cycles of 94° C. for 5 sec, 68° C. for 10 sec, and 72° C. for 3 min;

and final extension was at 72° C. for 7 min.

The PCR products were purified from agarose gel using the QIAquick Gel Extraction Kit (QIAGEN), and cloned into a pGEM-T Easy Vector (Promega). The nucleotide sequence was then determined using the ABI 3700 DNA Analyzer (Perkin Elmer).

The nucleotide sequence of cloned VB22B H chain variable region (hereinafter abbreviated as "VB22B-VH") is shown in SEQ ID NO: 117, and its amino acid sequence is shown in SEQ ID NO: 118. The nucleotide sequence of the L chain variable region (hereinafter abbreviated as "VB22B-VL") is shown in SEQ ID NO: 119, and its amino acid sequence is shown in SEQ ID NO: 120.

2.2 Preparation of Expression Vectors for Anti-Human Mpl Diabodies

The gene encoding VB22B single-chain Fv (hereinafter abbreviated as "VB22B diabody") containing a five-amino acid linker sequence was constructed, by linking a nucleotide sequence encoding a $(Gly_4Ser)_1$ linker to the VB22B-VH-encoding gene at its 3' end and to the VB22B-VL-encoding gene at its 5' end; both of which have been amplified by PCR.

The VB22B-VH forward primer, 70•115HF, (SEQ ID NO: 168) was designed to contain an EcoRI site. The VB22B-VH reverse primer, 33•115HR, (SEQ ID NO: 169) was designed to hybridize to a DNA encoding the C terminus of VB22B-VH, and to have a nucleotide sequence encoding the $(Gly_4Ser)_1$ linker and a nucleotide sequence hybridizing to the DNA encoding the N terminus of VB22B-VL. The VB22B-VL forward primer, 33•115LF, (SEQ ID NO: 170) was designed to have a nucleotide sequence encoding the N terminus of VB22B-VL, a nucleotide sequence encoding the $(Gly_4Ser)_1$ linker, and a nucleotide sequence encoding the C terminus of VB22B-VH. The VB22B-VL reverse primer, 33•115LR, (SEQ ID NO: 171) was designed to hybridize to a DNA encoding the C terminus of VB22B-VL and to have a nucleotide sequence encoding a FLAG tag (Asp Tyr Lys Asp Asp Asp Asp Lys/SEQ ID NO: 172) and a NotI site.

In the first round of PCR, two PCR products: one containing VB22B-VH and a linker sequence, and the other containing VB22B-VL and the identical linker sequence, were synthesized by the procedure described below.

The composition of the PCR reaction solution (50 μL in total) is shown below.

| | |
|---|---|
| 10x PCR Buffer (TaKaRa) | 5 μL |
| dNTPs (dATP, dGTP, dCTP, and dTTP) (TaKaRa) | 0.4 mM |
| DNA polymerase TaKaRa Ex Taq (TaKaRa) | 2.5 units |
| pGEM-T Easy vector comprising VB22B-VH or VB22B-VL gene | 10 ng |
| Synthetic oligonucleotides, 70.115HF and 33.115HR, or 33.115LF and 33.115LR | 10 pmol |

The PCR reaction conditions were:
94° C. (initial temperature) for 30 sec;
five cycles of: 94° C. for 15 sec and 72° C. for 2 min;
five cycles of 94° C. for 15 sec and 70° C. for 2 min;
28 cycles of 94° C. for 15 sec and 68° C. for 2 min;
and final extension was at 72° C. for 5 min.

After the PCR products of about 400 bp were purified from agarose gel using the QIAquick Gel Extraction Kit (QIAGEN), the second-round PCR was carried out using aliquots of the respective PCR products according to the protocol described below.

The composition of the PCR reaction solution (50 μL in total) is shown below.

| | |
|---|---|
| 10x PCR Buffer (TaKaRa) | 5 μL |
| dNTPs (dATP, dGTP, dCTP, and dTTP) (TaKaRa) | 0.4 mM |
| DNA polymerase TaKaRa Ex Taq (TaKaRa) | 2.5 unit |
| First-round PCR products (two types) | 1 μL |
| Synthetic oligonucleotides, 70.115HF and 33.115LR | 10 pmol |

The reaction conditions were:
94° C. (initial temperature) for 30 sec;
five cycles of 94° C. for 15 sec and 72° C. for 2 min;
five cycles of 94° C. for 15 sec and 70° C. for 2 min;
28 cycles of 94° C. for 15 sec and 68° C. for 2 min;
and final extension was at 72° C. for 5 min.

The PCR products of about 800 bp were purified from agarose gel using the QIAquick Gel Extraction Kit (QIAGEN), and then digested with EcoRI and NotI (both from TaKaRa). The resulting DNA fragments were purified using the QIAquick PCR Purification Kit (QIAGEN), and then cloned into pCXND3 to prepare pCXND3-VB22B db.

2.3 Preparation of Expression Vectors for Anti-Human Mpl Antibody sc(Fv)2

To prepare expression plasmids for the modified antibody [sc(Fv)2] comprising two units of H chain variable region and two units of L chain variable region derived from VB22B, the above-described pCXND3-VB22B db was modified by PCR using the procedure shown below. The process for constructing the sc(Fv)2 gene is illustrated in FIG. 1.

First, PCR method was carried out to amplify (a) the VB22B-VH-encoding gene in which a nucleotide sequence encoding a 15-amino acid linker $(Gly_4Ser)_3$ was added to its 3' end; and (b) the VB22B-VL-encoding gene containing the identical linker nucleotide sequence added to its 5' end. The desired construct was prepared by linking these amplified genes. Three new primers were designed in this construction process. The VB22B-VH forward primer, VB22B-fpvu, (primer A; SEQ ID NO: 173) was designed to have an EcoRI site at its 5' end and to convert Gln22 and Leu23 of VB22B db into a PvuII site. The VB22B-VH reverse primer, sc-rL15, (primer B; SEQ ID NO: 174) was designed to hybridize to a DNA encoding the C terminus of VB22B-VH, and to have a nucleotide sequence encoding the $(Gly_4Ser)_3$ linker, as well as a nucleotide sequence hybridizing to a DNA encoding the N terminus of VB22B-VL. The VB22B-VL forward primer, sc-fL15, (primer C; SEQ ID NO: 175) was designed to have a nucleotide sequence encoding the N terminus of VB22B-VL, a nucleotide sequence encoding the $(Gly_4Ser)_3$ linker, and a nucleotide sequence encoding the C terminus of VB22B-VH.

In the first-round PCR, two PCR products: one comprising VB22B-VH and a linker sequence, and the other comprising VB22B-VL and the identical linker sequence, were synthesized by the procedure described below.

The composition of the PCR reaction solution (50 μL in total) is shown below.

| | |
|---|---|
| 10x PCR Buffer (TaKaRa) | 5 μL |
| dNTPs (dATP, dGTP, dCTP, and dTTP) (TaKaRa) | 0.4 mM |
| DNA polymerase TaKaRa Ex Taq (TaKaRa) | 2.5 units |
| pCXND3-VB22B db | 10 ng |
| Synthetic oligonucleotides, VB22B-fpvu, sc-rL15 or sc-fL15, and 33.115LR (primer D) | 10 pmol |

The reaction conditions were:
94° C. (initial temperature) for 30 sec;
five cycles of 94° C. for 15 sec and 72° C. for 2 min;
five cycles of 94° C. for 15 sec and 70° C. for 2 min;
28 cycles of 94° C. for 15 sec and 68° C. for 2 min;
and final extension was at 72° C. for 5 min.

After the PCR products of about 400 bp were purified from agarose gel using the QIAquick Gel Extraction Kit (QIAGEN), the second-round PCR was carried out using aliquots of the respective PCR products according to the protocol described below.

The composition of the PCR reaction solution (50 μL in total) is shown below.

| | |
|---|---|
| 10x PCR Buffer (TaKaRa) | 5 μL |
| dNTPs (dATP, dGTP, dCTP, and dTTP) (TaKaRa) | 0.4 mM |
| DNA polymerase TaKaRa Ex Taq (TaKaRa) | 2.5 units |
| First-round PCR product (two types) | 1 μL |
| Synthetic oligonucleotide, 70.115HF and 33.115LR | 10 pmol |

The reaction conditions were:
94° C. (initial temperature) for 30 sec;
five cycles of 94° C. for 15 sec and 72° C. for 2 min;
five cycles of 94° C. for 15 sec and 70° C. for 2 min;
28 cycles of 94° C. for 15 sec and 68° C. for 2 min;
and final extension was at 72° C. for 5 min.

The PCR products of about 800 bp were purified from agarose gel using the QIAquick Gel Extraction Kit (QIAGEN), and then digested with EcoRI and NotI (both from TaKaRa). The resulting DNA fragments were purified using the QIAquick PCR Purification Kit (QIAGEN), and then cloned into pBacPAK9 (Clontech) to construct pBacPAK9-scVB22B.

A fragment to be inserted into the PvuII site of pBacPAK9-scVB22B was prepared. Specifically, the fragment has a PvuII recognition site at both ends and a nucleotide sequence, in which a gene encoding the VB22B-VH N-terminus is linked, via a $(Gly_4Ser)_3$ linker-encoding nucleotide sequence, to a gene encoding the amino acid sequence of an N terminus-deleted VB22B-VH linked to VB22B-VL via the $(Gly_4Ser)_3$ linker. Two primers were newly designed to prepare the fragment by PCR. The forward primer for the fragment of interest, Fv2-f (primer E; SEQ ID NO: 176), was designed to have a PvuII site at its 5' end and a VB22B-VH 5'-end sequence. The reverse primer for the fragment of interest, Fv2-r (primer F; SEQ ID NO: 177), was designed to hybridize to a DNA encoding the C terminus of VB22B-VL, and to have a PvuII site, a nucleotide sequence encoding the $(Gly_4Ser)_3$ linker, and a nucleotide sequence hybridizing to a DNA encoding the N terminus of VB22B-VH. PCR was carried out using pBacPAK9-scVB22B as a template as described below.

The composition of the PCR reaction solution (50 µL in total) is shown below.

| | |
|---|---|
| 10x PCR Buffer (TaKaRa) | 5 µL |
| dNTPs (dATP, dGTP, dCTP, and dTTP) (TaKaRa) | 0.4 mM |
| DNA polymerase TaKaRa Ex Taq (TaKaRa) | 2.5 units |
| pBacPAK9-scVB22B | 10 µg |
| Synthetic oligonucleotide, Fv2-f and Fv2-r | 10 pmol |

The reaction conditions were:
94° C. (initial temperature) for 30 sec;
five cycles of 94° C. for 15 sec and 72° C. for 2 min;
five cycles of 94° C. for 15 sec and 70° C. for 2 min;
28 cycles of 94° C. for 15 sec and 68° C. for 2 min;
and final extension was at 72° C. for 5 min.

The PCR products of about 800 bp were purified from agarose gel using the QIAquick Gel Extraction Kit (QIAGEN), and then cloned into the pGEM-T Easy Vector (Promega). After sequencing, the plasmid was digested with PvuII (TaKaRa), and the fragment of interest was recovered. The recovered fragment was ligated to pBacPAK9-scVB22B pre-digested with PvuII (TaKaRa) to construct pBacPAK9-VB22B sc (Fv) 2. After the resulting vector was digested with EcoRI and NotI (both from TaKaRa), the fragment of about 1, 600 bp was purified from agarose gel using the QIAquick Gel Extraction Kit (QIAGEN). The fragment was then cloned into a pCXND3 expression vector to construct pCXND3-VB22B sc(Fv)2.

2.4 Expression of Single-Chain Anti-Human Mpl Antibody in Animal Cells

A cell line stably expressing the single-chain antibody was prepared from CHO-DG44 cells as described below. Gene transfer was achieved by electroporation using a Gene Pulser II (Bio-Rad). An expression vector (25 µg) and 0.75 mL of CHO-DG44 cells suspended in PBS ($1\times10^7$ cells/mL) were mixed. The resulting mixture was cooled on ice for 10 min, transferred into a cuvette, and pulsed at 1.5-kV and 25 µFD. After a ten-minute restoration period at room temperature, the electroporated cells were plated in CHO-S-SFMII medium (Invitrogen) containing 500 µg/mL Geneticin (Invitrogen). CHO cell lines expressing the single-chain antibody were established through selection. A cell line stably expressing VB22B sc(Fv)2 and its culture supernatants were obtained by this method.

The transient expression of the single-chain antibody was achieved using COS7 cells as described below. An expression vector (10 µg) and 0.75 mL of COS7 cells suspended in PBS ($1\times10^7$ cells/mL) were mixed. The resulting mixture was cooled on ice for 10 min, transferred into a cuvette, and then pulsed at 1.5-kV and 25 µFD. After a ten-minute restoration period at room temperature, the electroporated cells were plated in DMEM/10% FBS medium (Invitrogen). The cells were incubated overnight and then washed with PBS. CHO-S-SFMII medium was added and the cells were cultured for about three days. The culture supernatants for preparing the VB22B diabody were thus prepared.

2.5 Quantitation of Single-Chain Anti-Human Mpl Antibodies in Culture Supernatants The culture supernatant concentration of the single-chain anti-human Mpl antibody transiently expressed in COS cells was determined using surface plasmon resonance. A sensor chip CM5 (Biacore) was placed in Biacore 2000 (Biacore). ANTI-FLAG® M2 Monoclonal Antibody (Sigma-Aldrich) was immobilized onto the chip. An appropriate concentration of sample was injected over the chip surface at a flow rate of 5 mL/sec, and 50 mM diethylamine was used to dissociate the bound antibody. Changes in the mass during sample injection were recorded, and the sample concentration was calculated from the calibration curve prepared using the mass changes of a standard sample. db12E10 (see WO 02/33073 and WO 02/33072) was used as the diabody standard, and 12E10 sc(Fv)2 which has the same gene structure as that of sc(Fv)2 was used as the sc(Fv)2 standard.

2.6 Purification of Anti-Human Mpl Diabodies and Single-Chain Antibodies

The culture supernatants of VB22B diabody-expressing COS7 cells or CHO cells was loaded onto an Anti-Flag M2 Affinity Gel (Sigma-Aldrich) column equilibrated with a 50 mM Tris-HCl buffer (pH7.4) containing 150 mM NaCl and 0.05% Tween 20. The absorbed antibodies were eluted with 100 mM glycine-HCl (pH3.5). The fractions eluted were immediately neutralized with 1 M Tris-HCl (pH8.0), and loaded onto a HiLoad 26/60 Superdex 200 pg (Amersham Biosciences) column for gel filtration chromatography. PBS/0.01% Tween 20 was used in the gel filtration chromatography.

VB22B sc(Fv)2 was purified from the culture supernatants of VB22B sc(Fv)2-expressing COS7 cells or CHO cells under the same conditions used for purifying the diabodies. A large-scale preparation of VB22B sc(Fv)2 was prepared by loading the CHO cell culture supernatants onto a Macro-Prep Ceramic Hydroxyapatite Type I (Bio-Rad) column equilibrated with a 20 mM phosphate buffer (pH6.8), and eluting the VB22B sc(Fv)2 in a stepwise manner with 250 mM phosphate buffer (pH6.8). The eluted fraction was concentrated on an ultrafilter, and then fractionated by gel filtration chromatography using a HiLoad 26/60 Superdex 200 pg (Amersham. Biosciences) column, and a fraction corresponding to the molecular weight range of about 40 kD to 70 kD was obtained. The fraction was loaded onto an Anti-Flag M2 Affinity Gel column equilibrated with a 50 mM Tris-HCl buffer (pH7.4) containing 150 mM NaCl and 0.05% Tween 20. The absorbed antibody was eluted with 100 mM glycine-HCl (pH3.5). The eluted fraction was immediately neutralized with 1 M Tris-HCl (pH8.0), and loaded onto a HiLoad 26/60 Superdex 200 pg (Amersham Biosciences) column for gel filtration chromatography. 20 mM acetate buffer (pH6.0)

containing 150 mM NaCl and 0.01% Tween 80 was used in the gel filtration chromatography. In each purification step, the presence of the diabody and sc(Fv)2 in the samples was confirmed by SDS-PAGE and Western blotting using an anti-Flag antibody (Sigma-Aldrich). Specifically, obtained fractions corresponding to each peak were subjected to the electrophoresis according to the method described by Laemli, and then stained using Coomassie Brilliant Blue. As a result, single band was detected apparently at about 29 kDa for the diabody; while single band was detected apparently at about 55 kDa for sc(Fv)2.

2.7 Binding Activity Analyses of Single-Chain Anti-Human Mpl Antibodies by Flow Cytometry CHO-human Mpl, CHO-monkey Mpl, and CHO-mouse Mpl cells were recovered and suspended in FACS buffer (1% FBS/PBS) to a final concentration of $1\times10^6$ cells/mL. Cell suspensions were aliquoted at 100-μL/well into the Multiscreen-HV Filter Plates (Millipore). After centrifugation, the supernatant was removed. An appropriate concentration of diabody or sc(Fv)2 was added into each well and incubated on ice for 30 min. The cells were washed once with 200 μL of FACS buffer, and incubated on ice for 30 min following the addition of 10 μg/mL ANTI-FLAG® M2 Monoclonal Antibody (Sigma-Aldrich). The cells were then washed once with 200 μL of FACS buffer, and a 100×-diluted FITC-labeled anti-mouse IgG antibody (Beckman Coulter) was added to the plate. The plate was incubated on ice for 30 min. After centrifugation, the supernatant was removed. The cells were suspended in 400 μL of FACS Buffer, and then analyzed by flow cytometry using EPICS ELITE ESP (Beckman Coulter). An analysis gate was set on the forward and side scatters of a histogram to include viable cell populations.

Figure 2:
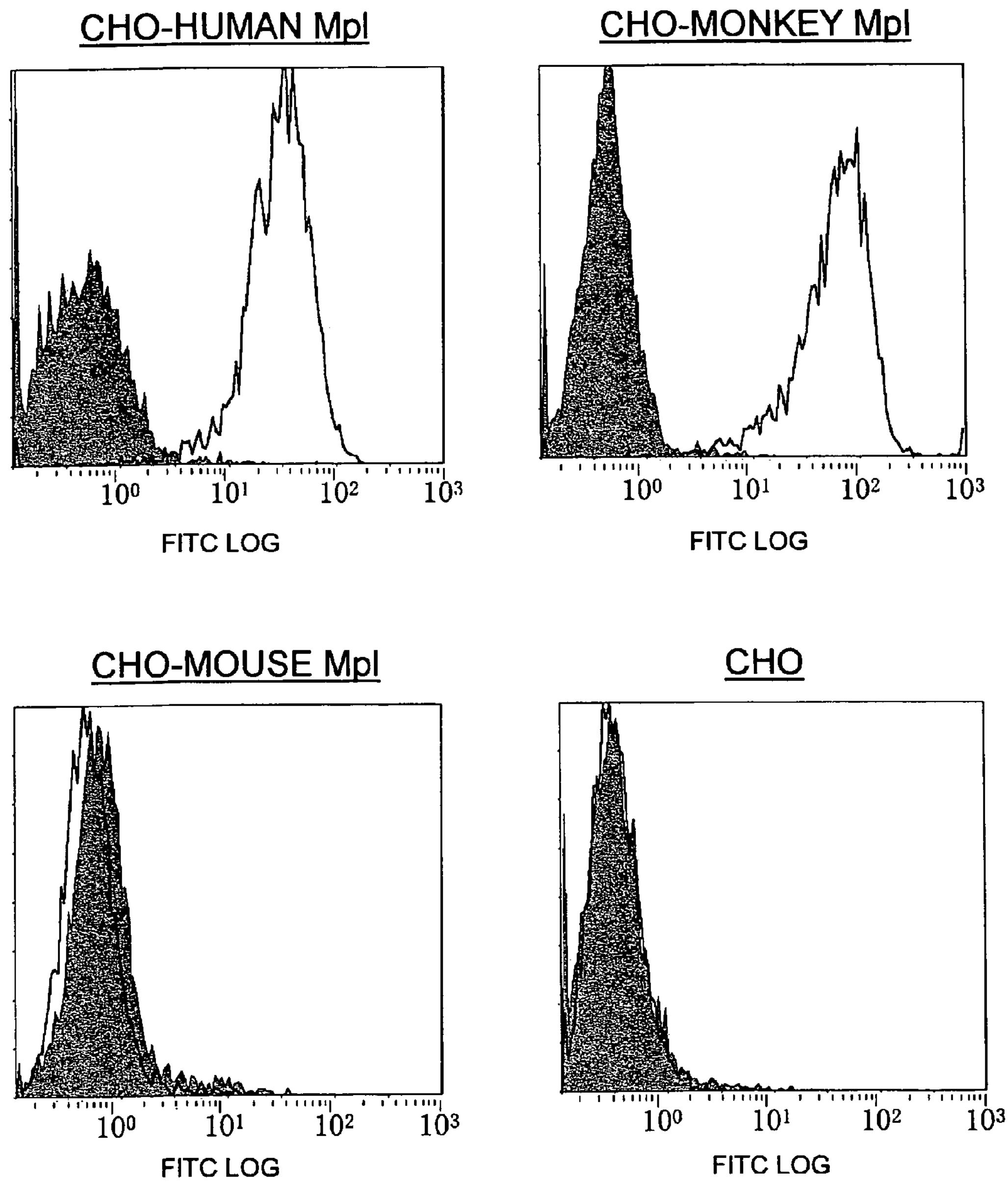
FIG. 2 illustrates the assessment of VB22B sc(Fv)2 binding activity using an Mpl-expressing CHO cell line. Purified VB22B sc(Fv)2 was used.

The binding activity of the purified VB22B sc(Fv)2 to various Mpl molecules expressed in CHO cells was determined (FIG. 2). VB22B sc (Fv) 2 was found to specifically bind to CHO-human Mpl and CHO-monkey Mpl but not to the host cell CHO or CHO-mouse Mpl. This binding characteristic of VB22B sc(Fv)2 is comparable to those of VB22B IgG, indicating that the antibody binding site remains unaltered by converting whole IgG to minibody.

2.8 Analyses of TPO-Like Agonistic Activity for Single-Chain Anti-Human Mpl Antibodies TPO-like agonistic activity was assessed using BaF3-human Mpl or BaF3-monkey Mpl that proliferate in a TPO-dependent manner.

Cells from each cell line were washed twice with RPMI 1640/1% FBS (fetal bovine serum) (Invitrogen), and then suspended in RPMI 1640/10% FBS to a concentration of $4\times10^5$ cells/mL. Cell suspensions were aliquoted at 60-μL/well into a 96-well plate. Various concentrations of rhTPO (R&D) and COS7 culture supernatants or purified samples were prepared, and a 40-μL aliquot was added into each well. The plates were then incubated at 37° C. under 5% $CO_2$ for 24 hr. Immediately after a 10-μL aliquot of WST-8 reagent (Cell Count Reagent SF; Nacalai Tesque) was added into each well, absorbance was measured at 450 nm (and at 655 nm as a control) using Benchmark Plus. After two hours of incubation, absorbance was again measured at 450 nm (and at 655 nm as a control). The WST-8 reagent changes colors at 450 nm in a color reaction that reflects the viable cell count. The TPO-like agonistic activity was assessed using the change in absorbance during the two-hour incubation as an index. $EC_{50}$ values were computed using GraphPad Prism.

TPO-like agonistic activity was assayed using the human leukemia cell line M-07e (purchased from DSMZ) which proliferates TPO-dependently. M-07e cells were washed twice with RPMI 1640/1% FBS, and then suspended in RPMI 1640/10% FBS to a concentration of $5\times10^5$ cells/mL. The resulting cell suspension was aliquoted at 50-μL/well into a 96-well plate. Various concentrations of rhTPO and COS7 culture supernatants or purified samples were prepared, and a 50-μL aliquot was added into each well. The plates were then incubated at 37° C. under 5% $CO_2$ for 48 hr. Immediately after a 10-μL aliquot of WST-8 reagent (Cell Count Reagent SF; Nacalai Tesque) was added to each well, absorbance of was measured at 450 nm (and at 655 nm as a control) using a Benchmark Plus. After four hours of incubation, absorbance was again measured at 450 nm (and at 655 nm as a control). The TPO-like agonistic activity was assayed using the change in absorbance during the four-hour incubation as an index.

Figure 3:
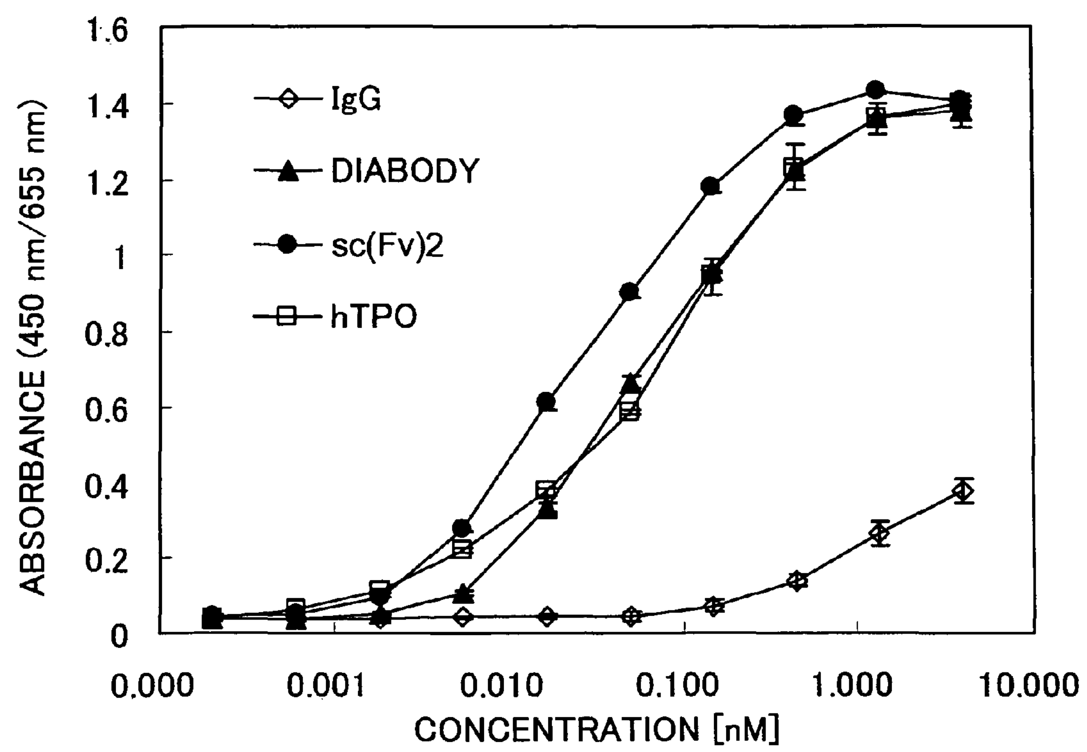
FIG. 3 illustrates the assessment of VB22B antibody agonistic activity using BaF3-human Mpl.
Figure 4:
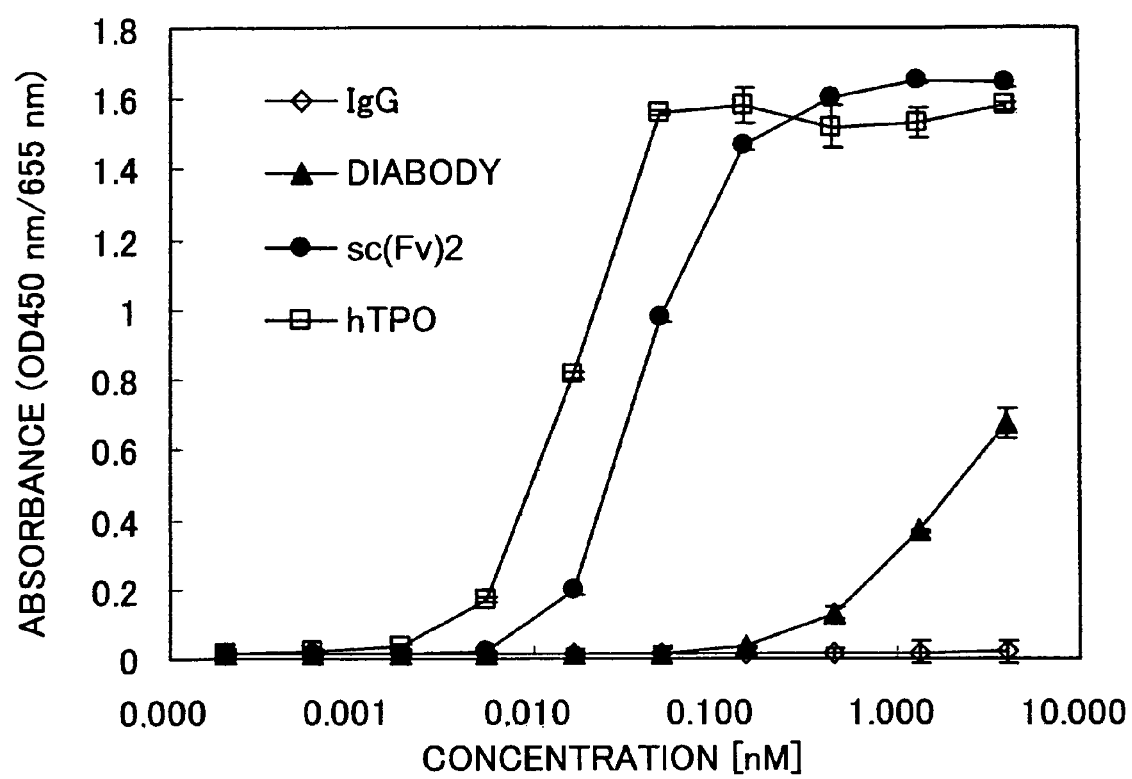
FIG. 4 illustrates the assessment of VB22B antibody agonistic activity using BaF3-monkey Mpl.
Figure 5:
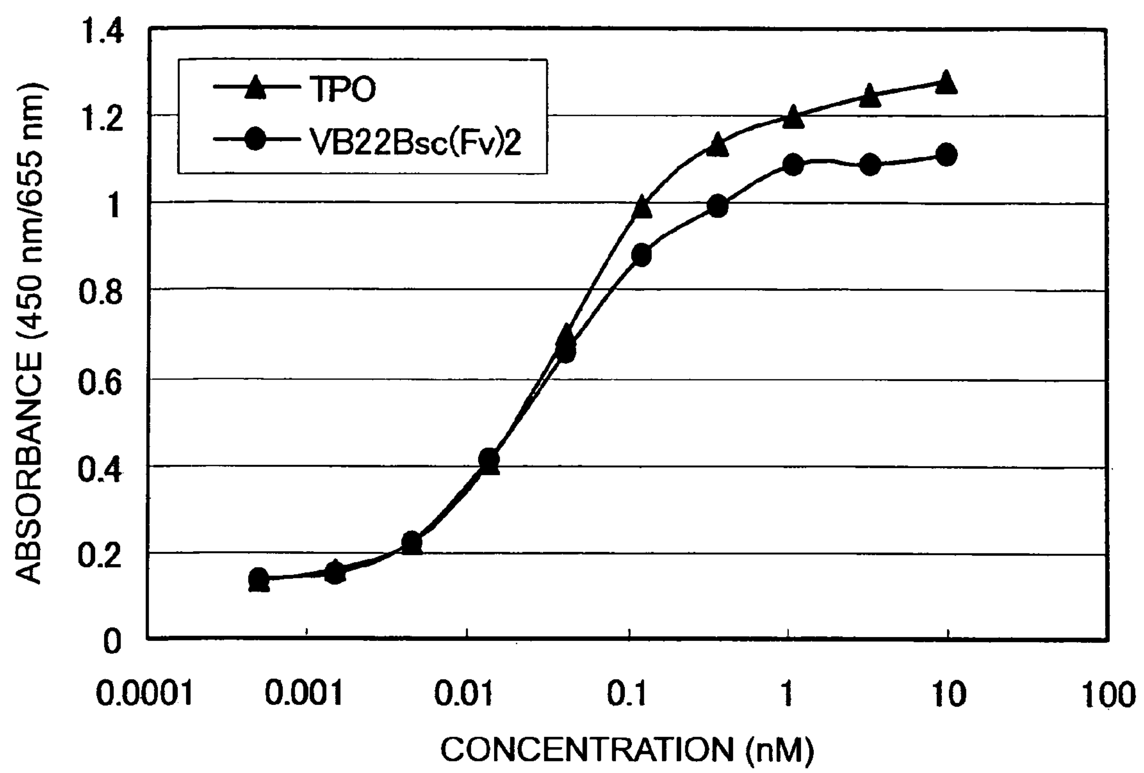
FIG. 5 illustrates the assessment of VB22B antibody agonistic activity using M-07e.

Purified VB22B IgG, VB22B diabody, and VB22B sc(Fv)2 were assayed for their TPO-like agonistic activities using BaF3-human Mpl, BaF3-monkey Mpl, and M-07e. The results are shown in FIGS. 3, 4, and 5, respectively. The presence of bivalent antigen-binding domains in a single antibody molecule is essential for its agonistic activity. The distance and angle between two antigen-binding domains can also be important factors (see WO 02/33073 and WO 02/33072). Similar results were obtained for the newly isolated anti-human Mpl antibodies. Specifically, the agonistic activities of VB22B diabody and VB22B sc(Fv)2 ($EC_{50}$=61 pM and 27 pM in BaF3-human Mpl, respectively) were higher than that of VB22B IgG ($EC_{50}$>30 nM in BaF3-human Mpl), and were equivalent to or higher than that of the naturally-occurring human TPO ligand ($EC_{50}$=76 pM in BaF3-human Mpl). The VB22B diabody activity was lower than that of VB22B sc(Fv)2. This suggests that the structure of a single-chain antibody is greatly altered by its molecular shape and the length of the linker sequence, which in turn changes the agonistic activity. Sixteen types of the single-chain anti-human Mpl antibodies were obtained, each exhibiting a high agonistic activity. The amino acid sequences of the H chain and L chain variable regions of the representative antibodies are shown in FIGS. 6 and 7, respectively.

2.9 Humanization of Single-Chain Anti-Human Mpl Antibody

Antibody sequence data for the humanization of VB22B sc(Fv)2 were obtained from the Kabat Database (ftp://ftp.ebi.ac.uk/pub/databases/kabat/), and homology searches were carried out independently for the H chain variable region and the L chain variable region. As a result, the H chain variable region was found to be highly homologous to DN13 (Smithson S. L. et al., Mol Immunol. 36, 113-124 (1999)). The L chain variable region was found to be highly homologous to ToP027 (Hougs L. et al., J. Immunol. 162, 224-237 (1999)). Humanized antibodies were prepared by inserting a complementarity-determining region (hereinafter abbreviated as "CDR") into the framework regions (hereinafter abbreviated as "FR") of the above antibodies. The humanized antibody sc(Fv)2 was expressed in CHO-DG44 cells, and its agonistic activity was assessed using BaF3-human Mpl. The agonistic activity was used as an index to generate a humanized VB22B sc (Fv) 2 which has agonistic activity equivalent to that of murine VB22B sc(Fv)2 by replacing one or more amino acids in its framework region.

Specifically, synthetic oligo-DNAs of approximately 50 nucleotides in length were designed as to make 20 of these nucleotides available for hybridization, and the synthetic oligo-DNAs were assembled by PCR to prepare genes that encode the respective variable regions. Using the resulting genes, sc(Fv)2 was similarly prepared by the method described in Example 2.3. The respective DNAs were cloned into a pCXND3 expression vector to construct expression vectors pCXND3-hVB22B p-z sc(Fv)2, pCXND3-hVB22B g-e sc(Fv)2, pCXND3-hVB22B e sc(Fv)2, pCXND3-hVB22B u2-wz4 sc(Fv)2, and pCXND3-hVB22B q-wz5 sc(Fv)2, to which the humanized VB22B sc(Fv)2 is inserted. The nucleotide sequences and the amino acid sequences of the fragments in each plasmid are shown below.

| Plasmid name | Nucleotide sequence | Amino acid sequence |
|---|---|---|
| hVB22B p-z sc(Fv)2 | SEQ ID NO: 1 | SEQ ID NO: 2 |
| hVB22B g-e sc(Fv)2 | SEQ ID NO: 253 | SEQ ID NO: 254 |
| hVB22B e sc(Fv)2 | SEQ ID NO: 259 | SEQ ID NO: 260 |
| hVB22B u2-wz4 sc(Fv)2 | SEQ ID NO: 286 | SEQ ID NO: 287 |
| hVB22B q-wz5 sc(Fv)2 | SEQ ID NO: 292 | SEQ ID NO: 293 |
| Murine VB22B sc(Fv)2 | SEQ ID NO: 263 | SEQ ID NO: 264 |

Figure 19:
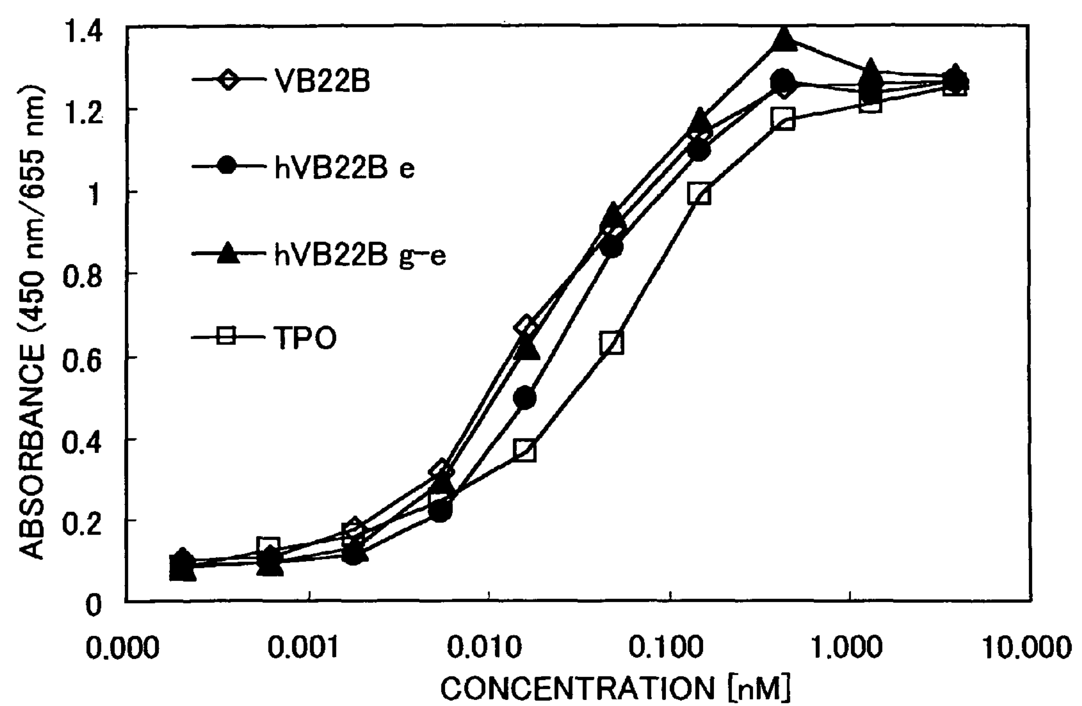
FIG. 19 shows the TPO-like agonistic activities of murine VB22B sc(Fv)2, hVB22B e sc(Fv)2, and hVB22B g-e sc(Fv)2 in BaF3-human Mpl. The X-axis shows absorbance ratio (450 nm/655 nm), and the Y-axis represents concentration.
Figure 20:
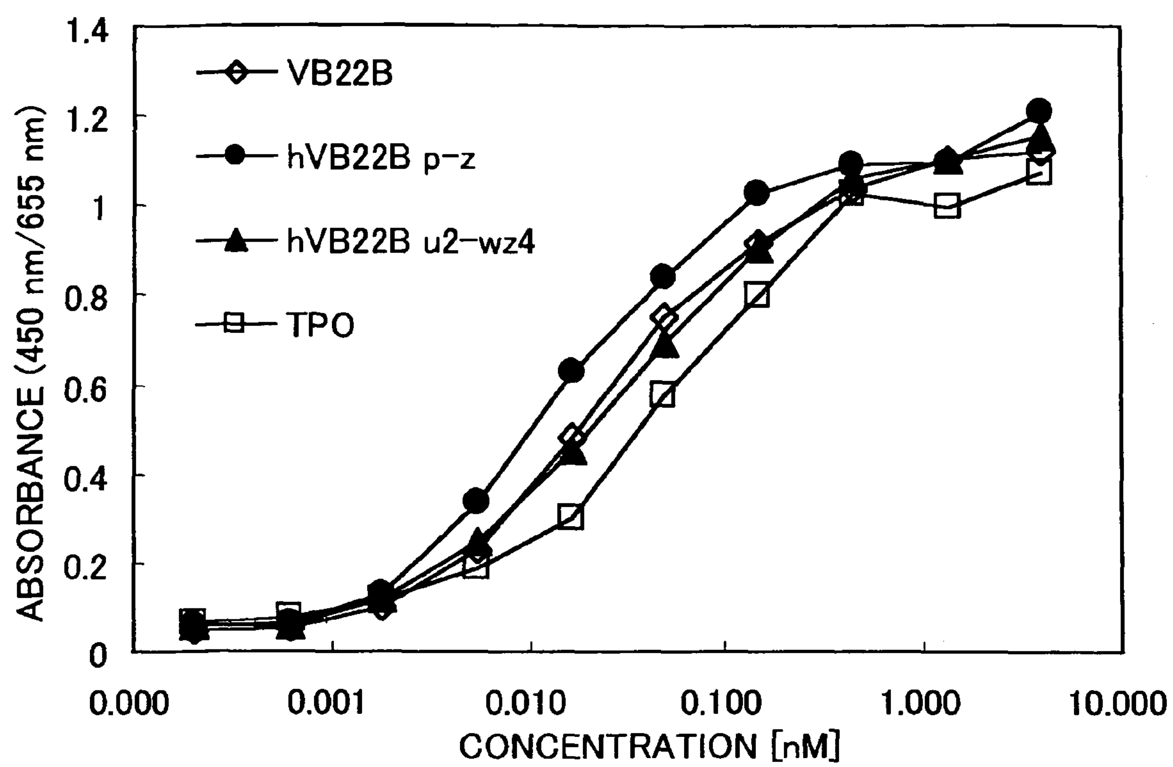
FIG. 20 shows the TPO-like agonistic activities of murine VB22B sc(Fv)2, hVB22B p-z sc(Fv)2, and hVB22B u2-wz4 sc(Fv)2 in BaF3-human Mpl. TheX-axis shows absorbance ratio (450 nm/655 nm), and theY-axis represents concentration.
Figure 21:
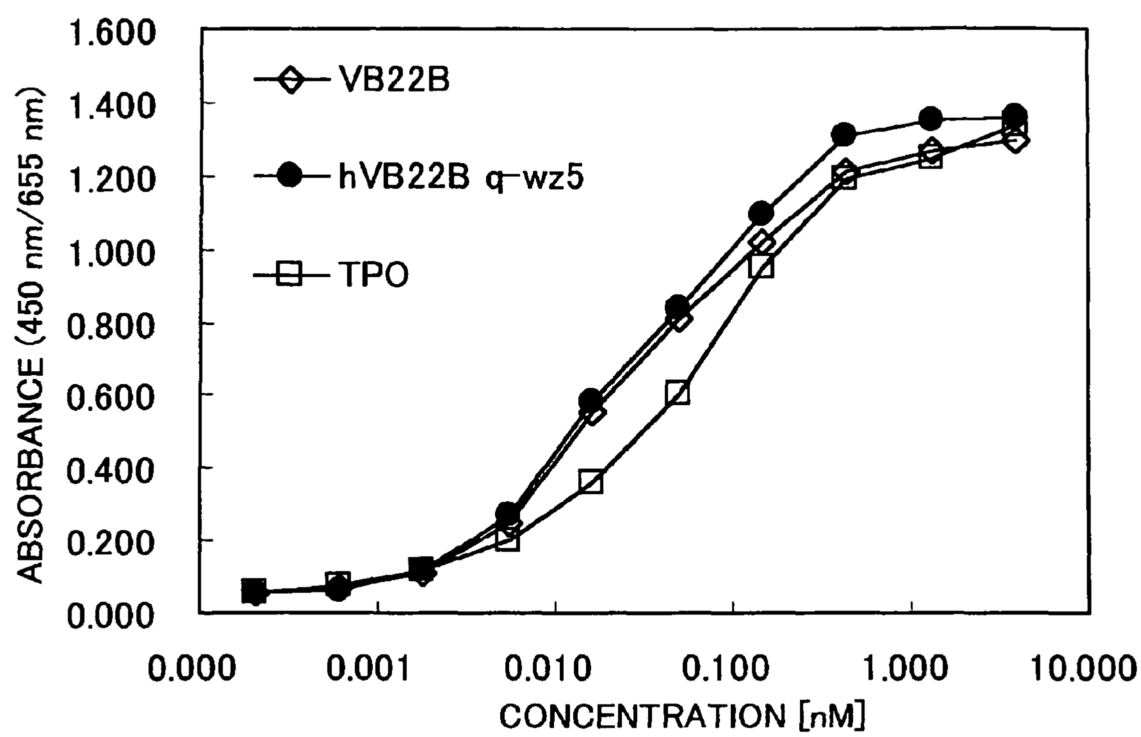
FIG. 21 shows the TPO-like agonistic activities of murine VB22B sc(Fv) 2 and hVB22B q-wz5 sc(Fv)2 in BaF3-human Mpl. The X-axis shows absorbance ratio (450 nm/655 nm), and the Y-axis represents concentration.

The plasmids were expressed in CHO-DG44 cells and the culture supernatants were recovered by the method described in Example 2.4. Since the humanized VB22B sc(Fv)2 does not contain a Flag tag, its purification from the culture supernatant was performed using a MG10-GST fusion protein. MG10 (Gln213 to Ala231) is one of the epitopes recognized by VB22B, as described in Example 1.8. The MG10-GST fusion protein was purified using Glutathione Sepharose 4B (Amersham Biosciences) according to the supplier's protocol. Then, the purified MG10-GST fusion protein was immobilized onto a HiTrap NHS-activated HP Column (Amersham Biosciences) to prepare an affinity column, according to the supplier's protocol. The culture supernatant of CHO cells expressing the humanized VB22B sc(Fv)2 was loaded onto the MG10-GST fusion protein-immobilized column, which has been equilibrated with 50 mM Tris-HCl (pH7.4)/150 mM NaCl/0.01% Tween 80. The adsorbed humanized VB22B sc(Fv)2 was eluted with 100 mM glycine-HCl (pH3.5)/0.01% Tween 80. Immediately after elution, the eluted fraction was neutralized with 1 M Tris-HCl (pH7.4), and was further subjected to gel filtration chromatography using a HiLoad 16/60 Superdex 200 pg (Amersham Biosciences). 20 mM citrate buffer (pH7.5) containing 300 mM NaCl and 0.01% Tween 80 was used in the gel filtration chromatography. The TPO-like agonistic activities of the purified samples were similarly determined using the method described in Example 2.8. The TPO-like agonistic activities of the purified murine VB22B sc(Fv)2, hVB22B p-z sc(Fv)2, hVB22B u2-wz4 sc(Fv)2, hVB22B q-wz5 sc(Fv)2, and humanized hVB22B e sc(Fv)2 and hVB22B g-e sc(Fv)2 were assessed in BaF3-human Mpl. The results are shown in FIGS. 19, 20, and 21. The humanized VB22B sc(Fv)2 showed comparable agonistic activities, suggesting that the humanization has no influence on the activity.

2.10 Kinetic Analyses of the Antigen-Antibody Reaction for Anti-Human Mpl Antibodies: VB22B IgG, VB22B sc(Fv)2, and Humanized VB22B sc(Fv)2

Using the soluble recombinant Mpl-binding characteristic of anti-human Mpl antibody VB22B, kinetic analyses of the antigen-antibody reactions between the MG10 (Gln 213 to Ala 231)-GST fusion protein and each of VB22B IgG, VB22B sc(Fv)2, and humanized VB22B sc (Fv) 2 were carried out as described in Example 1.8. The Sensor Chip CM5 (Biacore) was placed in Biacore 3000 (Biacore), and MG10-GST fusion protein was immobilized onto the chip by amine-coupling methods. HBS-EP Buffer (Biacore) was used as the running buffer, and the flow rate was 20 μL/min. 5.5 to 175.0 nM of VB22B IgG solution was prepared using HBS-EP Buffer, and injected over each of the chip surfaces for 2 min to obtain the binding region at the respective concentrations. Then, dissociation region for the 2 minutes was measured. VB22B IgG bound to the MG10-GST fusion protein on the sensor chip was removed by injecting 20 mM HCl over the sensor chip for 1 min, and the chip was recovered. Similarly, 4.7 to 150.1 nM of VB22B sc(Fv)2, 5.3 to 168.9 nM of hVB22B q-wz5 sc(Fv)2, and 4.9 to 156.8 nM of hVB22B u2-wz4 sc(Fv)2 were prepared and injected over the chip surfaces onto which MG10-GST fusion protein was immobilized, and the measurement was carried out.

All the antibodies used were bivalent antibodies, and thus the sensorgrams at each concentration were obtained in the presence of both monovalent and bivalent bindings. In this context, the reaction rate constant was determined as that for the monovalent antibody by analysis using the Bivalent analyte model of BIAevaluation ver.3.1 software (Biacore). The above analysis was carried out in triplicates for each antibody. The binding rate constant (ka), dissociation rate constant (kd), and dissociation constant (KD) were determined as those for the monovalent antibody by the procedure described above. The constants are indicated below in Table 1. The dissociation constants (KD) for VB22B IgG, VB22B sc(Fv)2, hVB22B q-wz5 sc(Fv)2, and hVB22B u2-wz4 sc(Fv)2 were determined to be $1.15\times10^{-6}$ M, $1.17\times10^{-8}$ M, $1.36\times10^{-8}$ M, and $1.02\times10^{-8}$ M, respectively, showing nearly equivalent binding activities towards the MG10-GST fusion protein.

TABLE 1

Kinetic analyses of the antigen-antibody reaction for anti-human Mpl antibodies

| Antibody Name | ka (1/Ms) [$\times10^5$] | kd (1/s) [$\times10^{-3}$] | KD (M) [$\times10^{-8}$] |
|---|---|---|---|
| VB22B IgG | 0.96 ± 0.78 | 1.10 ± 0.01 | 1.15 ± 0.09 |
| VB22B sc(Fv)2 | 4.23 ± 0.22 | 4.91 ± 0.72 | 1.17 ± 0.23 |
| hVB22B q-wz5 sc(Fv)2 | 3.76 ± 0.38 | 5.10 ± 0.56 | 1.36 ± 0.06 |
| hVB22B u2-wz4 sc(Fv)2 | 6.08 ± 0.30 | 6.17 ± 0.23 | 1.02 ± 0.08 |

Example 3

Preparation of Anti-Mpl Diabodies by the AGS Method

Anti-Mpl diabodies having agonistic activity were prepared by an Autocrine Growth Selection (AGS) method (see, WO 03/91424).

3.1 Construction of a Retrovirus Library

Spleens were isolated from MRL/lpr mice immunized with shMPL-Flag by the method described in Example 1.5, and homogenized in TRIZOL Reagent (Invitrogen) using a Dounce homogenizer. After chloroform addition, the homogenized sample was shaken vigorously, the aqueous phase was removed and total RNA was extracted by isopropanol precipitation. mRNA was purified using a PolyATract System 1000 (Promega). Reverse transcription of 2.5 μg mRNA was carried out at 42° C. for 50 min using the Superscript First strand synthesis system for RT-PCR (Invitrogen) and the included oligo-dT primers to prepare cDNA.

The composition of the PCR reaction solution (250 μL) is shown below.

| | |
|---|---|
| 10x KOD Plus Buffer (Toyobo) | 25 μL |
| 2 mM dNTPs (dATP, dGTP, dCTP, and dTTP) (Toyobo) | 25 μL |
| 2.5 mM $MgSO_4$ (Toyobo) | 10 μL |
| KOD Plus (Toyobo) | 7.5 μL |
| Reverse transcription products | 25 μL |

-continued

| | |
|---|---|
| Mixed primers complementary to H chain or L chain variable region | 500 pmol |

The reaction conditions were:

98° C. (initial temperature) for 3 min;

32 cycles of 98° C. for 20 sec, 58° C. for 20 sec, and 72° C. for 30 sec;

and final extension was at 72° C. for 6 min.

The H chain primer mix contained HS1 to HS19 (SEQ ID NOs: 178 to 196) and HA1 to HA4 (SEQ ID NOs: 197 to 200), which were mixed at the indicated ratios next to the sequence names in Table 2. The L chain primer mix contained LS1 to LS17 (SEQ ID NOs: 201 to 217), Lslambda (SEQ ID NO: 218), LA1 to LA5 (SEQ ID NOs: 219 to 222), and Lalambda (SEQ ID NO: 223). The respective PCR products were purified from agarose gel using the QIAquick Gel Extraction Kit (QIAGEN). The H chain and L chain variable regions were linked via the $(Gly_4Ser)_1$ linker sequence by PCR using sc-S (SEQ ID NO: 224) and sc-AS (SEQ ID NO: 225) as described below.

The composition of the PCR reaction solution (100 μL in total) is shown below.

| | |
|---|---|
| 10x KOD Plus Buffer (Toyobo) | 10 μL |
| 2 mM dNTPs (dATP, dGTP, dCTP, and dTTP) (Toyobo) | 10 μL |
| 2.5 mM $MgSO_4$ (Toyobo) | 4 μL |
| KOD Plus (Toyobo) | 2 μL |
| Fragment of H chain variable region | 4 μL |
| Fragment of L chain variable region | 4 μL |

The first-round PCR conditions were:

94° C. (initial temperature) for 3 min; and seven cycles of 94° C. for 1 min and 63° C. for 4 min.

Then, sc-S and sc-AS (25 pmol each) were added to the first-round products.

The second-round PCR conditions were:

30 cycles of 94° C. for 30 sec, 55° C. for 2 min, and 72° C. for 2 min;

and final extension was at 72° C. for 6 min.

The resulting product with an SfiI restriction site at both ends was purified using the QIAquick PCR Purification Kit (QIAGEN), and incubated with the SfiI restriction enzyme (TaKaRa) overnight at 50° C. The PCR product purified from agarose gel using the QIAquick Gel Extraction Kit (QIAGEN) was inserted into the SfiI site of the viral vector pMX/IL3ssGFPHis.

The resulting plasmid was constructed by inserting a GFP gene, which has an EcoRI site, mouse IL-3 signal sequence and SfiI site at its 5' end; and an SfiI site, His tag sequence, termination codon, and NotI site at its 3' end, between the EcoRI and NotI sites on the pMX viral vector (Onishi, M. et al., Mol. Cell. Biol. 18, 3871-3879). The plasmid was introduced into the ElectroMAX DH10B T1 phage resistant cells (Invitrogen) by electroporation (settings: 2.5 kV, 25 μF, and 100Ω) using a Gene Pulser II (Bio-Rad). The cells were plated onto an LB-Agar plate containing 100 μg/mL ampicillin. After overnight incubation, $1\times10^7$ colonies were obtained. Colonies were recovered from the plate and plasmids were then extracted using the QIAGEN Plasmid Maxi Kit (QIAGEN).

TABLE 2

| | |
|---|---|
| SEQ ID NO: 178 (HS1 (4)) | GCCCAGCCGGCCATGGCGGAKGTRMAGCTTCAGGAGTC |
| SEQ ID NO: 179 (HS2 (4)) | GCCCAGCCGGCCATGGCGGAGGTBCAGCTBCAGCAGTC |
| SEQ ID NO: 180 (HS3 (3)) | GCCCAGCCGGCCATGGCGCAGGTGCAGCTGAAGSASTC |
| SEQ ID NO: 181 (HS4 (4)) | GCCCAGCCGGCCATGGCGGAGGTCCARCTGCAACARTC |
| SEQ ID NO: 182 (HS5 (7)) | GCCCAGCCGGCCATGGCGCAGGTYCAGCTBCAGCARTC |
| SEQ ID NO: 183 (HS6 (2)) | GCCCAGCCGGCCATGGCGCAGGTYCARCTGCAGCAGTC |
| SEQ ID NO: 184 (HS7 (1)) | GCCCAGCCGGCCATGGCGCAGGTCCACGTGAAGCAGTC |
| SEQ ID NO: 185 (HS8 (2)) | GCCCAGCCGGCCATGGCGGAGGTGAASSTGGTGGAATC |
| SEQ ID NO: 186 (HS9 (5)) | GCCCAGCCGGCCATGGCGGAVGTGAWGYTGGTGGAGTC |
| SEQ ID NO: 187 (HS10 (2)) | GCCCAGCCGGCCATGGCGGAGGTGCAGSKGGTGGAGTC |
| SEQ ID NO: 188 (HS11 (2)) | GCCCAGCCGGCCATGGCGGAKGTGCAMCTGGTGGAGTC |
| SEQ ID NO: 189 (HS12 (2)) | GCCCAGCCGGCCATGGCGGAGGTGAAGCTGATGGARTC |
| SEQ ID NO: 190 (HS13 (1)) | GCCCAGCCGGCCATGGCGGAGGTGCARCTTGTTGAGTC |
| SEQ ID NO: 191 (HS14 (2)) | GCCCAGCCGGCCATGGCGGARGTRAAGCTTCTCGAGTC |
| SEQ ID NO: 192 (HS15 (2)) | GCCCAGCCGGCCATGGCGGAAGTGAARSTTGAGGAGTC |
| SEQ ID NO: 193 (HS16 (5)) | GCCCAGCCGGCCATGGCGCAGGTTACTCTRAAAGWGTSTG |
| SEQ ID NO: 194 (HS17 (3.5)) | GCCCAGCCGGCCATGGCGCAGGTCCAACTVCAGCARCC |
| SEQ ID NO: 195 (HS18 (0.7)) | GCCCAGCCGGCCATGGCGGATGTGAACTTGGAAGTGTC |
| SEQ ID NO: 196 (HS19 (0.7)) | GCCCAGCCGGCCATGGCGGAGGTGAAGGTCATCGAGTC |
| SEQ ID NO: 197 (HA1 (1)) | GGAGCCGCCGCCGCCCGAGGAAACGGTGACCGTGGT |

TABLE 2-continued

| | |
|---|---|
| SEQ ID NO: 198 (HA2 (1)) | GGAGCCGCCGCCGCCCGAGGAGACTGTGAGAGTGGT |
| SEQ ID NO: 199 (HA3 (1)) | GGAGCCGCCGCCGCCCGCAGAGACAGTGACCAGAGT |
| SEQ ID NO: 200 (HA4 (1)) | GGAGCCGCCGCCGCCCGAGGAGACGGTGACTGAGGT |
| SEQ ID NO: 201 (LS1 (1)) | GGCGGCGGCGGCTCCGAYATCCAGCTGACTCAGCC |
| SEQ ID NO: 202 (LS2 (2)) | GGCGGCGGCGGCTCCGAYATTGTTCTCWCCCAGTC |
| SEQ ID NO: 203 (LS3 (5)) | GGCGGCGGCGGCTCCGAYATTGTGMTMACTCAGTC |
| SEQ ID NO: 204 (LS4 (3.5)) | GGCGGCGGCGGCTCCGAYATTGTGYTRACACAGTC Z |
| SEQ ID NO: 205 (LS5 (4)) | GGCGGCGGCGGCTCCGAYATTGTRATGACMCAGTC |
| SEQ ID NO: 206 (LS6 (7)) | GGCGGCGGCGGCTCCGAYATTMAGATRAMCCAGTC |
| SEQ ID NO: 207 (LS7 (6)) | GGCGGCGGCGGCTCCGAYATTCAGATGAYDCAGTC |
| SEQ ID NO: 208 (LS8 (1.5)) | GGCGGCGGCGGCTCCGAYATYCAGATGACACAGAC |
| SEQ ID NO: 209 (LS9 (2)) | GGCGGCGGCGGCTCCGAYATTGTTCTCAWCCAGTC |
| SEQ ID NO: 210 (LS10 (3.5)) | GGCGGCGGCGGCTCCGAYATTGWGCTSACCCAATC |
| SEQ ID NO: 211 (LS11 (8)) | GGCGGCGGCGGCTCCGAYATTSTRATGACCCARTC |
| SEQ ID NO: 212 (LS12 (8)) | GGCGGCGGCGGCTCCGAYRTTKTGATGACCCARAC |
| SEQ ID NO: 213 (LS13 (6)) | GGCGGCGGCGGCTCCGAYATTGTGATGACBCAGKC |
| SEQ ID NO: 214 (LS14 (2)) | GGCGGCGGCGGCTCCGAYATTGTGATAACYCAGGA |
| SEQ ID NO: 215 (LS15 (2)) | GGCGGCGGCGGCTCCGAYATTGTGATGACCCAGWT |
| SEQ ID NO: 216 (LS16 (1)) | GGCGGCGGCGGCTCCGAYATTGTGATGACACAACC |
| SEQ ID NO: 217 (LS17 (1)) | GGCGGCGGCGGCTCCGAYATTTTGCTGACTCAGTC |
| SEQ ID NO: 218 (LSlambda (1)) | GGCGGCGGCGGCTCCGATGCTGTTGTGACTCAGGAATC |
| SEQ ID NO: 219 (LA1 (4)) | GGAATTCGGCCCCCGAGGCCTTGATTTCCAGCTTGG |
| SEQ ID NO: 220 (LA2 (4)) | GGAATTCGGCCCCCGAGGCCTTTATTTCCAGCTTGG |
| SEQ ID NO: 221 (LA4 (4)) | GGAATTCGGCCCCCGAGGCCTTTATTTCCAACTTTG |
| SEQ ID NO: 222 (LA5 (4)) | GGAATTCGGCCCCCGAGGCCTTCAGCTCCAGCTTGG |
| SEQ ID NO: 223 (LAlambda (1)) | GGAATTCGGCCCCCGAGGCCCCTAGGACAGTCAGTTTGG |

3.2 Establishment of Autonomously Replicating Cell Lines by the AGS Method

The resulting library was transfected into a packaging cell, Pt-E, (Morita, S. et al., Gene therapy 7, 1063-1066 (2003)) using FuGENE 6 (Roche Diagnostics). Specifically, Pt-E was plated onto 6-cm dishes and cultured in DMEM/10% FBS (Invitrogen). A mixture of FuGENE 6 and the library was added to the plate the following day. The culture medium was exchanged the next day, and the culture supernatant was collected 24 hours after that. 10 μg/mL polybrene (Hexadimethrine Bromide; Sigma) and 2 ng/mL mIL-3 were added to the culture supernatant containing recombinant virus particles. The viral solution was used to infect the BaF3-monkey Mpl target cells. The cells were washed with PBS the following day, and suspended in RPMI 1640/10% FBS minus mIL-3. The suspension was plated onto a 96-well plate at a cell density of 1,000 cells/well. Autonomously replicating cell lines (AB317 and AB324) were obtained after seven days of incubation. Genomic DNAs were extracted from these cells using a DNeasy Tissue Kit (QIAGEN), and the antibody genes were amplified by PCR.

The composition of the PCR reaction solution (50 μL in total) is shown below.

| | |
|---|---|
| 10x LA Taq Buffer (TaKaRa) | 5 μL |
| 2 mM dNTPs (dATP, dGTP, dCTP, and dTTP) (TaKaRa) | 5 μL |
| 2.5 mM $MgCl_4$ (TaKaRa) | 5 μL |
| TaKaRa LA Taq (TaKaRa) | 0.5 μL |
| Genomic DNA | 0.5 μg |
| AGSdbS1 (SEQ ID NO: 226) and AGSdbA1 (SEQ ID NO: 227) | 25 pmol |

The reaction conditions were:

94° C. (initial temperature) for 1 min;

30 cycles of 94° C. for 30 sec, 60° C. for 30 sec, and 70° C. for 1 min;

and final extension was at 72° C. for 6 min.

The nucleotide sequences and the amino acid sequences of the fragments of cloned antibodies are shown below.

| Fragment | | Nucleotide sequence | Amino acid sequence |
|---|---|---|---|
| AB317 | H chain | SEQ ID NO: 154 | SEQ ID NO: 155 |
| | L chain | SEQ ID NO: 156 | SEQ ID NO: 157 |
| AB324 | H chain | SEQ ID NO: 158 | SEQ ID NO: 159 |
| | L chain | SEQ ID NO: 160 | SEQ ID NO: 161 |

3.3 Activity Assays of the Diabodies Obtained by AGS Method

Each of the anti-Mpl diabodies obtained above was inserted into the pCXND3 expression vector. The PCR primers used are a synthetic oligonucleotide complementary to the 5' end of the diabody and containing an EcoRI site, and a synthetic oligonucleotide complementary to the nucleotide sequence of the 3' end of the diabody and containing a FLAG tag and a NotI site. The PCR product thus obtained was inserted into pCXND3 between the EcoRI and NotI sites. The diabody was expressed transiently in COS7 cells by the method described in Example 2.4. The culture supernatant was removed and the activity of the diabody was evaluated.

Figure 8:
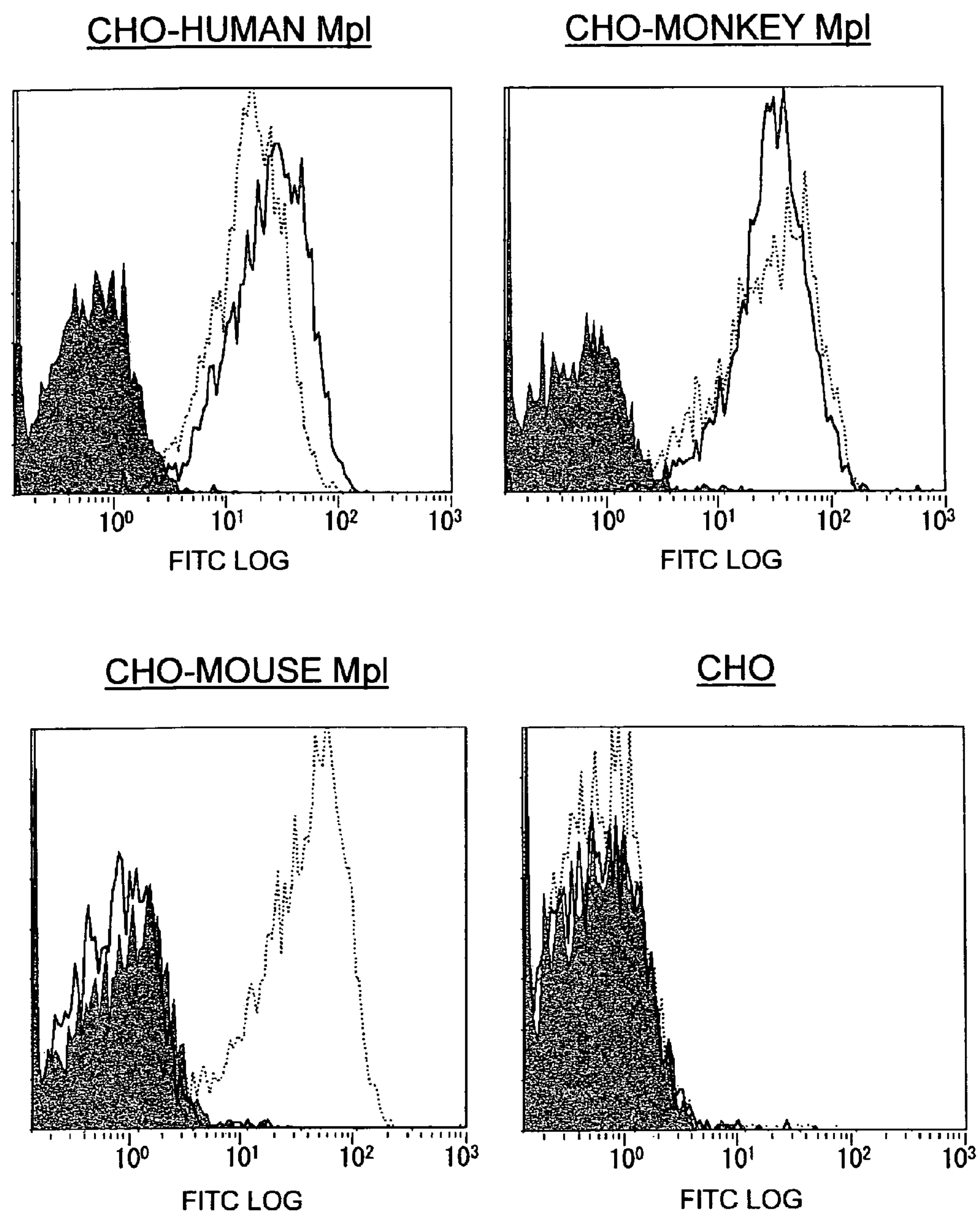
FIG. 8 illustrates the binding activity assessment of AB317 diabody using Mpl-expressing CHO cells. Both VB22B diabody (solid line) and AB317 diabody (broken line) were obtained from COS7 culture supernatants.

The binding activities of the diabodies were assessed by flow cytometry using CHO cells that express Mpl derived from various species (FIG. 8). AB317 was proven to bind to CHO-mouse Mpl.

Figure 9:
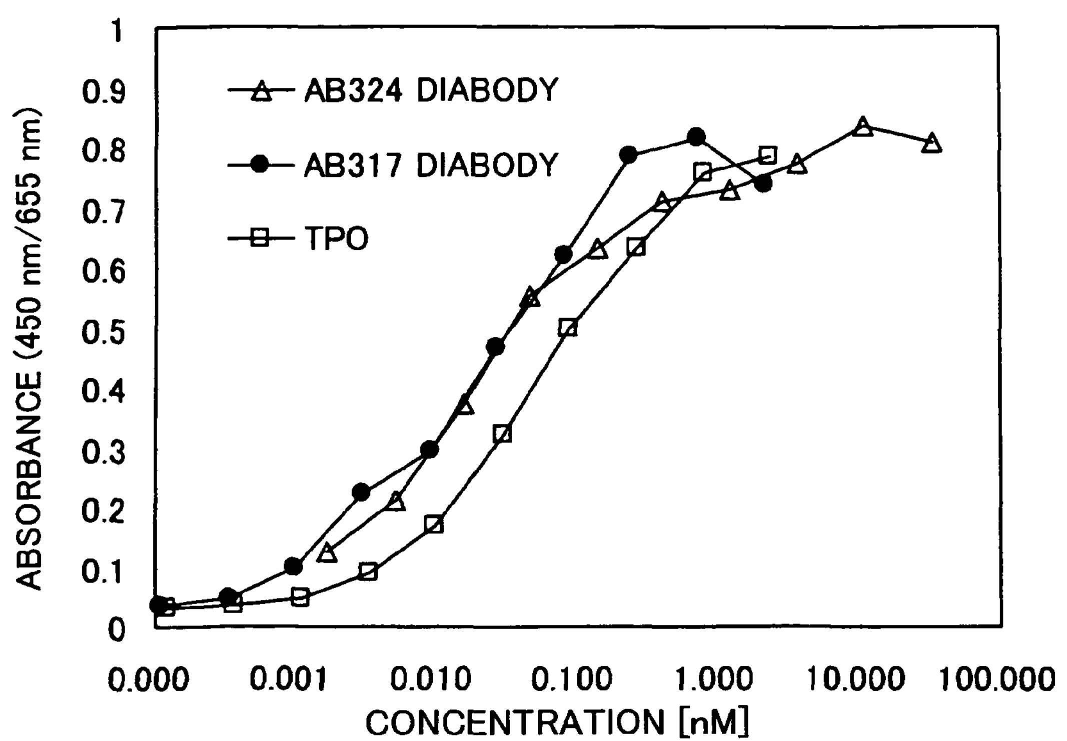
FIG. 9 illustrates the agnostic activity assessment of AB324 and AB317 diabodies using BaF3-human Mpl.
Figure 10:
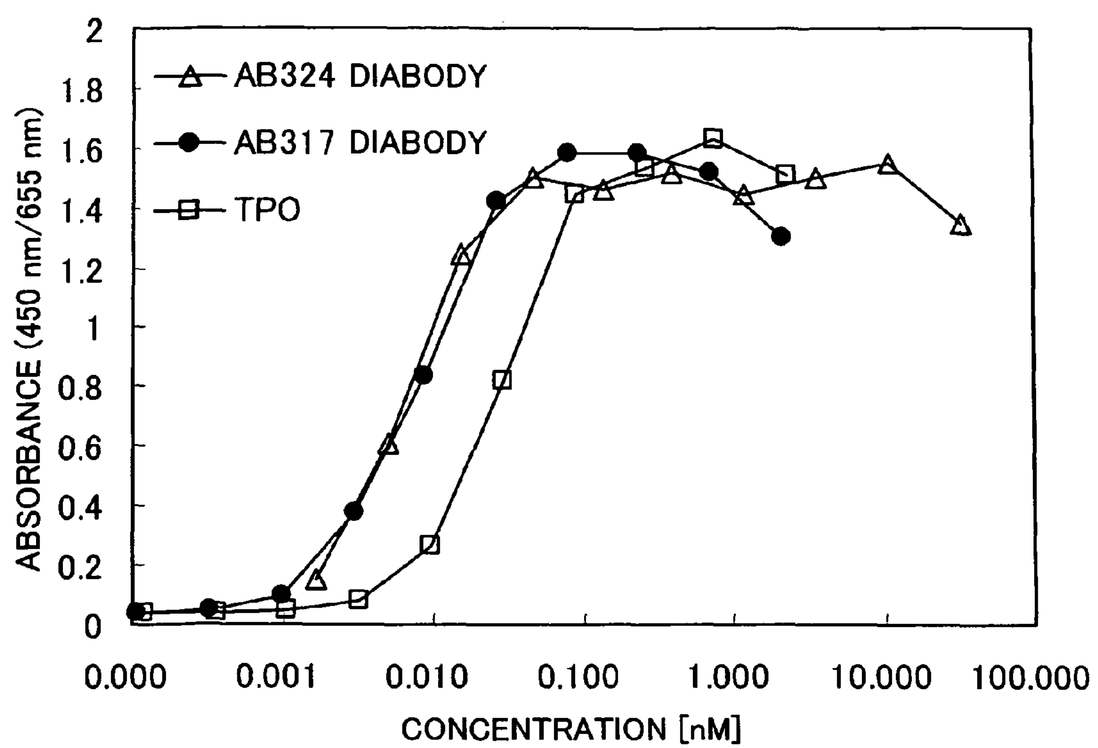
FIG. 10 illustrates the agnostic activity assessment of AB324 and AB317 diabodies using BaF3-monkey Mpl.
Figure 11:
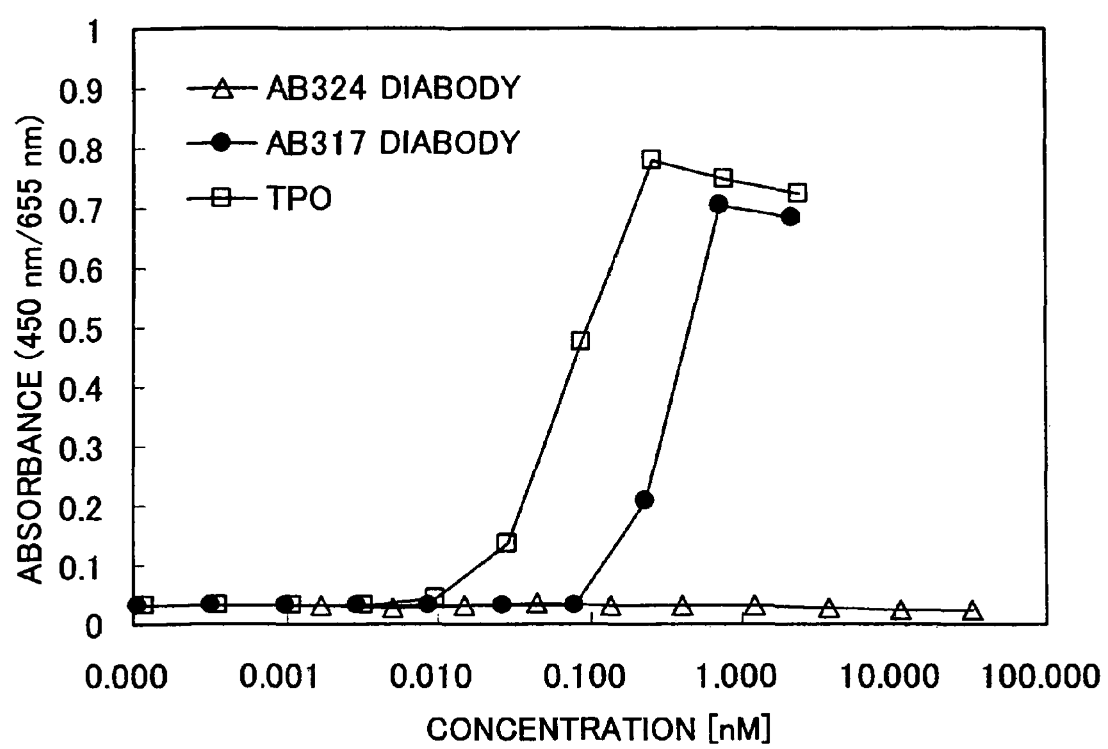
FIG. 11 illustrates the agnostic activity assessment of AB324 and AB317 diabodies using BaF3-mouse Mpl.

The TPO-like agonistic activities of the diabodies were evaluated using BaF3-human Mpl, BaF3-monkey Mpl, and BaF3-mouse Mpl (FIGS. 9, 10, and 11). AB317 had the highest agonistic activity against human, monkey, and mouse Mpl, whereas AB324 showed the highest agonistic activity against human and monkey Mpl.

This proves that anti-Mpl diabodies having high agonistic activity can be obtained by the AGS method.

Example 4

Agonistic Activity Assays of the Anti-Mpl Antibodies Against Mutant Mpl in Congenital Amegakaryocytic Thrombocytopenia (CAMT) Patients 4.1 Establishment of BaF3 Cell Lines Introduced with the Mutant Mpl Observed in CAMT Patients Mutations on G305C(R102P), C769T (R257C), and C823A (P275T) have been reported in the Mpl gene of CAMT patients. The respective expression vectors carrying the Mpl gene mutations were constructed and introduced into BaF3 cells. The following Mpl gene fragments were constructed.

| Fragment | Nucleotide sequence | Amino acid sequence |
|---|---|---|
| Normal Mpl gene | SEQ ID NO: 246 | SEQ ID NO: 123 |
| Mutant Mpl gene, G305C, in which C is substituted for 305th nucleotide G relative to the initiation codon | SEQ ID NO: 247 | SEQ ID NO: 248 |
| Mutant Mpl gene, C769T, in which T is substituted for 769th nucleotide C | SEQ ID NO: 249 | SEQ ID NO: 250 |
| Mutant Mpl gene, C823A, in which A is substituted for 823rd nucleotide C | SEQ ID NO: 251 | SEQ ID NO: 252 |

The above-described DNA fragments were digested with EcoRI and SalI, and inserted between the EcoRI and SalI sites on the animal cell expression vector pCOS2-Ha to prepare pCOS2-hMPLfullG305C, pCOS2-hMPLfullC769T, and pCOS2-hMPLfullC823A.

The genes were introduced into BaF3 cells by the procedure described in Example 1.1 to establish BaF3 cell lines expressing each Mpl gene: BaF3-human MPL (G305C), BaF3-human MPL (C769T), and BaF3-human MPL (C823A). After the selection, the cells were cultured and passaged using RPMI 1640 containing 1 ng/mL mIL-3 and 10% FBS.

4.2 Preparation of Anti-Human Mpl Diabody and sc(Fv)2

Among the amino acid sequences shown in FIGS. 6 and 7, expression vectors were prepared for the diabodies VB8B, VB45B, VB33, VB140, VB157, and TA136 using the same procedure described in Example 2.2. The prepared expression vectors were introduced into COS7 cells by the same procedure described in Example 2.4. The supernatant concentration of each diabody was determined by the method of Example 2.5. The sc(Fv)2 expression vector for TA136 was prepared by the same procedure described in Example 2.3. The vector was introduced into CHO-DG44 cells by the same procedure described in Example 2.4. sc(Fv)2 was purified from the culture supernatant thus obtained using the same method described in Example 2.6.

4.3 Agonistic Activity Assays of sc(Fv)2 and the Anti-Human Mpl Diabodies

Figure 12:
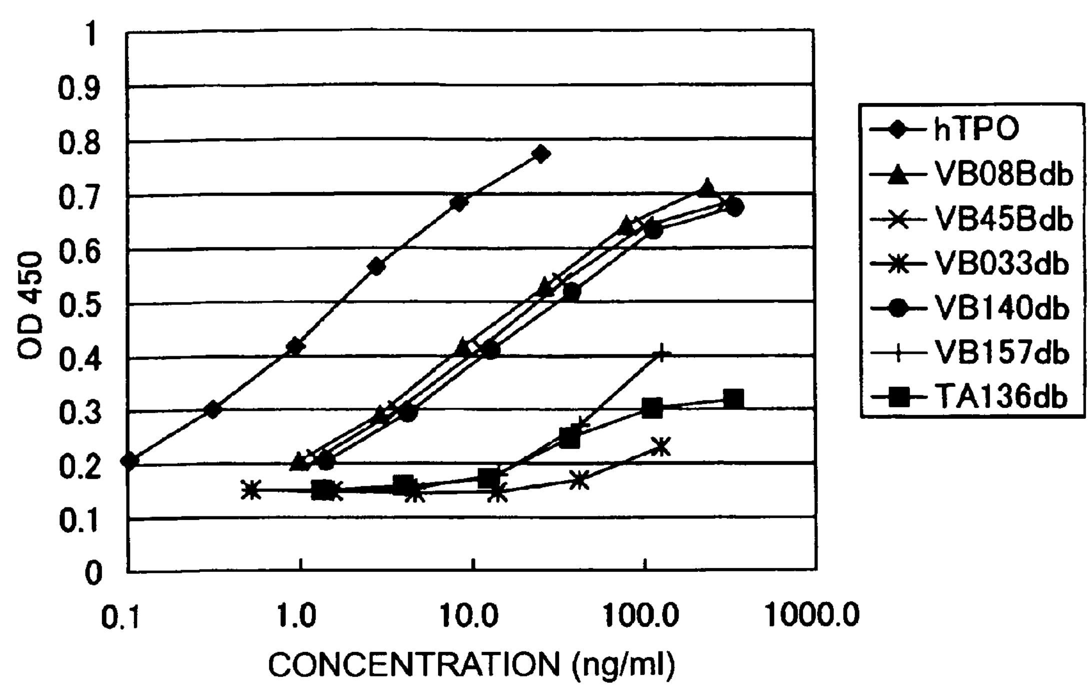
FIG. 12 shows the agonistic activities of diabodies in BaF3-human Mpl cells. The X-axis shows OD at 450/655 nm, and the Y-axis represents concentration.
Figure 13:
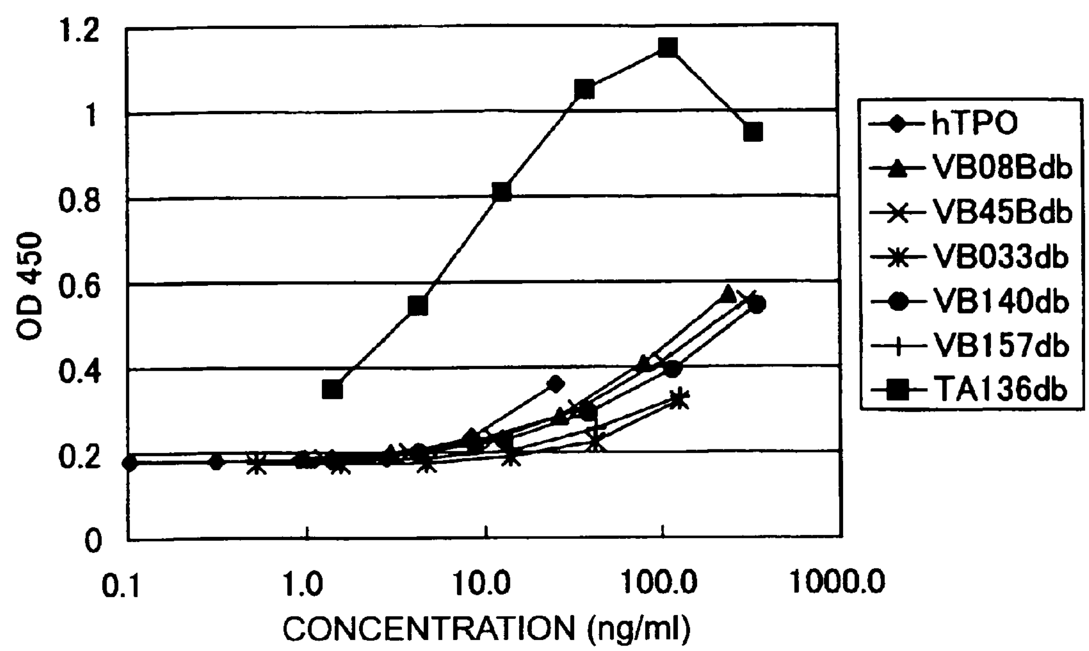
FIG. 13 shows the agonistic activities of diabodies in BaF3-human Mpl (G305C) cells. The X-axis shows OD at 450/655 nm, and the Y-axis represents concentration.

The prepared diabodies and sc(Fv)2 were assayed for their agonistic activities in normal Mpl and mutant Mpl in BaF3 cells by the same procedure described in Example 2.8. The agonistic activities in BaF3-human Mpl and BaF3-human Mpl (G305C) were compared using the culture supernatants of cells expressing the diabodies. The TA136 diabody (TA136 db) was shown to have a low agonistic activity in BaF3-human Mpl cells expressing the normal Mpl gene, and a high agonistic activity in BaF3-human Mpl (G305C) cells expressing the mutant Mpl gene. hTPO and the rest of the diabodies did not show a high agonistic activity in BaF3-human Mpl (G305C) cells (FIGS. 12 and 13).

Figure 14:
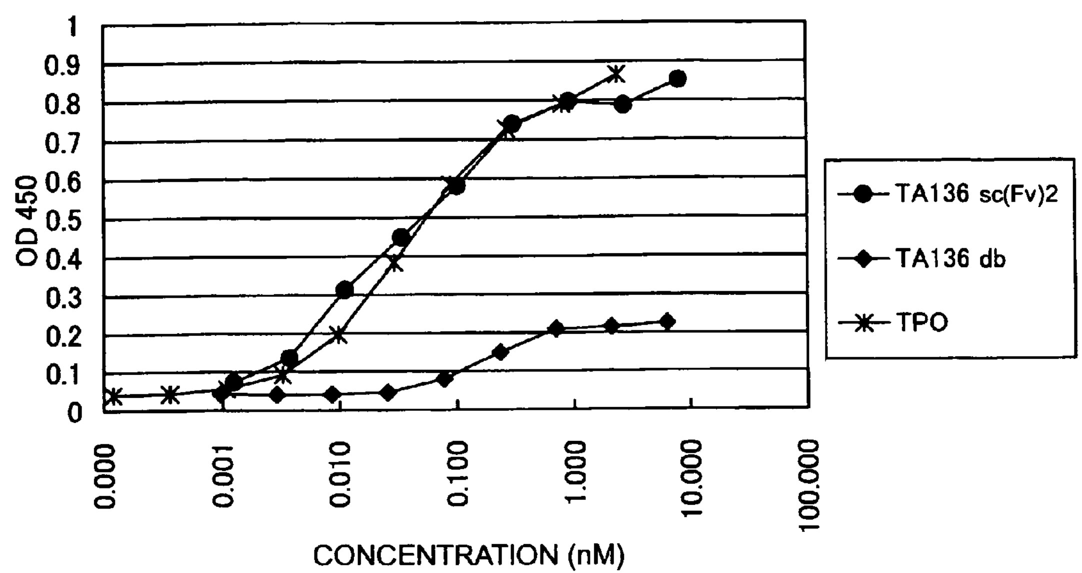
FIG. 14 shows the agonistic activities of TA136 db and TA136 sc(Fv)2 in BaF3-human Mpl cells. The X-axis shows OD at 450/655 nm and the Y-axis represents concentration.
Figure 15:
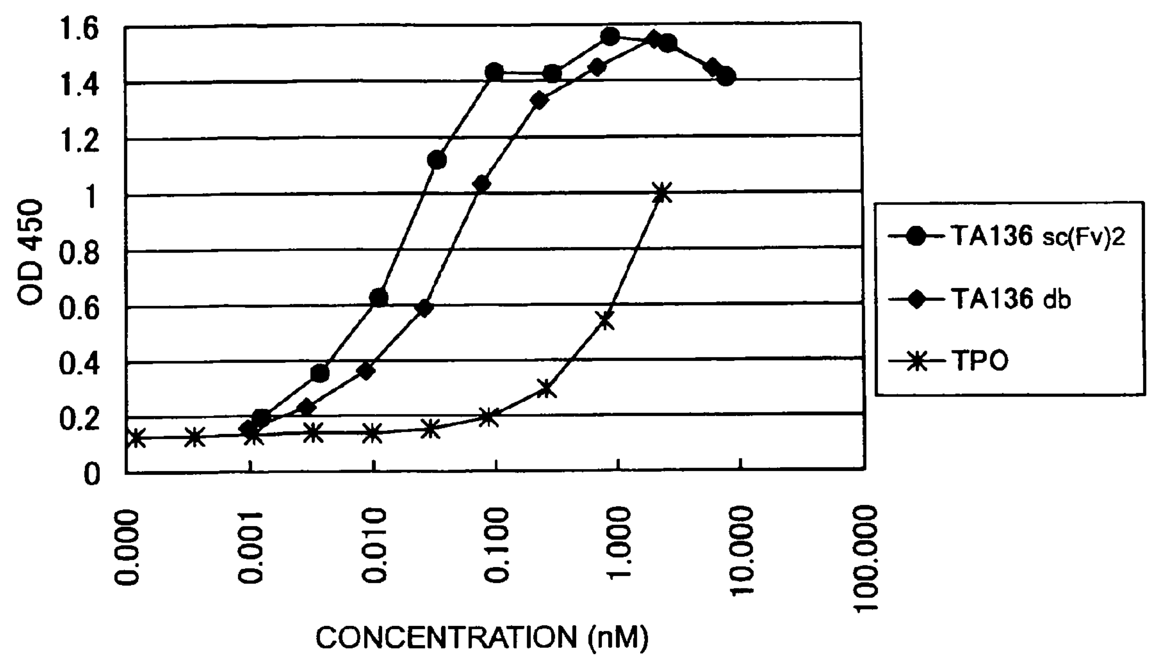
FIG. 15 shows the agonistic activities of TA136 db and TA136 sc(Fv)2 in BaF3-human Mpl (G305C) cells. The X-axis shows OD at 450/655 nm, and the Y-axis represents concentration.
Figure 16:
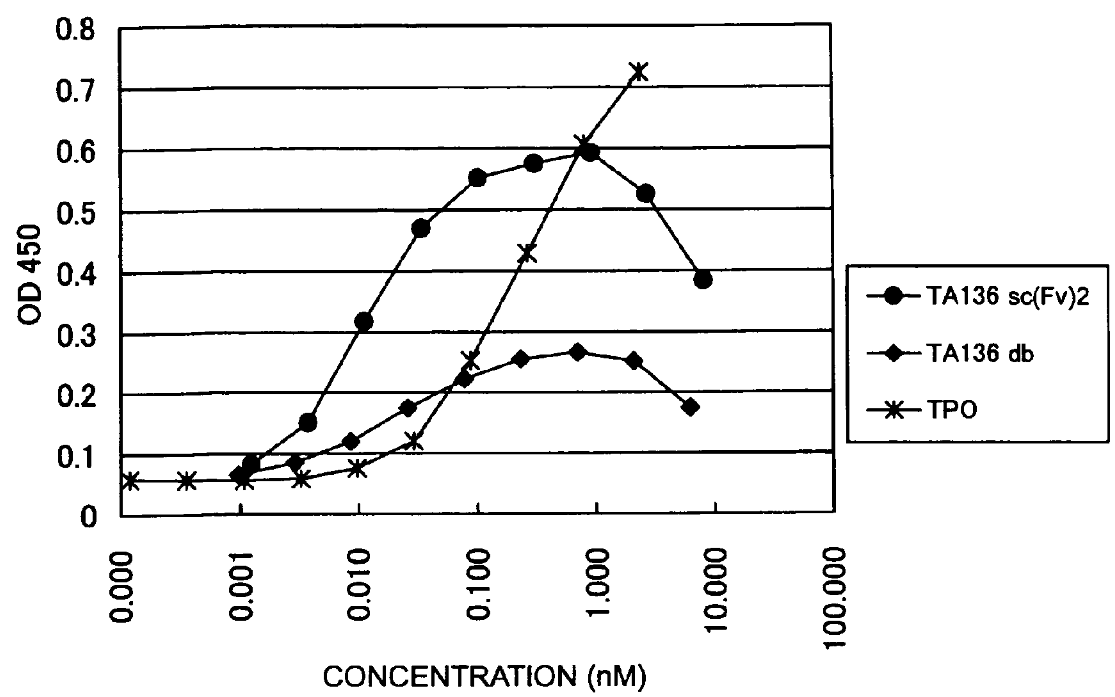
FIG. 16 shows the agonistic activities of TA136 db and TA136 sc(Fv)2 in BaF3-human Mpl (C769T) cells. The X-axis shows OD at 450/655 nm, and the Y-axis represents concentration.
Figure 17:
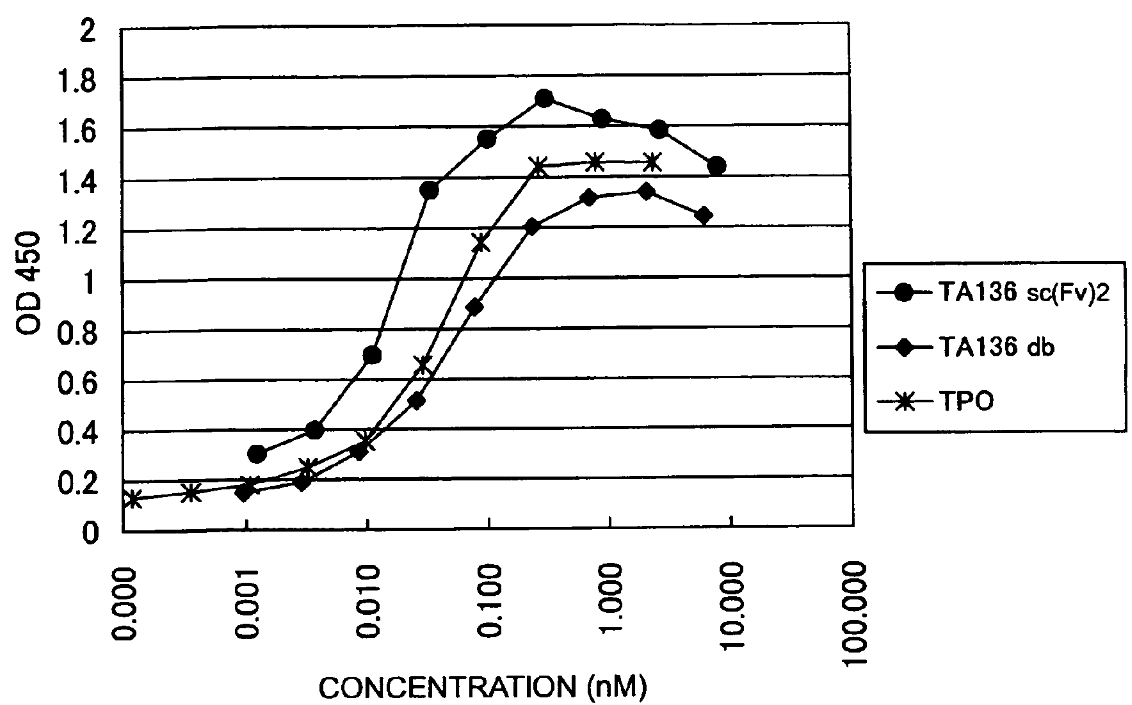
FIG. 17 shows the agonistic activities of TA136 db and TA136 sc(Fv)2 in BaF3-human Mpl (C823A) cells. The X-axis shows OD at 450/655 nm, and the Y-axis represents concentration.

In addition, the agonistic activities of the TA136 diabody and TA136 sc(Fv)2 in BaF3-human Mpl, BaF3-human Mpl (G305C), BaF3-human Mpl (C769T), and BaF3-human Mpl (C823A) cells were assessed using a purified sample of the diabody. Compared with hTPO and the TA136 diabody, TA136 sc(Fv)2 exhibited a higher agonistic activity in all three types of the TPO receptor mutant cell lines (FIGS. 15, 16 and 17). Furthermore, it was shown that in BaF3-human Mpl cells expressing the normal Mpl gene, the TA136 diabody exhibited a lower activity than hTPO. However, an agonistic activity equivalent to that of hTPO was achieved by converting the diabody into sc (Fv) 2 (FIG. 14).

INDUSTRIAL APPLICABILITY

Various clinical trials had been conducted on recombinant human TPO as a therapeutic agent for thrombocytopenia following chemotherapy. Some clinical trials reported a serious problem, namely, the production of anti-TPO antibodies due to TPO administration (Junzhi Li, et al., Blood 98, 3241-324 (2001); Saroj Vandhan-Raj. et al., Ann. Intern. Med. 132, 364-368 (2000)). Specifically, the production of neutralizing antibodies which inhibit the activity of endogenous TPO have been reported, triggering the onset of thrombocytopenia. In the present invention, the administration of agonistic minibodies against TPO receptor does not induce the production of antibodies against endogenous TPO. Reduction of the molecular weight of antibodies increases the specific activity of antibodies and shortens the half-life in blood. Thus, the effective concentration of an antibody in blood can be easily controlled, presenting an advantage in clinical applications. Accordingly, such an antibody can be used as an agent to treat thrombocytopenia more effectively than the naturally-occurring TPO or its agonistic antibodies. Since minibodies are not attached with sugar chains, the expression systems for expressing those recombinant proteins are not limited, and minibodies can be prepared by using any of the expression systems derived from mammalian cell lines, yeasts, insect cells, and *E. coli*. In addition, minibodies have a binding affinity towards mutant TPO receptor different from that of TPO. Therefore, minibodies are expected to bind and exhibit agonistic activities against specific TPO receptor mutants, which contain mutations commonly detected in CAMT patients with thrombocytopenia and genetically mutated TPO receptors.

The invention claimed is:

1. An antibody comprising a single-chain polypeptide that binds to the thrombopoietin (TPO) receptor (Mpl), wherein said antibody comprises two heavy chain variable regions and two light chain variable regions, and at least one of the heavy chain variable regions comprises a set of CDR1, CDR2 and CDR3 sequences selected from the group consisting of:

(a) SEQ ID NOs: 27, 28, and 29;

(b) SEQ ID NOs: 36, 37, and 38; and (c) SEQ ID NOs: 57, 58 and 59.

2. The antibody of claim 1, wherein the two heavy chain variable regions and the two light chain variable regions are arranged in the order, from the N-terminus of the single-chain polypeptide, of heavy chain variable region, light chain variable region, heavy chain variable region, and light chain variable region.

3. The antibody of claim 1, wherein the four variable regions are linked by linkers.

4. The antibody of claim 3, wherein each linker comprises 15 amino acids.

5. The antibody of claim 1, which is a humanized antibody.

6. The antibody of claim 1, wherein the antibody binds to soluble Mpl.

7. The antibody of claim 1, wherein the antibody binds to soluble Mpl with a $KD=10^{-6}$ M or lower.

8. The antibody of claim 1, wherein the antibody binds to soluble Mpl with a $KD=10^{-7}$ M or lower.

9. The antibody of claim 1, wherein the antibody has a TPO agonistic activity of EC50=100 nM or lower.

10. The antibody of claim 1, wherein the antibody has a TPO agonistic activity of EC50=30 nM or lower.

11. The antibody of claim 1, wherein the antibody has a TPO agonistic activity of EC50=10 nM or lower.

12. The antibody of claim 1, wherein at least one of the light chain variable regions comprises a set of CDR1, CDR2 and CDR3 sequences selected from the group consisting of:

(a) SEQ ID NOs: 84, 85, and 86:

(b) SEQ ID NOs: 93, 94, and 95; and (c) SEQ ID NOs: 114, 115, and 116.

13. The antibody of claim 1 comprising any one of:

(a) heavy chain variable region CDR1, CDR2, and CDR3 comprising amino acid sequences consisting of SEQ ID NOs: 27, 28, and 29, respectively, and light chain variable region CDR1, CDR2, and CDR3 comprising amino acid sequences consisting of SEQ ID NOs: 84, 85, and 86, respectively;

(b) heavy chain variable region CDR1, CDR2, and CDR3 comprising amino acid sequences consisting of SEQ ID NOs: 36, 37, and 38, respectively, and light chain variable region CDR1, CDR2, and CDR3 comprising amino acid sequences consisting of SEQ ID NOs: 93, 94, and 95, respectively; and (c) heavy chain variable region CDR1, CDR2, and CDR3 comprising amino acid sequences consisting of SEQ ID NOs: 57, 58 and 59, respectively, and light chain variable region CDR1, CDR2, and CDR3 comprising amino acid sequences consisting of SEQ ID NOs: 114, 115, and 116, respectively.

14. The antibody of claim 1, wherein at least one of the heavy chain variable regions comprises a set of FR1, FR2, FR3, and FR4 sequences selected from the group consisting of:

(a) SEQ ID NOs: 230, 232, 234, and 236; and (b) SEQ ID NOs: 265, 267, 269, and 271.

15. The antibody of claim 1, wherein at least one of the light chain variable regions comprises a set of FR1, FR2, FR3, and FR4 sequences selected from the group consisting of:

(a) SEQ ID NOs: 239, 241, 243, and 245; and (b) SEQ ID NOs: 272, 274, 276, and 278.

16. The antibody of claim 1, comprising any one of:

(a) heavy chain variable region FR1, FR2, FR3, and FR4 comprising amino acid sequences consisting of SEQ ID NOs: 230, 232, 234, and 236, respectively, and light chain variable region FR1, FR2, FR3, and FR4 comprising amino acid sequences consisting of SEQ ID NOs: 239, 241, 243, and 245, respectively; and (b) heavy chain variable region FR1, FR2, FR3, and FR4 comprising amino acid sequences consisting of SEQ ID NOs: 265, 267, 269, and 271, respectively, and light chain variable region FR1, FR2, FR3, and FR4 comprising amino acid sequences consisting of SEQ ID NOs: 272, 274, 276, and 278, respectively.

17. The antibody of claim 1, wherein at least one of said heavy chain variable regions comprises the amino acid sequence of SEQ ID NO: 140, 162, or 229.

18. The antibody of claim 1, wherein at least one of said light chain variable regions comprises the amino acid sequence of SEQ ID NO: 141, 163, or 238.

19. The antibody of claim 1, wherein (a) at least one of the heavy chain variable regions comprises the amino acid sequence of SEQ ID NO: 229, and at least one of the light chain variable regions comprises the amino acid sequence of SEQ ID NO: 238;

(b) at least one of the heavy chain variable regions comprises the amino acid sequence of SEQ ID NO: 140, and at least one of the light chain variable regions comprises the amino acid sequence of SEQ ID NO: 141; or (c) at least one of the heavy chain variable regions comprises the amino acid sequence of SEQ ID NO: 162, and at least one of the light chain variable regions comprises the amino acid sequence of SEQ ID NO: 163.

20. The antibody of claim 1, wherein the antibody recognizes an epitope within the region of amino acids 26 to 274 of human Mpl (SEQ ID NO: 123).

21. The antibody of claim 1, which has TPO agonistic activity.

22. A pharmaceutical composition comprising the antibody of claim 20.

23. A method of treating or reducing the incidence of thrombocytopenia in a subject in need thereof, comprising administering to the subject a therapeutically effective amount of the pharmaceutical composition of claim 22.

24. A method for increasing platelet number in a subject in need thereof, comprising administering to the subject a therapeutically effective amount of the pharmaceutical composition of claim 22.

25. The method of claim 24, wherein the pharmaceutical composition is administered to the subject after the administration of platelet components to the subject.

26. A method for increasing the amount of platelet components at the time of blood collection, the method comprising preadministering to a blood collection subject an effective amount of the pharmaceutical composition of claim 22.

27. The method of claim 26, further comprising collecting blood from the subject after said preadministration.

* * * * *

SEQUENCE LISTING

```
<160> NUMBER OF SEQ ID NOS: 308

<210> SEQ ID NO 1
<211> LENGTH: 1572
<212> TYPE: DNA
<213> ORGANISM: Homo sapiens

<400> SEQUENCE: 1

atggactgga cctggaggtt cctctttgtg gtggcagcag ctacaggtgt ccagtcccag     60

gtgcagctgg tgcagtctgg acctgaggtg aagaagcctg gggcctcagt gaaggtctcc    120

tgcaaggctt ctggatacac cttcaccaac tcctggatga actgggtgag gcagaggcct    180

ggaaagggtc ttgagtggat gggacggatt tatcctggag atggagaaac tatctacaat    240

gggaaattca gggtcagagt cacgattacc gcggacgaat ccacgagcac agcctacatg    300

gagctgagca gcctgagatc tgaggacacg gccgtgtatt actgtgcgag aggctatgat    360

gattactcgt ttgcttactg gggccaggga accacggtca ccgtctcttc aggtggtggt    420

ggatccggag gtggtggatc gggtggtgga ggatcggata ttgtgatgac tcagtctgca    480

ctctccctgc ccgtcacccc tggagagccg gcctccatct cctgcaggtc tagtaagagt    540

ctcctgcata gtaatggcaa cacttacttg tattggttcc agcagaagcc agggcagtct    600

ccacagctcc tgatctatcg gatgtccaac cttgcctcag gggtccctga caggttcagt    660

ggcagtggat caggcacagc ttttacactg aaaatcagca gagtggaggc tgaggatgtt    720

ggggtttatt actgcatgca acatatagaa tatcctttta cgttcggcca agggaccaaa    780

ctggaaatca aaggaggtgg tggatcgggt ggtggtggtt cgggaggcgg tggatcgcag    840

gtgcagctgg tgcagtctgg acctgaggtg aagaagcctg gggcctcagt gaaggtctcc    900

tgcaaggctt ctggatacac cttcaccaac tcctggatga actgggtgag gcagaggcct    960

ggaaagggtc ttgagtggat gggacggatt tatcctggag atggagaaac tatctacaat   1020

gggaaattca gggtcagagt cacgattacc gcggacgaat ccacgagcac agcctacatg   1080

gagctgagca gcctgagatc tgaggacacg gccgtgtatt actgtgcgag aggctatgat   1140

gattactcgt ttgcttactg gggccaggga accacggtca ccgtctcttc aggtggtggt   1200

ggatccggag gtggtggatc gggtggtgga ggatcggata ttgtgatgac tcagtctgca   1260

ctctccctgc ccgtcacccc tggagagccg gcctccatct cctgcaggtc tagtaagagt   1320

ctcctgcata gtaatggcaa cacttacttg tattggttcc agcagaagcc agggcagtct   1380

ccacagctcc tgatctatcg gatgtccaac cttgcctcag gggtccctga caggttcagt   1440

ggcagtggat caggcacagc ttttacactg aaaatcagca gagtggaggc tgaggatgtt   1500

ggggtttatt actgcatgca acatatagaa tatcctttta cgttcggcca agggaccaaa   1560

ctggaaatca aa                                                       1572

<210> SEQ ID NO 2
```

```
<211> LENGTH: 524
<212> TYPE: PRT
<213> ORGANISM: Homo sapiens

<400> SEQUENCE: 2

Met Asp Trp Thr Trp Arg Phe Leu Phe Val Val Ala Ala Ala Thr Gly
1               5                   10                  15

Val Gln Ser Gln Val Gln Leu Val Gln Ser Gly Pro Glu Val Lys Lys
            20                  25                  30

Pro Gly Ala Ser Val Lys Val Ser Cys Lys Ala Ser Gly Tyr Thr Phe
        35                  40                  45

Thr Asn Ser Trp Met Asn Trp Val Arg Gln Arg Pro Gly Lys Gly Leu
    50                  55                  60

Glu Trp Met Gly Arg Ile Tyr Pro Gly Asp Gly Glu Thr Ile Tyr Asn
65                  70                  75                  80

Gly Lys Phe Arg Val Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Tyr Asp Asp Tyr Ser Phe Ala Tyr Trp Gly
        115                 120                 125

Gln Gly Thr Thr Val Thr Val Ser Ser Gly Gly Gly Gly Ser Gly Gly
    130                 135                 140

Gly Gly Ser Gly Gly Gly Gly Ser Asp Ile Val Met Thr Gln Ser Ala
145                 150                 155                 160

Leu Ser Leu Pro Val Thr Pro Gly Glu Pro Ala Ser Ile Ser Cys Arg
                165                 170                 175

Ser Ser Lys Ser Leu Leu His Ser Asn Gly Asn Thr Tyr Leu Tyr Trp
            180                 185                 190

Phe Gln Gln Lys Pro Gly Gln Ser Pro Gln Leu Leu Ile Tyr Arg Met
        195                 200                 205

Ser Asn Leu Ala Ser Gly Val Pro Asp Arg Phe Ser Gly Ser Gly Ser
    210                 215                 220

Gly Thr Ala Phe Thr Leu Lys Ile Ser Arg Val Glu Ala Glu Asp Val
225                 230                 235                 240

Gly Val Tyr Tyr Cys Met Gln His Ile Glu Tyr Pro Phe Thr Phe Gly
                245                 250                 255

Gln Gly Thr Lys Leu Glu Ile Lys Gly Gly Gly Gly Ser Gly Gly Gly
            260                 265                 270

Gly Ser Gly Gly Gly Gly Ser Gln Val Gln Leu Val Gln Ser Gly Pro
        275                 280                 285

Glu Val Lys Lys Pro Gly Ala Ser Val Lys Val Ser Cys Lys Ala Ser
    290                 295                 300

Gly Tyr Thr Phe Thr Asn Ser Trp Met Asn Trp Val Arg Gln Arg Pro
305                 310                 315                 320

Gly Lys Gly Leu Glu Trp Met Gly Arg Ile Tyr Pro Gly Asp Gly Glu
                325                 330                 335

Thr Ile Tyr Asn Gly Lys Phe Arg Val Arg Val Thr Ile Thr Ala Asp
            340                 345                 350

Glu Ser Thr Ser Thr Ala Tyr Met Glu Leu Ser Ser Leu Arg Ser Glu
        355                 360                 365

Asp Thr Ala Val Tyr Tyr Cys Ala Arg Gly Tyr Asp Asp Tyr Ser Phe
    370                 375                 380

Ala Tyr Trp Gly Gln Gly Thr Thr Val Thr Val Ser Ser Gly Gly Gly
385                 390                 395                 400
```

```
Gly Ser Gly Gly Gly Gly Ser Gly Gly Gly Gly Ser Asp Ile Val Met
                405                 410                 415

Thr Gln Ser Ala Leu Ser Leu Pro Val Thr Pro Gly Glu Pro Ala Ser
            420                 425                 430

Ile Ser Cys Arg Ser Ser Lys Ser Leu Leu His Ser Asn Gly Asn Thr
        435                 440                 445

Tyr Leu Tyr Trp Phe Gln Gln Lys Pro Gly Gln Ser Pro Gln Leu Leu
    450                 455                 460

Ile Tyr Arg Met Ser Asn Leu Ala Ser Gly Val Pro Asp Arg Phe Ser
465                 470                 475                 480

Gly Ser Gly Ser Gly Thr Ala Phe Thr Leu Lys Ile Ser Arg Val Glu
                485                 490                 495

Ala Glu Asp Val Gly Val Tyr Tyr Cys Met Gln His Ile Glu Tyr Pro
            500                 505                 510

Phe Thr Phe Gly Gln Gly Thr Lys Leu Glu Ile Lys
        515                 520


<210> SEQ ID NO 3
<211> LENGTH: 5
<212> TYPE: PRT
<213> ORGANISM: Mus musculus

<400> SEQUENCE: 3

Ser Ser Trp Met Asn
1               5


<210> SEQ ID NO 4
<211> LENGTH: 17
<212> TYPE: PRT
<213> ORGANISM: Mus musculus

<400> SEQUENCE: 4

Arg Thr Tyr Pro Gly Asp Gly Asp Thr Asn Tyr Asn Gly Lys Phe Lys
1               5                   10                  15

Gly


<210> SEQ ID NO 5
<211> LENGTH: 13
<212> TYPE: PRT
<213> ORGANISM: Mus musculus

<400> SEQUENCE: 5

Gly Trp Ile Leu Ala Asp Gly Gly Tyr Ser Phe Ala Tyr
1               5                   10


<210> SEQ ID NO 6
<211> LENGTH: 5
<212> TYPE: PRT
<213> ORGANISM: Mus musculus

<400> SEQUENCE: 6

Ser Ser Trp Met Asn
1               5


<210> SEQ ID NO 7
<211> LENGTH: 17
<212> TYPE: PRT
<213> ORGANISM: Mus musculus

<400> SEQUENCE: 7

Arg Ile Tyr Pro Gly Asp Gly Asp Thr Asn Tyr Asn Gly Lys Phe Lys
```

```
1               5                   10                  15

Gly


<210> SEQ ID NO 8
<211> LENGTH: 9
<212> TYPE: PRT
<213> ORGANISM: Mus musculus

<400> SEQUENCE: 8

Gly Tyr Ala Asp Tyr Ser Phe Ala Tyr
1               5


<210> SEQ ID NO 9
<211> LENGTH: 5
<212> TYPE: PRT
<213> ORGANISM: Mus musculus

<400> SEQUENCE: 9

Ser Ser Trp Met Asn
1               5


<210> SEQ ID NO 10
<211> LENGTH: 17
<212> TYPE: PRT
<213> ORGANISM: Mus musculus

<400> SEQUENCE: 10

Arg Ile Tyr Pro Gly Asp Gly Glu Thr Asn Tyr Asn Gly Lys Phe Lys
1               5                   10                  15

Gly


<210> SEQ ID NO 11
<211> LENGTH: 9
<212> TYPE: PRT
<213> ORGANISM: Mus musculus

<400> SEQUENCE: 11

Gly Phe Gly Asp Tyr Ser Phe Ala Tyr
1               5


<210> SEQ ID NO 12
<211> LENGTH: 5
<212> TYPE: PRT
<213> ORGANISM: Mus musculus

<400> SEQUENCE: 12

Ser Ser Trp Met Asn
1               5


<210> SEQ ID NO 13
<211> LENGTH: 17
<212> TYPE: PRT
<213> ORGANISM: Mus musculus

<400> SEQUENCE: 13

Arg Ile Tyr Pro Gly Asp Gly Asp Thr Asn Tyr Asn Gly Lys Phe Lys
1               5                   10                  15

Gly


<210> SEQ ID NO 14
<211> LENGTH: 9
<212> TYPE: PRT
<213> ORGANISM: Mus musculus
```

<400> SEQUENCE: 14

Gly Tyr Ala Asp Tyr Ser Phe Ala Tyr
1 5

<210> SEQ ID NO 15
<211> LENGTH: 5
<212> TYPE: PRT
<213> ORGANISM: Mus musculus

<400> SEQUENCE: 15

Arg Ser Trp Met Asn
1 5

<210> SEQ ID NO 16
<211> LENGTH: 17
<212> TYPE: PRT
<213> ORGANISM: Mus musculus

<400> SEQUENCE: 16

Arg Ile Tyr Pro Gly Asp Gly Asp Thr Asn Tyr Asn Gly Lys Phe Lys
1 5 10 15

Gly

<210> SEQ ID NO 17
<211> LENGTH: 9
<212> TYPE: PRT
<213> ORGANISM: Mus musculus

<400> SEQUENCE: 17

Gly Tyr Asp Asp Tyr Ser Phe Ala Tyr
1 5

<210> SEQ ID NO 18
<211> LENGTH: 5
<212> TYPE: PRT
<213> ORGANISM: Mus musculus

<400> SEQUENCE: 18

Asn Ser Trp Met Asn
1 5

<210> SEQ ID NO 19
<211> LENGTH: 17
<212> TYPE: PRT
<213> ORGANISM: Mus musculus

<400> SEQUENCE: 19

Arg Ile Tyr Pro Gly Asp Gly Glu Thr Asn Asn Asn Gly Lys Phe Lys
1 5 10 15

Gly

<210> SEQ ID NO 20
<211> LENGTH: 9
<212> TYPE: PRT
<213> ORGANISM: Mus musculus

<400> SEQUENCE: 20

Gly Tyr Gly Asp Tyr Ser Phe Ala Tyr
1 5

<210> SEQ ID NO 21
<211> LENGTH: 5
<212> TYPE: PRT
<213> ORGANISM: Mus musculus

<400> SEQUENCE: 21

Asn Tyr Trp Val Asn
1 5

<210> SEQ ID NO 22
<211> LENGTH: 17
<212> TYPE: PRT
<213> ORGANISM: Mus musculus

<400> SEQUENCE: 22

Arg Ile His Pro Ser Asp Ser Glu Thr His Cys Asn Gln Lys Phe Lys
1 5 10 15

Arg

<210> SEQ ID NO 23
<211> LENGTH: 6
<212> TYPE: PRT
<213> ORGANISM: Mus musculus

<400> SEQUENCE: 23

Gly Gly Trp Phe Ala Tyr
1 5

<210> SEQ ID NO 24
<211> LENGTH: 5
<212> TYPE: PRT
<213> ORGANISM: Mus musculus

<400> SEQUENCE: 24

Ser Ser Trp Met Asn
1 5

<210> SEQ ID NO 25
<211> LENGTH: 17
<212> TYPE: PRT
<213> ORGANISM: Mus musculus

<400> SEQUENCE: 25

Arg Ile Tyr Pro Gly Asp Gly Glu Thr Asn Asn Asn Gly Lys Phe Lys
1 5 10 15

Gly

<210> SEQ ID NO 26
<211> LENGTH: 9
<212> TYPE: PRT
<213> ORGANISM: Mus musculus

<400> SEQUENCE: 26

Gly Tyr Gly Asp Tyr Ser Phe Ala Tyr
1 5

<210> SEQ ID NO 27
<211> LENGTH: 5
<212> TYPE: PRT
<213> ORGANISM: Mus musculus

<400> SEQUENCE: 27

Thr Ser Trp Met Asn
1 5

<210> SEQ ID NO 28
<211> LENGTH: 17
<212> TYPE: PRT

```
<213> ORGANISM: Mus musculus

<400> SEQUENCE: 28

Arg Ile Tyr Pro Gly Asp Gly Glu Ala Asn Tyr Asn Gly Lys Phe Lys
1               5                   10                  15

Gly


<210> SEQ ID NO 29
<211> LENGTH: 9
<212> TYPE: PRT
<213> ORGANISM: Mus musculus

<400> SEQUENCE: 29

Gly Tyr Gly Asp Tyr Ser Phe Ala Tyr
1               5


<210> SEQ ID NO 30
<211> LENGTH: 5
<212> TYPE: PRT
<213> ORGANISM: Mus musculus

<400> SEQUENCE: 30

Ser Ser Trp Met Asn
1               5


<210> SEQ ID NO 31
<211> LENGTH: 17
<212> TYPE: PRT
<213> ORGANISM: Mus musculus

<400> SEQUENCE: 31

Arg Ile Tyr Pro Gly Asp Gly Glu Thr Asn Tyr Asn Gly Lys Phe Lys
1               5                   10                  15

Gly


<210> SEQ ID NO 32
<211> LENGTH: 9
<212> TYPE: PRT
<213> ORGANISM: Mus musculus

<400> SEQUENCE: 32

Gly Tyr Gly Asp Tyr Ser Phe Ala Tyr
1               5


<210> SEQ ID NO 33
<211> LENGTH: 5
<212> TYPE: PRT
<213> ORGANISM: Mus musculus

<400> SEQUENCE: 33

Arg Ser Trp Met Asn
1               5


<210> SEQ ID NO 34
<211> LENGTH: 17
<212> TYPE: PRT
<213> ORGANISM: Mus musculus

<400> SEQUENCE: 34

Arg Ile Tyr Pro Gly Asp Gly Glu Thr Asn Tyr Asn Gly Lys Phe Lys
1               5                   10                  15

Gly
```

<210> SEQ ID NO 35
<211> LENGTH: 9
<212> TYPE: PRT
<213> ORGANISM: Mus musculus

<400> SEQUENCE: 35

Gly Asp Gly Asp Tyr Ser Phe Ala Tyr
1               5

<210> SEQ ID NO 36
<211> LENGTH: 5
<212> TYPE: PRT
<213> ORGANISM: Mus musculus

<400> SEQUENCE: 36

Asn Ser Trp Met Asn
1               5

<210> SEQ ID NO 37
<211> LENGTH: 17
<212> TYPE: PRT
<213> ORGANISM: Mus musculus

<400> SEQUENCE: 37

Arg Ile Tyr Pro Gly Asp Gly Glu Thr Ile Tyr Asn Gly Lys Phe Arg
1               5                   10                  15

Val

<210> SEQ ID NO 38
<211> LENGTH: 9
<212> TYPE: PRT
<213> ORGANISM: Mus musculus

<400> SEQUENCE: 38

Gly Tyr Asp Asp Tyr Ser Phe Ala Tyr
1               5

<210> SEQ ID NO 39
<211> LENGTH: 5
<212> TYPE: PRT
<213> ORGANISM: Mus musculus

<400> SEQUENCE: 39

Asp Tyr Trp Val Asn
1               5

<210> SEQ ID NO 40
<211> LENGTH: 17
<212> TYPE: PRT
<213> ORGANISM: Mus musculus

<400> SEQUENCE: 40

Arg Ile His Pro Tyr Asp Ser Glu Thr His Tyr Asn Gln Lys Phe Lys
1               5                   10                  15

Asn

<210> SEQ ID NO 41
<211> LENGTH: 6
<212> TYPE: PRT
<213> ORGANISM: Mus musculus

<400> SEQUENCE: 41

Gly Gly Trp Phe Ala Ser
1               5

<210> SEQ ID NO 42
<211> LENGTH: 5
<212> TYPE: PRT
<213> ORGANISM: Mus musculus

<400> SEQUENCE: 42

Asp Tyr Trp Met Asn
1               5

<210> SEQ ID NO 43
<211> LENGTH: 17
<212> TYPE: PRT
<213> ORGANISM: Mus musculus

<400> SEQUENCE: 43

Arg Ile His Pro Phe Asp Ser Glu Thr His Cys Ser Gln Lys Phe Lys
1               5                   10                  15

Asn

<210> SEQ ID NO 44
<211> LENGTH: 6
<212> TYPE: PRT
<213> ORGANISM: Mus musculus

<400> SEQUENCE: 44

Gly Gly Trp Phe Ala Tyr
1               5

<210> SEQ ID NO 45
<211> LENGTH: 5
<212> TYPE: PRT
<213> ORGANISM: Mus musculus

<400> SEQUENCE: 45

Asn Ser Trp Met Asn
1               5

<210> SEQ ID NO 46
<211> LENGTH: 17
<212> TYPE: PRT
<213> ORGANISM: Mus musculus

<400> SEQUENCE: 46

Arg Ile Tyr Pro Gly Asp Gly Glu Thr Ile Tyr Asn Gly Lys Phe Arg
1               5                   10                  15

Val

<210> SEQ ID NO 47
<211> LENGTH: 9
<212> TYPE: PRT
<213> ORGANISM: Mus musculus

<400> SEQUENCE: 47

Gly Tyr Asp Asp Tyr Ser Phe Ala Tyr
1               5

<210> SEQ ID NO 48
<211> LENGTH: 5
<212> TYPE: PRT
<213> ORGANISM: Mus musculus

<400> SEQUENCE: 48

Asn Ser Trp Met Asn
1               5

<210> SEQ ID NO 49
<211> LENGTH: 17
<212> TYPE: PRT
<213> ORGANISM: Mus musculus

<400> SEQUENCE: 49

Arg Ile Tyr Pro Gly Asp Gly Asp Thr Ile Tyr Asn Gly Asn Phe Lys
1 5 10 15

Gly

<210> SEQ ID NO 50
<211> LENGTH: 9
<212> TYPE: PRT
<213> ORGANISM: Mus musculus

<400> SEQUENCE: 50

Gly Tyr Asp Asp Tyr Ser Phe Ala Tyr
1 5

<210> SEQ ID NO 51
<211> LENGTH: 5
<212> TYPE: PRT
<213> ORGANISM: Mus musculus

<400> SEQUENCE: 51

Ser Tyr Thr Met Ser
1 5

<210> SEQ ID NO 52
<211> LENGTH: 17
<212> TYPE: PRT
<213> ORGANISM: Mus musculus

<400> SEQUENCE: 52

Thr Ile Ser Ser Gly Ser Ser Thr Ile Tyr Tyr Ala Asp Thr Val Lys
1 5 10 15

Gly

<210> SEQ ID NO 53
<211> LENGTH: 6
<212> TYPE: PRT
<213> ORGANISM: Mus musculus

<400> SEQUENCE: 53

Arg Trp Phe Leu Asp Cys
1 5

<210> SEQ ID NO 54
<211> LENGTH: 5
<212> TYPE: PRT
<213> ORGANISM: Mus musculus

<400> SEQUENCE: 54

Ser Ser Trp Met Asn
1 5

<210> SEQ ID NO 55
<211> LENGTH: 17
<212> TYPE: PRT
<213> ORGANISM: Mus musculus

<400> SEQUENCE: 55

Arg Ile Tyr Pro Gly Asp Gly Asp Thr Asn Tyr Asn Gly Lys Phe Lys 1 5 10 15

Gly

<210> SEQ ID NO 56
<211> LENGTH: 9
<212> TYPE: PRT
<213> ORGANISM: Mus musculus

<400> SEQUENCE: 56

Ala Arg Lys Thr Ser Trp Phe Ala Tyr
1 5

<210> SEQ ID NO 57
<211> LENGTH: 6
<212> TYPE: PRT
<213> ORGANISM: Mus musculus

<400> SEQUENCE: 57

Ser Asp Tyr Ala Trp Ser
1 5

<210> SEQ ID NO 58
<211> LENGTH: 16
<212> TYPE: PRT
<213> ORGANISM: Mus musculus

<400> SEQUENCE: 58

Tyr Ile Thr Tyr Ser Gly Tyr Ser Ile Tyr Asn Pro Ser Leu Lys Ser
1 5 10 15

<210> SEQ ID NO 59
<211> LENGTH: 7
<212> TYPE: PRT
<213> ORGANISM: Mus musculus

<400> SEQUENCE: 59

Gly Tyr Asp Asn Met Asp Tyr
1 5

<210> SEQ ID NO 60
<211> LENGTH: 16
<212> TYPE: PRT
<213> ORGANISM: Mus musculus

<400> SEQUENCE: 60

Arg Ser Ser Lys Ser Leu Leu His Ser Asn Gly Asn Thr Tyr Leu Tyr
1 5 10 15

<210> SEQ ID NO 61
<211> LENGTH: 7
<212> TYPE: PRT
<213> ORGANISM: Mus musculus

<400> SEQUENCE: 61

Arg Met Ser Asn Leu Ala Ser
1 5

<210> SEQ ID NO 62
<211> LENGTH: 9
<212> TYPE: PRT
<213> ORGANISM: Mus musculus

<400> SEQUENCE: 62

Met Gln His Leu Glu Tyr Pro Phe Thr
1 5

<210> SEQ ID NO 63
<211> LENGTH: 16
<212> TYPE: PRT
<213> ORGANISM: Mus musculus

<400> SEQUENCE: 63

Arg Ser Ser Lys Ser Leu Leu His Ser Asn Gly Asn Thr Tyr Leu Tyr
1 5 10 15

<210> SEQ ID NO 64
<211> LENGTH: 7
<212> TYPE: PRT
<213> ORGANISM: Mus musculus

<400> SEQUENCE: 64

Arg Met Ser Asn Leu Ala Ser
1 5

<210> SEQ ID NO 65
<211> LENGTH: 9
<212> TYPE: PRT
<213> ORGANISM: Mus musculus

<400> SEQUENCE: 65

Met Gln His Leu Glu Tyr Pro Tyr Thr
1 5

<210> SEQ ID NO 66
<211> LENGTH: 16
<212> TYPE: PRT
<213> ORGANISM: Mus musculus

<400> SEQUENCE: 66

Arg Ser Ser Lys Ser Leu Leu His Ser Asn Gly Asn Thr Tyr Leu Tyr
1 5 10 15

<210> SEQ ID NO 67
<211> LENGTH: 7
<212> TYPE: PRT
<213> ORGANISM: Mus musculus

<400> SEQUENCE: 67

Arg Met Ser Asn Leu Ala Ser
1 5

<210> SEQ ID NO 68
<211> LENGTH: 9
<212> TYPE: PRT
<213> ORGANISM: Mus musculus

<400> SEQUENCE: 68

Met Gln His Leu Glu Tyr Pro Tyr Thr
1 5

<210> SEQ ID NO 69
<211> LENGTH: 16
<212> TYPE: PRT
<213> ORGANISM: Mus musculus

<400> SEQUENCE: 69

Arg Ser Ser Lys Ser Leu Leu His Ser Asn Gly Asn Thr Tyr Leu Tyr
1 5 10 15

<210> SEQ ID NO 70

<211> LENGTH: 7
<212> TYPE: PRT
<213> ORGANISM: Mus musculus

<400> SEQUENCE: 70

Arg Met Ser Asn Leu Ala Ser
1 5

<210> SEQ ID NO 71
<211> LENGTH: 9
<212> TYPE: PRT
<213> ORGANISM: Mus musculus

<400> SEQUENCE: 71

Met Gln His Leu Glu Tyr Pro Tyr Thr
1 5

<210> SEQ ID NO 72
<211> LENGTH: 16
<212> TYPE: PRT
<213> ORGANISM: Mus musculus

<400> SEQUENCE: 72

Arg Ser Ser Lys Ser Leu Leu His Ser Asn Gly Asn Thr Tyr Leu Tyr
1 5 10 15

<210> SEQ ID NO 73
<211> LENGTH: 7
<212> TYPE: PRT
<213> ORGANISM: Mus musculus

<400> SEQUENCE: 73

Arg Met Ser Asn Leu Ala Ser
1 5

<210> SEQ ID NO 74
<211> LENGTH: 9
<212> TYPE: PRT
<213> ORGANISM: Mus musculus

<400> SEQUENCE: 74

Met Gln His Leu Glu Tyr Pro Tyr Thr
1 5

<210> SEQ ID NO 75
<211> LENGTH: 16
<212> TYPE: PRT
<213> ORGANISM: Mus musculus

<400> SEQUENCE: 75

Arg Ser Ser Lys Ser Leu Leu His Ser Asn Gly Asn Thr Tyr Leu Tyr
1 5 10 15

<210> SEQ ID NO 76
<211> LENGTH: 7
<212> TYPE: PRT
<213> ORGANISM: Mus musculus

<400> SEQUENCE: 76

Arg Met Ser Asn Leu Ala Ser
1 5

<210> SEQ ID NO 77
<211> LENGTH: 9
<212> TYPE: PRT
<213> ORGANISM: Mus musculus

<400> SEQUENCE: 77

Met Gln His Leu Glu Tyr Pro Tyr Thr
1               5

<210> SEQ ID NO 78
<211> LENGTH: 16
<212> TYPE: PRT
<213> ORGANISM: Mus musculus

<400> SEQUENCE: 78

Arg Ser Ser Lys Ser Leu Leu Tyr Ser Asn Gly Asn Ile Tyr Leu Tyr
1               5                   10                  15

<210> SEQ ID NO 79
<211> LENGTH: 7
<212> TYPE: PRT
<213> ORGANISM: Mus musculus

<400> SEQUENCE: 79

Arg Met Ser Asn Leu Ala Ser
1               5

<210> SEQ ID NO 80
<211> LENGTH: 9
<212> TYPE: PRT
<213> ORGANISM: Mus musculus

<400> SEQUENCE: 80

Met Gln His Leu Glu Tyr Pro Tyr Thr
1               5

<210> SEQ ID NO 81
<211> LENGTH: 16
<212> TYPE: PRT
<213> ORGANISM: Mus musculus

<400> SEQUENCE: 81

Arg Ser Ser Lys Ser Leu Leu His Ser Asn Gly Asn Thr Tyr Leu Tyr
1               5                   10                  15

<210> SEQ ID NO 82
<211> LENGTH: 7
<212> TYPE: PRT
<213> ORGANISM: Mus musculus

<400> SEQUENCE: 82

Arg Met Ser Asn Leu Ala Ser
1               5

<210> SEQ ID NO 83
<211> LENGTH: 9
<212> TYPE: PRT
<213> ORGANISM: Mus musculus

<400> SEQUENCE: 83

Met Gln His Leu Glu Tyr Pro Tyr Thr
1               5

<210> SEQ ID NO 84
<211> LENGTH: 16
<212> TYPE: PRT
<213> ORGANISM: Mus musculus

<400> SEQUENCE: 84

Arg Ser Ser Lys Ser Leu Leu His Ser Asn Gly Asn Thr Tyr Leu Tyr
1 5 10 15

<210> SEQ ID NO 85
<211> LENGTH: 7
<212> TYPE: PRT
<213> ORGANISM: Mus musculus

<400> SEQUENCE: 85

Arg Met Ser Asn Leu Ala Ser
1 5

<210> SEQ ID NO 86
<211> LENGTH: 9
<212> TYPE: PRT
<213> ORGANISM: Mus musculus

<400> SEQUENCE: 86

Met Gln His Val Glu Tyr Pro Tyr Thr
1 5

<210> SEQ ID NO 87
<211> LENGTH: 16
<212> TYPE: PRT
<213> ORGANISM: Mus musculus

<400> SEQUENCE: 87

Arg Ser Ser Lys Ser Leu Leu His Ser Asn Gly Asn Thr Tyr Leu Tyr
1 5 10 15

<210> SEQ ID NO 88
<211> LENGTH: 7
<212> TYPE: PRT
<213> ORGANISM: Mus musculus

<400> SEQUENCE: 88

Arg Met Ser Asn Leu Ala Ser
1 5

<210> SEQ ID NO 89
<211> LENGTH: 9
<212> TYPE: PRT
<213> ORGANISM: Mus musculus

<400> SEQUENCE: 89

Met Gln His Leu Glu Tyr Pro Tyr Thr
1 5

<210> SEQ ID NO 90
<211> LENGTH: 16
<212> TYPE: PRT
<213> ORGANISM: Mus musculus

<400> SEQUENCE: 90

Arg Ser Ser Lys Ser Leu Leu His Ser Asn Gly Asn Thr Tyr Leu Tyr
1 5 10 15

<210> SEQ ID NO 91
<211> LENGTH: 7
<212> TYPE: PRT
<213> ORGANISM: Mus musculus

<400> SEQUENCE: 91

Arg Met Ser Asn Leu Ala Ser
1 5

<210> SEQ ID NO 92
<211> LENGTH: 9
<212> TYPE: PRT
<213> ORGANISM: Mus musculus

<400> SEQUENCE: 92

Met Gln His Leu Glu Tyr Pro Tyr Thr
1               5

<210> SEQ ID NO 93
<211> LENGTH: 16
<212> TYPE: PRT
<213> ORGANISM: Mus musculus

<400> SEQUENCE: 93

Arg Ser Ser Lys Ser Leu Leu His Ser Asn Gly Asn Thr Tyr Leu Tyr
1               5                   10                  15

<210> SEQ ID NO 94
<211> LENGTH: 7
<212> TYPE: PRT
<213> ORGANISM: Mus musculus

<400> SEQUENCE: 94

Arg Met Ser Asn Leu Ala Ser
1               5

<210> SEQ ID NO 95
<211> LENGTH: 9
<212> TYPE: PRT
<213> ORGANISM: Mus musculus

<400> SEQUENCE: 95

Met Gln His Ile Glu Tyr Pro Phe Thr
1               5

<210> SEQ ID NO 96
<211> LENGTH: 16
<212> TYPE: PRT
<213> ORGANISM: Mus musculus

<400> SEQUENCE: 96

Arg Ser Ser Lys Ser Leu Leu Tyr Ser Asn Gly Asn Thr Tyr Leu Tyr
1               5                   10                  15

<210> SEQ ID NO 97
<211> LENGTH: 7
<212> TYPE: PRT
<213> ORGANISM: Mus musculus

<400> SEQUENCE: 97

Arg Met Ser Asn Leu Ala Ser
1               5

<210> SEQ ID NO 98
<211> LENGTH: 9
<212> TYPE: PRT
<213> ORGANISM: Mus musculus

<400> SEQUENCE: 98

Met Gln His Leu Glu Tyr Pro Tyr Thr
1               5

<210> SEQ ID NO 99
<211> LENGTH: 16

<212> TYPE: PRT
<213> ORGANISM: Mus musculus

<400> SEQUENCE: 99

Arg Ser Ser Lys Ser Leu Leu Tyr Ser Asn Gly Asn Ile Tyr Leu Tyr
1 5 10 15

<210> SEQ ID NO 100
<211> LENGTH: 7
<212> TYPE: PRT
<213> ORGANISM: Mus musculus

<400> SEQUENCE: 100

Arg Met Ser Asn Leu Ala Ser
1 5

<210> SEQ ID NO 101
<211> LENGTH: 9
<212> TYPE: PRT
<213> ORGANISM: Mus musculus

<400> SEQUENCE: 101

Met Gln His Leu Glu Tyr Pro Tyr Thr
1 5

<210> SEQ ID NO 102
<211> LENGTH: 16
<212> TYPE: PRT
<213> ORGANISM: Mus musculus

<400> SEQUENCE: 102

Arg Ser Ser Lys Ser Leu Leu His Asn Asn Gly Asn Thr Tyr Leu Tyr
1 5 10 15

<210> SEQ ID NO 103
<211> LENGTH: 7
<212> TYPE: PRT
<213> ORGANISM: Mus musculus

<400> SEQUENCE: 103

Arg Met Ser Asn Leu Ala Ser
1 5

<210> SEQ ID NO 104
<211> LENGTH: 9
<212> TYPE: PRT
<213> ORGANISM: Mus musculus

<400> SEQUENCE: 104

Met Gln His Ile Glu Tyr Pro Phe Thr
1 5

<210> SEQ ID NO 105
<211> LENGTH: 16
<212> TYPE: PRT
<213> ORGANISM: Mus musculus

<400> SEQUENCE: 105

Arg Ser Ser Lys Ser Leu Leu His Ser Asn Gly Asn Thr Tyr Leu Tyr
1 5 10 15

<210> SEQ ID NO 106
<211> LENGTH: 7
<212> TYPE: PRT
<213> ORGANISM: Mus musculus

<400> SEQUENCE: 106

Arg Met Ser Asn Leu Ala Ser
1 5

<210> SEQ ID NO 107
<211> LENGTH: 9
<212> TYPE: PRT
<213> ORGANISM: Mus musculus

<400> SEQUENCE: 107

Met Gln His Leu Glu Tyr Pro Tyr Thr
1 5

<210> SEQ ID NO 108
<211> LENGTH: 15
<212> TYPE: PRT
<213> ORGANISM: Mus musculus

<400> SEQUENCE: 108

Arg Ala Ser Glu Ser Val Glu Tyr Tyr Gly Thr Ser Leu Met Gln
1 5 10 15

<210> SEQ ID NO 109
<211> LENGTH: 7
<212> TYPE: PRT
<213> ORGANISM: Mus musculus

<400> SEQUENCE: 109

Gly Ala Ser Asn Val Glu Ser
1 5

<210> SEQ ID NO 110
<211> LENGTH: 9
<212> TYPE: PRT
<213> ORGANISM: Mus musculus

<400> SEQUENCE: 110

Gln Gln Ser Arg Lys Val Pro Trp Thr
1 5

<210> SEQ ID NO 111
<211> LENGTH: 11
<212> TYPE: PRT
<213> ORGANISM: Mus musculus

<400> SEQUENCE: 111

Lys Ala Ser Gln Asn Val Gly Asn Ile Ile Ala
1 5 10

<210> SEQ ID NO 112
<211> LENGTH: 7
<212> TYPE: PRT
<213> ORGANISM: Mus musculus

<400> SEQUENCE: 112

Leu Ala Ser Tyr Arg Tyr Ser
1 5

<210> SEQ ID NO 113
<211> LENGTH: 9
<212> TYPE: PRT
<213> ORGANISM: Mus musculus

<400> SEQUENCE: 113

Gln Gln Tyr Ser Ser Ser Pro Leu Thr 1 5

<210> SEQ ID NO 114
<211> LENGTH: 12
<212> TYPE: PRT
<213> ORGANISM: Mus musculus

<400> SEQUENCE: 114

Ser Ala Ser Ser Ser Val Ser Ser Ser His Leu Tyr
1 5 10

<210> SEQ ID NO 115
<211> LENGTH: 7
<212> TYPE: PRT
<213> ORGANISM: Mus musculus

<400> SEQUENCE: 115

Ser Thr Ser Asn Leu Ala Ser
1 5

<210> SEQ ID NO 116
<211> LENGTH: 9
<212> TYPE: PRT
<213> ORGANISM: Mus musculus

<400> SEQUENCE: 116

His Gln Trp Ser Ser Tyr Pro Trp Thr
1 5

<210> SEQ ID NO 117
<211> LENGTH: 354
<212> TYPE: DNA
<213> ORGANISM: Mus musculus

<400> SEQUENCE: 117
caggttcagc tgcagcagtc tggacctgag ctggtgaagc ctggggcctc agtgaagatt 60
tcctgcaagg cttctggcta tgcattcact aactcctgga tgaactgggt gaagcagagg 120
cctggaaagg gtcttgagtg gattggacgg atttatcctg gagatggaga aactatctac 180
aatgggaaat tcagggtcaa ggccacactg actgcagaca aatcctccag cacagcctac 240
atggatatca gcagcctgac atctgaggac tctgcggtct acttctgtgc aagaggctat 300
gatgattact cgtttgctta ctggggccaa gggactctgg tcactgtctc tgca 354

<210> SEQ ID NO 118
<211> LENGTH: 118
<212> TYPE: PRT
<213> ORGANISM: Mus musculus

<400> SEQUENCE: 118

Gln Val Gln Leu Gln Gln Ser Gly Pro Glu Leu Val Lys Pro Gly Ala
1 5 10 15

Ser Val Lys Ile Ser Cys Lys Ala Ser Gly Tyr Ala Phe Thr Asn Ser
20 25 30

Trp Met Asn Trp Val Lys Gln Arg Pro Gly Lys Gly Leu Glu Trp Ile
35 40 45

Gly Arg Ile Tyr Pro Gly Asp Gly Glu Thr Ile Tyr Asn Gly Lys Phe
50 55 60

Arg Val Lys Ala Thr Leu Thr Ala Asp Lys Ser Ser Ser Thr Ala Tyr
65 70 75 80

Met Asp Ile Ser Ser Leu Thr Ser Glu Asp Ser Ala Val Tyr Phe Cys
85 90 95

```
Ala Arg Gly Tyr Asp Asp Tyr Ser Phe Ala Tyr Trp Gly Gln Gly Thr
            100                 105                 110

Leu Val Thr Val Ser Ala
        115


<210> SEQ ID NO 119
<211> LENGTH: 336
<212> TYPE: DNA
<213> ORGANISM: Mus musculus

<400> SEQUENCE: 119

gatattgtga tgactcaggc tgcaccctct atacctgtca ctcctggaga gtcagtatcc      60

atctcctgta ggtctagtaa gagtctcctg catagtaatg gcaacactta cttgtattgg     120

ttcctgcaga ggccaggcca gtctcctcaa ctcctgatat atcggatgtc caaccttgcc     180

tcaggagtcc cagataggtt cagtggcagt gggtcaggaa ctgctttcac actgagaatc     240

agtagagtgg aggctgagga tgtgggtgtt tattactgta tgcaacatat agaatatcct     300

tttacgttcg gatcggggac caagctggaa ataaaa                               336


<210> SEQ ID NO 120
<211> LENGTH: 112
<212> TYPE: PRT
<213> ORGANISM: Mus musculus

<400> SEQUENCE: 120

Asp Ile Val Met Thr Gln Ala Ala Pro Ser Ile Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Ile Glu Tyr Pro Phe Thr Phe Gly Ser Gly Thr Lys Leu Glu Ile Lys
            100                 105                 110


<210> SEQ ID NO 121
<211> LENGTH: 762
<212> TYPE: DNA
<213> ORGANISM: Mus musculus

<400> SEQUENCE: 121

atggaatggc ctttgatctt tctcttcctc ctgtcaggaa ctgcaggtgt ccactcccag      60

gttcagctgc agcagtctgg acctgagctg gtgaagcctg gggcctcagt gaagatttcc     120

tgcaaggctt ctggctatgc attcactaac tcctggatga actgggtgaa gcagaggcct     180

ggaaagggtc ttgagtggat tggacggatt tatcctggag atggagaaac tatctacaat     240

gggaaattca gggtcaaggc cacactgact gcagacaaat cctccagcac agcctacatg     300

gatatcagca gcctgacatc tgaggactct gcggtctact tctgtgcaag aggctatgat     360

gattactcgt ttgcttactg gggccaaggg actctggtca ctgtctctgc aggtggtggt     420

ggttcggata ttgtgatgac tcaggctgca ccctctatac ctgtcactcc tggagagtca     480
```

```
gtatccatct cctgtaggtc tagtaagagt ctcctgcata gtaatggcaa cacttacttg    540

tattggttcc tgcagaggcc aggccagtct cctcaactcc tgatatatcg gatgtccaac    600

cttgcctcag gagtcccaga taggttcagt ggcagtgggt caggaactgc tttcacactg    660

agaatcagta gagtggaggc tgaggatgtg ggtgtttatt actgtatgca acatatagaa    720

tatcctttta cgttcggatc ggggaccaag ctggaaataa aa                      762


<210> SEQ ID NO 122
<211> LENGTH: 254
<212> TYPE: PRT
<213> ORGANISM: Mus musculus

<400> SEQUENCE: 122

Met Glu Trp Pro Leu Ile Phe Leu Phe Leu Leu Ser Gly Thr Ala Gly
1               5                   10                  15

Val His Ser Gln Val Gln Leu Gln Gln Ser Gly Pro Glu Leu Val Lys
            20                  25                  30

Pro Gly Ala Ser Val Lys Ile Ser Cys Lys Ala Ser Gly Tyr Ala Phe
        35                  40                  45

Thr Asn Ser Trp Met Asn Trp Val Lys Gln Arg Pro Gly Lys Gly Leu
    50                  55                  60

Glu Trp Ile Gly Arg Ile Tyr Pro Gly Asp Gly Glu Thr Ile Tyr Asn
65                  70                  75                  80

Gly Lys Phe Arg Val Lys Ala Thr Leu Thr Ala Asp Lys Ser Ser Ser
                85                  90                  95

Thr Ala Tyr Met Asp Ile Ser Ser Leu Thr Ser Glu Asp Ser Ala Val
            100                 105                 110

Tyr Phe Cys Ala Arg Gly Tyr Asp Asp Tyr Ser Phe Ala Tyr Trp Gly
        115                 120                 125

Gln Gly Thr Leu Val Thr Val Ser Ala Gly Gly Gly Gly Ser Asp Ile
    130                 135                 140

Val Met Thr Gln Ala Ala Pro Ser Ile Pro Val Thr Pro Gly Glu Ser
145                 150                 155                 160

Val Ser Ile Ser Cys Arg Ser Ser Lys Ser Leu Leu His Ser Asn Gly
                165                 170                 175

Asn Thr Tyr Leu Tyr Trp Phe Leu Gln Arg Pro Gly Gln Ser Pro Gln
            180                 185                 190

Leu Leu Ile Tyr Arg Met Ser Asn Leu Ala Ser Gly Val Pro Asp Arg
        195                 200                 205

Phe Ser Gly Ser Gly Ser Gly Thr Ala Phe Thr Leu Arg Ile Ser Arg
    210                 215                 220

Val Glu Ala Glu Asp Val Gly Val Tyr Tyr Cys Met Gln His Ile Glu
225                 230                 235                 240

Tyr Pro Phe Thr Phe Gly Ser Gly Thr Lys Leu Glu Ile Lys
                245                 250


<210> SEQ ID NO 123
<211> LENGTH: 635
<212> TYPE: PRT
<213> ORGANISM: Homo sapiens

<400> SEQUENCE: 123

Met Pro Ser Trp Ala Leu Phe Met Val Thr Ser Cys Leu Leu Leu Ala
1               5                   10                  15

Pro Gln Asn Leu Ala Gln Val Ser Ser Gln Asp Val Ser Leu Leu Ala
            20                  25                  30
```

```
Ser Asp Ser Glu Pro Leu Lys Cys Phe Ser Arg Thr Phe Glu Asp Leu
        35                  40                  45

Thr Cys Phe Trp Asp Glu Glu Glu Ala Ala Pro Ser Gly Thr Tyr Gln
    50                  55                  60

Leu Leu Tyr Ala Tyr Pro Arg Glu Lys Pro Arg Ala Cys Pro Leu Ser
65                  70                  75                  80

Ser Gln Ser Met Pro His Phe Gly Thr Arg Tyr Val Cys Gln Phe Pro
                85                  90                  95

Asp Gln Glu Glu Val Arg Leu Phe Phe Pro Leu His Leu Trp Val Lys
            100                 105                 110

Asn Val Phe Leu Asn Gln Thr Arg Thr Gln Arg Val Leu Phe Val Asp
        115                 120                 125

Ser Val Gly Leu Pro Ala Pro Pro Ser Ile Ile Lys Ala Met Gly Gly
    130                 135                 140

Ser Gln Pro Gly Glu Leu Gln Ile Ser Trp Glu Glu Pro Ala Pro Glu
145                 150                 155                 160

Ile Ser Asp Phe Leu Arg Tyr Glu Leu Arg Tyr Gly Pro Arg Asp Pro
                165                 170                 175

Lys Asn Ser Thr Gly Pro Thr Val Ile Gln Leu Ile Ala Thr Glu Thr
            180                 185                 190

Cys Cys Pro Ala Leu Gln Arg Pro His Ser Ala Ser Ala Leu Asp Gln
        195                 200                 205

Ser Pro Cys Ala Gln Pro Thr Met Pro Trp Gln Asp Gly Pro Lys Gln
    210                 215                 220

Thr Ser Pro Ser Arg Glu Ala Ser Ala Leu Thr Ala Glu Gly Gly Ser
225                 230                 235                 240

Cys Leu Ile Ser Gly Leu Gln Pro Gly Asn Ser Tyr Trp Leu Gln Leu
                245                 250                 255

Arg Ser Glu Pro Asp Gly Ile Ser Leu Gly Gly Ser Trp Gly Ser Trp
            260                 265                 270

Ser Leu Pro Val Thr Val Asp Leu Pro Gly Asp Ala Val Ala Leu Gly
        275                 280                 285

Leu Gln Cys Phe Thr Leu Asp Leu Lys Asn Val Thr Cys Gln Trp Gln
    290                 295                 300

Gln Gln Asp His Ala Ser Ser Gln Gly Phe Phe Tyr His Ser Arg Ala
305                 310                 315                 320

Arg Cys Cys Pro Arg Asp Arg Tyr Pro Ile Trp Glu Asn Cys Glu Glu
                325                 330                 335

Glu Glu Lys Thr Asn Pro Gly Leu Gln Thr Pro Gln Phe Ser Arg Cys
            340                 345                 350

His Phe Lys Ser Arg Asn Asp Ser Ile Ile His Ile Leu Val Glu Val
        355                 360                 365

Thr Thr Ala Pro Gly Thr Val His Ser Tyr Leu Gly Ser Pro Phe Trp
    370                 375                 380

Ile His Gln Ala Val Arg Leu Pro Thr Pro Asn Leu His Trp Arg Glu
385                 390                 395                 400

Ile Ser Ser Gly His Leu Glu Leu Glu Trp Gln His Pro Ser Ser Trp
                405                 410                 415

Ala Ala Gln Glu Thr Cys Tyr Gln Leu Arg Tyr Thr Gly Glu Gly His
            420                 425                 430

Gln Asp Trp Lys Val Leu Glu Pro Pro Leu Gly Ala Arg Gly Gly Thr
        435                 440                 445

Leu Glu Leu Arg Pro Arg Ser Arg Tyr Arg Leu Gln Leu Arg Ala Arg
    450                 455                 460
```

```
Leu Asn Gly Pro Thr Tyr Gln Gly Pro Trp Ser Ser Trp Ser Asp Pro
465                 470                 475                 480

Thr Arg Val Glu Thr Ala Thr Glu Thr Ala Trp Ile Ser Leu Val Thr
                485                 490                 495

Ala Leu His Leu Val Leu Gly Leu Ser Ala Val Leu Gly Leu Leu Leu
            500                 505                 510

Leu Arg Trp Gln Phe Pro Ala His Tyr Arg Arg Leu Arg His Ala Leu
        515                 520                 525

Trp Pro Ser Leu Pro Asp Leu His Arg Val Leu Gly Gln Tyr Leu Arg
    530                 535                 540

Asp Thr Ala Ala Leu Ser Pro Pro Lys Ala Thr Val Ser Asp Thr Cys
545                 550                 555                 560

Glu Glu Val Glu Pro Ser Leu Leu Glu Ile Leu Pro Lys Ser Ser Glu
                565                 570                 575

Arg Thr Pro Leu Pro Leu Cys Ser Ser Gln Ala Gln Met Asp Tyr Arg
            580                 585                 590

Arg Leu Gln Pro Ser Cys Leu Gly Thr Met Pro Leu Ser Val Cys Pro
        595                 600                 605

Pro Met Ala Glu Ser Gly Ser Cys Cys Thr Thr His Ile Ala Asn His
    610                 615                 620

Ser Tyr Leu Pro Leu Ser Tyr Trp Gln Gln Pro
625                 630                 635


<210> SEQ ID NO 124
<211> LENGTH: 122
<212> TYPE: PRT
<213> ORGANISM: Mus musculus

<400> SEQUENCE: 124

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Lys Gly Leu Glu Trp Ile
        35                  40                  45

Gly Arg Thr Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Trp Ile Leu Ala Asp Gly Gly Tyr Ser Phe Ala Tyr Trp
            100                 105                 110

Gly Gln Gly Thr Leu Val Thr Val Ser Ala
        115                 120


<210> SEQ ID NO 125
<211> LENGTH: 112
<212> TYPE: PRT
<213> ORGANISM: Mus musculus

<400> SEQUENCE: 125

Asp Ile Val Met Thr Gln Ala Ala Pro Ser Ile Pro Val Thr Pro Gly
1               5                   10                  15

Glu Ser Val Ser Ile Ser Cys Arg Ser Ser Lys Ser Leu Leu His Ser
            20                  25                  30
```

```
Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Ile Tyr Tyr Cys Met Gln His
                85                  90                  95

Leu Glu Tyr Pro Phe Thr Phe Gly Thr Gly Thr Lys Leu Glu Ile Lys
            100                 105                 110


<210> SEQ ID NO 126
<211> LENGTH: 118
<212> TYPE: PRT
<213> ORGANISM: Mus musculus

<400> SEQUENCE: 126

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Ile Gln Leu Ser Ser Leu Thr Ser Glu Asp Ser Ala Val Tyr Phe Cys
                85                  90                  95

Ala Arg Gly Tyr Ala Asp Tyr Ser Phe Ala Tyr Trp Gly Gln Gly Thr
            100                 105                 110

Leu Val Thr Val Ser Ala
        115


<210> SEQ ID NO 127
<211> LENGTH: 112
<212> TYPE: PRT
<213> ORGANISM: Mus musculus

<400> SEQUENCE: 127

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Ser Gly Thr Lys Leu Glu Ile Lys
            100                 105                 110


<210> SEQ ID NO 128
<211> LENGTH: 118
<212> TYPE: PRT
```

<213> ORGANISM: Mus musculus

<400> SEQUENCE: 128

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Glu Thr Asn Tyr Asn Gly Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Gly Phe Gly Asp Tyr Ser Phe Ala Tyr Trp Gly Gln Gly Thr
            100                 105                 110

Leu Val Thr Val Ser Ala
        115
```

<210> SEQ ID NO 129
<211> LENGTH: 112
<212> TYPE: PRT
<213> ORGANISM: Mus musculus

<400> SEQUENCE: 129

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Ala Pro
    50                  55                  60

Asp Arg Phe Ser Gly Ser Gly Ser Gly Thr Ala Phe Thr Leu Arg Ile
65                  70                  75                  80

Ser Arg Val Glu Thr Glu Asp Val Gly Val Tyr Tyr Cys Met Gln His
                85                  90                  95

Leu Glu Tyr Pro Tyr Thr Phe Gly Ser Gly Thr Lys Leu Glu Ile Lys
            100                 105                 110
```

<210> SEQ ID NO 130
<211> LENGTH: 118
<212> TYPE: PRT
<213> ORGANISM: Mus musculus

<400> SEQUENCE: 130

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Ser Ser Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80
```

```
Met Gln Leu Ser Ser Leu Thr Ser Glu Asp Ser Ala Val Tyr Phe Cys
                85                  90                  95

Ala Ser Gly Tyr Ala Asp Tyr Ser Phe Ala Tyr Trp Gly Gln Gly Thr
            100                 105                 110

Leu Val Thr Val Ser Ala
        115


<210> SEQ ID NO 131
<211> LENGTH: 112
<212> TYPE: PRT
<213> ORGANISM: Mus musculus

<400> SEQUENCE: 131

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Ser Gly Thr Lys Leu Glu Ile Lys
            100                 105                 110


<210> SEQ ID NO 132
<211> LENGTH: 118
<212> TYPE: PRT
<213> ORGANISM: Mus musculus

<400> SEQUENCE: 132

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Arg Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Ser Gly Tyr Asp Asp Tyr Ser Phe Ala Tyr Trp Gly Gln Gly Thr
            100                 105                 110

Leu Val Thr Val Ser Ala
        115


<210> SEQ ID NO 133
<211> LENGTH: 112
<212> TYPE: PRT
<213> ORGANISM: Mus musculus

<400> SEQUENCE: 133

Asp Ile Val Met Thr Gln Ala Ala Pro Ser Val Pro Val Thr Pro Gly
1               5                   10                  15
```

```
Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Ser Gly Thr Lys Leu Glu Ile Lys
            100                 105                 110


<210> SEQ ID NO 134
<211> LENGTH: 118
<212> TYPE: PRT
<213> ORGANISM: Mus musculus

<400> SEQUENCE: 134

Gln Val Gln Leu Gln Gln Ser Gly Pro Glu Leu Val Lys Pro Gly Ala
1               5                   10                  15

Ser Val Lys Ile Ser Cys Arg Ala Phe Gly Tyr Ala Phe Ser Asn Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Glu Thr Asn Asn Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Tyr Gly Asp Tyr Ser Phe Ala Tyr Trp Gly Gln Gly Thr
            100                 105                 110

Leu Val Thr Val Ser Ala
        115


<210> SEQ ID NO 135
<211> LENGTH: 112
<212> TYPE: PRT
<213> ORGANISM: Mus musculus

<400> SEQUENCE: 135

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Ala Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Ser Gly Thr Lys Leu Glu Ile Lys
            100                 105                 110
```

<210> SEQ ID NO 136
<211> LENGTH: 115
<212> TYPE: PRT
<213> ORGANISM: Mus musculus

<400> SEQUENCE: 136

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Val Asn Trp Val Lys Gln Arg Pro Gly Arg Gly Leu Glu Trp Ile
        35                  40                  45

Gly Arg Ile His Pro Ser Asp Ser Glu Thr His Cys Asn Gln Lys Phe
    50                  55                  60

Lys Arg Lys Ala Thr Leu Thr Val Asn Lys Ser Ser Ser Thr Ala Tyr
65                  70                  75                  80

Ile Gln Leu His Ser Leu Thr Ser Glu Asp Ser Ala Val Tyr Tyr Cys
                85                  90                  95

Thr Ser Gly Gly Trp Phe Ala Tyr Trp Gly Gln Gly Thr Leu Val Thr
            100                 105                 110

Val Ser Ala
        115
```

<210> SEQ ID NO 137
<211> LENGTH: 112
<212> TYPE: PRT
<213> ORGANISM: Mus musculus

<400> SEQUENCE: 137

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu Tyr Ser
            20                  25                  30

Asn Gly Asn Ile Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Ser Gly Thr Lys Leu Glu Ile Lys
            100                 105                 110
```

<210> SEQ ID NO 138
<211> LENGTH: 118
<212> TYPE: PRT
<213> ORGANISM: Mus musculus

<400> SEQUENCE: 138

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Glu Thr Asn Asn Asn Gly Lys Phe
    50                  55                  60
```

```
Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Phe Cys
                85                  90                  95

Ala Arg Gly Tyr Gly Asp Tyr Ser Phe Ala Tyr Trp Gly Gln Gly Thr
            100                 105                 110

Leu Val Thr Val Ser Ala
        115


<210> SEQ ID NO 139
<211> LENGTH: 112
<212> TYPE: PRT
<213> ORGANISM: Mus musculus

<400> SEQUENCE: 139

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Ala Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Ser Gly Thr Lys Leu Glu Ile Lys
            100                 105                 110


<210> SEQ ID NO 140
<211> LENGTH: 118
<212> TYPE: PRT
<213> ORGANISM: Mus musculus

<400> SEQUENCE: 140

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Thr Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Glu Ala Asn Tyr Asn Gly Lys Phe
    50                  55                  60

Lys Gly Lys Ala Thr Leu Thr Ala Asp Lys Ser Ser Ser Ser Ala Tyr
65                  70                  75                  80

Met Gln Leu Ser Ser Leu Thr Ser Glu Asp Ser Ala Val Tyr Phe Cys
                85                  90                  95

Ala Arg Gly Tyr Gly Asp Tyr Ser Phe Ala Tyr Trp Gly Gln Gly Thr
            100                 105                 110

Leu Val Thr Val Ser Ala
        115


<210> SEQ ID NO 141
<211> LENGTH: 112
<212> TYPE: PRT
<213> ORGANISM: Mus musculus
```

<400> SEQUENCE: 141

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Met Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Val Glu Tyr Pro Tyr Thr Phe Gly Ser Gly Thr Lys Leu Glu Ile Lys
            100                 105                 110
```

<210> SEQ ID NO 142
<211> LENGTH: 118
<212> TYPE: PRT
<213> ORGANISM: Mus musculus

<400> SEQUENCE: 142

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Lys Gly Pro Glu Trp Ile
        35                  40                  45

Gly Arg Ile Tyr Pro Gly Asp Gly Glu Thr Asn Tyr Asn Gly Lys Phe
    50                  55                  60

Lys Gly Lys Ala Thr Leu Thr Ala Asp Lys Ser Ser Ser Thr Val Tyr
65                  70                  75                  80

Met Gln Leu Ser Ser Leu Thr Ser Glu Asp Ser Ala Val Tyr Phe Cys
                85                  90                  95

Ala Arg Gly Tyr Gly Asp Tyr Ser Phe Ala Tyr Trp Gly Gln Gly Thr
            100                 105                 110

Leu Val Thr Val Ser Ala
        115
```

<210> SEQ ID NO 143
<211> LENGTH: 112
<212> TYPE: PRT
<213> ORGANISM: Mus musculus

<400> SEQUENCE: 143

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95
```

```
Leu Glu Tyr Pro Tyr Thr Phe Gly Ser Gly Thr Lys Leu Glu Ile Lys
            100                 105                 110


<210> SEQ ID NO 144
<211> LENGTH: 118
<212> TYPE: PRT
<213> ORGANISM: Mus musculus

<400> SEQUENCE: 144

Gln Val Gln Leu Gln Gln Ser Gly Pro Glu Leu Leu Asn Pro Gly Ala
1               5                   10                  15

Ser Val Lys Ile Ser Cys Lys Ala Ser Gly Tyr Ala Phe Ser Arg Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Glu Thr Asn Tyr Asn Gly Lys Phe
    50                  55                  60

Lys Gly Lys Ala Thr Leu Thr Ala Asp Lys Ser Ser Thr Thr Ala Tyr
65                  70                  75                  80

Met Gln Phe Ser Ser Leu Thr Ser Glu Asp Ser Ala Val Tyr Phe Cys
                85                  90                  95

Ala Arg Gly Asp Gly Asp Tyr Ser Phe Ala Tyr Trp Gly Gln Gly Thr
            100                 105                 110

Leu Val Thr Val Ser Ala
        115


<210> SEQ ID NO 145
<211> LENGTH: 112
<212> TYPE: PRT
<213> ORGANISM: Mus musculus

<400> SEQUENCE: 145

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Ser Gly Thr Lys Leu Glu Ile Lys
            100                 105                 110


<210> SEQ ID NO 146
<211> LENGTH: 115
<212> TYPE: PRT
<213> ORGANISM: Mus musculus

<400> SEQUENCE: 146

Gln Val Gln Leu Gln Gln Pro Gly Thr Glu Leu Val Arg Pro Gly Ala
1               5                   10                  15

Ser Val Lys Leu Ser Cys Lys Ala Ser Gly Tyr Thr Phe Thr Asp Tyr
            20                  25                  30

Trp Val Asn Trp Val Lys Gln Arg Pro Gly Arg Gly Leu Glu Trp Ile
```

```
        35                  40                  45

Gly Arg Ile His Pro Tyr Asp Ser Glu Thr His Tyr Asn Gln Lys Phe
    50                  55                  60

Lys Asn Lys Ala Thr Leu Thr Val Asp Lys Ser Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Ser Gly Gly Trp Phe Ala Ser Trp Gly Gln Gly Thr Leu Val Thr
            100                 105                 110

Val Ser Ala
        115


<210> SEQ ID NO 147
<211> LENGTH: 112
<212> TYPE: PRT
<213> ORGANISM: Mus musculus

<400> SEQUENCE: 147

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu Tyr Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Thr Ile
65                  70                  75                  80

Ser Ser Val Glu Ala Glu Asp Val Gly Val Tyr Tyr Cys Met Gln His
                85                  90                  95

Leu Glu Tyr Pro Tyr Thr Phe Gly Ser Gly Thr Lys Leu Glu Ile Lys
            100                 105                 110


<210> SEQ ID NO 148
<211> LENGTH: 115
<212> TYPE: PRT
<213> ORGANISM: Mus musculus

<400> SEQUENCE: 148

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asp Tyr
            20                  25                  30

Trp Met Asn Trp Val Lys Gln Arg Pro Gly Arg Gly Leu Glu Trp Ile
        35                  40                  45

Gly Arg Ile His Pro Phe Asp Ser Glu Thr His Cys Ser Gln Lys Phe
    50                  55                  60

Lys Asn Lys Ala Thr Leu Thr Val Asp Lys Ser Ser Asn Thr Ala Tyr
65                  70                  75                  80

Ile Gln Phe Ser Ser Leu Thr Ser Glu Asp Ser Ala Val Tyr Tyr Cys
                85                  90                  95

Ser Ser Gly Gly Trp Phe Ala Tyr Trp Gly Gln Gly Thr Leu Val Thr
            100                 105                 110

Val Ser Ala
        115


<210> SEQ ID NO 149
```

<211> LENGTH: 112
<212> TYPE: PRT
<213> ORGANISM: Mus musculus

<400> SEQUENCE: 149

```
Asp Ile Val Met Thr Gln Ala Ala Pro Ser Val Ser Val Thr Pro Gly
1               5                   10                  15

Glu Ser Val Ser Ile Ser Cys Arg Ser Ser Lys Ser Leu Leu Tyr Ser
            20                  25                  30

Asn Gly Asn Ile Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Ser Gly Thr Lys Leu Glu Ile Lys
            100                 105                 110
```

<210> SEQ ID NO 150
<211> LENGTH: 118
<212> TYPE: PRT
<213> ORGANISM: Mus musculus

<400> SEQUENCE: 150

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Thr Asn Ser
            20                  25                  30

Trp Met Asn Trp Val Arg Gln Arg Pro Gly Lys Gly Leu Glu Trp Ile
        35                  40                  45

Gly Arg Ile Tyr Pro Gly Asp Gly Glu Thr Ile Tyr Asn Gly Lys Phe
    50                  55                  60

Arg Val Lys Ala Thr Leu Thr Ala Asp Lys Ser Ser Ser Thr Ala Tyr
65                  70                  75                  80

Met Glu Ile Ser Ser Leu Thr Ser Glu Asp Ser Ala Val Tyr Phe Cys
                85                  90                  95

Ala Arg Gly Tyr Asp Asp Tyr Ser Phe Ala Tyr Trp Gly Gln Gly Thr
            100                 105                 110

Leu Val Thr Val Ser Ala
        115
```

<210> SEQ ID NO 151
<211> LENGTH: 112
<212> TYPE: PRT
<213> ORGANISM: Mus musculus

<400> SEQUENCE: 151

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Asn
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
```

```
65                  70                  75                  80

Ser Arg Val Glu Ala Glu Asp Val Gly Val Tyr Tyr Cys Met Gln His
                85                  90                  95

Ile Glu Tyr Pro Phe Thr Phe Gly Ser Gly Thr Lys Leu Glu Ile Lys
            100                 105                 110


<210> SEQ ID NO 152
<211> LENGTH: 118
<212> TYPE: PRT
<213> ORGANISM: Mus musculus

<400> SEQUENCE: 152

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Asn Ser
            20                  25                  30

Trp Met Asn Trp Val Asn Gln Arg Pro Gly Lys Gly Leu Glu Trp Ile
        35                  40                  45

Gly Arg Ile Tyr Pro Gly Asp Gly Asp Thr Ile Tyr Asn Gly Asn Phe
    50                  55                  60

Lys Gly Lys Ala Thr Leu Thr Ala Asp Lys Ser Ser Ser Ile Ala Tyr
65                  70                  75                  80

Met Gln Leu Ser Ser Leu Thr Ser Glu Asp Ser Ala Val Tyr Phe Cys
                85                  90                  95

Thr Ser Gly Tyr Asp Asp Tyr Ser Phe Ala Tyr Trp Gly Gln Gly Thr
            100                 105                 110

Leu Val Thr Val Ser Ala
        115


<210> SEQ ID NO 153
<211> LENGTH: 112
<212> TYPE: PRT
<213> ORGANISM: Mus musculus

<400> SEQUENCE: 153

Asp Ile Val Met Thr Gln Ala Ala Pro Ser Leu Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Ser Gly Thr Lys Leu Glu Ile Lys
            100                 105                 110


<210> SEQ ID NO 154
<211> LENGTH: 423
<212> TYPE: DNA
<213> ORGANISM: Mus musculus
<220> FEATURE:
<221> NAME/KEY: CDS
<222> LOCATION: (1)..(423)

<400> SEQUENCE: 154
```

```
atg gtt ctt gcc agc tct acc acc agc atc cac acc atg ctg ctc ctg       48
Met Val Leu Ala Ser Ser Thr Thr Ser Ile His Thr Met Leu Leu Leu
1               5                   10                  15

ctc ctg atg ctg gcc cag ccg gcc atg gcg gaa gtg aag ctg gtg gag       96
Leu Leu Met Leu Ala Gln Pro Ala Met Ala Glu Val Lys Leu Val Glu
            20                  25                  30

tct ggg gga ggc tta gtg aag cct gga ggg tcc cgg aaa ctc tcc tgt      144
Ser Gly Gly Gly Leu Val Lys Pro Gly Gly Ser Arg Lys Leu Ser Cys
        35                  40                  45

gca gcc tct gga ttc act ttc agt agc tat acc atg tct tgg gtt cgc      192
Ala Ala Ser Gly Phe Thr Phe Ser Ser Tyr Thr Met Ser Trp Val Arg
    50                  55                  60

cag act ccg gcg aag agg ctg gag tgg gtc gca acc att agt agt ggc      240
Gln Thr Pro Ala Lys Arg Leu Glu Trp Val Ala Thr Ile Ser Ser Gly
65                  70                  75                  80

agt agt acc atc tac tat gca gac aca gtg aag ggc cga ttc acc atc      288
Ser Ser Thr Ile Tyr Tyr Ala Asp Thr Val Lys Gly Arg Phe Thr Ile
                85                  90                  95

tcc aga gac aat gcc aag aac acc ctg ttc ctg caa atg acc agt cta      336
Ser Arg Asp Asn Ala Lys Asn Thr Leu Phe Leu Gln Met Thr Ser Leu
            100                 105                 110

agg tct gag gac aca gcc atg tat tac tgt gca agg aga tgg ttt ctt      384
Arg Ser Glu Asp Thr Ala Met Tyr Tyr Cys Ala Arg Arg Trp Phe Leu
        115                 120                 125

gac tgc tgg ggc caa ggc acc act ctc aca gtc tcc tcg                  423
Asp Cys Trp Gly Gln Gly Thr Thr Leu Thr Val Ser Ser
    130                 135                 140


<210> SEQ ID NO 155
<211> LENGTH: 141
<212> TYPE: PRT
<213> ORGANISM: Mus musculus

<400> SEQUENCE: 155

Met Val Leu Ala Ser Ser Thr Thr Ser Ile His Thr Met Leu Leu Leu
1               5                   10                  15

Leu Leu Met Leu Ala Gln Pro Ala Met Ala Glu Val Lys Leu Val Glu
            20                  25                  30

Ser Gly Gly Gly Leu Val Lys Pro Gly Gly Ser Arg Lys Leu Ser Cys
        35                  40                  45

Ala Ala Ser Gly Phe Thr Phe Ser Ser Tyr Thr Met Ser Trp Val Arg
    50                  55                  60

Gln Thr Pro Ala Lys Arg Leu Glu Trp Val Ala Thr Ile Ser Ser Gly
65                  70                  75                  80

Ser Ser Thr Ile Tyr Tyr Ala Asp Thr Val Lys Gly Arg Phe Thr Ile
                85                  90                  95

Ser Arg Asp Asn Ala Lys Asn Thr Leu Phe Leu Gln Met Thr Ser Leu
            100                 105                 110

Arg Ser Glu Asp Thr Ala Met Tyr Tyr Cys Ala Arg Arg Trp Phe Leu
        115                 120                 125

Asp Cys Trp Gly Gln Gly Thr Thr Leu Thr Val Ser Ser
    130                 135                 140


<210> SEQ ID NO 156
<211> LENGTH: 357
<212> TYPE: DNA
<213> ORGANISM: Mus musculus
<220> FEATURE:
<221> NAME/KEY: CDS
<222> LOCATION: (1)..(357)
```

```
<400> SEQUENCE: 156

gat att gtg ctc acc caa tct cca gct tct ttg gct gtg tct cta ggg       48
Asp Ile Val Leu Thr Gln Ser Pro Ala Ser Leu Ala Val Ser Leu Gly
1               5                   10                  15

cag agt gtc acc atc tcc tgc aga gcc agt gaa agt gtt gaa tat tat       96
Gln Ser Val Thr Ile Ser Cys Arg Ala Ser Glu Ser Val Glu Tyr Tyr
            20                  25                  30

ggc act agt tta atg cag tgg tac caa cag aaa cca gga cag cca ccc      144
Gly Thr Ser Leu Met Gln Trp Tyr Gln Gln Lys Pro Gly Gln Pro Pro
        35                  40                  45

aaa ctc ctc atc tat ggt gca tcc aac gta gaa tct ggg gtc cct gcc      192
Lys Leu Leu Ile Tyr Gly Ala Ser Asn Val Glu Ser Gly Val Pro Ala
    50                  55                  60

agg ttt agt ggc agt ggg tct ggg aca gac ttc agc ctc aac atc cat      240
Arg Phe Ser Gly Ser Gly Ser Gly Thr Asp Phe Ser Leu Asn Ile His
65                  70                  75                  80

cct gtg gag gag gat gat att gca atg tat ttc tgt cag caa agt agg      288
Pro Val Glu Glu Asp Asp Ile Ala Met Tyr Phe Cys Gln Gln Ser Arg
                85                  90                  95

aag gtt ccg tgg acg ttc ggt gga ggc acc aag ctg gaa ata aag gac      336
Lys Val Pro Trp Thr Phe Gly Gly Gly Thr Lys Leu Glu Ile Lys Asp
            100                 105                 110

tac aag gat gac gac gat aag                                          357
Tyr Lys Asp Asp Asp Asp Lys
        115


<210> SEQ ID NO 157
<211> LENGTH: 119
<212> TYPE: PRT
<213> ORGANISM: Mus musculus

<400> SEQUENCE: 157

Asp Ile Val Leu Thr Gln Ser Pro Ala Ser Leu Ala Val Ser Leu Gly
1               5                   10                  15

Gln Ser Val Thr Ile Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Gly Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                85                  90                  95

Lys Val Pro Trp Thr Phe Gly Gly Gly Thr Lys Leu Glu Ile Lys Asp
            100                 105                 110

Tyr Lys Asp Asp Asp Asp Lys
        115


<210> SEQ ID NO 158
<211> LENGTH: 432
<212> TYPE: DNA
<213> ORGANISM: Mus musculus
<220> FEATURE:
<221> NAME/KEY: CDS
<222> LOCATION: (1)..(432)

<400> SEQUENCE: 158

atg gtt ctt gcc agc tct acc acc agc atc cac acc atg ctg ctc ctg       48
Met Val Leu Ala Ser Ser Thr Thr Ser Ile His Thr Met Leu Leu Leu
1               5                   10                  15
```

```
ctc ctg atg ctg gcc cag ccg gcc atg gcg cag gtt cag ctc cag caa       96
Leu Leu Met Leu Ala Gln Pro Ala Met Ala Gln Val Gln Leu Gln Gln
            20                  25                  30

tct gga cct gag ctg gtg aag cct ggg gcc tca gtg aag att tcc tgc      144
Ser Gly Pro Glu Leu Val Lys Pro Gly Ala Ser Val Lys Ile Ser Cys
        35                  40                  45

aag gct tct ggc tat gca ttc agt agc tcc tgg atg aac tgg atg aag      192
Lys Ala Ser Gly Tyr Ala Phe Ser Ser Ser Trp Met Asn Trp Met Lys
    50                  55                  60

cag agg cct gga aag ggt ctt gag tgg att ggg cgg att tat cct gga      240
Gln Arg Pro Gly Lys Gly Leu Glu Trp Ile Gly Arg Ile Tyr Pro Gly
65                  70                  75                  80

gat gga gat act aac tac aat ggg aag ttc aag ggc aag gcc aca ctg      288
Asp Gly Asp Thr Asn Tyr Asn Gly Lys Phe Lys Gly Lys Ala Thr Leu
                85                  90                  95

act gca gac aaa tcc tcc agc aca gcc tac atg caa ctc agc agc ctg      336
Thr Ala Asp Lys Ser Ser Ser Thr Ala Tyr Met Gln Leu Ser Ser Leu
            100                 105                 110

aca tct gag gac tct gcg gtc tac ttc tgt gca aga gcg agg aaa act      384
Thr Ser Glu Asp Ser Ala Val Tyr Phe Cys Ala Arg Ala Arg Lys Thr
        115                 120                 125

tcc tgg ttt gct tac tgg ggc caa ggg act ctg gtc act gtc tct gcg      432
Ser Trp Phe Ala Tyr Trp Gly Gln Gly Thr Leu Val Thr Val Ser Ala
    130                 135                 140


<210> SEQ ID NO 159
<211> LENGTH: 144
<212> TYPE: PRT
<213> ORGANISM: Mus musculus

<400> SEQUENCE: 159

Met Val Leu Ala Ser Ser Thr Thr Ser Ile His Thr Met Leu Leu Leu
1               5                   10                  15

Leu Leu Met Leu Ala Gln Pro Ala Met Ala Gln Val Gln Leu Gln Gln
            20                  25                  30

Ser Gly Pro Glu Leu Val Lys Pro Gly Ala Ser Val Lys Ile Ser Cys
        35                  40                  45

Lys Ala Ser Gly Tyr Ala Phe Ser Ser Ser Trp Met Asn Trp Met Lys
    50                  55                  60

Gln Arg Pro Gly Lys Gly Leu Glu Trp Ile Gly Arg Ile Tyr Pro Gly
65                  70                  75                  80

Asp Gly Asp Thr Asn Tyr Asn Gly Lys Phe Lys Gly Lys Ala Thr Leu
                85                  90                  95

Thr Ala Asp Lys Ser Ser Ser Thr Ala Tyr Met Gln Leu Ser Ser Leu
            100                 105                 110

Thr Ser Glu Asp Ser Ala Val Tyr Phe Cys Ala Arg Ala Arg Lys Thr
        115                 120                 125

Ser Trp Phe Ala Tyr Trp Gly Gln Gly Thr Leu Val Thr Val Ser Ala
    130                 135                 140


<210> SEQ ID NO 160
<211> LENGTH: 345
<212> TYPE: DNA
<213> ORGANISM: Mus musculus
<220> FEATURE:
<221> NAME/KEY: CDS
<222> LOCATION: (1)..(345)

<400> SEQUENCE: 160

gac att gtg ttg aca cag tct caa aaa ttc atg tcc aca tca gta gga       48
```

```
Asp Ile Val Leu Thr Gln Ser Gln Lys Phe Met Ser Thr Ser Val Gly
1               5                   10                  15

gac agg gtc agc atc agc tgc aag gcc agt cag aat gtg ggt aat att       96
Asp Arg Val Ser Ile Ser Cys Lys Ala Ser Gln Asn Val Gly Asn Ile
            20                  25                  30

ata gcc tgg tat caa cag aaa cca ggg caa tct cct aaa gca ctg att      144
Ile Ala Trp Tyr Gln Gln Lys Pro Gly Gln Ser Pro Lys Ala Leu Ile
        35                  40                  45

tac ttg gca tcc tac cgg tac agt gga gtc cct gat cgc ttc aca ggc      192
Tyr Leu Ala Ser Tyr Arg Tyr Ser Gly Val Pro Asp Arg Phe Thr Gly
    50                  55                  60

agt gga tct ggg aca gat ttc act ctc acc att agt aat gtg cag tct      240
Ser Gly Ser Gly Thr Asp Phe Thr Leu Thr Ile Ser Asn Val Gln Ser
65                  70                  75                  80

gaa gac ttg gca gag tat ttc tgt cag caa tat agc agc tct ccg ctc      288
Glu Asp Leu Ala Glu Tyr Phe Cys Gln Gln Tyr Ser Ser Ser Pro Leu
                85                  90                  95

acg ttc ggt gct ggg acc aag ctg gaa ata aag gac tac aag gat gac      336
Thr Phe Gly Ala Gly Thr Lys Leu Glu Ile Lys Asp Tyr Lys Asp Asp
            100                 105                 110

gac gat aag                                                          345
Asp Asp Lys
        115


<210> SEQ ID NO 161
<211> LENGTH: 115
<212> TYPE: PRT
<213> ORGANISM: Mus musculus

<400> SEQUENCE: 161

Asp Ile Val Leu Thr Gln Ser Gln Lys Phe Met Ser Thr Ser Val Gly
1               5                   10                  15

Asp Arg Val Ser Ile Ser Cys Lys Ala Ser Gln Asn Val Gly Asn Ile
            20                  25                  30

Ile Ala Trp Tyr Gln Gln Lys Pro Gly Gln Ser Pro Lys Ala Leu Ile
        35                  40                  45

Tyr Leu Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Ser Ser Ser Pro Leu
                85                  90                  95

Thr Phe Gly Ala Gly Thr Lys Leu Glu Ile Lys Asp Tyr Lys Asp Asp
            100                 105                 110

Asp Asp Lys
        115


<210> SEQ ID NO 162
<211> LENGTH: 116
<212> TYPE: PRT
<213> ORGANISM: Mus musculus

<400> SEQUENCE: 162

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Ser Trp Ile Arg Gln Leu Pro Gly Asn Lys Leu Glu Trp
        35                  40                  45
```

```
Met Gly Tyr Ile Thr Tyr Ser Gly Tyr Ser Ile Tyr Asn Pro Ser Leu
    50                  55                  60

Lys Ser Arg Ile Ser Ile Ser Arg Asp Thr Ser Lys Asn Gln Leu Phe
65                  70                  75                  80

Leu Gln Leu Asn Ser Val Thr Thr Glu Asp Thr Ala Thr Tyr Tyr Cys
                85                  90                  95

Val Gly Gly Tyr Asp Asn Met Asp Tyr Trp Gly Gln Gly Thr Ser Val
            100                 105                 110

Thr Val Ser Ser
        115


<210> SEQ ID NO 163
<211> LENGTH: 108
<212> TYPE: PRT
<213> ORGANISM: Mus musculus

<400> SEQUENCE: 163

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Ser Ser Ser
            20                  25                  30

His Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Asn Met Glu
65                  70                  75                  80

Thr Glu Asp Ala Ala Ser Tyr Phe Cys His Gln Trp Ser Ser Tyr Pro
                85                  90                  95

Trp Thr Phe Gly Gly Gly Thr Lys Leu Glu Ile Lys
            100                 105


<210> SEQ ID NO 164
<211> LENGTH: 1924
<212> TYPE: DNA
<213> ORGANISM: Macaca fascicularis
<220> FEATURE:
<221> NAME/KEY: CDS
<222> LOCATION: (11)..(1918)

<400> SEQUENCE: 164

gaattccacc atg ccc tcc tgg gcc ctc ttc atg gtc acc tcc tgc ctc        49

                 Met Pro Ser Trp Ala Leu Phe Met Val Thr Ser Cys Leu
                 1               5                   10

ctc ctg gcc cct caa aac ctg gcc caa gtc agc agc caa gat gtc tcc       97
Leu Leu Ala Pro Gln Asn Leu Ala Gln Val Ser Ser Gln Asp Val Ser
    15                  20                  25

ttg ctg gcc tcg gac tca gag ccc ctg aag tgt ttc tcc cga aca ttt      145
Leu Leu Ala Ser Asp Ser Glu Pro Leu Lys Cys Phe Ser Arg Thr Phe
30                  35                  40                  45

gag gac ctc act tgc ttc tgg gat gag gaa gag gca gca ccc agt ggg      193
Glu Asp Leu Thr Cys Phe Trp Asp Glu Glu Glu Ala Ala Pro Ser Gly
                50                  55                  60

aca tac cag ctg ctg tat gcc tac ccg ggg gag aag ccc cgt gcc tgc      241
Thr Tyr Gln Leu Leu Tyr Ala Tyr Pro Gly Glu Lys Pro Arg Ala Cys
            65                  70                  75

ccc ctg agt tct cag agc gtg ccc cgc ttt gga acc cga tac gtg tgc      289
Pro Leu Ser Ser Gln Ser Val Pro Arg Phe Gly Thr Arg Tyr Val Cys
        80                  85                  90
```

```
cag ttt cca gcc cag gaa gaa gtg cgt ctc ttc tct ccg ctg cac ctc      337
Gln Phe Pro Ala Gln Glu Glu Val Arg Leu Phe Ser Pro Leu His Leu
    95                  100                 105

tgg gtg aag aat gtg ttc cta aac cag act cag att cag cga gtc ctc      385
Trp Val Lys Asn Val Phe Leu Asn Gln Thr Gln Ile Gln Arg Val Leu
110                 115                 120                 125

ttt gtg gac agt gta ggc ctg ccg gct ccc ccc agt atc atc aag gcc      433
Phe Val Asp Ser Val Gly Leu Pro Ala Pro Pro Ser Ile Ile Lys Ala
                130                 135                 140

atg ggt ggg agc cag cca ggg gaa ctt cag atc agc tgg gag gcc cca      481
Met Gly Gly Ser Gln Pro Gly Glu Leu Gln Ile Ser Trp Glu Ala Pro
            145                 150                 155

gct cca gaa atc agt gat ttc ctg agg tac gaa ctc cgc tat ggc ccc      529
Ala Pro Glu Ile Ser Asp Phe Leu Arg Tyr Glu Leu Arg Tyr Gly Pro
        160                 165                 170

aaa gat ctc aag aac tcc act ggt ccc acg gtc ata cag ttg atc gcc      577
Lys Asp Leu Lys Asn Ser Thr Gly Pro Thr Val Ile Gln Leu Ile Ala
    175                 180                 185

aca gaa acc tgc tgc cct gct ctg cag agg cca cac tca gcc tct gct      625
Thr Glu Thr Cys Cys Pro Ala Leu Gln Arg Pro His Ser Ala Ser Ala
190                 195                 200                 205

ctg gac cag tct cca tgt gct cag ccc aca atg ccc tgg caa gat gga      673
Leu Asp Gln Ser Pro Cys Ala Gln Pro Thr Met Pro Trp Gln Asp Gly
                210                 215                 220

cca aag cag acc tcc cca act aga gaa gct tca gct ctg aca gca gtg      721
Pro Lys Gln Thr Ser Pro Thr Arg Glu Ala Ser Ala Leu Thr Ala Val
            225                 230                 235

ggt gga agc tgc ctc atc tca gga ctc cag cct ggc aac tcc tac tgg      769
Gly Gly Ser Cys Leu Ile Ser Gly Leu Gln Pro Gly Asn Ser Tyr Trp
        240                 245                 250

ctg cag ctg cgc agc gaa cct gat ggg atc tcc ctc ggt ggc tcc tgg      817
Leu Gln Leu Arg Ser Glu Pro Asp Gly Ile Ser Leu Gly Gly Ser Trp
    255                 260                 265

gga tcc tgg tcc ctc cct gtg act gtg gac ctg cct gga gat gca gtg      865
Gly Ser Trp Ser Leu Pro Val Thr Val Asp Leu Pro Gly Asp Ala Val
270                 275                 280                 285

gca att gga ctg caa tgc ttt acc ttg gac ctg aag aat gtt acc tgt      913
Ala Ile Gly Leu Gln Cys Phe Thr Leu Asp Leu Lys Asn Val Thr Cys
                290                 295                 300

caa tgg cag caa gag gac cat gct agt tcc caa ggt ttc ttc tac cac      961
Gln Trp Gln Gln Glu Asp His Ala Ser Ser Gln Gly Phe Phe Tyr His
            305                 310                 315

agc agg gca cgg tgc tgc ccc aga gac agg tac ccc atc tgg gag gac     1009
Ser Arg Ala Arg Cys Cys Pro Arg Asp Arg Tyr Pro Ile Trp Glu Asp
        320                 325                 330

tgt gaa gag gaa gag aaa aca aat cca gga tta cag acc cca cag ttc     1057
Cys Glu Glu Glu Glu Lys Thr Asn Pro Gly Leu Gln Thr Pro Gln Phe
    335                 340                 345

tct cgc tgc cac ttc aag tca cga aat gac agc gtt att cac atc ctt     1105
Ser Arg Cys His Phe Lys Ser Arg Asn Asp Ser Val Ile His Ile Leu
350                 355                 360                 365

gtg gag gtg acc aca gcc ctg ggt gct gtt cac agt tac ctg ggc tcc     1153
Val Glu Val Thr Thr Ala Leu Gly Ala Val His Ser Tyr Leu Gly Ser
                370                 375                 380

cct ttc tgg atc cac cag gct gtg cgc ctc ccc acc cca aac ttg cac     1201
Pro Phe Trp Ile His Gln Ala Val Arg Leu Pro Thr Pro Asn Leu His
            385                 390                 395

tgg agg gag atc tcc agc ggg cat ctg gaa ttg gag tgg cag cac cca     1249
Trp Arg Glu Ile Ser Ser Gly His Leu Glu Leu Glu Trp Gln His Pro
        400                 405                 410
```

```
tca tcc tgg gca gcc caa gag acc tgc tat caa ctc cga tac aca gga      1297
Ser Ser Trp Ala Ala Gln Glu Thr Cys Tyr Gln Leu Arg Tyr Thr Gly
    415                 420                 425

gaa ggc cat cag gac tgg aag gtg ctg gag ccg cct ctc ggg gcc cga      1345
Glu Gly His Gln Asp Trp Lys Val Leu Glu Pro Pro Leu Gly Ala Arg
430                 435                 440                 445

gga ggg acc ctg gag ctg cgc ccg cga tct cgc tac cgt tta cag ctg      1393
Gly Gly Thr Leu Glu Leu Arg Pro Arg Ser Arg Tyr Arg Leu Gln Leu
                450                 455                 460

cgc gcc agg ctc aat ggc ccc acc tac caa ggt ccc tgg agc tcg tgg      1441
Arg Ala Arg Leu Asn Gly Pro Thr Tyr Gln Gly Pro Trp Ser Ser Trp
            465                 470                 475

tcg gac cca gct agg gtg gag acc gcc acc gag acc gcc tgg att tcc      1489
Ser Asp Pro Ala Arg Val Glu Thr Ala Thr Glu Thr Ala Trp Ile Ser
        480                 485                 490

ttg gtg acc gct ctg ctg cta gtg ctg ggc ctc agc gcc gtc ctg ggc      1537
Leu Val Thr Ala Leu Leu Leu Val Leu Gly Leu Ser Ala Val Leu Gly
    495                 500                 505

ctg ctg ctg ctg agg tgg cag ttt cct gca cac tac agg aga ctg agg      1585
Leu Leu Leu Leu Arg Trp Gln Phe Pro Ala His Tyr Arg Arg Leu Arg
510                 515                 520                 525

cat gcc ctg tgg ccc tca ctt cca gat ctg cac cga gtc cta ggc cag      1633
His Ala Leu Trp Pro Ser Leu Pro Asp Leu His Arg Val Leu Gly Gln
                530                 535                 540

tac ctt agg gac act gca gcc ctg agt ccg ccc aag gcc aca gtc tca      1681
Tyr Leu Arg Asp Thr Ala Ala Leu Ser Pro Pro Lys Ala Thr Val Ser
            545                 550                 555

gat acc tgt gaa gaa gtg gaa ccc agc ctc ctt gaa atc ctc ccc aag      1729
Asp Thr Cys Glu Glu Val Glu Pro Ser Leu Leu Glu Ile Leu Pro Lys
        560                 565                 570

tcc tca gag agg act cct ttg ccc ctg tgt tcc tcc cag tcc cag atg      1777
Ser Ser Glu Arg Thr Pro Leu Pro Leu Cys Ser Ser Gln Ser Gln Met
    575                 580                 585

gac tac cga aga ttg cag cct tct tgc ctg ggg acc atg ccc ctg tct      1825
Asp Tyr Arg Arg Leu Gln Pro Ser Cys Leu Gly Thr Met Pro Leu Ser
590                 595                 600                 605

gtg tgc cca ccc atg gct gag tca ggg tcc tgc tgt acc acc cac att      1873
Val Cys Pro Pro Met Ala Glu Ser Gly Ser Cys Cys Thr Thr His Ile
                610                 615                 620

gcc aac cat tcc tac cta cca cta agc tat tgg cag cag cct tga          1918
Ala Asn His Ser Tyr Leu Pro Leu Ser Tyr Trp Gln Gln Pro
            625                 630                 635

gtcgac                                                               1924


<210> SEQ ID NO 165
<211> LENGTH: 635
<212> TYPE: PRT
<213> ORGANISM: Macaca fascicularis

<400> SEQUENCE: 165

Met Pro Ser Trp Ala Leu Phe Met Val Thr Ser Cys Leu Leu Leu Ala
1               5                   10                  15

Pro Gln Asn Leu Ala Gln Val Ser Ser Gln Asp Val Ser Leu Leu Ala
            20                  25                  30

Ser Asp Ser Glu Pro Leu Lys Cys Phe Ser Arg Thr Phe Glu Asp Leu
        35                  40                  45

Thr Cys Phe Trp Asp Glu Glu Glu Ala Ala Pro Ser Gly Thr Tyr Gln
    50                  55                  60

Leu Leu Tyr Ala Tyr Pro Gly Glu Lys Pro Arg Ala Cys Pro Leu Ser
65                  70                  75                  80
```

```
Ser Gln Ser Val Pro Arg Phe Gly Thr Arg Tyr Val Cys Gln Phe Pro
                85                  90                  95

Ala Gln Glu Glu Val Arg Leu Phe Ser Pro Leu His Leu Trp Val Lys
            100                 105                 110

Asn Val Phe Leu Asn Gln Thr Gln Ile Gln Arg Val Leu Phe Val Asp
        115                 120                 125

Ser Val Gly Leu Pro Ala Pro Pro Ser Ile Ile Lys Ala Met Gly Gly
    130                 135                 140

Ser Gln Pro Gly Glu Leu Gln Ile Ser Trp Glu Ala Pro Ala Pro Glu
145                 150                 155                 160

Ile Ser Asp Phe Leu Arg Tyr Glu Leu Arg Tyr Gly Pro Lys Asp Leu
                165                 170                 175

Lys Asn Ser Thr Gly Pro Thr Val Ile Gln Leu Ile Ala Thr Glu Thr
            180                 185                 190

Cys Cys Pro Ala Leu Gln Arg Pro His Ser Ala Ser Ala Leu Asp Gln
        195                 200                 205

Ser Pro Cys Ala Gln Pro Thr Met Pro Trp Gln Asp Gly Pro Lys Gln
    210                 215                 220

Thr Ser Pro Thr Arg Glu Ala Ser Ala Leu Thr Ala Val Gly Gly Ser
225                 230                 235                 240

Cys Leu Ile Ser Gly Leu Gln Pro Gly Asn Ser Tyr Trp Leu Gln Leu
                245                 250                 255

Arg Ser Glu Pro Asp Gly Ile Ser Leu Gly Gly Ser Trp Gly Ser Trp
            260                 265                 270

Ser Leu Pro Val Thr Val Asp Leu Pro Gly Asp Ala Val Ala Ile Gly
        275                 280                 285

Leu Gln Cys Phe Thr Leu Asp Leu Lys Asn Val Thr Cys Gln Trp Gln
    290                 295                 300

Gln Glu Asp His Ala Ser Ser Gln Gly Phe Phe Tyr His Ser Arg Ala
305                 310                 315                 320

Arg Cys Cys Pro Arg Asp Arg Tyr Pro Ile Trp Glu Asp Cys Glu Glu
                325                 330                 335

Glu Glu Lys Thr Asn Pro Gly Leu Gln Thr Pro Gln Phe Ser Arg Cys
            340                 345                 350

His Phe Lys Ser Arg Asn Asp Ser Val Ile His Ile Leu Val Glu Val
        355                 360                 365

Thr Thr Ala Leu Gly Ala Val His Ser Tyr Leu Gly Ser Pro Phe Trp
    370                 375                 380

Ile His Gln Ala Val Arg Leu Pro Thr Pro Asn Leu His Trp Arg Glu
385                 390                 395                 400

Ile Ser Ser Gly His Leu Glu Leu Glu Trp Gln His Pro Ser Ser Trp
                405                 410                 415

Ala Ala Gln Glu Thr Cys Tyr Gln Leu Arg Tyr Thr Gly Glu Gly His
            420                 425                 430

Gln Asp Trp Lys Val Leu Glu Pro Pro Leu Gly Ala Arg Gly Gly Thr
        435                 440                 445

Leu Glu Leu Arg Pro Arg Ser Arg Tyr Arg Leu Gln Leu Arg Ala Arg
    450                 455                 460

Leu Asn Gly Pro Thr Tyr Gln Gly Pro Trp Ser Ser Trp Ser Asp Pro
465                 470                 475                 480

Ala Arg Val Glu Thr Ala Thr Glu Thr Ala Trp Ile Ser Leu Val Thr
                485                 490                 495

Ala Leu Leu Leu Val Leu Gly Leu Ser Ala Val Leu Gly Leu Leu Leu
```

```
            500                 505                 510

Leu Arg Trp Gln Phe Pro Ala His Tyr Arg Arg Leu Arg His Ala Leu
        515                 520                 525

Trp Pro Ser Leu Pro Asp Leu His Arg Val Leu Gly Gln Tyr Leu Arg
    530                 535                 540

Asp Thr Ala Ala Leu Ser Pro Pro Lys Ala Thr Val Ser Asp Thr Cys
545                 550                 555                 560

Glu Glu Val Glu Pro Ser Leu Leu Glu Ile Leu Pro Lys Ser Ser Glu
                565                 570                 575

Arg Thr Pro Leu Pro Leu Cys Ser Ser Gln Ser Gln Met Asp Tyr Arg
            580                 585                 590

Arg Leu Gln Pro Ser Cys Leu Gly Thr Met Pro Leu Ser Val Cys Pro
        595                 600                 605

Pro Met Ala Glu Ser Gly Ser Cys Cys Thr Thr His Ile Ala Asn His
    610                 615                 620

Ser Tyr Leu Pro Leu Ser Tyr Trp Gln Gln Pro
625                 630                 635


<210> SEQ ID NO 166
<211> LENGTH: 24
<212> TYPE: DNA
<213> ORGANISM: Artificial
<220> FEATURE:
<223> OTHER INFORMATION: an artificially synthesized sequence

<400> SEQUENCE: 166

caggggccag tggatagact gatg                                            24


<210> SEQ ID NO 167
<211> LENGTH: 23
<212> TYPE: DNA
<213> ORGANISM: Artificial
<220> FEATURE:
<223> OTHER INFORMATION: an artificially synthesized sequence

<400> SEQUENCE: 167

gctcactgga tggtgggaag atg                                             23


<210> SEQ ID NO 168
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 168

tagaattcca ccatggaatg gcctttgatc                                      30


<210> SEQ ID NO 169
<211> LENGTH: 56
<212> TYPE: DNA
<213> ORGANISM: Artificial
<220> FEATURE:
<223> OTHER INFORMATION: an artificially synthesized primer sequence

<400> SEQUENCE: 169

agcctgagtc atcacaatat ccgatccgcc tccacctgca gagacagtga ccagag         56


<210> SEQ ID NO 170
<211> LENGTH: 56
<212> TYPE: DNA
<213> ORGANISM: Artificial
<220> FEATURE:
```

<223> OTHER INFORMATION: an artificially synthesized primer sequence

<400> SEQUENCE: 170
actctggtca ctgtctctgc aggtggaggc ggatcggata ttgtgatgac tcaggc 56

<210> SEQ ID NO 171
<211> LENGTH: 60
<212> TYPE: DNA
<213> ORGANISM: Artificial
<220> FEATURE:
<223> OTHER INFORMATION: an artificially synthesized primer sequence

<400> SEQUENCE: 171
attgcggccg cttatcactt atcgtcgtca tccttgtagt cttttatttc cagcttggtc 60

<210> SEQ ID NO 172
<211> LENGTH: 8
<212> TYPE: PRT
<213> ORGANISM: Artificial
<220> FEATURE:
<223> OTHER INFORMATION: an artificially synthesized FLAG tag sequence

<400> SEQUENCE: 172

Asp Tyr Lys Asp Asp Asp Asp Lys
1 5

<210> SEQ ID NO 173
<211> LENGTH: 85
<212> TYPE: DNA
<213> ORGANISM: Artificial
<220> FEATURE:
<223> OTHER INFORMATION: an artificially synthesized primer sequence

<400> SEQUENCE: 173
tagaattcca ccatggaatg gcctttgatc tttctcttcc tcctgtcagg aactgcaggt 60
gtccactccc aggttcagct gcagc 85

<210> SEQ ID NO 174
<211> LENGTH: 82
<212> TYPE: DNA
<213> ORGANISM: Artificial
<220> FEATURE:
<223> OTHER INFORMATION: an artificially synthesized primer sequence

<400> SEQUENCE: 174
tggtcactgt ctctgcaggt ggtggtggtt cgggtggtgg tggttcgggt ggtggcggat 60
cggatattgt gatgactcag gc 82

<210> SEQ ID NO 175
<211> LENGTH: 82
<212> TYPE: DNA
<213> ORGANISM: Artificial
<220> FEATURE:
<223> OTHER INFORMATION: an artificially synthesized primer sequence

<400> SEQUENCE: 175
tgagtcatca caatatccga tccgccacca cccgaaccac caccacccga accaccacca 60
cctgcagaga cagtgaccag ag 82

<210> SEQ ID NO 176
<211> LENGTH: 25
<212> TYPE: DNA
<213> ORGANISM: Artificial
<220> FEATURE:
<223> OTHER INFORMATION: an artificially synthesized primer sequence

<400> SEQUENCE: 176
caggttcagc tgcagcagtc tggac 25

<210> SEQ ID NO 177
<211> LENGTH: 81
<212> TYPE: DNA
<213> ORGANISM: Artificial
<220> FEATURE:
<223> OTHER INFORMATION: an artificially synthesized primer sequence

<400> SEQUENCE: 177
gctgcagctg aacctgcgat ccaccgcctc ccgaaccacc accacccgat ccaccacctc 60
cttttatttc cagcttggtc c 81

<210> SEQ ID NO 178
<211> LENGTH: 38
<212> TYPE: DNA
<213> ORGANISM: Artificial
<220> FEATURE:
<223> OTHER INFORMATION: an artificially synthesized primer sequence

<400> SEQUENCE: 178
gcccagccgg ccatggcgga kgtrmagctt caggagtc 38

<210> SEQ ID NO 179
<211> LENGTH: 38
<212> TYPE: DNA
<213> ORGANISM: Artificial
<220> FEATURE:
<223> OTHER INFORMATION: an artificially synthesized primer sequence

<400> SEQUENCE: 179
gcccagccgg ccatggcgga ggtbcagctb cagcagtc 38

<210> SEQ ID NO 180
<211> LENGTH: 38
<212> TYPE: DNA
<213> ORGANISM: Artificial
<220> FEATURE:
<223> OTHER INFORMATION: an artificially synthesized primer sequence

<400> SEQUENCE: 180
gcccagccgg ccatggcgca ggtgcagctg aagsastc 38

<210> SEQ ID NO 181
<211> LENGTH: 38
<212> TYPE: DNA
<213> ORGANISM: Artificial
<220> FEATURE:
<223> OTHER INFORMATION: an artificially synthesized primer sequence

<400> SEQUENCE: 181
gcccagccgg ccatggcgga ggtccarctg caacartc 38

<210> SEQ ID NO 182
<211> LENGTH: 38
<212> TYPE: DNA
<213> ORGANISM: Artificial
<220> FEATURE:
<223> OTHER INFORMATION: an artificially synthesized primer sequence

<400> SEQUENCE: 182
gcccagccgg ccatggcgca ggtycagctb cagcartc 38

<210> SEQ ID NO 183
<211> LENGTH: 38
<212> TYPE: DNA
<213> ORGANISM: Artificial
<220> FEATURE:
<223> OTHER INFORMATION: an artificially synthesized primer sequence

<400> SEQUENCE: 183
gcccagccgg ccatggcgca ggtycarctg cagcagtc 38

<210> SEQ ID NO 184
<211> LENGTH: 38
<212> TYPE: DNA
<213> ORGANISM: Artificial
<220> FEATURE:
<223> OTHER INFORMATION: an artificially synthesized primer sequence

<400> SEQUENCE: 184
gcccagccgg ccatggcgca ggtccacgtg aagcagtc 38

<210> SEQ ID NO 185
<211> LENGTH: 38
<212> TYPE: DNA
<213> ORGANISM: Artificial
<220> FEATURE:
<223> OTHER INFORMATION: an artificially synthesized primer sequence

<400> SEQUENCE: 185
gcccagccgg ccatggcgga ggtgaasstg gtggaatc 38

<210> SEQ ID NO 186
<211> LENGTH: 38
<212> TYPE: DNA
<213> ORGANISM: Artificial
<220> FEATURE:
<223> OTHER INFORMATION: an artificially synthesized primer sequence

<400> SEQUENCE: 186
gcccagccgg ccatggcgga vgtgawgytg gtggagtc 38

<210> SEQ ID NO 187
<211> LENGTH: 38
<212> TYPE: DNA
<213> ORGANISM: Artificial
<220> FEATURE:
<223> OTHER INFORMATION: an artificially synthesized primer sequence

<400> SEQUENCE: 187
gcccagccgg ccatggcgga ggtgcagskg gtggagtc 38

<210> SEQ ID NO 188
<211> LENGTH: 38
<212> TYPE: DNA
<213> ORGANISM: Artificial
<220> FEATURE:
<223> OTHER INFORMATION: an artificially synthesized primer sequence

<400> SEQUENCE: 188
gcccagccgg ccatggcgga kgtgcamctg gtggagtc 38

<210> SEQ ID NO 189
<211> LENGTH: 38
<212> TYPE: DNA
<213> ORGANISM: Artificial
<220> FEATURE:
<223> OTHER INFORMATION: an artificially synthesized primer sequence

<400> SEQUENCE: 189
gcccagccgg ccatggcgga ggtgaagctg atggartc 38

<210> SEQ ID NO 190
<211> LENGTH: 38
<212> TYPE: DNA
<213> ORGANISM: Artificial
<220> FEATURE:
<223> OTHER INFORMATION: an artificially synthesized primer sequence

<400> SEQUENCE: 190
gcccagccgg ccatggcgga ggtgcarctt gttgagtc 38

<210> SEQ ID NO 191
<211> LENGTH: 38
<212> TYPE: DNA
<213> ORGANISM: Artificial
<220> FEATURE:
<223> OTHER INFORMATION: an artificially synthesized primer sequence

<400> SEQUENCE: 191
gcccagccgg ccatggcgga rgtraagctt ctcgagtc 38

<210> SEQ ID NO 192
<211> LENGTH: 38
<212> TYPE: DNA
<213> ORGANISM: Artificial
<220> FEATURE:
<223> OTHER INFORMATION: an artificially synthesized primer sequence

<400> SEQUENCE: 192
gcccagccgg ccatggcgga agtgaarstt gaggagtc 38

<210> SEQ ID NO 193
<211> LENGTH: 40
<212> TYPE: DNA
<213> ORGANISM: Artificial
<220> FEATURE:
<223> OTHER INFORMATION: an artificially synthesized primer sequence

<400> SEQUENCE: 193
gcccagccgg ccatggcgca ggttactctr aaagwgtstg 40

<210> SEQ ID NO 194
<211> LENGTH: 38
<212> TYPE: DNA
<213> ORGANISM: Artificial
<220> FEATURE:
<223> OTHER INFORMATION: an artificially synthesized primer sequence

<400> SEQUENCE: 194
gcccagccgg ccatggcgca ggtccaactv cagcarcc 38

<210> SEQ ID NO 195
<211> LENGTH: 38
<212> TYPE: DNA
<213> ORGANISM: Artificial
<220> FEATURE:
<223> OTHER INFORMATION: an artificially synthesized primer sequence

<400> SEQUENCE: 195
gcccagccgg ccatggcgga tgtgaacttg gaagtgtc 38

<210> SEQ ID NO 196
<211> LENGTH: 38
<212> TYPE: DNA
<213> ORGANISM: Artificial

<220> FEATURE:
<223> OTHER INFORMATION: an artificially synthesized primer sequence

<400> SEQUENCE: 196
gcccagccgg ccatggcgga ggtgaaggtc atcgagtc 38

<210> SEQ ID NO 197
<211> LENGTH: 36
<212> TYPE: DNA
<213> ORGANISM: Artificial
<220> FEATURE:
<223> OTHER INFORMATION: an artificially synthesized primer sequence

<400> SEQUENCE: 197
ggagccgccg ccgcccgagg aaacggtgac cgtggt 36

<210> SEQ ID NO 198
<211> LENGTH: 36
<212> TYPE: DNA
<213> ORGANISM: Artificial
<220> FEATURE:
<223> OTHER INFORMATION: an artificially synthesized primer sequence

<400> SEQUENCE: 198
ggagccgccg ccgcccgagg agactgtgag agtggt 36

<210> SEQ ID NO 199
<211> LENGTH: 36
<212> TYPE: DNA
<213> ORGANISM: Artificial
<220> FEATURE:
<223> OTHER INFORMATION: an artificially synthesized primer sequence

<400> SEQUENCE: 199
ggagccgccg ccgcccgcag agacagtgac cagagt 36

<210> SEQ ID NO 200
<211> LENGTH: 36
<212> TYPE: DNA
<213> ORGANISM: Artificial
<220> FEATURE:
<223> OTHER INFORMATION: an artificially synthesized primer sequence

<400> SEQUENCE: 200
ggagccgccg ccgcccgagg agacggtgac tgaggt 36

<210> SEQ ID NO 201
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 201
ggcggcggcg gctccgayat ccagctgact cagcc 35

<210> SEQ ID NO 202
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 202
ggcggcggcg gctccgayat tgttctcwcc cagtc 35

<210> SEQ ID NO 203
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 203
ggcggcggcg gctccgayat tgtgmtmact cagtc 35

<210> SEQ ID NO 204
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 204
ggcggcggcg gctccgayat tgtgytraca cagtc 35

<210> SEQ ID NO 205
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 205
ggcggcggcg gctccgayat tgtratgacm cagtc 35

<210> SEQ ID NO 206
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 206
ggcggcggcg gctccgayat tmagatramc cagtc 35

<210> SEQ ID NO 207
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 207
ggcggcggcg gctccgayat tcagatgayd cagtc 35

<210> SEQ ID NO 208
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 208
ggcggcggcg gctccgayat ycagatgaca cagac 35

<210> SEQ ID NO 209
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 209

```
ggcggcggcg gctccgayat tgttctcawc cagtc                              35


<210> SEQ ID NO 210
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 210

ggcggcggcg gctccgayat tgwgctsacc caatc                              35


<210> SEQ ID NO 211
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 211

ggcggcggcg gctccgayat tstratgacc cartc                              35


<210> SEQ ID NO 212
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 212

ggcggcggcg gctccgayrt tktgatgacc carac                              35


<210> SEQ ID NO 213
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 213

ggcggcggcg gctccgayat tgtgatgacb cagkc                              35


<210> SEQ ID NO 214
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 214

ggcggcggcg gctccgayat tgtgataacy cagga                              35


<210> SEQ ID NO 215
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 215

ggcggcggcg gctccgayat tgtgatgacc cagwt                              35


<210> SEQ ID NO 216
<211> LENGTH: 35
<212> TYPE: DNA
<213> ORGANISM: Artificial
```

<220> FEATURE:
<223> OTHER INFORMATION: an artificially synthesized primer sequence

<400> SEQUENCE: 216
ggcggcggcg gctccgayat tgtgatgaca caacc 35

<210> SEQ ID NO 217
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 217
ggcggcggcg gctccgayat tttgctgact cagtc 35

<210> SEQ ID NO 218
<211> LENGTH: 38
<212> TYPE: DNA
<213> ORGANISM: Artificial
<220> FEATURE:
<223> OTHER INFORMATION: an artificially synthesized primer sequence

<400> SEQUENCE: 218
ggcggcggcg gctccgatgc tgttgtgact caggaatc 38

<210> SEQ ID NO 219
<211> LENGTH: 36
<212> TYPE: DNA
<213> ORGANISM: Artificial
<220> FEATURE:
<223> OTHER INFORMATION: an artificially synthesized primer sequence

<400> SEQUENCE: 219
ggaattcggc ccccgaggcc ttgatttcca gcttgg 36

<210> SEQ ID NO 220
<211> LENGTH: 36
<212> TYPE: DNA
<213> ORGANISM: Artificial
<220> FEATURE:
<223> OTHER INFORMATION: an artificially synthesized primer sequence

<400> SEQUENCE: 220
ggaattcggc ccccgaggcc tttatttcca gcttgg 36

<210> SEQ ID NO 221
<211> LENGTH: 36
<212> TYPE: DNA
<213> ORGANISM: Artificial
<220> FEATURE:
<223> OTHER INFORMATION: an artificially synthesized primer sequence

<400> SEQUENCE: 221
ggaattcggc ccccgaggcc tttatttcca actttg 36

<210> SEQ ID NO 222
<211> LENGTH: 36
<212> TYPE: DNA
<213> ORGANISM: Artificial
<220> FEATURE:
<223> OTHER INFORMATION: an artificially synthesized primer sequence

<400> SEQUENCE: 222
ggaattcggc ccccgaggcc ttcagctcca gcttgg 36

<210> SEQ ID NO 223
<211> LENGTH: 39
<212> TYPE: DNA
<213> ORGANISM: Artificial
<220> FEATURE:
<223> OTHER INFORMATION: an artificially synthesized primer sequence

<400> SEQUENCE: 223
ggaattcggc ccccgaggcc cctaggacag tcagtttgg 39

<210> SEQ ID NO 224
<211> LENGTH: 27
<212> TYPE: DNA
<213> ORGANISM: Artificial
<220> FEATURE:
<223> OTHER INFORMATION: an artificially synthesized sequence

<400> SEQUENCE: 224
ttactcgcgg cccagccggc catggcg 27

<210> SEQ ID NO 225
<211> LENGTH: 17
<212> TYPE: DNA
<213> ORGANISM: Artificial
<220> FEATURE:
<223> OTHER INFORMATION: an artificially synthesized sequence

<400> SEQUENCE: 225
ggaattcggc ccccgag 17

<210> SEQ ID NO 226
<211> LENGTH: 20
<212> TYPE: DNA
<213> ORGANISM: Artificial
<220> FEATURE:
<223> OTHER INFORMATION: an artificially synthesized sequence

<400> SEQUENCE: 226
tcacttacag gctctctact 20

<210> SEQ ID NO 227
<211> LENGTH: 20
<212> TYPE: DNA
<213> ORGANISM: Artificial
<220> FEATURE:
<223> OTHER INFORMATION: an artificially synthesized sequence

<400> SEQUENCE: 227
caggtggggt ctttcattcc 20

<210> SEQ ID NO 228
<211> LENGTH: 354
<212> TYPE: DNA
<213> ORGANISM: Homo sapiens

<400> SEQUENCE: 228
caggtgcagc tggtgcagtc tggacctgag gtgaagaagc ctggggcctc agtgaaggtc 60
tcctgcaagg cttctggata caccttcacc aactcctgga tgaactgggt gaggcagagg 120
cctggaaagg gtcttgagtg gatgggacgg atttatcctg gagatggaga aactatctac 180
aatgggaaat tcagggtcag agtcacgatt accgcggacg aatccacgag cacagcctac 240
atggagctga gcagcctgag atctgaggac acggccgtgt attactgtgc gagaggctat 300
gatgattact cgtttgctta ctggggccag ggaaccacgg tcaccgtctc ttca 354

<210> SEQ ID NO 229
<211> LENGTH: 118
<212> TYPE: PRT
<213> ORGANISM: Homo sapiens

<400> SEQUENCE: 229

```
Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asn Ser
            20                  25                  30

Trp Met Asn Trp Val Arg Gln Arg Pro Gly Lys Gly Leu Glu Trp Met
        35                  40                  45

Gly Arg Ile Tyr Pro Gly Asp Gly Glu Thr Ile Tyr Asn Gly Lys Phe
    50                  55                  60

Arg Val Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Asp Tyr Ser Phe Ala Tyr Trp Gly Gln Gly Thr
            100                 105                 110

Thr Val Thr Val Ser Ser
        115
```

<210> SEQ ID NO 230
<211> LENGTH: 30
<212> TYPE: PRT
<213> ORGANISM: Homo sapiens

<400> SEQUENCE: 230

```
Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr
            20                  25                  30
```

<210> SEQ ID NO 231
<211> LENGTH: 5
<212> TYPE: PRT
<213> ORGANISM: Homo sapiens

<400> SEQUENCE: 231

```
Asn Ser Trp Met Asn
1               5
```

<210> SEQ ID NO 232
<211> LENGTH: 14
<212> TYPE: PRT
<213> ORGANISM: Homo sapiens

<400> SEQUENCE: 232

```
Trp Val Arg Gln Arg Pro Gly Lys Gly Leu Glu Trp Met Gly
1               5                   10
```

<210> SEQ ID NO 233
<211> LENGTH: 17
<212> TYPE: PRT
<213> ORGANISM: Homo sapiens

<400> SEQUENCE: 233

```
Arg Ile Tyr Pro Gly Asp Gly Glu Thr Ile Tyr Asn Gly Lys Phe Arg
1               5                   10                  15

Val
```

<210> SEQ ID NO 234
<211> LENGTH: 32
<212> TYPE: PRT
<213> ORGANISM: Homo sapiens

<400> SEQUENCE: 234

Arg Val Thr Ile Thr Ala Asp Glu Ser Thr Ser Thr Ala Tyr Met Glu
1 5 10 15

Leu Ser Ser Leu Arg Ser Glu Asp Thr Ala Val Tyr Tyr Cys Ala Arg
20 25 30

<210> SEQ ID NO 235
<211> LENGTH: 9
<212> TYPE: PRT
<213> ORGANISM: Homo sapiens

<400> SEQUENCE: 235

Gly Tyr Asp Asp Tyr Ser Phe Ala Tyr
1 5

<210> SEQ ID NO 236
<211> LENGTH: 11
<212> TYPE: PRT
<213> ORGANISM: Homo sapiens

<400> SEQUENCE: 236

Trp Gly Gln Gly Thr Thr Val Thr Val Ser Ser
1 5 10

<210> SEQ ID NO 237
<211> LENGTH: 336
<212> TYPE: DNA
<213> ORGANISM: Homo sapiens

<400> SEQUENCE: 237
gatattgtga tgactcagtc tgcactctcc ctgcccgtca cccctggaga gccggcctcc 60
atctcctgca ggtctagtaa gagtctcctg catagtaatg gcaacactta cttgtattgg 120
ttccagcaga agccagggca gtctccacag ctcctgatct atcggatgtc caaccttgcc 180
tcaggggtcc ctgacaggtt cagtggcagt ggatcaggca cagcttttac actgaaaatc 240
agcagagtgg aggctgagga tgttggggtt tattactgca tgcaacatat agaatatcct 300
tttacgttcg gccaagggac caaactggaa atcaaa 336

<210> SEQ ID NO 238
<211> LENGTH: 112
<212> TYPE: PRT
<213> ORGANISM: Homo sapiens

<400> SEQUENCE: 238

Asp Ile Val Met Thr Gln Ser Ala Leu Ser Leu Pro Val Thr Pro Gly
1 5 10 15

Glu Pro Ala Ser Ile Ser Cys Arg Ser Ser Lys Ser Leu Leu His Ser
20 25 30

Asn Gly Asn Thr Tyr Leu Tyr Trp Phe Gln Gln Lys Pro Gly Gln Ser
35 40 45

Pro Gln Leu Leu Ile Tyr Arg Met Ser Asn Leu Ala Ser Gly Val Pro
50 55 60

Asp Arg Phe Ser Gly Ser Gly Ser Gly Thr Ala Phe Thr Leu Lys Ile
65 70 75 80

Ser Arg Val Glu Ala Glu Asp Val Gly Val Tyr Tyr Cys Met Gln His

```
                85                  90                  95

Ile Glu Tyr Pro Phe Thr Phe Gly Gln Gly Thr Lys Leu Glu Ile Lys
            100                 105                 110


<210> SEQ ID NO 239
<211> LENGTH: 23
<212> TYPE: PRT
<213> ORGANISM: Homo sapiens

<400> SEQUENCE: 239

Asp Ile Val Met Thr Gln Ser Ala Leu Ser Leu Pro Val Thr Pro Gly
1               5                   10                  15

Glu Pro Ala Ser Ile Ser Cys
            20


<210> SEQ ID NO 240
<211> LENGTH: 16
<212> TYPE: PRT
<213> ORGANISM: Homo sapiens

<400> SEQUENCE: 240

Arg Ser Ser Lys Ser Leu Leu His Ser Asn Gly Asn Thr Tyr Leu Tyr
1               5                   10                  15


<210> SEQ ID NO 241
<211> LENGTH: 15
<212> TYPE: PRT
<213> ORGANISM: Homo sapiens

<400> SEQUENCE: 241

Trp Phe Gln Gln Lys Pro Gly Gln Ser Pro Gln Leu Leu Ile Tyr
1               5                   10                  15


<210> SEQ ID NO 242
<211> LENGTH: 7
<212> TYPE: PRT
<213> ORGANISM: Homo sapiens

<400> SEQUENCE: 242

Arg Met Ser Asn Leu Ala Ser
1               5


<210> SEQ ID NO 243
<211> LENGTH: 32
<212> TYPE: PRT
<213> ORGANISM: Homo sapiens

<400> SEQUENCE: 243

Gly Val Pro Asp Arg Phe Ser Gly Ser Gly Ser Gly Thr Ala Phe Thr
1               5                   10                  15

Leu Lys Ile Ser Arg Val Glu Ala Glu Asp Val Gly Val Tyr Tyr Cys
            20                  25                  30


<210> SEQ ID NO 244
<211> LENGTH: 9
<212> TYPE: PRT
<213> ORGANISM: Homo sapiens

<400> SEQUENCE: 244

Met Gln His Ile Glu Tyr Pro Phe Thr
1               5


<210> SEQ ID NO 245
<211> LENGTH: 10
```

<212> TYPE: PRT
<213> ORGANISM: Homo sapiens

<400> SEQUENCE: 245

Phe Gly Gln Gly Thr Lys Leu Glu Ile Lys
1               5                   10

<210> SEQ ID NO 246
<211> LENGTH: 1924
<212> TYPE: DNA
<213> ORGANISM: Homo sapiens

<400> SEQUENCE: 246
gaattccacc atgccctcct gggccctctt catggtcacc tcctgcctcc tcctggcccc 60
tcaaaacctg gcccaagtca gcagccaaga tgtctccttg ctggcatcag actcagagcc 120
cctgaagtgt ttctcccgaa catttgagga cctcacttgc ttctgggatg aggaagaggc 180
agcgcccagt gggacatacc agctgctgta tgcctacccg cgggagaagc cccgtgcttg 240
ccccctgagt tcccagagca tgccccactt tggaacccga tacgtgtgcc agtttccaga 300
ccaggaggaa gtgcgtctct tctttccgct gcacctctgg gtgaagaatg tgttcctaaa 360
ccagactcgg actcagcgag tcctctttgt ggacagtgta ggcctgccgg ctccccccag 420
tatcatcaag gccatgggtg ggagccagcc aggggaactt cagatcagct gggaggagcc 480
agctccagaa atcagtgatt tcctgaggta cgaactccgc tatggcccca gagatcccaa 540
gaactccact ggtcccacgg tcatacagct gattgccaca gaaacctgct gccctgctct 600
gcagagacct cactcagcct ctgctctgga ccagtctcca tgtgctcagc ccacaatgcc 660
ctggcaagat ggaccaaagc agacctcccc aagtagagaa gcttcagctc tgacagcaga 720
gggtggaagc tgcctcatct caggactcca gcctggcaac tcctactggc tgcagctgcg 780
cagcgaacct gatgggatct ccctcggtgg ctcctgggga tcctggtccc tccctgtgac 840
tgtggacctg cctggagatg cagtggcact tggactgcaa tgctttacct tggacctgaa 900
gaatgttacc tgtcaatggc agcaacagga ccatgctagc tcccaaggct tcttctacca 960
cagcagggca cggtgctgcc ccagagacag gtaccccatc tgggagaact gcgaagagga 1020
agagaaaaca aatccaggac tacagacccc acagttctct cgctgccact tcaagtcacg 1080
aaatgacagc attattcaca tccttgtgga ggtgaccaca gccccgggta ctgttcacag 1140
ctacctgggc tcccctttct ggatccacca ggctgtgcgc ctccccaccc caaacttgca 1200
ctggagggag atctccagtg ggcatctgga attggagtgg cagcacccat cgtcctgggc 1260
agcccaagag acctgttatc aactccgata cacaggagaa ggccatcagg actggaaggt 1320
gctggagccg cctctcgggg cccgaggagg gaccctggag ctgcgcccgc gatctcgcta 1380
ccgtttacag ctgcgcgcca ggctcaacgg ccccacctac caaggtccct ggagctcgtg 1440
gtcggaccca actagggtgg agaccgccac cgagaccgcc tggatctcct tggtgaccgc 1500
tctgcatcta gtgctgggcc tcagcgccgt cctgggcctg ctgctgctga ggtggcagtt 1560
tcctgcacac tacaggagac tgaggcatgc cctgtggccc tcacttccag acctgcaccg 1620
ggtcctaggc cagtacctta gggacactgc agccctgagc ccgcccaagg ccacagtctc 1680
agatacctgt gaagaagtgg aacccagcct ccttgaaatc ctccccaagt cctcagagag 1740
gactcctttg cccctgtgtt cctcccaggc ccagatggac taccgaagat tgcagccttc 1800
ttgcctgggg accatgcccc tgtctgtgtg cccacccatg gctgagtcag ggtcctgctg 1860
taccacccac attgccaacc attcctacct accactaagc tattggcagc agccttgagt 1920

```
cgac                                                            1924


<210> SEQ ID NO 247
<211> LENGTH: 1924
<212> TYPE: DNA
<213> ORGANISM: Homo sapiens
<220> FEATURE:
<221> NAME/KEY: CDS
<222> LOCATION: (11)..(1918)

<400> SEQUENCE: 247

gaattccacc atg ccc tcc tgg gcc ctc ttc atg gtc acc tcc tgc ctc        49
           Met Pro Ser Trp Ala Leu Phe Met Val Thr Ser Cys Leu
           1               5                   10

ctc ctg gcc cct caa aac ctg gcc caa gtc agc agc caa gat gtc tcc       97
Leu Leu Ala Pro Gln Asn Leu Ala Gln Val Ser Ser Gln Asp Val Ser
    15                  20                  25

ttg ctg gca tca gac tca gag ccc ctg aag tgt ttc tcc cga aca ttt      145
Leu Leu Ala Ser Asp Ser Glu Pro Leu Lys Cys Phe Ser Arg Thr Phe
30                  35                  40                  45

gag gac ctc act tgc ttc tgg gat gag gaa gag gca gcg ccc agt ggg      193
Glu Asp Leu Thr Cys Phe Trp Asp Glu Glu Glu Ala Ala Pro Ser Gly
                50                  55                  60

aca tac cag ctg ctg tat gcc tac ccg cgg gag aag ccc cgt gct tgc      241
Thr Tyr Gln Leu Leu Tyr Ala Tyr Pro Arg Glu Lys Pro Arg Ala Cys
            65                  70                  75

ccc ctg agt tcc cag agc atg ccc cac ttt gga acc cga tac gtg tgc      289
Pro Leu Ser Ser Gln Ser Met Pro His Phe Gly Thr Arg Tyr Val Cys
        80                  85                  90

cag ttt cca gac cag gag gaa gtg cct ctc ttc ttt ccg ctg cac ctc      337
Gln Phe Pro Asp Gln Glu Glu Val Pro Leu Phe Phe Pro Leu His Leu
    95                  100                 105

tgg gtg aag aat gtg ttc cta aac cag act cgg act cag cga gtc ctc      385
Trp Val Lys Asn Val Phe Leu Asn Gln Thr Arg Thr Gln Arg Val Leu
110                 115                 120                 125

ttt gtg gac agt gta ggc ctg ccg gct ccc ccc agt atc atc aag gcc      433
Phe Val Asp Ser Val Gly Leu Pro Ala Pro Pro Ser Ile Ile Lys Ala
                130                 135                 140

atg ggt ggg agc cag cca ggg gaa ctt cag atc agc tgg gag gag cca      481
Met Gly Gly Ser Gln Pro Gly Glu Leu Gln Ile Ser Trp Glu Glu Pro
            145                 150                 155

gct cca gaa atc agt gat ttc ctg agg tac gaa ctc cgc tat ggc ccc      529
Ala Pro Glu Ile Ser Asp Phe Leu Arg Tyr Glu Leu Arg Tyr Gly Pro
        160                 165                 170

aga gat ccc aag aac tcc act ggt ccc acg gtc ata cag ctg att gcc      577
Arg Asp Pro Lys Asn Ser Thr Gly Pro Thr Val Ile Gln Leu Ile Ala
    175                 180                 185

aca gaa acc tgc tgc cct gct ctg cag aga cct cac tca gcc tct gct      625
Thr Glu Thr Cys Cys Pro Ala Leu Gln Arg Pro His Ser Ala Ser Ala
190                 195                 200                 205

ctg gac cag tct cca tgt gct cag ccc aca atg ccc tgg caa gat gga      673
Leu Asp Gln Ser Pro Cys Ala Gln Pro Thr Met Pro Trp Gln Asp Gly
                210                 215                 220

cca aag cag acc tcc cca agt aga gaa gct tca gct ctg aca gca gag      721
Pro Lys Gln Thr Ser Pro Ser Arg Glu Ala Ser Ala Leu Thr Ala Glu
            225                 230                 235

ggt gga agc tgc ctc atc tca gga ctc cag cct ggc aac tcc tac tgg      769
Gly Gly Ser Cys Leu Ile Ser Gly Leu Gln Pro Gly Asn Ser Tyr Trp
        240                 245                 250

ctg cag ctg cgc agc gaa cct gat ggg atc tcc ctc ggt ggc tcc tgg      817
Leu Gln Leu Arg Ser Glu Pro Asp Gly Ile Ser Leu Gly Gly Ser Trp
    255                 260                 265
```

```
gga tcc tgg tcc ctc cct gtg act gtg gac ctg cct gga gat gca gtg      865
Gly Ser Trp Ser Leu Pro Val Thr Val Asp Leu Pro Gly Asp Ala Val
270                 275                 280                 285

gca ctt gga ctg caa tgc ttt acc ttg gac ctg aag aat gtt acc tgt      913
Ala Leu Gly Leu Gln Cys Phe Thr Leu Asp Leu Lys Asn Val Thr Cys
                290                 295                 300

caa tgg cag caa cag gac cat gct agc tcc caa ggc ttc ttc tac cac      961
Gln Trp Gln Gln Gln Asp His Ala Ser Ser Gln Gly Phe Phe Tyr His
            305                 310                 315

agc agg gca cgg tgc tgc ccc aga gac agg tac ccc atc tgg gag aac     1009
Ser Arg Ala Arg Cys Cys Pro Arg Asp Arg Tyr Pro Ile Trp Glu Asn
        320                 325                 330

tgc gaa gag gaa gag aaa aca aat cca gga cta cag acc cca cag ttc     1057
Cys Glu Glu Glu Glu Lys Thr Asn Pro Gly Leu Gln Thr Pro Gln Phe
    335                 340                 345

tct cgc tgc cac ttc aag tca cga aat gac agc att att cac atc ctt     1105
Ser Arg Cys His Phe Lys Ser Arg Asn Asp Ser Ile Ile His Ile Leu
350                 355                 360                 365

gtg gag gtg acc aca gcc ccg ggt act gtt cac agc tac ctg ggc tcc     1153
Val Glu Val Thr Thr Ala Pro Gly Thr Val His Ser Tyr Leu Gly Ser
                370                 375                 380

cct ttc tgg atc cac cag gct gtg cgc ctc ccc acc cca aac ttg cac     1201
Pro Phe Trp Ile His Gln Ala Val Arg Leu Pro Thr Pro Asn Leu His
            385                 390                 395

tgg agg gag atc tcc agt ggg cat ctg gaa ttg gag tgg cag cac cca     1249
Trp Arg Glu Ile Ser Ser Gly His Leu Glu Leu Glu Trp Gln His Pro
        400                 405                 410

tcg tcc tgg gca gcc caa gag acc tgt tat caa ctc cga tac aca gga     1297
Ser Ser Trp Ala Ala Gln Glu Thr Cys Tyr Gln Leu Arg Tyr Thr Gly
    415                 420                 425

gaa ggc cat cag gac tgg aag gtg ctg gag ccg cct ctc ggg gcc cga     1345
Glu Gly His Gln Asp Trp Lys Val Leu Glu Pro Pro Leu Gly Ala Arg
430                 435                 440                 445

gga ggg acc ctg gag ctg cgc ccg cga tct cgc tac cgt tta cag ctg     1393
Gly Gly Thr Leu Glu Leu Arg Pro Arg Ser Arg Tyr Arg Leu Gln Leu
                450                 455                 460

cgc gcc agg ctc aac ggc ccc acc tac caa ggt ccc tgg agc tcg tgg     1441
Arg Ala Arg Leu Asn Gly Pro Thr Tyr Gln Gly Pro Trp Ser Ser Trp
            465                 470                 475

tcg gac cca act agg gtg gag acc gcc acc gag acc gcc tgg atc tcc     1489
Ser Asp Pro Thr Arg Val Glu Thr Ala Thr Glu Thr Ala Trp Ile Ser
        480                 485                 490

ttg gtg acc gct ctg cat cta gtg ctg ggc ctc agc gcc gtc ctg ggc     1537
Leu Val Thr Ala Leu His Leu Val Leu Gly Leu Ser Ala Val Leu Gly
    495                 500                 505

ctg ctg ctg ctg agg tgg cag ttt cct gca cac tac agg aga ctg agg     1585
Leu Leu Leu Leu Arg Trp Gln Phe Pro Ala His Tyr Arg Arg Leu Arg
510                 515                 520                 525

cat gcc ctg tgg ccc tca ctt cca gac ctg cac cgg gtc cta ggc cag     1633
His Ala Leu Trp Pro Ser Leu Pro Asp Leu His Arg Val Leu Gly Gln
                530                 535                 540

tac ctt agg gac act gca gcc ctg agc ccg ccc aag gcc aca gtc tca     1681
Tyr Leu Arg Asp Thr Ala Ala Leu Ser Pro Pro Lys Ala Thr Val Ser
            545                 550                 555

gat acc tgt gaa gaa gtg gaa ccc agc ctc ctt gaa atc ctc ccc aag     1729
Asp Thr Cys Glu Glu Val Glu Pro Ser Leu Leu Glu Ile Leu Pro Lys
        560                 565                 570

tcc tca gag agg act cct ttg ccc ctg tgt tcc tcc cag gcc cag atg     1777
Ser Ser Glu Arg Thr Pro Leu Pro Leu Cys Ser Ser Gln Ala Gln Met
    575                 580                 585
```

```
gac tac cga aga ttg cag cct tct tgc ctg ggg acc atg ccc ctg tct      1825
Asp Tyr Arg Arg Leu Gln Pro Ser Cys Leu Gly Thr Met Pro Leu Ser
590                 595                 600                 605

gtg tgc cca ccc atg gct gag tca ggg tcc tgc tgt acc acc cac att      1873
Val Cys Pro Pro Met Ala Glu Ser Gly Ser Cys Cys Thr Thr His Ile
                610                 615                 620

gcc aac cat tcc tac cta cca cta agc tat tgg cag cag cct tga          1918
Ala Asn His Ser Tyr Leu Pro Leu Ser Tyr Trp Gln Gln Pro
            625                 630                 635

gtcgac                                                               1924


<210> SEQ ID NO 248
<211> LENGTH: 635
<212> TYPE: PRT
<213> ORGANISM: Homo sapiens

<400> SEQUENCE: 248

Met Pro Ser Trp Ala Leu Phe Met Val Thr Ser Cys Leu Leu Leu Ala
1               5                   10                  15

Pro Gln Asn Leu Ala Gln Val Ser Ser Gln Asp Val Ser Leu Leu Ala
            20                  25                  30

Ser Asp Ser Glu Pro Leu Lys Cys Phe Ser Arg Thr Phe Glu Asp Leu
        35                  40                  45

Thr Cys Phe Trp Asp Glu Glu Glu Ala Ala Pro Ser Gly Thr Tyr Gln
    50                  55                  60

Leu Leu Tyr Ala Tyr Pro Arg Glu Lys Pro Arg Ala Cys Pro Leu Ser
65                  70                  75                  80

Ser Gln Ser Met Pro His Phe Gly Thr Arg Tyr Val Cys Gln Phe Pro
                85                  90                  95

Asp Gln Glu Glu Val Pro Leu Phe Phe Pro Leu His Leu Trp Val Lys
            100                 105                 110

Asn Val Phe Leu Asn Gln Thr Arg Thr Gln Arg Val Leu Phe Val Asp
        115                 120                 125

Ser Val Gly Leu Pro Ala Pro Pro Ser Ile Ile Lys Ala Met Gly Gly
    130                 135                 140

Ser Gln Pro Gly Glu Leu Gln Ile Ser Trp Glu Glu Pro Ala Pro Glu
145                 150                 155                 160

Ile Ser Asp Phe Leu Arg Tyr Glu Leu Arg Tyr Gly Pro Arg Asp Pro
                165                 170                 175

Lys Asn Ser Thr Gly Pro Thr Val Ile Gln Leu Ile Ala Thr Glu Thr
            180                 185                 190

Cys Cys Pro Ala Leu Gln Arg Pro His Ser Ala Ser Ala Leu Asp Gln
        195                 200                 205

Ser Pro Cys Ala Gln Pro Thr Met Pro Trp Gln Asp Gly Pro Lys Gln
    210                 215                 220

Thr Ser Pro Ser Arg Glu Ala Ser Ala Leu Thr Ala Glu Gly Gly Ser
225                 230                 235                 240

Cys Leu Ile Ser Gly Leu Gln Pro Gly Asn Ser Tyr Trp Leu Gln Leu
                245                 250                 255

Arg Ser Glu Pro Asp Gly Ile Ser Leu Gly Gly Ser Trp Gly Ser Trp
            260                 265                 270

Ser Leu Pro Val Thr Val Asp Leu Pro Gly Asp Ala Val Ala Leu Gly
        275                 280                 285

Leu Gln Cys Phe Thr Leu Asp Leu Lys Asn Val Thr Cys Gln Trp Gln
    290                 295                 300
```

```
Gln Gln Asp His Ala Ser Ser Gln Gly Phe Phe Tyr His Ser Arg Ala
305                 310                 315                 320

Arg Cys Cys Pro Arg Asp Arg Tyr Pro Ile Trp Glu Asn Cys Glu Glu
                325                 330                 335

Glu Glu Lys Thr Asn Pro Gly Leu Gln Thr Pro Gln Phe Ser Arg Cys
            340                 345                 350

His Phe Lys Ser Arg Asn Asp Ser Ile Ile His Ile Leu Val Glu Val
        355                 360                 365

Thr Thr Ala Pro Gly Thr Val His Ser Tyr Leu Gly Ser Pro Phe Trp
    370                 375                 380

Ile His Gln Ala Val Arg Leu Pro Thr Pro Asn Leu His Trp Arg Glu
385                 390                 395                 400

Ile Ser Ser Gly His Leu Glu Leu Glu Trp Gln His Pro Ser Ser Trp
                405                 410                 415

Ala Ala Gln Glu Thr Cys Tyr Gln Leu Arg Tyr Thr Gly Glu Gly His
            420                 425                 430

Gln Asp Trp Lys Val Leu Glu Pro Pro Leu Gly Ala Arg Gly Gly Thr
        435                 440                 445

Leu Glu Leu Arg Pro Arg Ser Arg Tyr Arg Leu Gln Leu Arg Ala Arg
    450                 455                 460

Leu Asn Gly Pro Thr Tyr Gln Gly Pro Trp Ser Ser Trp Ser Asp Pro
465                 470                 475                 480

Thr Arg Val Glu Thr Ala Thr Glu Thr Ala Trp Ile Ser Leu Val Thr
                485                 490                 495

Ala Leu His Leu Val Leu Gly Leu Ser Ala Val Leu Gly Leu Leu Leu
            500                 505                 510

Leu Arg Trp Gln Phe Pro Ala His Tyr Arg Arg Leu Arg His Ala Leu
        515                 520                 525

Trp Pro Ser Leu Pro Asp Leu His Arg Val Leu Gly Gln Tyr Leu Arg
    530                 535                 540

Asp Thr Ala Ala Leu Ser Pro Pro Lys Ala Thr Val Ser Asp Thr Cys
545                 550                 555                 560

Glu Glu Val Glu Pro Ser Leu Leu Glu Ile Leu Pro Lys Ser Ser Glu
                565                 570                 575

Arg Thr Pro Leu Pro Leu Cys Ser Ser Gln Ala Gln Met Asp Tyr Arg
            580                 585                 590

Arg Leu Gln Pro Ser Cys Leu Gly Thr Met Pro Leu Ser Val Cys Pro
        595                 600                 605

Pro Met Ala Glu Ser Gly Ser Cys Cys Thr Thr His Ile Ala Asn His
    610                 615                 620

Ser Tyr Leu Pro Leu Ser Tyr Trp Gln Gln Pro
625                 630                 635


<210> SEQ ID NO 249
<211> LENGTH: 1924
<212> TYPE: DNA
<213> ORGANISM: Homo sapiens
<220> FEATURE:
<221> NAME/KEY: CDS
<222> LOCATION: (11)..(1918)

<400> SEQUENCE: 249

gaattccacc atg ccc tcc tgg gcc ctc ttc atg gtc acc tcc tgc ctc        49
           Met Pro Ser Trp Ala Leu Phe Met Val Thr Ser Cys Leu
           1               5                   10

ctc ctg gcc cct caa aac ctg gcc caa gtc agc agc caa gat gtc tcc        97
Leu Leu Ala Pro Gln Asn Leu Ala Gln Val Ser Ser Gln Asp Val Ser
```

```
    15                  20                  25

ttg ctg gca tca gac tca gag ccc ctg aag tgt ttc tcc cga aca ttt      145
Leu Leu Ala Ser Asp Ser Glu Pro Leu Lys Cys Phe Ser Arg Thr Phe
30                  35                  40                  45

gag gac ctc act tgc ttc tgg gat gag gaa gag gca gcg ccc agt ggg      193
Glu Asp Leu Thr Cys Phe Trp Asp Glu Glu Glu Ala Ala Pro Ser Gly
                50                  55                  60

aca tac cag ctg ctg tat gcc tac ccg cgg gag aag ccc cgt gct tgc      241
Thr Tyr Gln Leu Leu Tyr Ala Tyr Pro Arg Glu Lys Pro Arg Ala Cys
            65                  70                  75

ccc ctg agt tcc cag agc atg ccc cac ttt gga acc cga tac gtg tgc      289
Pro Leu Ser Ser Gln Ser Met Pro His Phe Gly Thr Arg Tyr Val Cys
        80                  85                  90

cag ttt cca gac cag gag gaa gtg cgt ctc ttc ttt ccg ctg cac ctc      337
Gln Phe Pro Asp Gln Glu Glu Val Arg Leu Phe Phe Pro Leu His Leu
    95                  100                 105

tgg gtg aag aat gtg ttc cta aac cag act cgg act cag cga gtc ctc      385
Trp Val Lys Asn Val Phe Leu Asn Gln Thr Arg Thr Gln Arg Val Leu
110                 115                 120                 125

ttt gtg gac agt gta ggc ctg ccg gct ccc ccc agt atc atc aag gcc      433
Phe Val Asp Ser Val Gly Leu Pro Ala Pro Pro Ser Ile Ile Lys Ala
                130                 135                 140

atg ggt ggg agc cag cca ggg gaa ctt cag atc agc tgg gag gag cca      481
Met Gly Gly Ser Gln Pro Gly Glu Leu Gln Ile Ser Trp Glu Glu Pro
            145                 150                 155

gct cca gaa atc agt gat ttc ctg agg tac gaa ctc cgc tat ggc ccc      529
Ala Pro Glu Ile Ser Asp Phe Leu Arg Tyr Glu Leu Arg Tyr Gly Pro
        160                 165                 170

aga gat ccc aag aac tcc act ggt ccc acg gtc ata cag ctg att gcc      577
Arg Asp Pro Lys Asn Ser Thr Gly Pro Thr Val Ile Gln Leu Ile Ala
    175                 180                 185

aca gaa acc tgc tgc cct gct ctg cag aga cct cac tca gcc tct gct      625
Thr Glu Thr Cys Cys Pro Ala Leu Gln Arg Pro His Ser Ala Ser Ala
190                 195                 200                 205

ctg gac cag tct cca tgt gct cag ccc aca atg ccc tgg caa gat gga      673
Leu Asp Gln Ser Pro Cys Ala Gln Pro Thr Met Pro Trp Gln Asp Gly
                210                 215                 220

cca aag cag acc tcc cca agt aga gaa gct tca gct ctg aca gca gag      721
Pro Lys Gln Thr Ser Pro Ser Arg Glu Ala Ser Ala Leu Thr Ala Glu
            225                 230                 235

ggt gga agc tgc ctc atc tca gga ctc cag cct ggc aac tcc tac tgg      769
Gly Gly Ser Cys Leu Ile Ser Gly Leu Gln Pro Gly Asn Ser Tyr Trp
        240                 245                 250

ctg cag ctg tgc agc gaa cct gat ggg atc tcc ctc ggt ggc tcc tgg      817
Leu Gln Leu Cys Ser Glu Pro Asp Gly Ile Ser Leu Gly Gly Ser Trp
    255                 260                 265

gga tcc tgg tcc ctc cct gtg act gtg gac ctg cct gga gat gca gtg      865
Gly Ser Trp Ser Leu Pro Val Thr Val Asp Leu Pro Gly Asp Ala Val
270                 275                 280                 285

gca ctt gga ctg caa tgc ttt acc ttg gac ctg aag aat gtt acc tgt      913
Ala Leu Gly Leu Gln Cys Phe Thr Leu Asp Leu Lys Asn Val Thr Cys
                290                 295                 300

caa tgg cag caa cag gac cat gct agc tcc caa ggc ttc ttc tac cac      961
Gln Trp Gln Gln Gln Asp His Ala Ser Ser Gln Gly Phe Phe Tyr His
            305                 310                 315

agc agg gca cgg tgc tgc ccc aga gac agg tac ccc atc tgg gag aac     1009
Ser Arg Ala Arg Cys Cys Pro Arg Asp Arg Tyr Pro Ile Trp Glu Asn
        320                 325                 330

tgc gaa gag gaa gag aaa aca aat cca gga cta cag acc cca cag ttc     1057
Cys Glu Glu Glu Glu Lys Thr Asn Pro Gly Leu Gln Thr Pro Gln Phe
```

-continued

```
    335                 340                 345

tct cgc tgc cac ttc aag tca cga aat gac agc att att cac atc ctt      1105
Ser Arg Cys His Phe Lys Ser Arg Asn Asp Ser Ile Ile His Ile Leu
350                 355                 360                 365

gtg gag gtg acc aca gcc ccg ggt act gtt cac agc tac ctg ggc tcc      1153
Val Glu Val Thr Thr Ala Pro Gly Thr Val His Ser Tyr Leu Gly Ser
                370                 375                 380

cct ttc tgg atc cac cag gct gtg cgc ctc ccc acc cca aac ttg cac      1201
Pro Phe Trp Ile His Gln Ala Val Arg Leu Pro Thr Pro Asn Leu His
            385                 390                 395

tgg agg gag atc tcc agt ggg cat ctg gaa ttg gag tgg cag cac cca      1249
Trp Arg Glu Ile Ser Ser Gly His Leu Glu Leu Glu Trp Gln His Pro
        400                 405                 410

tcg tcc tgg gca gcc caa gag acc tgt tat caa ctc cga tac aca gga      1297
Ser Ser Trp Ala Ala Gln Glu Thr Cys Tyr Gln Leu Arg Tyr Thr Gly
    415                 420                 425

gaa ggc cat cag gac tgg aag gtg ctg gag ccg cct ctc ggg gcc cga      1345
Glu Gly His Gln Asp Trp Lys Val Leu Glu Pro Pro Leu Gly Ala Arg
430                 435                 440                 445

gga ggg acc ctg gag ctg cgc ccg cga tct cgc tac cgt tta cag ctg      1393
Gly Gly Thr Leu Glu Leu Arg Pro Arg Ser Arg Tyr Arg Leu Gln Leu
                450                 455                 460

cgc gcc agg ctc aac ggc ccc acc tac caa ggt ccc tgg agc tcg tgg      1441
Arg Ala Arg Leu Asn Gly Pro Thr Tyr Gln Gly Pro Trp Ser Ser Trp
            465                 470                 475

tcg gac cca act agg gtg gag acc gcc acc gag acc gcc tgg atc tcc      1489
Ser Asp Pro Thr Arg Val Glu Thr Ala Thr Glu Thr Ala Trp Ile Ser
        480                 485                 490

ttg gtg acc gct ctg cat cta gtg ctg ggc ctc agc gcc gtc ctg ggc      1537
Leu Val Thr Ala Leu His Leu Val Leu Gly Leu Ser Ala Val Leu Gly
    495                 500                 505

ctg ctg ctg ctg agg tgg cag ttt cct gca cac tac agg aga ctg agg      1585
Leu Leu Leu Leu Arg Trp Gln Phe Pro Ala His Tyr Arg Arg Leu Arg
510                 515                 520                 525

cat gcc ctg tgg ccc tca ctt cca gac ctg cac cgg gtc cta ggc cag      1633
His Ala Leu Trp Pro Ser Leu Pro Asp Leu His Arg Val Leu Gly Gln
                530                 535                 540

tac ctt agg gac act gca gcc ctg agc ccg ccc aag gcc aca gtc tca      1681
Tyr Leu Arg Asp Thr Ala Ala Leu Ser Pro Pro Lys Ala Thr Val Ser
            545                 550                 555

gat acc tgt gaa gaa gtg gaa ccc agc ctc ctt gaa atc ctc ccc aag      1729
Asp Thr Cys Glu Glu Val Glu Pro Ser Leu Leu Glu Ile Leu Pro Lys
        560                 565                 570

tcc tca gag agg act cct ttg ccc ctg tgt tcc tcc cag gcc cag atg      1777
Ser Ser Glu Arg Thr Pro Leu Pro Leu Cys Ser Ser Gln Ala Gln Met
    575                 580                 585

gac tac cga aga ttg cag cct tct tgc ctg ggg acc atg ccc ctg tct      1825
Asp Tyr Arg Arg Leu Gln Pro Ser Cys Leu Gly Thr Met Pro Leu Ser
590                 595                 600                 605

gtg tgc cca ccc atg gct gag tca ggg tcc tgc tgt acc acc cac att      1873
Val Cys Pro Pro Met Ala Glu Ser Gly Ser Cys Cys Thr Thr His Ile
                610                 615                 620

gcc aac cat tcc tac cta cca cta agc tat tgg cag cag cct tga          1918
Ala Asn His Ser Tyr Leu Pro Leu Ser Tyr Trp Gln Gln Pro
            625                 630                 635

gtcgac                                                               1924

<210> SEQ ID NO 250
<211> LENGTH: 635
<212> TYPE: PRT
```

<213> ORGANISM: Homo sapiens

<400> SEQUENCE: 250

```
Met Pro Ser Trp Ala Leu Phe Met Val Thr Ser Cys Leu Leu Leu Ala
1               5                   10                  15

Pro Gln Asn Leu Ala Gln Val Ser Ser Gln Asp Val Ser Leu Leu Ala
            20                  25                  30

Ser Asp Ser Glu Pro Leu Lys Cys Phe Ser Arg Thr Phe Glu Asp Leu
        35                  40                  45

Thr Cys Phe Trp Asp Glu Glu Glu Ala Ala Pro Ser Gly Thr Tyr Gln
    50                  55                  60

Leu Leu Tyr Ala Tyr Pro Arg Glu Lys Pro Arg Ala Cys Pro Leu Ser
65                  70                  75                  80

Ser Gln Ser Met Pro His Phe Gly Thr Arg Tyr Val Cys Gln Phe Pro
                85                  90                  95

Asp Gln Glu Glu Val Arg Leu Phe Phe Pro Leu His Leu Trp Val Lys
            100                 105                 110

Asn Val Phe Leu Asn Gln Thr Arg Thr Gln Arg Val Leu Phe Val Asp
        115                 120                 125

Ser Val Gly Leu Pro Ala Pro Pro Ser Ile Ile Lys Ala Met Gly Gly
    130                 135                 140

Ser Gln Pro Gly Glu Leu Gln Ile Ser Trp Glu Glu Pro Ala Pro Glu
145                 150                 155                 160

Ile Ser Asp Phe Leu Arg Tyr Glu Leu Arg Tyr Gly Pro Arg Asp Pro
                165                 170                 175

Lys Asn Ser Thr Gly Pro Thr Val Ile Gln Leu Ile Ala Thr Glu Thr
            180                 185                 190

Cys Cys Pro Ala Leu Gln Arg Pro His Ser Ala Ser Ala Leu Asp Gln
        195                 200                 205

Ser Pro Cys Ala Gln Pro Thr Met Pro Trp Gln Asp Gly Pro Lys Gln
    210                 215                 220

Thr Ser Pro Ser Arg Glu Ala Ser Ala Leu Thr Ala Glu Gly Gly Ser
225                 230                 235                 240

Cys Leu Ile Ser Gly Leu Gln Pro Gly Asn Ser Tyr Trp Leu Gln Leu
                245                 250                 255

Cys Ser Glu Pro Asp Gly Ile Ser Leu Gly Gly Ser Trp Gly Ser Trp
            260                 265                 270

Ser Leu Pro Val Thr Val Asp Leu Pro Gly Asp Ala Val Ala Leu Gly
        275                 280                 285

Leu Gln Cys Phe Thr Leu Asp Leu Lys Asn Val Thr Cys Gln Trp Gln
    290                 295                 300

Gln Gln Asp His Ala Ser Ser Gln Gly Phe Phe Tyr His Ser Arg Ala
305                 310                 315                 320

Arg Cys Cys Pro Arg Asp Arg Tyr Pro Ile Trp Glu Asn Cys Glu Glu
                325                 330                 335

Glu Glu Lys Thr Asn Pro Gly Leu Gln Thr Pro Gln Phe Ser Arg Cys
            340                 345                 350

His Phe Lys Ser Arg Asn Asp Ser Ile Ile His Ile Leu Val Glu Val
        355                 360                 365

Thr Thr Ala Pro Gly Thr Val His Ser Tyr Leu Gly Ser Pro Phe Trp
    370                 375                 380

Ile His Gln Ala Val Arg Leu Pro Thr Pro Asn Leu His Trp Arg Glu
385                 390                 395                 400

Ile Ser Ser Gly His Leu Glu Leu Glu Trp Gln His Pro Ser Ser Trp
```

```
                405                 410                 415

Ala Ala Gln Glu Thr Cys Tyr Gln Leu Arg Tyr Thr Gly Glu Gly His
            420                 425                 430

Gln Asp Trp Lys Val Leu Glu Pro Pro Leu Gly Ala Arg Gly Gly Thr
        435                 440                 445

Leu Glu Leu Arg Pro Arg Ser Arg Tyr Arg Leu Gln Leu Arg Ala Arg
    450                 455                 460

Leu Asn Gly Pro Thr Tyr Gln Gly Pro Trp Ser Ser Trp Ser Asp Pro
465                 470                 475                 480

Thr Arg Val Glu Thr Ala Thr Glu Thr Ala Trp Ile Ser Leu Val Thr
                485                 490                 495

Ala Leu His Leu Val Leu Gly Leu Ser Ala Val Leu Gly Leu Leu Leu
            500                 505                 510

Leu Arg Trp Gln Phe Pro Ala His Tyr Arg Arg Leu Arg His Ala Leu
        515                 520                 525

Trp Pro Ser Leu Pro Asp Leu His Arg Val Leu Gly Gln Tyr Leu Arg
    530                 535                 540

Asp Thr Ala Ala Leu Ser Pro Pro Lys Ala Thr Val Ser Asp Thr Cys
545                 550                 555                 560

Glu Glu Val Glu Pro Ser Leu Leu Glu Ile Leu Pro Lys Ser Ser Glu
                565                 570                 575

Arg Thr Pro Leu Pro Leu Cys Ser Ser Gln Ala Gln Met Asp Tyr Arg
            580                 585                 590

Arg Leu Gln Pro Ser Cys Leu Gly Thr Met Pro Leu Ser Val Cys Pro
        595                 600                 605

Pro Met Ala Glu Ser Gly Ser Cys Cys Thr Thr His Ile Ala Asn His
    610                 615                 620

Ser Tyr Leu Pro Leu Ser Tyr Trp Gln Gln Pro
625                 630                 635


<210> SEQ ID NO 251
<211> LENGTH: 1924
<212> TYPE: DNA
<213> ORGANISM: Homo sapiens
<220> FEATURE:
<221> NAME/KEY: CDS
<222> LOCATION: (11)..(1918)

<400> SEQUENCE: 251

gaattccacc atg ccc tcc tgg gcc ctc ttc atg gtc acc tcc tgc ctc        49
           Met Pro Ser Trp Ala Leu Phe Met Val Thr Ser Cys Leu
           1               5                   10

ctc ctg gcc cct caa aac ctg gcc caa gtc agc agc caa gat gtc tcc       97
Leu Leu Ala Pro Gln Asn Leu Ala Gln Val Ser Ser Gln Asp Val Ser
    15                  20                  25

ttg ctg gca tca gac tca gag ccc ctg aag tgt ttc tcc cga aca ttt      145
Leu Leu Ala Ser Asp Ser Glu Pro Leu Lys Cys Phe Ser Arg Thr Phe
30                  35                  40                  45

gag gac ctc act tgc ttc tgg gat gag gaa gag gca gcg ccc agt ggg      193
Glu Asp Leu Thr Cys Phe Trp Asp Glu Glu Glu Ala Ala Pro Ser Gly
                50                  55                  60

aca tac cag ctg ctg tat gcc tac ccg cgg gag aag ccc cgt gct tgc      241
Thr Tyr Gln Leu Leu Tyr Ala Tyr Pro Arg Glu Lys Pro Arg Ala Cys
            65                  70                  75

ccc ctg agt tcc cag agc atg ccc cac ttt gga acc cga tac gtg tgc      289
Pro Leu Ser Ser Gln Ser Met Pro His Phe Gly Thr Arg Tyr Val Cys
        80                  85                  90

cag ttt cca gac cag gag gaa gtg cgt ctc ttc ttt ccg ctg cac ctc      337
```

```
Gln Phe Pro Asp Gln Glu Glu Val Arg Leu Phe Phe Pro Leu His Leu
    95                  100                 105

tgg gtg aag aat gtg ttc cta aac cag act cgg act cag cga gtc ctc      385
Trp Val Lys Asn Val Phe Leu Asn Gln Thr Arg Thr Gln Arg Val Leu
110                 115                 120                 125

ttt gtg gac agt gta ggc ctg ccg gct ccc ccc agt atc atc aag gcc      433
Phe Val Asp Ser Val Gly Leu Pro Ala Pro Pro Ser Ile Ile Lys Ala
                130                 135                 140

atg ggt ggg agc cag cca ggg gaa ctt cag atc agc tgg gag gag cca      481
Met Gly Gly Ser Gln Pro Gly Glu Leu Gln Ile Ser Trp Glu Glu Pro
            145                 150                 155

gct cca gaa atc agt gat ttc ctg agg tac gaa ctc cgc tat ggc ccc      529
Ala Pro Glu Ile Ser Asp Phe Leu Arg Tyr Glu Leu Arg Tyr Gly Pro
        160                 165                 170

aga gat ccc aag aac tcc act ggt ccc acg gtc ata cag ctg att gcc      577
Arg Asp Pro Lys Asn Ser Thr Gly Pro Thr Val Ile Gln Leu Ile Ala
    175                 180                 185

aca gaa acc tgc tgc cct gct ctg cag aga cct cac tca gcc tct gct      625
Thr Glu Thr Cys Cys Pro Ala Leu Gln Arg Pro His Ser Ala Ser Ala
190                 195                 200                 205

ctg gac cag tct cca tgt gct cag ccc aca atg ccc tgg caa gat gga      673
Leu Asp Gln Ser Pro Cys Ala Gln Pro Thr Met Pro Trp Gln Asp Gly
                210                 215                 220

cca aag cag acc tcc cca agt aga gaa gct tca gct ctg aca gca gag      721
Pro Lys Gln Thr Ser Pro Ser Arg Glu Ala Ser Ala Leu Thr Ala Glu
            225                 230                 235

ggt gga agc tgc ctc atc tca gga ctc cag cct ggc aac tcc tac tgg      769
Gly Gly Ser Cys Leu Ile Ser Gly Leu Gln Pro Gly Asn Ser Tyr Trp
        240                 245                 250

ctg cag ctg cgc agc gaa cct gat ggg atc tcc ctc ggt ggc tcc tgg      817
Leu Gln Leu Arg Ser Glu Pro Asp Gly Ile Ser Leu Gly Gly Ser Trp
    255                 260                 265

gga tcc tgg tcc ctc act gtg act gtg gac ctg cct gga gat gca gtg      865
Gly Ser Trp Ser Leu Thr Val Thr Val Asp Leu Pro Gly Asp Ala Val
270                 275                 280                 285

gca ctt gga ctg caa tgc ttt acc ttg gac ctg aag aat gtt acc tgt      913
Ala Leu Gly Leu Gln Cys Phe Thr Leu Asp Leu Lys Asn Val Thr Cys
                290                 295                 300

caa tgg cag caa cag gac cat gct agc tcc caa ggc ttc ttc tac cac      961
Gln Trp Gln Gln Gln Asp His Ala Ser Ser Gln Gly Phe Phe Tyr His
            305                 310                 315

agc agg gca cgg tgc tgc ccc aga gac agg tac ccc atc tgg gag aac     1009
Ser Arg Ala Arg Cys Cys Pro Arg Asp Arg Tyr Pro Ile Trp Glu Asn
        320                 325                 330

tgc gaa gag gaa gag aaa aca aat cca gga cta cag acc cca cag ttc     1057
Cys Glu Glu Glu Glu Lys Thr Asn Pro Gly Leu Gln Thr Pro Gln Phe
    335                 340                 345

tct cgc tgc cac ttc aag tca cga aat gac agc att att cac atc ctt     1105
Ser Arg Cys His Phe Lys Ser Arg Asn Asp Ser Ile Ile His Ile Leu
350                 355                 360                 365

gtg gag gtg acc aca gcc ccg ggt act gtt cac agc tac ctg ggc tcc     1153
Val Glu Val Thr Thr Ala Pro Gly Thr Val His Ser Tyr Leu Gly Ser
                370                 375                 380

cct ttc tgg atc cac cag gct gtg cgc ctc ccc acc cca aac ttg cac     1201
Pro Phe Trp Ile His Gln Ala Val Arg Leu Pro Thr Pro Asn Leu His
            385                 390                 395

tgg agg gag atc tcc agt ggg cat ctg gaa ttg gag tgg cag cac cca     1249
Trp Arg Glu Ile Ser Ser Gly His Leu Glu Leu Glu Trp Gln His Pro
        400                 405                 410

tcg tcc tgg gca gcc caa gag acc tgt tat caa ctc cga tac aca gga     1297
```

```
Ser Ser Trp Ala Ala Gln Glu Thr Cys Tyr Gln Leu Arg Tyr Thr Gly
    415                 420                 425

gaa ggc cat cag gac tgg aag gtg ctg gag ccg cct ctc ggg gcc cga     1345
Glu Gly His Gln Asp Trp Lys Val Leu Glu Pro Pro Leu Gly Ala Arg
430                 435                 440                 445

gga ggg acc ctg gag ctg cgc ccg cga tct cgc tac cgt tta cag ctg     1393
Gly Gly Thr Leu Glu Leu Arg Pro Arg Ser Arg Tyr Arg Leu Gln Leu
                450                 455                 460

cgc gcc agg ctc aac ggc ccc acc tac caa ggt ccc tgg agc tcg tgg     1441
Arg Ala Arg Leu Asn Gly Pro Thr Tyr Gln Gly Pro Trp Ser Ser Trp
            465                 470                 475

tcg gac cca act agg gtg gag acc gcc acc gag acc gcc tgg atc tcc     1489
Ser Asp Pro Thr Arg Val Glu Thr Ala Thr Glu Thr Ala Trp Ile Ser
        480                 485                 490

ttg gtg acc gct ctg cat cta gtg ctg ggc ctc agc gcc gtc ctg ggc     1537
Leu Val Thr Ala Leu His Leu Val Leu Gly Leu Ser Ala Val Leu Gly
    495                 500                 505

ctg ctg ctg ctg agg tgg cag ttt cct gca cac tac agg aga ctg agg     1585
Leu Leu Leu Leu Arg Trp Gln Phe Pro Ala His Tyr Arg Arg Leu Arg
510                 515                 520                 525

cat gcc ctg tgg ccc tca ctt cca gac ctg cac cgg gtc cta ggc cag     1633
His Ala Leu Trp Pro Ser Leu Pro Asp Leu His Arg Val Leu Gly Gln
                530                 535                 540

tac ctt agg gac act gca gcc ctg agc ccg ccc aag gcc aca gtc tca     1681
Tyr Leu Arg Asp Thr Ala Ala Leu Ser Pro Pro Lys Ala Thr Val Ser
            545                 550                 555

gat acc tgt gaa gaa gtg gaa ccc agc ctc ctt gaa atc ctc ccc aag     1729
Asp Thr Cys Glu Glu Val Glu Pro Ser Leu Leu Glu Ile Leu Pro Lys
        560                 565                 570

tcc tca gag agg act cct ttg ccc ctg tgt tcc tcc cag gcc cag atg     1777
Ser Ser Glu Arg Thr Pro Leu Pro Leu Cys Ser Ser Gln Ala Gln Met
    575                 580                 585

gac tac cga aga ttg cag cct tct tgc ctg ggg acc atg ccc ctg tct     1825
Asp Tyr Arg Arg Leu Gln Pro Ser Cys Leu Gly Thr Met Pro Leu Ser
590                 595                 600                 605

gtg tgc cca ccc atg gct gag tca ggg tcc tgc tgt acc acc cac att     1873
Val Cys Pro Pro Met Ala Glu Ser Gly Ser Cys Cys Thr Thr His Ile
                610                 615                 620

gcc aac cat tcc tac cta cca cta agc tat tgg cag cag cct tga         1918
Ala Asn His Ser Tyr Leu Pro Leu Ser Tyr Trp Gln Gln Pro
            625                 630                 635

gtcgac                                                              1924


<210> SEQ ID NO 252
<211> LENGTH: 635
<212> TYPE: PRT
<213> ORGANISM: Homo sapiens

<400> SEQUENCE: 252

Met Pro Ser Trp Ala Leu Phe Met Val Thr Ser Cys Leu Leu Leu Ala
1               5                   10                  15

Pro Gln Asn Leu Ala Gln Val Ser Ser Gln Asp Val Ser Leu Leu Ala
            20                  25                  30

Ser Asp Ser Glu Pro Leu Lys Cys Phe Ser Arg Thr Phe Glu Asp Leu
        35                  40                  45

Thr Cys Phe Trp Asp Glu Glu Glu Ala Ala Pro Ser Gly Thr Tyr Gln
    50                  55                  60

Leu Leu Tyr Ala Tyr Pro Arg Glu Lys Pro Arg Ala Cys Pro Leu Ser
65                  70                  75                  80
```

```
Ser Gln Ser Met Pro His Phe Gly Thr Arg Tyr Val Cys Gln Phe Pro
                85                  90                  95

Asp Gln Glu Glu Val Arg Leu Phe Phe Pro Leu His Leu Trp Val Lys
            100                 105                 110

Asn Val Phe Leu Asn Gln Thr Arg Thr Gln Arg Val Leu Phe Val Asp
        115                 120                 125

Ser Val Gly Leu Pro Ala Pro Pro Ser Ile Ile Lys Ala Met Gly Gly
    130                 135                 140

Ser Gln Pro Gly Glu Leu Gln Ile Ser Trp Glu Glu Pro Ala Pro Glu
145                 150                 155                 160

Ile Ser Asp Phe Leu Arg Tyr Glu Leu Arg Tyr Gly Pro Arg Asp Pro
                165                 170                 175

Lys Asn Ser Thr Gly Pro Thr Val Ile Gln Leu Ile Ala Thr Glu Thr
            180                 185                 190

Cys Cys Pro Ala Leu Gln Arg Pro His Ser Ala Ser Ala Leu Asp Gln
        195                 200                 205

Ser Pro Cys Ala Gln Pro Thr Met Pro Trp Gln Asp Gly Pro Lys Gln
    210                 215                 220

Thr Ser Pro Ser Arg Glu Ala Ser Ala Leu Thr Ala Glu Gly Gly Ser
225                 230                 235                 240

Cys Leu Ile Ser Gly Leu Gln Pro Gly Asn Ser Tyr Trp Leu Gln Leu
                245                 250                 255

Arg Ser Glu Pro Asp Gly Ile Ser Leu Gly Gly Ser Trp Gly Ser Trp
            260                 265                 270

Ser Leu Thr Val Thr Val Asp Leu Pro Gly Asp Ala Val Ala Leu Gly
        275                 280                 285

Leu Gln Cys Phe Thr Leu Asp Leu Lys Asn Val Thr Cys Gln Trp Gln
    290                 295                 300

Gln Gln Asp His Ala Ser Ser Gln Gly Phe Phe Tyr His Ser Arg Ala
305                 310                 315                 320

Arg Cys Cys Pro Arg Asp Arg Tyr Pro Ile Trp Glu Asn Cys Glu Glu
                325                 330                 335

Glu Glu Lys Thr Asn Pro Gly Leu Gln Thr Pro Gln Phe Ser Arg Cys
            340                 345                 350

His Phe Lys Ser Arg Asn Asp Ser Ile Ile His Ile Leu Val Glu Val
        355                 360                 365

Thr Thr Ala Pro Gly Thr Val His Ser Tyr Leu Gly Ser Pro Phe Trp
    370                 375                 380

Ile His Gln Ala Val Arg Leu Pro Thr Pro Asn Leu His Trp Arg Glu
385                 390                 395                 400

Ile Ser Ser Gly His Leu Glu Leu Glu Trp Gln His Pro Ser Ser Trp
                405                 410                 415

Ala Ala Gln Glu Thr Cys Tyr Gln Leu Arg Tyr Thr Gly Glu Gly His
            420                 425                 430

Gln Asp Trp Lys Val Leu Glu Pro Pro Leu Gly Ala Arg Gly Gly Thr
        435                 440                 445

Leu Glu Leu Arg Pro Arg Ser Arg Tyr Arg Leu Gln Leu Arg Ala Arg
    450                 455                 460

Leu Asn Gly Pro Thr Tyr Gln Gly Pro Trp Ser Ser Trp Ser Asp Pro
465                 470                 475                 480

Thr Arg Val Glu Thr Ala Thr Glu Thr Ala Trp Ile Ser Leu Val Thr
                485                 490                 495

Ala Leu His Leu Val Leu Gly Leu Ser Ala Val Leu Gly Leu Leu Leu
            500                 505                 510
```

```
Leu Arg Trp Gln Phe Pro Ala His Tyr Arg Arg Leu Arg His Ala Leu
        515                 520                 525

Trp Pro Ser Leu Pro Asp Leu His Arg Val Leu Gly Gln Tyr Leu Arg
    530                 535                 540

Asp Thr Ala Ala Leu Ser Pro Pro Lys Ala Thr Val Ser Asp Thr Cys
545                 550                 555                 560

Glu Glu Val Glu Pro Ser Leu Leu Glu Ile Leu Pro Lys Ser Ser Glu
                565                 570                 575

Arg Thr Pro Leu Pro Leu Cys Ser Ser Gln Ala Gln Met Asp Tyr Arg
            580                 585                 590

Arg Leu Gln Pro Ser Cys Leu Gly Thr Met Pro Leu Ser Val Cys Pro
        595                 600                 605

Pro Met Ala Glu Ser Gly Ser Cys Cys Thr Thr His Ile Ala Asn His
    610                 615                 620

Ser Tyr Leu Pro Leu Ser Tyr Trp Gln Gln Pro
625                 630                 635


<210> SEQ ID NO 253
<211> LENGTH: 1572
<212> TYPE: DNA
<213> ORGANISM: Homo sapiens

<400> SEQUENCE: 253

atggactgga cctggaggtt cctctttgtg gtggcagcag ctacaggtgt ccagtcccag      60

gtgcagctgg tgcagtctgg acctgaggtg aagaagcctg ggcctcagt gaaggtctcc      120

tgcaaggctt ctggatacac cttcaccaac tcctggatga actgggtgag gcagaggcct     180

ggaaagggtc ttgagtgggt tggacggatt tatcctggag atggagaaac tatctacaat     240

gggaaattca gggtcagagt cacgattacc gcggacgaat ccacgagcac agcctacatg     300

gagctgagca gcctgagatc tgaggacacg gccgtgtatt actgtgcgag aggctatgat     360

gattactcgt ttgcttactg gggccaggga accacggtca ccgtctcttc aggtggtggt     420

ggatccggag gtggtggatc gggtggtgga ggatcggata ttgtgatgac tcagtctgca     480

ctctccctgc ccgtcacccc tggagagccg gcctccatct cctgcaggtc tagtaagagt     540

ctcctgcata gtaatggcaa cacttacttg tattggtacc tgcagaagcc agggcagtct     600

ccacagctcc tgatctatcg gatgtccaac cttgcctcag ggtccctga caggttcagt      660

ggcagtggat caggcacagc ttttacactg aaaatcagca gagtggaggc tgaggatgtt     720

ggggtttatt actgcatgca acatatagaa tatcctttta cgttcggcca agggaccaaa     780

ctggaaatca aaggaggtgg tggatcgggt ggtggtggtt cgggaggcgg tggatcgcag     840

gtgcagctgg tgcagtctgg acctgaggtg aagaagcctg ggcctcagt gaaggtctcc      900

tgcaaggctt ctggatacac cttcaccaac tcctggatga actgggtgag gcagaggcct     960

ggaaagggtc ttgagtgggt tggacggatt tatcctggag atggagaaac tatctacaat    1020

gggaaattca gggtcagagt cacgattacc gcggacgaat ccacgagcac agcctacatg    1080

gagctgagca gcctgagatc tgaggacacg gccgtgtatt actgtgcgag aggctatgat    1140

gattactcgt ttgcttactg gggccaggga accacggtca ccgtctcttc aggtggtggt    1200

ggatccggag gtggtggatc gggtggtgga ggatcggata ttgtgatgac tcagtctgca    1260

ctctccctgc ccgtcacccc tggagagccg gcctccatct cctgcaggtc tagtaagagt    1320

ctcctgcata gtaatggcaa cacttacttg tattggtacc tgcagaagcc agggcagtct    1380

ccacagctcc tgatctatcg gatgtccaac cttgcctcag ggtccctga caggttcagt     1440
```

```
ggcagtggat caggcacagc ttttacactg aaaatcagca gagtggaggc tgaggatgtt   1500

ggggtttatt actgcatgca acatatagaa tatcctttta cgttcggcca agggaccaaa   1560

ctggaaatca aa                                                       1572


<210> SEQ ID NO 254
<211> LENGTH: 524
<212> TYPE: PRT
<213> ORGANISM: Homo sapiens

<400> SEQUENCE: 254

Met Asp Trp Thr Trp Arg Phe Leu Phe Val Val Ala Ala Ala Thr Gly
1               5                   10                  15

Val Gln Ser Gln Val Gln Leu Val Gln Ser Gly Pro Glu Val Lys Lys
            20                  25                  30

Pro Gly Ala Ser Val Lys Val Ser Cys Lys Ala Ser Gly Tyr Thr Phe
        35                  40                  45

Thr Asn Ser Trp Met Asn Trp Val Arg Gln Arg Pro Gly Lys Gly Leu
    50                  55                  60

Glu Trp Val Gly Arg Ile Tyr Pro Gly Asp Gly Glu Thr Ile Tyr Asn
65                  70                  75                  80

Gly Lys Phe Arg Val Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Tyr Asp Asp Tyr Ser Phe Ala Tyr Trp Gly
        115                 120                 125

Gln Gly Thr Thr Val Thr Val Ser Ser Gly Gly Gly Gly Ser Gly Gly
    130                 135                 140

Gly Gly Ser Gly Gly Gly Gly Ser Asp Ile Val Met Thr Gln Ser Ala
145                 150                 155                 160

Leu Ser Leu Pro Val Thr Pro Gly Glu Pro Ala Ser Ile Ser Cys Arg
                165                 170                 175

Ser Ser Lys Ser Leu Leu His Ser Asn Gly Asn Thr Tyr Leu Tyr Trp
            180                 185                 190

Tyr Leu Gln Lys Pro Gly Gln Ser Pro Gln Leu Leu Ile Tyr Arg Met
        195                 200                 205

Ser Asn Leu Ala Ser Gly Val Pro Asp Arg Phe Ser Gly Ser Gly Ser
    210                 215                 220

Gly Thr Ala Phe Thr Leu Lys Ile Ser Arg Val Glu Ala Glu Asp Val
225                 230                 235                 240

Gly Val Tyr Tyr Cys Met Gln His Ile Glu Tyr Pro Phe Thr Phe Gly
                245                 250                 255

Gln Gly Thr Lys Leu Glu Ile Lys Gly Gly Gly Gly Ser Gly Gly Gly
            260                 265                 270

Gly Ser Gly Gly Gly Gly Ser Gln Val Gln Leu Val Gln Ser Gly Pro
        275                 280                 285

Glu Val Lys Lys Pro Gly Ala Ser Val Lys Val Ser Cys Lys Ala Ser
    290                 295                 300

Gly Tyr Thr Phe Thr Asn Ser Trp Met Asn Trp Val Arg Gln Arg Pro
305                 310                 315                 320

Gly Lys Gly Leu Glu Trp Val Gly Arg Ile Tyr Pro Gly Asp Gly Glu
                325                 330                 335

Thr Ile Tyr Asn Gly Lys Phe Arg Val Arg Val Thr Ile Thr Ala Asp
            340                 345                 350
```

```
Glu Ser Thr Ser Thr Ala Tyr Met Glu Leu Ser Ser Leu Arg Ser Glu
        355                 360                 365

Asp Thr Ala Val Tyr Tyr Cys Ala Arg Gly Tyr Asp Asp Tyr Ser Phe
    370                 375                 380

Ala Tyr Trp Gly Gln Gly Thr Thr Val Thr Val Ser Ser Gly Gly Gly
385                 390                 395                 400

Gly Ser Gly Gly Gly Gly Ser Gly Gly Gly Gly Ser Asp Ile Val Met
                405                 410                 415

Thr Gln Ser Ala Leu Ser Leu Pro Val Thr Pro Gly Glu Pro Ala Ser
            420                 425                 430

Ile Ser Cys Arg Ser Ser Lys Ser Leu Leu His Ser Asn Gly Asn Thr
        435                 440                 445

Tyr Leu Tyr Trp Tyr Leu Gln Lys Pro Gly Gln Ser Pro Gln Leu Leu
    450                 455                 460

Ile Tyr Arg Met Ser Asn Leu Ala Ser Gly Val Pro Asp Arg Phe Ser
465                 470                 475                 480

Gly Ser Gly Ser Gly Thr Ala Phe Thr Leu Lys Ile Ser Arg Val Glu
                485                 490                 495

Ala Glu Asp Val Gly Val Tyr Tyr Cys Met Gln His Ile Glu Tyr Pro
            500                 505                 510

Phe Thr Phe Gly Gln Gly Thr Lys Leu Glu Ile Lys
        515                 520


<210> SEQ ID NO 255
<211> LENGTH: 354
<212> TYPE: DNA
<213> ORGANISM: Homo sapiens

<400> SEQUENCE: 255

caggtgcagc tggtgcagtc tggacctgag gtgaagaagc ctggggcctc agtgaaggtc      60

tcctgcaagg cttctggata caccttcacc aactcctgga tgaactgggt gaggcagagg     120

cctggaaagg gtcttgagtg ggttggacgg atttatcctg gagatggaga aactatctac     180

aatgggaaat tcagggtcag agtcacgatt accgcggacg aatccacgag cacagcctac     240

atggagctga gcagcctgag atctgaggac acggccgtgt attactgtgc gagaggctat     300

gatgattact cgtttgctta ctggggccag ggaaccacgg tcaccgtctc ttca           354


<210> SEQ ID NO 256
<211> LENGTH: 118
<212> TYPE: PRT
<213> ORGANISM: Homo sapiens

<400> SEQUENCE: 256

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asn Ser
            20                  25                  30

Trp Met Asn Trp Val Arg Gln Arg Pro Gly Lys Gly Leu Glu Trp Val
        35                  40                  45

Gly Arg Ile Tyr Pro Gly Asp Gly Glu Thr Ile Tyr Asn Gly Lys Phe
    50                  55                  60

Arg Val Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Gly Tyr Asp Asp Tyr Ser Phe Ala Tyr Trp Gly Gln Gly Thr
            100                 105                 110

Thr Val Thr Val Ser Ser
        115


<210> SEQ ID NO 257
<211> LENGTH: 336
<212> TYPE: DNA
<213> ORGANISM: Homo sapiens

<400> SEQUENCE: 257

gatattgtga tgactcagtc tgcactctcc ctgcccgtca cccctggaga gccggcctcc     60

atctcctgca ggtctagtaa gagtctcctg catagtaatg gcaacactta cttgtattgg    120

tacctgcaga agccagggca gtctccacag ctcctgatct atcggatgtc caaccttgcc    180

tcaggggtcc ctgacaggtt cagtggcagt ggatcaggca cagcttttac actgaaaatc    240

agcagagtgg aggctgagga tgttggggtt tattactgca tgcaacatat agaatatcct    300

tttacgttcg gccaagggac caaactggaa atcaaa                              336


<210> SEQ ID NO 258
<211> LENGTH: 112
<212> TYPE: PRT
<213> ORGANISM: Homo sapiens

<400> SEQUENCE: 258

Asp Ile Val Met Thr Gln Ser Ala Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Tyr Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Lys Ile
65                  70                  75                  80

Ser Arg Val Glu Ala Glu Asp Val Gly Val Tyr Tyr Cys Met Gln His
                85                  90                  95

Ile Glu Tyr Pro Phe Thr Phe Gly Gln Gly Thr Lys Leu Glu Ile Lys
            100                 105                 110


<210> SEQ ID NO 259
<211> LENGTH: 1572
<212> TYPE: DNA
<213> ORGANISM: Homo sapiens

<400> SEQUENCE: 259

atggactgga cctggaggtt cctctttgtg gtggcagcag ctacaggtgt ccagtcccag     60

gtgcagctgg tgcagtctgg acctgaggtg aagaagcctg gggcctcagt gaaggtctcc    120

tgcaaggctt ctggatacac cttcaccaac tcctggatga actggatcag gcagaggcct    180

ggaaagggtc ttgagtggat tggacggatt tatcctggag atggagaaac tatctacaat    240

gggaaattca gggtcagagt cacgattacc gcggacgaat ccacgagcac agcctacatg    300

gagctgagca gcctgagatc tgaggacacg gccgtgtatt actgtgcgag aggctatgat    360

gattactcgt ttgcttactg gggccaggga accctggtca ccgtctcttc aggtggtggt    420

ggatccggag gtggtggatc gggtggtgga ggatcggata ttgtgatgac tcagtctgca    480

ctctccctgc ccgtcacccc tggagagccg gcctccatct cctgcaggtc tagtaagagt    540
```

```
ctcctgcata gtaatggcaa cacttacttg tattggtacc tgcagaagcc agggcagtct    600
ccacagctcc tgatctatcg gatgtccaac cttgcctcag ggtccctga caggttcagt    660
ggcagtggat caggcacagc ttttacactg aaaatcagca gagtggaggc tgaggatgtt    720
ggggtttatt actgcatgca acatatagaa tatcctttta cgttcggcca agggaccaaa    780
ctggaaatca aaggaggtgg tggatcgggt ggtggtggtt cgggaggcgg tggatcgcag    840
gtgcagctgg tgcagtctgg acctgaggtg aagaagcctg gggcctcagt gaaggtctcc    900
tgcaaggctt ctggatacac cttcaccaac tcctggatga actggatcag gcagaggcct    960
ggaaagggtc ttgagtggat tggacggatt tatcctggag atggagaaac tatctacaat   1020
gggaaattca gggtcagagt cacgattacc gcggacgaat ccacgagcac agcctacatg   1080
gagctgagca gcctgagatc tgaggacacg gccgtgtatt actgtgcgag aggctatgat   1140
gattactcgt ttgcttactg gggccaggga accctggtca ccgtctcttc aggtggtggt   1200
ggatccggag gtggtggatc gggtggtgga ggatcggata ttgtgatgac tcagtctgca   1260
ctctccctgc ccgtcacccc tggagagccg gcctccatct cctgcaggtc tagtaagagt   1320
ctcctgcata gtaatggcaa cacttacttg tattggtacc tgcagaagcc agggcagtct   1380
ccacagctcc tgatctatcg gatgtccaac cttgcctcag ggtccctga caggttcagt   1440
ggcagtggat caggcacagc ttttacactg aaaatcagca gagtggaggc tgaggatgtt   1500
ggggtttatt actgcatgca acatatagaa tatcctttta cgttcggcca agggaccaaa   1560
ctggaaatca aa                                                       1572
```

```
<210> SEQ ID NO 260
<211> LENGTH: 524
<212> TYPE: PRT
<213> ORGANISM: Homo sapiens

<400> SEQUENCE: 260

Met Asp Trp Thr Trp Arg Phe Leu Phe Val Val Ala Ala Ala Thr Gly
1               5                   10                  15

Val Gln Ser Gln Val Gln Leu Val Gln Ser Gly Pro Glu Val Lys Lys
            20                  25                  30

Pro Gly Ala Ser Val Lys Val Ser Cys Lys Ala Ser Gly Tyr Thr Phe
        35                  40                  45

Thr Asn Ser Trp Met Asn Trp Ile Arg Gln Arg Pro Gly Lys Gly Leu
    50                  55                  60

Glu Trp Ile Gly Arg Ile Tyr Pro Gly Asp Gly Glu Thr Ile Tyr Asn
65                  70                  75                  80

Gly Lys Phe Arg Val Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Tyr Asp Asp Tyr Ser Phe Ala Tyr Trp Gly
        115                 120                 125

Gln Gly Thr Leu Val Thr Val Ser Ser Gly Gly Gly Gly Ser Gly Gly
    130                 135                 140

Gly Gly Ser Gly Gly Gly Gly Ser Asp Ile Val Met Thr Gln Ser Ala
145                 150                 155                 160

Leu Ser Leu Pro Val Thr Pro Gly Glu Pro Ala Ser Ile Ser Cys Arg
                165                 170                 175

Ser Ser Lys Ser Leu Leu His Ser Asn Gly Asn Thr Tyr Leu Tyr Trp
            180                 185                 190
```

```
Tyr Leu Gln Lys Pro Gly Gln Ser Pro Gln Leu Leu Ile Tyr Arg Met
        195                 200                 205

Ser Asn Leu Ala Ser Gly Val Pro Asp Arg Phe Ser Gly Ser Gly Ser
    210                 215                 220

Gly Thr Ala Phe Thr Leu Lys Ile Ser Arg Val Glu Ala Glu Asp Val
225                 230                 235                 240

Gly Val Tyr Tyr Cys Met Gln His Ile Glu Tyr Pro Phe Thr Phe Gly
                245                 250                 255

Gln Gly Thr Lys Leu Glu Ile Lys Gly Gly Gly Gly Ser Gly Gly Gly
            260                 265                 270

Gly Ser Gly Gly Gly Gly Ser Gln Val Gln Leu Val Gln Ser Gly Pro
        275                 280                 285

Glu Val Lys Lys Pro Gly Ala Ser Val Lys Val Ser Cys Lys Ala Ser
    290                 295                 300

Gly Tyr Thr Phe Thr Asn Ser Trp Met Asn Trp Ile Arg Gln Arg Pro
305                 310                 315                 320

Gly Lys Gly Leu Glu Trp Ile Gly Arg Ile Tyr Pro Gly Asp Gly Glu
                325                 330                 335

Thr Ile Tyr Asn Gly Lys Phe Arg Val Arg Val Thr Ile Thr Ala Asp
            340                 345                 350

Glu Ser Thr Ser Thr Ala Tyr Met Glu Leu Ser Ser Leu Arg Ser Glu
        355                 360                 365

Asp Thr Ala Val Tyr Tyr Cys Ala Arg Gly Tyr Asp Asp Tyr Ser Phe
    370                 375                 380

Ala Tyr Trp Gly Gln Gly Thr Leu Val Thr Val Ser Ser Gly Gly Gly
385                 390                 395                 400

Gly Ser Gly Gly Gly Gly Ser Gly Gly Gly Gly Ser Asp Ile Val Met
                405                 410                 415

Thr Gln Ser Ala Leu Ser Leu Pro Val Thr Pro Gly Glu Pro Ala Ser
            420                 425                 430

Ile Ser Cys Arg Ser Ser Lys Ser Leu Leu His Ser Asn Gly Asn Thr
        435                 440                 445

Tyr Leu Tyr Trp Tyr Leu Gln Lys Pro Gly Gln Ser Pro Gln Leu Leu
    450                 455                 460

Ile Tyr Arg Met Ser Asn Leu Ala Ser Gly Val Pro Asp Arg Phe Ser
465                 470                 475                 480

Gly Ser Gly Ser Gly Thr Ala Phe Thr Leu Lys Ile Ser Arg Val Glu
                485                 490                 495

Ala Glu Asp Val Gly Val Tyr Tyr Cys Met Gln His Ile Glu Tyr Pro
            500                 505                 510

Phe Thr Phe Gly Gln Gly Thr Lys Leu Glu Ile Lys
        515                 520
```

<210> SEQ ID NO 261
<211> LENGTH: 354
<212> TYPE: DNA
<213> ORGANISM: Homo sapiens

<400> SEQUENCE: 261

```
caggtgcagc tggtgcagtc tggacctgag gtgaagaagc ctggggcctc agtgaaggtc     60

tcctgcaagg cttctggata caccttcacc aactcctgga tgaactggat caggcagagg    120

cctggaaagg gtcttgagtg gattggacgg atttatcctg gagatggaga aactatctac    180

aatgggaaat tcagggtcag agtcacgatt accgcggacg aatccacgag cacagcctac    240
```

```
atggagctga gcagcctgag atctgaggac acggccgtgt attactgtgc gagaggctat    300

gatgattact cgtttgctta ctggggccag ggaaccctgg tcaccgtctc ttca          354
```

<210> SEQ ID NO 262
<211> LENGTH: 118
<212> TYPE: PRT
<213> ORGANISM: Homo sapiens

<400> SEQUENCE: 262

```
Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asn Ser
            20                  25                  30

Trp Met Asn Trp Ile Arg Gln Arg Pro Gly Lys Gly Leu Glu Trp Ile
        35                  40                  45

Gly Arg Ile Tyr Pro Gly Asp Gly Glu Thr Ile Tyr Asn Gly Lys Phe
    50                  55                  60

Arg Val Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Asp Tyr Ser Phe Ala Tyr Trp Gly Gln Gly Thr
            100                 105                 110

Leu Val Thr Val Ser Ser
        115
```

<210> SEQ ID NO 263
<211> LENGTH: 1572
<212> TYPE: DNA
<213> ORGANISM: Mus musculus

<400> SEQUENCE: 263

```
atggaatggc ctttgatctt tctcttcctc ctgtcaggaa ctgcaggtgt ccactcccag     60

gttcagctgc agcagtctgg acctgagctg gtgaagcctg gggcctcagt gaagatttcc    120

tgcaaggctt ctggctatgc attcactaac tcctggatga actgggtgaa gcagaggcct    180

ggaaagggtc ttgagtggat tggacggatt tatcctggag atggagaaac tatctacaat    240

gggaaattca gggtcaaggc cacactgact gcagacaaat cctccagcac agcctacatg    300

gatatcagca gcctgacatc tgaggactct gcggtctact tctgtgcaag aggctatgat    360

gattactcgt ttgcttactg gggccaaggg actctggtca ctgtctctgc aggtggtggt    420

ggttcgggtg gtggtggttc gggtggtggc ggatcggata ttgtgatgac tcaggctgca    480

ccctctatac ctgtcactcc tggagagtca gtatccatct cctgtaggtc tagtaagagt    540

ctcctgcata gtaatggcaa cacttacttg tattggttcc tgcagaggcc aggccagtct    600

cctcaactcc tgatatatcg gatgtccaac cttgcctcag gagtcccaga taggttcagt    660

ggcagtgggt caggaactgc tttcacactg agaatcagta gagtggaggc tgaggatgtg    720

ggtgtttatt actgtatgca acatatagaa tatcctttta cgttcggatc ggggaccaag    780

ctggaaataa aaggaggtgg tggatcgggt ggtggtggtt cgggaggcgg tggatcgcag    840

gttcagctgc agcagtctgg acctgagctg gtgaagcctg gggcctcagt gaagatttcc    900

tgcaaggctt ctggctatgc attcactaac tcctggatga actgggtgaa gcagaggcct    960

ggaaagggtc ttgagtggat tggacggatt tatcctggag atggagaaac tatctacaat   1020

gggaaattca gggtcaaggc cacactgact gcagacaaat cctccagcac agcctacatg   1080
```

```
gatatcagca gcctgacatc tgaggactct gcggtctact tctgtgcaag aggctatgat   1140

gattactcgt ttgcttactg gggccaaggg actctggtca ctgtctctgc aggtggtggt   1200

ggttcgggtg gtggtggttc gggtggtggc ggatcggata ttgtgatgac tcaggctgca   1260

ccctctatac ctgtcactcc tggagagtca gtatccatct cctgtaggtc tagtaagagt   1320

ctcctgcata gtaatggcaa cacttacttg tattggttcc tgcagaggcc aggccagtct   1380

cctcaactcc tgatatatcg gatgtccaac cttgcctcag gagtcccaga taggttcagt   1440

ggcagtgggt caggaactgc tttcacactg agaatcagta gagtggaggc tgaggatgtg   1500

ggtgtttatt actgtatgca acatatagaa tatccttta cgttcggatc ggggaccaag   1560

ctggaaataa aa                                                        1572
```

<210> SEQ ID NO 264
<211> LENGTH: 524
<212> TYPE: PRT
<213> ORGANISM: Mus musculus

<400> SEQUENCE: 264

```
Met Glu Trp Pro Leu Ile Phe Leu Phe Leu Leu Ser Gly Thr Ala Gly
1               5                   10                  15

Val His Ser Gln Val Gln Leu Gln Gln Ser Gly Pro Glu Leu Val Lys
            20                  25                  30

Pro Gly Ala Ser Val Lys Ile Ser Cys Lys Ala Ser Gly Tyr Ala Phe
        35                  40                  45

Thr Asn Ser Trp Met Asn Trp Val Lys Gln Arg Pro Gly Lys Gly Leu
    50                  55                  60

Glu Trp Ile Gly Arg Ile Tyr Pro Gly Asp Gly Glu Thr Ile Tyr Asn
65                  70                  75                  80

Gly Lys Phe Arg Val Lys Ala Thr Leu Thr Ala Asp Lys Ser Ser Ser
                85                  90                  95

Thr Ala Tyr Met Asp Ile Ser Ser Leu Thr Ser Glu Asp Ser Ala Val
            100                 105                 110

Tyr Phe Cys Ala Arg Gly Tyr Asp Asp Tyr Ser Phe Ala Tyr Trp Gly
        115                 120                 125

Gln Gly Thr Leu Val Thr Val Ser Ala Gly Gly Gly Gly Ser Gly Gly
    130                 135                 140

Gly Gly Ser Gly Gly Gly Gly Ser Asp Ile Val Met Thr Gln Ala Ala
145                 150                 155                 160

Pro Ser Ile Pro Val Thr Pro Gly Glu Ser Val Ser Ile Ser Cys Arg
                165                 170                 175

Ser Ser Lys Ser Leu Leu His Ser Asn Gly Asn Thr Tyr Leu Tyr Trp
            180                 185                 190

Phe Leu Gln Arg Pro Gly Gln Ser Pro Gln Leu Leu Ile Tyr Arg Met
        195                 200                 205

Ser Asn Leu Ala Ser Gly Val Pro Asp Arg Phe Ser Gly Ser Gly Ser
    210                 215                 220

Gly Thr Ala Phe Thr Leu Arg Ile Ser Arg Val Glu Ala Glu Asp Val
225                 230                 235                 240

Gly Val Tyr Tyr Cys Met Gln His Ile Glu Tyr Pro Phe Thr Phe Gly
                245                 250                 255

Ser Gly Thr Lys Leu Glu Ile Lys Gly Gly Gly Gly Ser Gly Gly Gly
            260                 265                 270

Gly Ser Gly Gly Gly Gly Ser Gln Val Gln Leu Gln Gln Ser Gly Pro
        275                 280                 285
```

```
Glu Leu Val Lys Pro Gly Ala Ser Val Lys Ile Ser Cys Lys Ala Ser
    290                 295                 300

Gly Tyr Ala Phe Thr Asn Ser Trp Met Asn Trp Val Lys Gln Arg Pro
305                 310                 315                 320

Gly Lys Gly Leu Glu Trp Ile Gly Arg Ile Tyr Pro Gly Asp Gly Glu
                325                 330                 335

Thr Ile Tyr Asn Gly Lys Phe Arg Val Lys Ala Thr Leu Thr Ala Asp
            340                 345                 350

Lys Ser Ser Ser Thr Ala Tyr Met Asp Ile Ser Ser Leu Thr Ser Glu
        355                 360                 365

Asp Ser Ala Val Tyr Phe Cys Ala Arg Gly Tyr Asp Asp Tyr Ser Phe
    370                 375                 380

Ala Tyr Trp Gly Gln Gly Thr Leu Val Thr Val Ser Ala Gly Gly Gly
385                 390                 395                 400

Gly Ser Gly Gly Gly Gly Ser Gly Gly Gly Gly Ser Asp Ile Val Met
                405                 410                 415

Thr Gln Ala Ala Pro Ser Ile Pro Val Thr Pro Gly Glu Ser Val Ser
            420                 425                 430

Ile Ser Cys Arg Ser Ser Lys Ser Leu Leu His Ser Asn Gly Asn Thr
        435                 440                 445

Tyr Leu Tyr Trp Phe Leu Gln Arg Pro Gly Gln Ser Pro Gln Leu Leu
    450                 455                 460

Ile Tyr Arg Met Ser Asn Leu Ala Ser Gly Val Pro Asp Arg Phe Ser
465                 470                 475                 480

Gly Ser Gly Ser Gly Thr Ala Phe Thr Leu Arg Ile Ser Arg Val Glu
                485                 490                 495

Ala Glu Asp Val Gly Val Tyr Tyr Cys Met Gln His Ile Glu Tyr Pro
            500                 505                 510

Phe Thr Phe Gly Ser Gly Thr Lys Leu Glu Ile Lys
        515                 520


<210> SEQ ID NO 265
<211> LENGTH: 30
<212> TYPE: PRT
<213> ORGANISM: Homo sapiens

<400> SEQUENCE: 265

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr
            20                  25                  30


<210> SEQ ID NO 266
<211> LENGTH: 5
<212> TYPE: PRT
<213> ORGANISM: Homo sapiens

<400> SEQUENCE: 266

Asn Ser Trp Met Asn
1               5


<210> SEQ ID NO 267
<211> LENGTH: 14
<212> TYPE: PRT
<213> ORGANISM: Homo sapiens

<400> SEQUENCE: 267

Trp Val Arg Gln Arg Pro Gly Lys Gly Leu Glu Trp Val Gly
1               5                   10
```

<210> SEQ ID NO 268
<211> LENGTH: 17
<212> TYPE: PRT
<213> ORGANISM: Homo sapiens

<400> SEQUENCE: 268

Arg Ile Tyr Pro Gly Asp Gly Glu Thr Ile Tyr Asn Gly Lys Phe Arg
1 5 10 15

Val

<210> SEQ ID NO 269
<211> LENGTH: 32
<212> TYPE: PRT
<213> ORGANISM: Homo sapiens

<400> SEQUENCE: 269

Arg Val Thr Ile Thr Ala Asp Glu Ser Thr Ser Thr Ala Tyr Met Glu
1 5 10 15

Leu Ser Ser Leu Arg Ser Glu Asp Thr Ala Val Tyr Tyr Cys Ala Arg
20 25 30

<210> SEQ ID NO 270
<211> LENGTH: 9
<212> TYPE: PRT
<213> ORGANISM: Homo sapiens

<400> SEQUENCE: 270

Gly Tyr Asp Asp Tyr Ser Phe Ala Tyr
1 5

<210> SEQ ID NO 271
<211> LENGTH: 11
<212> TYPE: PRT
<213> ORGANISM: Homo sapiens

<400> SEQUENCE: 271

Trp Gly Gln Gly Thr Thr Val Thr Val Ser Ser
1 5 10

<210> SEQ ID NO 272
<211> LENGTH: 23
<212> TYPE: PRT
<213> ORGANISM: Homo sapiens

<400> SEQUENCE: 272

Asp Ile Val Met Thr Gln Ser Ala Leu Ser Leu Pro Val Thr Pro Gly
1 5 10 15

Glu Pro Ala Ser Ile Ser Cys
20

<210> SEQ ID NO 273
<211> LENGTH: 16
<212> TYPE: PRT
<213> ORGANISM: Homo sapiens

<400> SEQUENCE: 273

Arg Ser Ser Lys Ser Leu Leu His Ser Asn Gly Asn Thr Tyr Leu Tyr
1 5 10 15

<210> SEQ ID NO 274
<211> LENGTH: 15
<212> TYPE: PRT
<213> ORGANISM: Homo sapiens

<400> SEQUENCE: 274

Trp Tyr Leu Gln Lys Pro Gly Gln Ser Pro Gln Leu Leu Ile Tyr
1               5                   10                  15

<210> SEQ ID NO 275
<211> LENGTH: 7
<212> TYPE: PRT
<213> ORGANISM: Homo sapiens

<400> SEQUENCE: 275

Arg Met Ser Asn Leu Ala Ser
1               5

<210> SEQ ID NO 276
<211> LENGTH: 32
<212> TYPE: PRT
<213> ORGANISM: Homo sapiens

<400> SEQUENCE: 276

Gly Val Pro Asp Arg Phe Ser Gly Ser Gly Ser Gly Thr Ala Phe Thr
1               5                   10                  15

Leu Lys Ile Ser Arg Val Glu Ala Glu Asp Val Gly Val Tyr Tyr Cys
            20                  25                  30

<210> SEQ ID NO 277
<211> LENGTH: 9
<212> TYPE: PRT
<213> ORGANISM: Homo sapiens

<400> SEQUENCE: 277

Met Gln His Ile Glu Tyr Pro Phe Thr
1               5

<210> SEQ ID NO 278
<211> LENGTH: 10
<212> TYPE: PRT
<213> ORGANISM: Homo sapiens

<400> SEQUENCE: 278

Phe Gly Gln Gly Thr Lys Leu Glu Ile Lys
1               5                   10

<210> SEQ ID NO 279
<211> LENGTH: 30
<212> TYPE: PRT
<213> ORGANISM: Homo sapiens

<400> SEQUENCE: 279

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 280
<211> LENGTH: 5
<212> TYPE: PRT
<213> ORGANISM: Homo sapiens

<400> SEQUENCE: 280

Asn Ser Trp Met Asn
1               5

<210> SEQ ID NO 281

<211> LENGTH: 14
<212> TYPE: PRT
<213> ORGANISM: Homo sapiens

<400> SEQUENCE: 281

Trp Ile Arg Gln Arg Pro Gly Lys Gly Leu Glu Trp Ile Gly
1               5                   10

<210> SEQ ID NO 282
<211> LENGTH: 17
<212> TYPE: PRT
<213> ORGANISM: Homo sapiens

<400> SEQUENCE: 282

Arg Ile Tyr Pro Gly Asp Gly Glu Thr Ile Tyr Asn Gly Lys Phe Arg
1               5                   10                  15

Val

<210> SEQ ID NO 283
<211> LENGTH: 32
<212> TYPE: PRT
<213> ORGANISM: Homo sapiens

<400> SEQUENCE: 283

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 284
<211> LENGTH: 9
<212> TYPE: PRT
<213> ORGANISM: Homo sapiens

<400> SEQUENCE: 284

Gly Tyr Asp Asp Tyr Ser Phe Ala Tyr
1               5

<210> SEQ ID NO 285
<211> LENGTH: 11
<212> TYPE: PRT
<213> ORGANISM: Homo sapiens

<400> SEQUENCE: 285

Trp Gly Gln Gly Thr Leu Val Thr Val Ser Ser
1               5                   10

<210> SEQ ID NO 286
<211> LENGTH: 1572
<212> TYPE: DNA
<213> ORGANISM: Homo sapiens

<400> SEQUENCE: 286
atggactgga cctggaggtt cctctttgtg gtggcagcag ctacaggtgt ccagtcccag     60
gtgcagctgg tgcagtctgg acctgaggtg aagaagcctg gggcctcagt gaaggtctcc    120
tgcaaggctt ctggatacac cttcaccaac tcctggatga actgggtgag gcagaggcct    180
ggaaagggtc ttgagtggat tggacggatt tatcctggag atggagaaac tatctacaat    240
gggaaattca gggtcagagt cacgattacc gcggacgaat ccacgagcac agcctacatg    300
caactgagca gcctgagatc tgaggacacg gccgtgtatt actgtgcgag aggctatgat    360
gattactcgt ttgcttactg gggccaggga accacggtca ccgtctcttc aggtggtggt    420

```
ggatccggag gtggtggatc gggtggtgga ggatcggata ttgtgatgac tcagtctcca    480

ctctccctgc ccgtcacccc tggagagccg gcctccatct cctgcaggtc tagtaagagt    540

ctcctgcata gtaatggcaa cacttacttg tattggttcc tgcagaagcc agggcagtct    600

ccacagctcc tgatctatcg gatgtccaac cttgcctcag ggtccctga caggttcagt     660

ggcagtggat caggcacaga ttttacactg aaaatcagca gagtggaggc tgaggatgtt    720

ggggtttatt actgcatgca acatatagaa tatcctttta cgttcggcca agggaccaaa    780

ctggaaatca aaggaggtgg tggatcgggt ggtggtggtt cgggaggcgg tggatcgcag    840

gtgcagctgg tgcagtctgg acctgaggtg aagaagcctg gggcctcagt gaaggtctcc    900

tgcaaggctt ctggatacac cttcaccaac tcctggatga actgggtgag gcagaggcct    960

ggaaagggtc ttgagtggat tggacggatt tatcctggag atggagaaac tatctacaat   1020

gggaaattca gggtcagagt cacgattacc gcggacgaat ccacgagcac agcctacatg   1080

caactgagca gcctgagatc tgaggacacg gccgtgtatt actgtgcgag aggctatgat   1140

gattactcgt ttgcttactg gggccaggga accacggtca ccgtctcttc aggtggtggt   1200

ggatccggag gtggtggatc gggtggtgga ggatcggata ttgtgatgac tcagtctcca   1260

ctctccctgc ccgtcacccc tggagagccg gcctccatct cctgcaggtc tagtaagagt   1320

ctcctgcata gtaatggcaa cacttacttg tattggttcc tgcagaagcc agggcagtct   1380

ccacagctcc tgatctatcg gatgtccaac cttgcctcag ggtccctga caggttcagt    1440

ggcagtggat caggcacaga ttttacactg aaaatcagca gagtggaggc tgaggatgtt   1500

ggggtttatt actgcatgca acatatagaa tatcctttta cgttcggcca agggaccaaa   1560

ctggaaatca aa                                                       1572
```

<210> SEQ ID NO 287
<211> LENGTH: 524
<212> TYPE: PRT
<213> ORGANISM: Homo sapiens

<400> SEQUENCE: 287

```
Met Asp Trp Thr Trp Arg Phe Leu Phe Val Val Ala Ala Ala Thr Gly
1               5                   10                  15

Val Gln Ser Gln Val Gln Leu Val Gln Ser Gly Pro Glu Val Lys Lys
            20                  25                  30

Pro Gly Ala Ser Val Lys Val Ser Cys Lys Ala Ser Gly Tyr Thr Phe
        35                  40                  45

Thr Asn Ser Trp Met Asn Trp Val Arg Gln Arg Pro Gly Lys Gly Leu
    50                  55                  60

Glu Trp Ile Gly Arg Ile Tyr Pro Gly Asp Gly Glu Thr Ile Tyr Asn
65                  70                  75                  80

Gly Lys Phe Arg Val Arg Val Thr Ile Thr Ala Asp Glu Ser Thr Ser
                85                  90                  95

Thr Ala Tyr Met Gln Leu Ser Ser Leu Arg Ser Glu Asp Thr Ala Val
            100                 105                 110

Tyr Tyr Cys Ala Arg Gly Tyr Asp Asp Tyr Ser Phe Ala Tyr Trp Gly
        115                 120                 125

Gln Gly Thr Thr Val Thr Val Ser Ser Gly Gly Gly Gly Ser Gly Gly
    130                 135                 140

Gly Gly Ser Gly Gly Gly Gly Ser Asp Ile Val Met Thr Gln Ser Pro
145                 150                 155                 160

Leu Ser Leu Pro Val Thr Pro Gly Glu Pro Ala Ser Ile Ser Cys Arg
                165                 170                 175
```

```
Ser Ser Lys Ser Leu Leu His Ser Asn Gly Asn Thr Tyr Leu Tyr Trp
            180                 185                 190

Phe Leu Gln Lys Pro Gly Gln Ser Pro Gln Leu Leu Ile Tyr Arg Met
        195                 200                 205

Ser Asn Leu Ala Ser Gly Val Pro Asp Arg Phe Ser Gly Ser Gly Ser
    210                 215                 220

Gly Thr Asp Phe Thr Leu Lys Ile Ser Arg Val Glu Ala Glu Asp Val
225                 230                 235                 240

Gly Val Tyr Tyr Cys Met Gln His Ile Glu Tyr Pro Phe Thr Phe Gly
                245                 250                 255

Gln Gly Thr Lys Leu Glu Ile Lys Gly Gly Gly Gly Ser Gly Gly Gly
            260                 265                 270

Gly Ser Gly Gly Gly Gly Ser Gln Val Gln Leu Val Gln Ser Gly Pro
        275                 280                 285

Glu Val Lys Lys Pro Gly Ala Ser Val Lys Val Ser Cys Lys Ala Ser
    290                 295                 300

Gly Tyr Thr Phe Thr Asn Ser Trp Met Asn Trp Val Arg Gln Arg Pro
305                 310                 315                 320

Gly Lys Gly Leu Glu Trp Ile Gly Arg Ile Tyr Pro Gly Asp Gly Glu
                325                 330                 335

Thr Ile Tyr Asn Gly Lys Phe Arg Val Arg Val Thr Ile Thr Ala Asp
            340                 345                 350

Glu Ser Thr Ser Thr Ala Tyr Met Gln Leu Ser Ser Leu Arg Ser Glu
        355                 360                 365

Asp Thr Ala Val Tyr Tyr Cys Ala Arg Gly Tyr Asp Asp Tyr Ser Phe
    370                 375                 380

Ala Tyr Trp Gly Gln Gly Thr Thr Val Thr Val Ser Ser Gly Gly Gly
385                 390                 395                 400

Gly Ser Gly Gly Gly Gly Ser Gly Gly Gly Gly Ser Asp Ile Val Met
                405                 410                 415

Thr Gln Ser Pro Leu Ser Leu Pro Val Thr Pro Gly Glu Pro Ala Ser
            420                 425                 430

Ile Ser Cys Arg Ser Ser Lys Ser Leu Leu His Ser Asn Gly Asn Thr
        435                 440                 445

Tyr Leu Tyr Trp Phe Leu Gln Lys Pro Gly Gln Ser Pro Gln Leu Leu
    450                 455                 460

Ile Tyr Arg Met Ser Asn Leu Ala Ser Gly Val Pro Asp Arg Phe Ser
465                 470                 475                 480

Gly Ser Gly Ser Gly Thr Asp Phe Thr Leu Lys Ile Ser Arg Val Glu
                485                 490                 495

Ala Glu Asp Val Gly Val Tyr Tyr Cys Met Gln His Ile Glu Tyr Pro
            500                 505                 510

Phe Thr Phe Gly Gln Gly Thr Lys Leu Glu Ile Lys
        515                 520
```

<210> SEQ ID NO 288
<211> LENGTH: 354
<212> TYPE: DNA
<213> ORGANISM: Homo sapiens

<400> SEQUENCE: 288

```
caggtgcagc tggtgcagtc tggacctgag gtgaagaagc ctggggcctc agtgaaggtc     60

tcctgcaagg cttctggata caccttcacc aactcctgga tgaactgggt gaggcagagg    120

cctggaaagg gtcttgagtg gattggacgg atttatcctg gagatggaga aactatctac    180
```

```
aatgggaaat tcagggtcag agtcacgatt accgcggacg aatccacgag cacagcctac    240

atgcaactga gcagcctgag atctgaggac acggccgtgt attactgtgc gagaggctat    300

gatgattact cgtttgctta ctggggccag ggaaccacgg tcaccgtctc ttca          354


<210> SEQ ID NO 289
<211> LENGTH: 118
<212> TYPE: PRT
<213> ORGANISM: Homo sapiens

<400> SEQUENCE: 289

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asn Ser
            20                  25                  30

Trp Met Asn Trp Val Arg Gln Arg Pro Gly Lys Gly Leu Glu Trp Ile
        35                  40                  45

Gly Arg Ile Tyr Pro Gly Asp Gly Glu Thr Ile Tyr Asn Gly Lys Phe
    50                  55                  60

Arg Val Arg Val Thr Ile Thr Ala Asp Glu Ser Thr Ser Thr Ala Tyr
65                  70                  75                  80

Met Gln Leu Ser Ser Leu Arg Ser Glu Asp Thr Ala Val Tyr Tyr Cys
                85                  90                  95

Ala Arg Gly Tyr Asp Asp Tyr Ser Phe Ala Tyr Trp Gly Gln Gly Thr
            100                 105                 110

Thr Val Thr Val Ser Ser
        115


<210> SEQ ID NO 290
<211> LENGTH: 336
<212> TYPE: DNA
<213> ORGANISM: Homo sapiens

<400> SEQUENCE: 290

gatattgtga tgactcagtc tccactctcc ctgcccgtca cccctggaga gccggcctcc     60

atctcctgca ggtctagtaa gagtctcctg catagtaatg gcaacactta cttgtattgg    120

ttcctgcaga agccagggca gtctccacag ctcctgatct atcggatgtc caaccttgcc    180

tcaggggtcc ctgacaggtt cagtggcagt ggatcaggca cagattttac actgaaaatc    240

agcagagtgg aggctgagga tgttggggtt tattactgca tgcaacatat agaatatcct    300

tttacgttcg gccaagggac caaactggaa atcaaa                              336


<210> SEQ ID NO 291
<211> LENGTH: 112
<212> TYPE: PRT
<213> ORGANISM: Homo sapiens

<400> SEQUENCE: 291

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
```

```
65                  70                  75                  80

Ser Arg Val Glu Ala Glu Asp Val Gly Val Tyr Tyr Cys Met Gln His
                85                  90                  95

Ile Glu Tyr Pro Phe Thr Phe Gly Gln Gly Thr Lys Leu Glu Ile Lys
            100                 105                 110


<210> SEQ ID NO 292
<211> LENGTH: 1572
<212> TYPE: DNA
<213> ORGANISM: Homo sapiens

<400> SEQUENCE: 292

atggactgga cctggaggtt cctctttgtg gtggcagcag ctacaggtgt ccagtcccag      60

gtgcagctgg tgcagtctgg acctgaggtg aagaagcctg gggcctcagt gaaggtctcc     120

tgcaaggctt ctggatacac cttcaccaac tcctggatga actgggtgag gcagaggcct     180

ggaaagggtc ttgagtggat tggacggatt tatcctggag atggagaaac tatctacaat     240

gggaaattca gggtcagagt cacgattacc gcggacgaat ccacgagcac agcctacatg     300

gagctgagca gcctgagatc tgaggacacg gccgtgtatt actgtgcgag aggctatgat     360

gattactcgt ttgcttactg gggccaggga accacggtca ccgtctcttc aggtggtggt     420

ggatccggag gtggtggatc gggtggtgga ggatcggata ttgtgatgac tcagtctcca     480

ctctccctgc ccgtcacccc tggagagccg gcctccatct cctgcaggtc tagtaagagt     540

ctcctgcata gtaatggcaa cacttacttg tattggttcc agcagaagcc agggcaggct     600

ccacggctcc tgatctatcg gatgtccaac cttgcctcag gggtccctga caggttcagt     660

ggcagtggat caggcacagc ttttacactg aaaatcagca gagtggaggc tgaggatgtt     720

ggggtttatt actgcatgca acatatagaa tatcctttta cgttcggcca agggaccaaa     780

ctggaaatca aaggaggtgg tggatcgggt ggtggtggtt cgggaggcgg tggatcgcag     840

gtgcagctgg tgcagtctgg acctgaggtg aagaagcctg gggcctcagt gaaggtctcc     900

tgcaaggctt ctggatacac cttcaccaac tcctggatga actgggtgag gcagaggcct     960

ggaaagggtc ttgagtggat tggacggatt tatcctggag atggagaaac tatctacaat    1020

gggaaattca gggtcagagt cacgattacc gcggacgaat ccacgagcac agcctacatg    1080

gagctgagca gcctgagatc tgaggacacg gccgtgtatt actgtgcgag aggctatgat    1140

gattactcgt ttgcttactg gggccaggga accacggtca ccgtctcttc aggtggtggt    1200

ggatccggag gtggtggatc gggtggtgga ggatcggata ttgtgatgac tcagtctcca    1260

ctctccctgc ccgtcacccc tggagagccg gcctccatct cctgcaggtc tagtaagagt    1320

ctcctgcata gtaatggcaa cacttacttg tattggttcc agcagaagcc agggcaggct    1380

ccacggctcc tgatctatcg gatgtccaac cttgcctcag gggtccctga caggttcagt    1440

ggcagtggat caggcacagc ttttacactg aaaatcagca gagtggaggc tgaggatgtt    1500

ggggtttatt actgcatgca acatatagaa tatcctttta cgttcggcca agggaccaaa    1560

ctggaaatca aa                                                        1572


<210> SEQ ID NO 293
<211> LENGTH: 524
<212> TYPE: PRT
<213> ORGANISM: Homo sapiens

<400> SEQUENCE: 293

Met Asp Trp Thr Trp Arg Phe Leu Phe Val Val Ala Ala Ala Thr Gly
1               5                   10                  15
```

```
Val Gln Ser Gln Val Gln Leu Val Gln Ser Gly Pro Glu Val Lys Lys
            20                  25                  30

Pro Gly Ala Ser Val Lys Val Ser Cys Lys Ala Ser Gly Tyr Thr Phe
        35                  40                  45

Thr Asn Ser Trp Met Asn Trp Val Arg Gln Arg Pro Gly Lys Gly Leu
    50                  55                  60

Glu Trp Ile Gly Arg Ile Tyr Pro Gly Asp Gly Glu Thr Ile Tyr Asn
65                  70                  75                  80

Gly Lys Phe Arg Val Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Tyr Asp Asp Tyr Ser Phe Ala Tyr Trp Gly
        115                 120                 125

Gln Gly Thr Thr Val Thr Val Ser Ser Gly Gly Gly Gly Ser Gly Gly
    130                 135                 140

Gly Gly Ser Gly Gly Gly Gly Ser Asp Ile Val Met Thr Gln Ser Pro
145                 150                 155                 160

Leu Ser Leu Pro Val Thr Pro Gly Glu Pro Ala Ser Ile Ser Cys Arg
                165                 170                 175

Ser Ser Lys Ser Leu Leu His Ser Asn Gly Asn Thr Tyr Leu Tyr Trp
            180                 185                 190

Phe Gln Gln Lys Pro Gly Gln Ala Pro Arg Leu Leu Ile Tyr Arg Met
        195                 200                 205

Ser Asn Leu Ala Ser Gly Val Pro Asp Arg Phe Ser Gly Ser Gly Ser
    210                 215                 220

Gly Thr Ala Phe Thr Leu Lys Ile Ser Arg Val Glu Ala Glu Asp Val
225                 230                 235                 240

Gly Val Tyr Tyr Cys Met Gln His Ile Glu Tyr Pro Phe Thr Phe Gly
                245                 250                 255

Gln Gly Thr Lys Leu Glu Ile Lys Gly Gly Gly Gly Ser Gly Gly Gly
            260                 265                 270

Gly Ser Gly Gly Gly Gly Ser Gln Val Gln Leu Val Gln Ser Gly Pro
        275                 280                 285

Glu Val Lys Lys Pro Gly Ala Ser Val Lys Val Ser Cys Lys Ala Ser
    290                 295                 300

Gly Tyr Thr Phe Thr Asn Ser Trp Met Asn Trp Val Arg Gln Arg Pro
305                 310                 315                 320

Gly Lys Gly Leu Glu Trp Ile Gly Arg Ile Tyr Pro Gly Asp Gly Glu
                325                 330                 335

Thr Ile Tyr Asn Gly Lys Phe Arg Val Arg Val Thr Ile Thr Ala Asp
            340                 345                 350

Glu Ser Thr Ser Thr Ala Tyr Met Glu Leu Ser Ser Leu Arg Ser Glu
        355                 360                 365

Asp Thr Ala Val Tyr Tyr Cys Ala Arg Gly Tyr Asp Asp Tyr Ser Phe
    370                 375                 380

Ala Tyr Trp Gly Gln Gly Thr Thr Val Thr Val Ser Ser Gly Gly Gly
385                 390                 395                 400

Gly Ser Gly Gly Gly Gly Ser Gly Gly Gly Gly Ser Asp Ile Val Met
                405                 410                 415

Thr Gln Ser Pro Leu Ser Leu Pro Val Thr Pro Gly Glu Pro Ala Ser
            420                 425                 430

Ile Ser Cys Arg Ser Ser Lys Ser Leu Leu His Ser Asn Gly Asn Thr
```

```
        435                 440                 445

Tyr Leu Tyr Trp Phe Gln Gln Lys Pro Gly Gln Ala Pro Arg Leu Leu
    450                 455                 460

Ile Tyr Arg Met Ser Asn Leu Ala Ser Gly Val Pro Asp Arg Phe Ser
465                 470                 475                 480

Gly Ser Gly Ser Gly Thr Ala Phe Thr Leu Lys Ile Ser Arg Val Glu
                485                 490                 495

Ala Glu Asp Val Gly Val Tyr Tyr Cys Met Gln His Ile Glu Tyr Pro
            500                 505                 510

Phe Thr Phe Gly Gln Gly Thr Lys Leu Glu Ile Lys
        515                 520


<210> SEQ ID NO 294
<211> LENGTH: 354
<212> TYPE: DNA
<213> ORGANISM: Homo sapiens

<400> SEQUENCE: 294

caggtgcagc tggtgcagtc tggacctgag gtgaagaagc ctggggcctc agtgaaggtc      60

tcctgcaagg cttctggata caccttcacc aactcctgga tgaactgggt gaggcagagg     120

cctggaaagg gtcttgagtg gattggacgg atttatcctg gagatggaga aactatctac     180

aatgggaaat tcagggtcag agtcacgatt accgcggacg aatccacgag cacagcctac     240

atggagctga gcagcctgag atctgaggac acggccgtgt attactgtgc gagaggctat     300

gatgattact cgtttgctta ctggggccag ggaaccacgg tcaccgtctc ttca           354


<210> SEQ ID NO 295
<211> LENGTH: 118
<212> TYPE: PRT
<213> ORGANISM: Homo sapiens

<400> SEQUENCE: 295

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asn Ser
            20                  25                  30

Trp Met Asn Trp Val Arg Gln Arg Pro Gly Lys Gly Leu Glu Trp Ile
        35                  40                  45

Gly Arg Ile Tyr Pro Gly Asp Gly Glu Thr Ile Tyr Asn Gly Lys Phe
    50                  55                  60

Arg Val Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Asp Tyr Ser Phe Ala Tyr Trp Gly Gln Gly Thr
            100                 105                 110

Thr Val Thr Val Ser Ser
        115


<210> SEQ ID NO 296
<211> LENGTH: 336
<212> TYPE: DNA
<213> ORGANISM: Homo sapiens

<400> SEQUENCE: 296

gatattgtga tgactcagtc tccactctcc ctgcccgtca cccctggaga gccggcctcc      60

atctcctgca ggtctagtaa gagtctcctg catagtaatg gcaacactta cttgtattgg     120
```

```
ttccagcaga agccagggca ggctccacgg ctcctgatct atcggatgtc caaccttgcc    180

tcaggggtcc ctgacaggtt cagtggcagt ggatcaggca cagcttttac actgaaaatc    240

agcagagtgg aggctgagga tgttggggtt tattactgca tgcaacatat agaatatcct    300

tttacgttcg gccaagggac caaactggaa atcaaa                              336
```

<210> SEQ ID NO 297
<211> LENGTH: 112
<212> TYPE: PRT
<213> ORGANISM: Homo sapiens

<400> SEQUENCE: 297

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Phe Gln Gln Lys Pro Gly Gln Ala
        35                  40                  45

Pro Arg Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Lys Ile
65                  70                  75                  80

Ser Arg Val Glu Ala Glu Asp Val Gly Val Tyr Tyr Cys Met Gln His
                85                  90                  95

Ile Glu Tyr Pro Phe Thr Phe Gly Gln Gly Thr Lys Leu Glu Ile Lys
            100                 105                 110
```

<210> SEQ ID NO 298
<211> LENGTH: 30
<212> TYPE: PRT
<213> ORGANISM: Homo sapiens

<400> SEQUENCE: 298

```
Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr
            20                  25                  30
```

<210> SEQ ID NO 299
<211> LENGTH: 14
<212> TYPE: PRT
<213> ORGANISM: Homo sapiens

<400> SEQUENCE: 299

```
Trp Val Arg Gln Arg Pro Gly Lys Gly Leu Glu Trp Ile Gly
1               5                   10
```

<210> SEQ ID NO 300
<211> LENGTH: 32
<212> TYPE: PRT
<213> ORGANISM: Homo sapiens

<400> SEQUENCE: 300

```
Arg Val Thr Ile Thr Ala Asp Glu Ser Thr Ser Thr Ala Tyr Met Gln
1               5                   10                  15

Leu Ser Ser Leu Arg Ser Glu Asp Thr Ala Val Tyr Tyr Cys Ala Arg
            20                  25                  30
```

<210> SEQ ID NO 301
<211> LENGTH: 11

<212> TYPE: PRT
<213> ORGANISM: Homo sapiens

<400> SEQUENCE: 301

Trp Gly Gln Gly Thr Thr Val Thr Val Ser Ser
1 5 10

<210> SEQ ID NO 302
<211> LENGTH: 23
<212> TYPE: PRT
<213> ORGANISM: Homo sapiens

<400> SEQUENCE: 302

Asp Ile Val Met Thr Gln Ser Pro Leu Ser Leu Pro Val Thr Pro Gly
1 5 10 15

Glu Pro Ala Ser Ile Ser Cys
20

<210> SEQ ID NO 303
<211> LENGTH: 15
<212> TYPE: PRT
<213> ORGANISM: Homo sapiens

<400> SEQUENCE: 303

Trp Phe Leu Gln Lys Pro Gly Gln Ser Pro Gln Leu Leu Ile Tyr
1 5 10 15

<210> SEQ ID NO 304
<211> LENGTH: 32
<212> TYPE: PRT
<213> ORGANISM: Homo sapiens

<400> SEQUENCE: 304

Gly Val Pro Asp Arg Phe Ser Gly Ser Gly Ser Gly Thr Asp Phe Thr
1 5 10 15

Leu Lys Ile Ser Arg Val Glu Ala Glu Asp Val Gly Val Tyr Tyr Cys
20 25 30

<210> SEQ ID NO 305
<211> LENGTH: 10
<212> TYPE: PRT
<213> ORGANISM: Homo sapiens

<400> SEQUENCE: 305

Phe Gly Gln Gly Thr Lys Leu Glu Ile Lys
1 5 10

<210> SEQ ID NO 306
<211> LENGTH: 32
<212> TYPE: PRT
<213> ORGANISM: Homo sapiens

<400> SEQUENCE: 306

Arg Val Thr Ile Thr Ala Asp Glu Ser Thr Ser Thr Ala Tyr Met Glu
1 5 10 15

Leu Ser Ser Leu Arg Ser Glu Asp Thr Ala Val Tyr Tyr Cys Ala Arg
20 25 30

<210> SEQ ID NO 307
<211> LENGTH: 15
<212> TYPE: PRT
<213> ORGANISM: Homo sapiens

<400> SEQUENCE: 307

-continued

```
Trp Phe Gln Gln Lys Pro Gly Gln Ala Pro Arg Leu Leu Ile Tyr
1               5                   10                  15


<210> SEQ ID NO 308
<211> LENGTH: 32
<212> TYPE: PRT
<213> ORGANISM: Homo sapiens

<400> SEQUENCE: 308

Gly Val Pro Asp Arg Phe Ser Gly Ser Gly Ser Gly Thr Ala Phe Thr
1               5                   10                  15

Leu Lys Ile Ser Arg Val Glu Ala Glu Asp Val Gly Val Tyr Tyr Cys
            20                  25                  30
```